US012807660B2

(12) United States Patent
Xu

(10) Patent No.: US 12,807,660 B2
(45) Date of Patent: Nov. 24, 2026

(54) NEUROD1 AND DLX2 VECTOR

(71) Applicant: NeuExcell Therapeutics Inc., State College, PA (US)

(72) Inventor: Jie Xu, State College, PA (US)

(73) Assignee: NeuExcell Therapeutics Inc., State College, PA (US)

( * ) Notice: Subject to any disclaimer, the term of this patent is extended or adjusted under 35 U.S.C. 154(b) by 0 days.

(21) Appl. No.: 17/487,169

(22) Filed: Sep. 28, 2021

(65) Prior Publication Data

US 2022/0098254 A1 Mar. 31, 2022

Related U.S. Application Data

(60) Provisional application No. 63/247,442, filed on Sep. 23, 2021, provisional application No. 63/084,945, filed on Sep. 29, 2020.

(51) Int. Cl.

| | |
|---|---|
| ***C07K 14/47*** | (2006.01) |
| ***C12N 5/0793*** | (2010.01) |
| ***C12N 15/86*** | (2006.01) |
| *A61K 48/00* | (2006.01) |

(52) U.S. Cl.

CPC ........ *C07K 14/4702* (2013.01); *C12N 5/0619* (2013.01); *C12N 15/86* (2013.01); *A61K 48/00* (2013.01); *C12N 2501/60* (2013.01); *C12N 2506/08* (2013.01); *C12N 2750/14143* (2013.01); *C12N 2750/14171* (2013.01); *C12N 2830/008* (2013.01); *C12N 2830/48* (2013.01); *C12N 2830/50* (2013.01); *C12N 2840/203* (2013.01)

(58) Field of Classification Search

CPC ............ C12N 2501/60; C12N 2830/48; C12N 2830/50; C12N 2840/203

See application file for complete search history.

(56) References Cited

U.S. PATENT DOCUMENTS

| | | | |
|---|---|---|---|
| 5,648,097 | A | 7/1997 | Nuwayser |
| 5,695,995 | A | 12/1997 | Weintraub et al. |
| 6,444,463 | B1 | 9/2002 | Tapscott |
| 6,602,680 | B2 | 8/2003 | Rubenstein et al. |
| 6,630,486 | B1 | 10/2003 | Royer |
| 7,041,507 | B1 | 5/2006 | Levesque et al. |
| 8,257,969 | B2 | 9/2012 | Farrar et al. |
| 8,440,431 | B2 | 5/2013 | Voytas et al. |
| 8,440,432 | B2 | 5/2013 | Voytas et al. |
| 8,450,471 | B2 | 5/2013 | Voytas et al. |
| 8,586,363 | B2 | 11/2013 | Voytas et al. |
| 8,617,876 | B2 | 12/2013 | Farrar et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 9,260,752 | B1 | 2/2016 | May et al. |
| 9,410,198 | B2 | 8/2016 | May et al. |
| 9,717,804 | B2 | 8/2017 | Chen et al. |
| 9,725,714 | B2 | 8/2017 | May et al. |
| 9,738,908 | B2 | 8/2017 | Wu |
| 9,803,194 | B2 | 10/2017 | May et al. |
| 9,809,814 | B1 | 11/2017 | May et al. |
| 10,076,574 | B2 | 9/2018 | Wang et al. |
| 10,201,619 | B2 | 2/2019 | Chen et al. |
| 10,561,742 | B2 | 2/2020 | Chen et al. |
| 10,973,930 | B2 | 4/2021 | Chen et al. |
| 11,014,976 | B2 | 5/2021 | Esteves et al. |
| 11,104,881 | B2 | 8/2021 | Ying et al. |
| 11,167,044 | B2 | 11/2021 | Chen et al. |
| 11,851,491 | B2 | 12/2023 | Baeuerle et al. |
| 2002/0151066 | A1 | 10/2002 | Rubenstein et al. |
| 2002/0172952 | A1 | 11/2002 | Henderson et al. |
| 2002/0187951 | A1 | 12/2002 | Aebischer et al. |
| 2004/0141946 | A1 | 7/2004 | Schaebitz et al. |
| 2004/0192630 | A1 | 9/2004 | Kyrkanides |
| 2005/0265981 | A1 | 12/2005 | Salim-Nordstrom |
| 2006/0127358 | A1 | 6/2006 | Muzyczka et al. |
| 2008/0050393 | A1 | 2/2008 | Tang et al. |
| 2009/0055941 | A1 | 2/2009 | Wang et al. |
| 2009/0238795 | A1 | 9/2009 | Sehgal et al. |
| 2010/0226912 | A1 | 9/2010 | Mehtali |
| 2010/0247487 | A1 | 9/2010 | Sehgal et al. |
| 2011/0003327 | A1 | 1/2011 | Chien et al. |

(Continued)

FOREIGN PATENT DOCUMENTS

| | | | |
|---|---|---|---|
| CA | 2903933 | A1 | 3/2017 |
| CN | 1756556 | A | 4/2006 |

(Continued)

OTHER PUBLICATIONS

Cell biolab pAAV-MCS Expression vector sequence (pAAV-MCS) (Year: 2023).*

Fan (Plasmids 101: Multicistronic Vectors, Addgene Blog, Published Sep. 9, 2014) (Year: 2014).*

AmCyan-P2A-mCherry vector sequence (P2A sequence) (Year: 2023).*

Boulaire et al (Transcriptional targeting to brain cells: Engineering cell type-specific promoter containing cassettes for enhanced transgene expression. Advanced Drug Delivery Reviews, vol. 61, Apr. 2009) (Year: 2009).*

Powell et al (Viral Expression Cassette Elements to Enhance Transgene Target Specificity and Expression in Gene Therapy. Discov Med., vol. 19, Jan. 2015). (Year: 2015).*

HGFAP-Cre (Year: 2001).*

(Continued)

*Primary Examiner* — Peter Paras, Jr.
*Assistant Examiner* — Matasha Dhar
(74) *Attorney, Agent, or Firm* — Jones Day

(57) ABSTRACT

The present disclosure relates to AAV vectors, compositions, and methods related to converting glial cells to neurons by the use of NeuroD1 and Dlx2 coding sequences in an AAV vector.

11 Claims, 64 Drawing Sheets

Specification includes a Sequence Listing.

(56) References Cited

U.S. PATENT DOCUMENTS

| | | | |
|---|---|---|---|
| 2011/0207828 | A1 | 8/2011 | Miller et al. |
| 2011/0217274 | A1 | 9/2011 | Reld |
| 2011/0223635 | A1 | 9/2011 | Deisseroth et al. |
| 2012/0040393 | A1 | 2/2012 | Zhang et al. |
| 2012/0278912 | A1 | 11/2012 | Farrar et al. |
| 2012/0301446 | A1 | 11/2012 | Zhu et al. |
| 2013/0022583 | A1 | 1/2013 | Wernig et al. |
| 2013/0095118 | A1 | 4/2013 | Smith et al. |
| 2014/0010861 | A1 | 1/2014 | Bancel et al. |
| 2014/0024599 | A1 | 1/2014 | Chen et al. |
| 2014/0051171 | A1 | 2/2014 | Christensen et al. |
| 2014/0068797 | A1 | 3/2014 | Doudna et al. |
| 2014/0273235 | A1 | 9/2014 | Voytas et al. |
| 2014/0315782 | A1 | 10/2014 | Tremblay et al. |
| 2015/0023927 | A1 | 1/2015 | Eggan et al. |
| 2015/0065376 | A1 | 3/2015 | Knaut et al. |
| 2015/0067922 | A1 | 3/2015 | Yang et al. |
| 2015/0079680 | A1 | 3/2015 | Bradley |
| 2015/0132821 | A1 | 5/2015 | Fine et al. |
| 2015/0190481 | A1 | 7/2015 | Finn |
| 2015/0250900 | A1 | 9/2015 | Chen et al. |
| 2015/0283065 | A1 | 10/2015 | Frey, II et al. |
| 2015/0335708 | A1 | 11/2015 | Froelich et al. |
| 2016/0024600 | A1 | 1/2016 | Inglese et al. |
| 2016/0046700 | A1 | 2/2016 | Foster et al. |
| 2016/0115447 | A1 | 4/2016 | Blumenstein et al. |
| 2016/0175462 | A1 | 6/2016 | Zhang et al. |
| 2016/0194625 | A1 | 7/2016 | Hoge et al. |
| 2016/0199412 | A1 | 7/2016 | Tareen |
| 2016/0234600 | A1 | 8/2016 | Kajihara et al. |
| 2016/0263233 | A1 | 9/2016 | Wang et al. |
| 2016/0296605 | A1 | 10/2016 | Zhang |
| 2016/0355797 | A1 | 12/2016 | Konermann et al. |
| 2017/0035839 | A1 | 2/2017 | Miller et al. |
| 2017/0073382 | A1 | 3/2017 | Wong et al. |
| 2017/0096683 | A1 | 4/2017 | Scaria et al. |
| 2017/0101622 | A1 | 4/2017 | Ahlfors et al. |
| 2017/0152528 | A1 | 6/2017 | Zhang |
| 2017/0216456 | A1 | 8/2017 | Alexander et al. |
| 2017/0224843 | A1 | 8/2017 | Deglon et al. |
| 2017/0239373 | A1 * | 8/2017 | Chen .................. C07K 14/4702 |
| 2017/0304463 | A1 | 10/2017 | Chen et al. |
| 2017/0320968 | A1 | 11/2017 | Tremblay et al. |
| 2018/0087052 | A1 | 3/2018 | Hung et al. |
| 2018/0187188 | A1 | 7/2018 | Lee et al. |
| 2018/0282759 | A1 | 10/2018 | Hu et al. |
| 2018/0311290 | A1 | 11/2018 | Sena-Esteves et al. |
| 2018/0320200 | A1 | 11/2018 | Hajitou et al. |
| 2019/0000982 | A1 | 1/2019 | Wang et al. |
| 2019/0024056 | A1 | 1/2019 | Ahlfors et al. |
| 2019/0032078 | A1 | 1/2019 | Kielian et al. |
| 2019/0046664 | A1 | 2/2019 | Schnieders et al. |
| 2019/0055552 | A1 | 2/2019 | Davidson et al. |
| 2019/0111157 | A1 | 4/2019 | Stanek et al. |
| 2019/0117797 | A1 | 4/2019 | Chen et al. |
| 2019/0153412 | A1 | 5/2019 | Zhang et al. |
| 2019/0276540 | A1 | 9/2019 | Baeuerle et al. |
| 2020/0054711 | A1 | 2/2020 | Chen et al. |
| 2020/0056159 | A1 | 2/2020 | Wilson et al. |
| 2020/0080107 | A1 | 3/2020 | Rezania |
| 2020/0106958 | A1 | 4/2020 | Yang et al. |
| 2020/0108193 | A1 | 4/2020 | Glaser |
| 2020/0123517 | A1 | 4/2020 | Mijts et al. |
| 2020/0181592 | A1 | 6/2020 | Mijts et al. |
| 2020/0190494 | A1 | 6/2020 | Hou et al. |
| 2020/0190504 | A1 | 6/2020 | Baltes |
| 2020/0255859 | A1 | 8/2020 | Yang et al. |
| 2020/0270635 | A1 | 8/2020 | Hou et al. |
| 2020/0384076 | A1 | 12/2020 | Passini et al. |
| 2020/0405801 | A1 | 12/2020 | Chen et al. |
| 2021/0032300 | A1 | 2/2021 | Chen et al. |
| 2021/0155664 | A1 | 5/2021 | Chen et al. |
| 2021/0162002 | A1 | 6/2021 | Chen et al. |
| 2021/0162003 | A1 | 6/2021 | Chen et al. |
| 2021/0162072 | A1 | 6/2021 | Moullier et al. |
| 2021/0163985 | A1 | 6/2021 | Sah et al. |
| 2021/0260217 | A1 | 8/2021 | Chen et al. |
| 2021/0324044 | A1 | 10/2021 | Esteves et al. |
| 2021/0346473 | A1 | 11/2021 | McIvor et al. |
| 2021/0395692 | A1 | 12/2021 | Ko et al. |
| 2021/0395777 | A1 | 12/2021 | Slack et al. |
| 2022/0040236 | A1 | 2/2022 | Chen |
| 2022/0064671 | A1 | 3/2022 | Maranga et al. |
| 2022/0072153 | A1 | 3/2022 | Chen et al. |
| 2022/0098254 | A1 | 3/2022 | Xu |
| 2022/0098255 | A1 | 3/2022 | Xu |
| 2022/0098616 | A1 | 3/2022 | Xu |
| 2022/0098617 | A1 | 3/2022 | Xu |
| 2022/0106613 | A1 | 4/2022 | Xu |
| 2022/0106614 | A1 | 4/2022 | Xu |
| 2022/0152224 | A1 | 5/2022 | Chen et al. |
| 2022/0160825 | A1 | 5/2022 | Chen et al. |
| 2022/0175970 | A1 | 6/2022 | Kerr et al. |
| 2022/0186256 | A1 | 6/2022 | Danos et al. |
| 2022/0211871 | A1 | 7/2022 | Abeliovich et al. |
| 2022/0339270 | A1 | 10/2022 | Liu et al. |
| 2022/0395586 | A1 | 12/2022 | Stanek et al. |
| 2023/0021959 | A1 | 1/2023 | Small et al. |
| 2023/0075314 | A1 | 3/2023 | Hou et al. |
| 2023/0084580 | A1 | 3/2023 | Passini et al. |
| 2023/0135379 | A1 | 5/2023 | Passini et al. |
| 2023/0142867 | A1 | 5/2023 | Ramu |
| 2023/0220014 | A1 | 7/2023 | Cheng et al. |
| 2023/0242939 | A1 | 8/2023 | Mathur et al. |
| 2023/0302158 | A1 | 9/2023 | Daigle et al. |
| 2023/0304032 | A1 | 9/2023 | Sah et al. |
| 2023/0330267 | A1 | 10/2023 | Cao et al. |
| 2024/0082352 | A1 | 3/2024 | Chen et al. |
| 2024/0117322 | A1 | 4/2024 | Wilson et al. |

FOREIGN PATENT DOCUMENTS

| | | | |
|---|---|---|---|
| CN | 101553245 | A | 10/2007 |
| CN | 101693107 | A | 4/2010 |
| CN | 102083964 | A | 6/2011 |
| CN | 102858985 | A | 1/2013 |
| CN | 103667190 | A | 3/2014 |
| CN | 104870634 | A | 8/2015 |
| CN | 105377039 | A | 3/2016 |
| CN | 105745326 | A | 7/2016 |
| CN | 102459611 | B | 11/2016 |
| CN | 106170295 | A | 11/2016 |
| CN | 106460054 | A | 2/2017 |
| CN | 107530447 | A | 1/2018 |
| CN | 107683289 | A | 2/2018 |
| CN | 109069544 | A | 12/2018 |
| CN | 110741082 | A | 1/2020 |
| CN | 111448308 | A | 7/2020 |
| CN | 111630170 | A | 9/2020 |
| CN | 111886343 | A | 11/2020 |
| CN | 112245592 | A | 1/2021 |
| CN | 113966400 | A | 1/2022 |
| CN | 114026242 | A | 2/2022 |
| CN | 114127089 | A | 3/2022 |
| CN | 115997011 | A | 4/2023 |
| CN | 116209768 | A | 6/2023 |
| KR | 10-2016-0143651 | A | 12/2016 |
| WO | WO 2005/021704 | A2 | 3/2005 |
| WO | WO 2005/037226 | A2 | 4/2005 |
| WO | WO 2005/056807 | A2 | 6/2005 |
| WO | WO 2005/113812 | A2 | 12/2005 |
| WO | WO 2008/013737 | A2 | 1/2008 |
| WO | WO 2008/083931 | A1 | 7/2008 |
| WO | WO 2009/100131 | A2 | 8/2009 |
| WO | WO 2009/136168 | A1 | 11/2009 |
| WO | WO 2009/142602 | A1 | 11/2009 |
| WO | WO 2009/143578 | A1 | 12/2009 |
| WO | WO 2010/053522 | A2 | 5/2010 |
| WO | WO 2010/129021 | A1 | 11/2010 |
| WO | WO 2011/011767 | A1 | 1/2011 |
| WO | WO 2011/050476 | A1 | 5/2011 |
| WO | WO 2011/072246 | A2 | 6/2011 |
| WO | WO 2011/097181 | A2 | 8/2011 |
| WO | WO 2012/010675 | A2 | 1/2012 |

(56) References Cited

FOREIGN PATENT DOCUMENTS

| | | | |
|---|---|---|---|
| WO | WO 2013/025963 A1 | 2/2013 | |
| WO | WO 2013/071440 A1 | 5/2013 | |
| WO | WO 2014/003553 | 1/2014 | |
| WO | WO 2014/015261 A1 | 1/2014 | |
| WO | WO 2014/153230 A1 | 9/2014 | |
| WO | WO 2014/186579 A1 | 11/2014 | |
| WO | WO 2014/204729 A1 | 12/2014 | |
| WO | WO 2015/060722 A1 | 4/2015 | |
| WO | WO 2015/061779 A1 | 4/2015 | |
| WO | WO 2015/069736 A1 | 5/2015 | |
| WO | WO 2015/120776 A1 | 8/2015 | |
| WO | WO 2015/131788 A1 | 9/2015 | |
| WO | WO 2015/142293 A1 | 9/2015 | |
| WO | WO 2016/123142 A1 | 8/2016 | |
| WO | WO 2016/125148 A1 | 8/2016 | |
| WO | WO 2016/130591 A2 | 8/2016 | |
| WO | WO 2016/161124 A1 | 10/2016 | |
| WO | WO 2017/100671 A1 | 6/2017 | |
| WO | WO 2017/112859 A1 | 6/2017 | |
| WO | WO 2017/143207 A1 | 8/2017 | |
| WO | WO 2018/160582 A1 | 9/2018 | |
| WO | WO 2018/160712 A1 | 9/2018 | |
| WO | WO 2019/025984 A1 | 2/2019 | |
| WO | WO 2019/028306 A2 | 2/2019 | |
| WO | WO 2019/032320 A1 | 2/2019 | |
| WO | WO 2019/094694 A1 | 5/2019 | |
| WO | WO 2019/152857 A1 | 8/2019 | |
| WO | WO 2019/165050 A1 | 8/2019 | |
| WO | WO 2019/204503 A1 | 10/2019 | |
| WO | WO 2020/033601 A1 | 2/2020 | |
| WO | WO 2020/072873 A1 | 4/2020 | |
| WO | WO 2020/097155 A1 | 5/2020 | |
| WO | WO 2020/106916 A1 | 5/2020 | |
| WO | WO 2020/163102 A1 | 8/2020 | |
| WO | WO 2020/198485 A1 | 10/2020 | |
| WO | WO 2020/206189 A1 | 10/2020 | |
| WO | WO 2020/210615 A1 | 10/2020 | |
| WO | WO-2020219563 A1 * | 10/2020 | ............ C12N 15/85 |
| WO | WO 2020/223276 A1 | 11/2020 | |
| WO | WO 2020/223279 A1 | 11/2020 | |
| WO | WO 2020/245169 A1 | 12/2020 | |
| WO | WO 2020/263639 A1 | 12/2020 | |
| WO | WO 2021/076947 A1 | 4/2021 | |
| WO | WO 2021/076951 A1 | 4/2021 | |
| WO | WO 2021/076983 A1 | 4/2021 | |
| WO | WO 2021/108609 A1 | 6/2021 | |
| WO | WO 2021/154923 A2 | 8/2021 | |
| WO | WO 2021/216456 A2 | 10/2021 | |
| WO | WO 2021/216975 A1 | 10/2021 | |
| WO | WO 2022/003211 A1 | 1/2022 | |
| WO | WO 2022/036255 A1 | 2/2022 | |
| WO | WO 2022/051633 A2 | 3/2022 | |
| WO | WO 2022/072308 A1 | 4/2022 | |
| WO | WO 2022/072309 A1 | 4/2022 | |
| WO | WO 2022/072310 A1 | 4/2022 | |
| WO | WO 2022/072322 | 4/2022 | |
| WO | WO 2022/072324 A1 | 4/2022 | |
| WO | WO/2022/072325 A1 | 4/2022 | |

OTHER PUBLICATIONS

GenBank: LT738798.1 (NCBI, available since Feb. 15, 2017), (Year: 2017).*

GenBank: HQ258018.1 (NCBI, available since Jul. 25, 2016), (Year: 2016).*

Lee et al (GFAP promoter elements required for region-specific and astrocyte-specific expression. Glia, vol. 56, Apr. 2008), (Year: 2008).*

Wu et al (Optimization of Self-complementary AAV Vectors for Liver-directed Expression Results in Sustained Correction of Hemophilia B at Low Vector Dose. Mol. Therapy, vol. 16 No. 2, 280-289 Feb. 2008), (Year: 2008).*

Wang et al (Astrocytic expression of transgene in the rat brain mediated by baculovirus vectors containing an astrocyte-specific promoter. Gene Therapy (2006) 13, 1447-1456), (Year: 2006).*

PWPI vector sequence (IRES sequence), (Year: 2014).*

PUltra vector sequence (T2A sequence), (Year: 2014).*

PGfaABC1D-nLac vector sequence (truncated hGFAp promoter), (Year: 2008).*

PRc/CMV2 vector sequence (CMV enhancer) (Year: 2006).*

PCI-Neo vector sequence (chimeric intron), (Year: 2008).*

PcDNA3.1 vector sequence (bGH poly A). (Year: 2008).*

Altschul et al., "Basic local alignment search tool." *Journal of Molecular Biology*, 215(3):403-410 (1990).

Chenna et al., "Multiple sequence alignment with the Clustal series of programs," *Nucleic Acids Research*, 31: 3497-3500 (2003).

Cong et al., "Multiplex Genome Engineering Using CRISPR/Cas Systems," *Science*, 339(6121): 819-823 (2013).

Larkin et al., "Clustal W and Clustal X version 2.0," *Bioinformatics*, 23(21): 2947-48 (2007).

Livak et al., "Analysis of Relative Gene Expression Data Using Real-Time Quantitative PCR and the 2-ΔΔCT Method." *Methods*, 25(4): 402-408 (2001).

Makarova et al., "An updated evolutionary classification of CRISPR—Cas systems," *Nature Reviews Microbiology*, 13: 722-736 (2015) doi: 10.1038/nrmicro3569.

Song et al., "Astroglia induce neurogenesis from adult neural stem cells," *Nature*, 417: 39-44 (2002).

Thompson et al., "Clustal W: Improving the sensitivity of progressive multiple sequence alignment through sequence weighting, position-specific gap penalties and weight matrix choice," *Nucleic Acids Research*, 22: 4673-4680 (1994).

Zetsche et al., "Cpf1 Is a Single RNA-Guided Endonuclease of a Class 2 CRISPR-Cas System," *Cell*, 163(3): 759-771 (2015) doi: 10.1016/j.cell.2015.09.038.

International Search Report dated Feb. 17, 2022, PCT/US2021/52348.

Abernathy et al., "MicroRNAs Induce a Permissive Chromatin Environment that Enables Neuronal Subtype-Specific Reprogramming of Adult Human Fibroblasts," *Cell Stem Cell*, 21(3), pp. 332-348 (Sep. 2017) (electronic publication).

Abraira et al., "The sensory neurons of touch," *Neuron*, 79(4), pp. 618-639 (Aug. 2013) (electronic publication).

Adams et al., "Spasticity after spinal cord injury," *Spinal Cord*, 43(10), pp. 577-586 (Apr. 2005) (electronic publication).

Addis et al., "Efficient conversion of astrocytes to functional midbrain dopaminergic neurons using a single polycistronic vector," *PLoS One*, 6(12): e28719, pp. 1-8 (Dec. 2011) (electronic publication).

Adil et al., "hPSC-derived striatal cells generated using a sealable 3D hydrogel promote recovery in a Huntington disease mouse model," *Stern Cell Reports*, 10(5), pp. 1481-1491 (May 2018) (electronic publication).

Aguirre et al., "NG2-expressing cells in the subventricular zone are type C-likes cells and contribute to interneuron generation in the postnatal hippocampus," *The Journal of Cell Biology*, 165(4), pp. 575-589 (May 2004) (electronic publication).

Aguirre et al., "Postnatal neurogenesis and gliogenesis in the olfactory bulb from NG2-expressing progenitors of the subventricular zone," *The Journal of Neurosciene*, 24(46), pp. 10530-10541 (Nov. 2004) (electronic publication).

Alaoui-Ismaili, et al. "Design of second generation therapeutic recombinant bone morphogenetic proteins," Cytokine & Growth Factor Reviews, vol. 20, pp. 501-507 (2009) (Amsterdam, Netherlands).

Altschul et al., "Gapped BLAST and PSI-BLAST: a new generation of protein database search programs," *Nucleic Acids Research*, 25(17), pp. 3389-3402 (1997) (electronic publication).

Amador-Arjona et al., "SOX2 primes the epigenetic landscape in neural precursors enabling proper gene activation during hippocampal neurogenesis," *PNAS*, 112(15), pp. E1936-E1945 (Mar. 2015) (electronic publication).

Anderson et al., "Astrocyte scar formation aids central nervous system axon regeneration," *Nature*, 532(7598), pp. 195-200 (Mar. 2016) (electronic publication).

(56) References Cited

OTHER PUBLICATIONS

Anderson et al., "Differential origins of neocortical projection and local circuit neurons: role of Dlx genes in neocortical interneuronogenesis," *Cerebral Cortex*, 9(6), pp. 646-654 (Sep. 1999) (electronic publication).
Anderson et al., "Interneuron migration from basal forebrain to neocortex: dependence on Dlx genes," *Science*, 278(5337), pp. 474-476 (Oct. 1997) (electronic publication).
Animal Research Info, "Huntington's disease," published Nov. 5, 2014 [retrieved on Oct. 21, 2020], Retrieved from: URL<http://www.animalresearch.info/en/medical-advances/diseases-research/huntingtons-disease/> 5 pages.
Araújo et al., "Direct Reprogramming of Adult Human Somatic Stem Cells Into Functional Neurons Using Sox2, Ascl1, and Neurog2," *Frontiers in Cellular Neuroscience*, 12(155), pp. 1-15 (Jun. 2018) (electronic publication).
Ascoli et al., "Petilla terminology: nomenclature of features of GABAergic interneurons of the cerebral cortex," *Nature Review Neuroscience*, 9(7), pp. 557-568 (Jul. 2008) (electronic publication).
Atasoy et al., "A FLEX switch targets Channelrhodopsin-2 to multiple cell types for imaging and long-range circuit mapping," *Journal of Neuroscience*, 28(28), pp. 7025-7030 (Jul. 2008) (electronic publication).
Baird et al., "The staircase test of skilled reaching in mice," *Brain Research Bulletin*, 54(2), pp. 243-250 (Jan. 2001) (electronic publication).
Bani-Yaghoub et al., "Role of Sox2 in the development of the mouse neocortex," *Developmental Biology*, 295(1), pp. 52-66 (Jul. 2006) (electronic publication).
Bardehle et al., "Live imaging of astrocyte responses to acute injury reveals selective juxtavascular proliferation," *Nature Neuroscience*, vol. 16, pp. 580-586 (Mar. 2013) (electronic publication).
Barker et al., "New approaches for brain repair—from rescue to reprogramming," *Nature*, 557(7705), pp. 329-334 (May 2018) (electronic publication).
Barry et al., "Striatal direct and indirect pathway output structures are differentially altered in mouse models of Huntington's disease," *Journal of Neuroscience*, 38(20), pp. 4678-4694 (May 2018) (electronic publication).
Baskin et al., "Two effective behavioral tasks for evaluating sensorimotor dysfunction following traumatic brain injury in mice," *Journal of Neuroscience Methods*, 129(1): 87-93 (Oct. 2003) (electronic publication).
Bates et al., "Huntington disease," *Nature Reviews Disease Primers*, vol. 1, article 15005, pp. 1-21 (Apr. 2015) (electronic publication).
Bayer et al., "Intracellular accumulation of amyloid-Beta—a predictor for synaptic dysfunction and neuron loss in Alzheimer's disease," *Frontiers in Aging Neuroscience*, vol. 2, article 8, pp. 1-10 (Mar. 2010) (electronic publication).
Bermingham et al., "Proprioceptor pathway development is dependent on Isdathi," *Neuron*, 30(2), pp. 411-422 (May 2001) (electronic publication).
Berninger et al., "Functional properties of neurons derived from in vitro reprogrammed postnatal astroglia," *The Journal of Neuroscience*, 27(32), pp. 8654-8664 (Aug. 2007) (electronic publication).
Bertrand et al., "Proneural genes and the specification of neural cell types," *Nature Reviews Neuroscience*, vol. 3, pp. 517-530 (Jul. 2002) (electronic publication).
Bonnard et al., "Recent advances in Nanomedicine for ischemic and hemorrhagic stroke," Stroke, 50(5), pp. 1318-1324 (Apr. 2019) (electronic publication).
Boutin et al., "NeuroD1 induces terminal neuronal differentiation in olfactory neurogenesis," *PNAS*, vol. 107, pp. 1201-1206 (Dec. 2010) (electronic publication).
Bowie, et al. "Deciphering the Message in Protein Sequences: Tolerance to Amino Acid Substitutions," *Science*, New Series, vol. 247, No. 4948. pp. 1306-1313 ((Mar. 1990) (London, UK).
Brandao et al., "Interplay of environmental signals and progenitor diversity on fate specification of cortical GABAergic neurons," *Frontiers in Cellular Neuroscience*, vol. 9, article 149, pp. 1-11 (Apr. 2015) (electronic publication).
Brennan et al., "The Somatic Genomic Landscape of Glioblastoma," *Cell*, 155(2), pp. 462-477 (Oct. 2013) (electronic publication).
Brill et al., "A Dlx2-and Pax6-Dependent Transcriptional Code for Periglomerular Neuron Specification in the Adult Olfactory Bulb," *The Journal of Neuroscience*, 28(25), pp. 6439-6452 (Jun. 2008) (electronic publication).
Brulet et al., "NEUROD1 instructs neuronal conversion in non-reactive astrocytes," *Stem Cell Reports*, 8(6), pp. 1506-1515 (Jun. 2017) (electronic publication).
Buffo et al., "Origin and progeny of reactive gliosis: A source of multipotent cells in the injured brain," *PNAS*, 105(9), pp. 3581-3586 (Mar. 2008) (electronic publication).
Burda et al., "Reactive gliosis and the multicellular response to CNS damage and disease," *Neuron*, 81(2):229-248 (Jan. 2014) (electronic publication).
Burgess, et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology*, vol. 111, pp. 2129-2138 (Nov. 1990) (New York, NY).
Busch et al., "Alzheimer's disease and retinal neurodegeneration share a consistent stress response of the neurovascular unit," *Cellular Physiology and Biochemistry*, 30(6), pp. 1436-1443 (Nov. 2012) (electronic publication).
Bush et al., "Leukocyte Infiltration, Neuronal Degeneration, and Neurite Outgrowth after Ablation of Scar-Forming, Reactive Astrocytes in Adult Transgenic Mice," *Neuron* 23(2), pp. 297-308 (Jun. 1999) (electronic publication).
Bylund et al., "Vertebrate neurogenesis is counteracted by Soxl-3 activity," *Nature Neuroscience*, 6(11), pp. 1162-1168 (Sep. 2003) (electronic publication).
Cai et al., "Misexpression of basic helix-loop-helix genes in the murine cerebral cortex affects cell fate choices and neuronal survival," *Development*, 127(14), pp. 3021-3030 (Jul. 2000) (electronic publication).
Caiazzo et al., "Direct generation of functional dopaminergic neurons from mouse and human fibroblasts," *Nature*, vol. 476, pp. 224-227 (Jul. 2011) (electronic publication).
Cancer Genome Atlas Research Network, "Comprehensive genomic characterization defines human glioblastoma genes and core pathways," *Nature*, 455(7216), pp. 1061-1068 (Sep. 2008) (electronic publication).
Castillo et al., "Comparative profiling of cortical gene expression in Alzheimer's disease patients and mouse models demonstrates. a link between amyloidosis and neuroinflammation," *Scientific Reports*, 7(1), pp. 1-6 (Dec. 2017) (electronic publication).
Celis et al., "High-resolution two-dimensional gel electrophoresis of proteins: isoelectric focusing and nonequilibrium pH gradient electrophoresis (NEPHGE)," *Cell Biology*, A Laboratory Handbook(3): 222-230 (1994) (electronic publication).
Chan et al., "Engineered AAVs for efficient noninvasive gene delivery to the central and peripheral nervous systems," *Nature Neuroscience*, 20(8), pp. 1172-1179 (Jun. 2017) (electronic publication).
Chanda et al., "Generation of Induced Neuronal Cells by the Single Reprogramming Factor ASCL1," *Stem Cell Reports*, 3(2), pp. 282-296 (Aug. 2014) (electronic publication).
Chen et al., "A NeuroD1 AAV-based gene therapy for functional brain repair after ischemic injury through in vivo astrocyte-to-neuron conversion," *Molecular Therapy*, 28(1), pp. 217-234 (Jan. 2020) (electronic publication).
Chen et al., "GAD67-GFP knock-in mice have normal sleep-wake patterns and sleep homeostasis," *Neuroreport*, 21(3), pp. 216-220 (Feb. 2010) (electronic publication).
Chen, "Functional Brain Repair Through In Vivo Cell Conversion," International Society for Stem Cell Research (ISSCR) 2017 Annual Meeting—Poster Abstract Book, Abstract F-1155 p. 401 (2017) (electronic publication).

(56) References Cited

OTHER PUBLICATIONS

Chen et al., "The basic helix-loop-helix transcription factor olig2 is critical for reactive astrocyte proliferation after cortical injury," *Journal of Neuroscience*, 28(43), pp. 10983-10989 (Oct. 2008) (electronic publication).
Cheng et al., "Lbx1 and Tlx3 are opposing switches in determining GABAergic versus glutamatergic transmitter phenotypes," *Nature Neuroscience*, 8(11), pp. 1510-1515 (Oct. 2005) (electronic publication).
Cheng et al., "Neurogenin 2 converts mesenchymal stem cells into a neural precursor fate and improves functional recovery after experimental stroke," *Cellular Physiology and Biochemistry*, 33(3), pp. 847-858 (Apr. 2014) (electronic publication).
Chittajallu et al., "NG2-positive cells in the mouse white and grey matter display distinct physiological properties," *The Journal Physiology*, 561(1), pp. 109-122 (Nov. 2004) (electronic publication).
Cho et al., "Targeted genome engineering in human cells with the Cas9 RNA-guided endonuclease," *Nature Biotechnology*, vol. 31, pp. 230-232 (Jan. 2013) (electronic publication).
Cho et al., "The role of BETA2/NeuroDI in the development of the nervous system," *Molecular Neurobiology*, 30(1), pp. 35-47 (Aug. 2004) (electronic publication).
Choi et al., "Hippocampus-based contextual memory alters the morphological characteristics of astrocytes in the dentate gyrus," *Molecular Brain*, 9(1):72 (Jul. 2016) (electronic publication).
Chouchane et al., "Lineage Reprogramming of Astroglial Cells from Different Origins into Distinct Neuronal Subtypes," *Stem Cell Reports*, 9(1), pp. 162-176 (Jul. 2017) (electronic publication).
Chuang et al., "Partial Reprogramming of Pluripotent Stem Cell-Derived Cardiomyocytes into Neurons," *Scientific Reports*, 7(44840), pp. 1-10 (Mar. 2017) (electronic publication).
Claassen et al., "Tetrabenazine Treatment Patterns and Outcomes for Chorea Associated with Huntington Disease: A Retrospective Chart Review," *Journal of Huntington's Disease*, 7(4), pp. 345-353 (Nov. 2018) (electronic publication).
Clarkson et al., "Reducing excessive GABA-mediated tonic inhibition promotes functional recovery after stroke," *Nature*, 468(7321), pp. 305-309 (Nov. 2010) (electronic publication).
Cobos et al., "Mice lacking Dlx1 show subtype-specific loss of interneurons, reduced inhibition and epilepsy," *Nature Neuroscience*, vol. 8, pp. 1059-1068 (Jul. 2005) (electronic publication).
Colasante et al., "Rapid Conversion of Fibroblasts into Functional Forebrain GABAergic Interneurons by Direct Genetic Reprogramming," *Cell Stem Cell*, 17(6), pp. 719-734, (Dec. 2015) (electronic publication).
Cong et al., "Multiplex genome engineering using CRISPR/Cas systems," *Science*, 339(6121), pp. 819-823 (Jan. 2013) (electronic publication).
Corti et al., "Direct reprogramming of human astrocytes into neural stem cells and neurons," *Experimental Cell Research*, 318(13), pp. 1528-1541 (Aug. 2012) (electronic publication).
Cregg et al., "Functional regeneration beyond the glial scar," *Experimental Neurology*, vol. 253, pp. 197-207 (Mar. 2014) (electronic publication).
Crooke, "Zonis: The Leader in RNA-Targeted," [retrieved on Oct. 21, 2020], Retrieved from: Therapeuticshttps://ir.ionispharma.comistatic-files/e034473b-e000-084-88a6-0dfOc5b6a79e>, 94 pages.
Dayton, et al., "More expansive gene transfer to the rat CNS: AAV PHP.EB vector dose-response and comparison to AAV PHP.B," Gene Therapy, vol. 25, pp. 392-400 (Jul. 2018), (Berlin, Germany).
Deng et al., "Sequential Postsynaptic Maturation Governs the Temporal Order of GABAergic and Glutamatergic Synaptogenesis in Rat Embryonic Cultures," *The Journal of Neuroscience*, 27(40), pp. 1086010869 (Oct. 2007) (electronic publication).
Di Val Cervo et al., "Induction of functional dopamine neurons from human astrocytes in vitro and mouse astrocytes in a Parkinson's disease model," *Nature Biotechnology*, vol. 35, pp. 444-452 (Apr. 2017) (electronic publication).
Di-Carlo et al., "Genome engineering in *Saccharomyces cerevisiae* using CRISPR-Cas systems," *Nucleic Acids Research*, 41(7), pp. 4336-4343 (Mar. 2013) (electronic publication).
Dittgen et al., "Lentivirus-based genetic manipulations of cortical neurons and their optical and electrophysiological monitoring in vivo," *Proceedings of the National Academy of Sciences*, 101(52), pp. 18206-18211 (Dec. 2004) (electronic publication).
Duff et al., "Transgenic mouse models of Alzheimer's disease: How useful have they been for therapeutic development?," *Briefing in Functional Genomics and Proteomics*, 3(1), pp. 47-59, (Apr. 2004) (electronic publication).
El-Serag, "Epidemiology of viral hepatitis and hepatocellular carcinoma," *Gastroenterology*, 142(6), pp. 1264-1273 (May 2012) (electronic publication).
Escartin et al., "Targeted Activation of Astrocytes: A Potential Neuroprotective Strategy," *Molecular Neurobiology*, vol. 33, pp. 231-241 (Oct. 2008) (electronic publication).
Extended European Search Report in European Patent Application No. 17753935.0, dated Jan. 18, 2019, 277 pages.
Extended European Search Report in European Patent Application No. 19747921.5, dated Oct. 1, 2021, 136 pages.
Extended European Search Report in European Patent Application No. 21156322.4, dated Jun. 23, 2022, 9 pages.
Extended European Search Report in European Patent Application No. 21167319.9, dated Jul. 28, 2021, 8 pages.
Fang, "The Molecular Mechanism of the NeuroD1 Gene Regulation Induced by Alt-trans Retinoic Acid in Neural Cells Differential," Dissertation Full-text Database (Electronic Journal) Basic Science, 11: A006-4 (Oct. 2010) (electronic publication).
Ferreira et al., "From the periphery to the brain: Lipocalin-2, a friend or foe?" *Progress in Neurobiology*, vol. 131, pp. 120-136 (Aug. 2015) (electronic publication).
Filous et al., "Determinants of Axon Growth, Plasticity, and Regeneration in the Context of Spinal Cord Injury," *The American Journal of Pathology*, vol. 188, pp. 53-62 (Jan. 2018) (electronic publication).
Foust et al., "Intravascular AAV9 preferentially targets neonatal neurons and adult astrocytes," *Nature Biotechnology*, 27(1), pp. 59-65 (Dec. 2009) (electronic publication).
Freeman, "Specification and morphogenesis of astrocytes," *Science*, 330(6005), pp. 774-778 (Nov. 2010) (electronic publication).
Frost et al., "The role of astrocytes in amyloid production and Alzheimer's disease," *Open Biology*, 7(12), pp. 1-14 (Dec. 2017) (electronic publication).
Fu et al., "MiR-30a-5p ameliorates spinal cord injury-induced inflammatory responses and oxidative stress by targeting Neurod 1 through MAPK/ERK signalling," *Clinical and Experimental Pharmacology and Physiology*, 45(1), pp. 68-74 (Jan. 2018) (electronic publication).
Fuxe et al., "Endothelin-1 induced lesions of the frontoparietal cortex of the rat. A possible model of focal cortical ischemia," *NeuroReport*, 8(11), pp. 2623-2629 (Jul. 1997) (electronic publication).
Gallo et al., "Glial Development: The Crossroads of Regeneration and Repair in the CNS," *Neuron*, 83(2), pp. 283-308 (Jul. 2014) (electronic publication).
Games et al., "Alzheimer-type neuropathology in transgenic mice overexpressing V717F β-amyloid precursor protein," *Nature*, vol. 373, pp. 523-527 (Feb. 1995) (electronic publication).
Gangarossa et al., "Distribution and compartmental organization of GABAergic medium-sized spiny neurons in the mouse nucleus accumbens," *Frontiers in Neural Circuits*, vol. 7, article 22, pp. 1-20 (Feb. 2013) (electronic publication).
Gao et al., "Neurod1 is essential for the survival and maturation of adult-born neurons," *Nature Neuroscience*, 12(9), pp. 1090-1092 (Sep. 2009) (electronic publication).
Gascón et al., "Identification and successful negotiation of a metabolic checkpoint in direct neuronal reprogramming," *Cell Stem Cell*, 18(3), pp. 396-409 (Mar. 2016) (electronic publication).
GenBank Accession No. AAB32188.1, "Nrf2 [*Homo sapiens*]," dated Mar. 3, 1995, 2 pages.
GenBank Accession No. AAH06545.2, "FOXA2 protein, partial [*Homo sapiens*]," dated Oct. 8, 2003, 2 pages.

(56) References Cited

OTHER PUBLICATIONS

GenBank Accession No. AAH11780.1, "Forkhead box A2 [*Homo sapiens*]," dated Jul. 15, 2006, 2 pages.
GenBank Accession No. AAH33890.1, "Forkhead box A1 [*Homo sapiens*]," dated Jul. 17, 2006, 2 pages.
GenBank Accession No. AAH36847.1, "Neurogenin 2 [*Homo sapiens*]," dated Jul. 15, 2006, 2 pages.
GenBank Accession No. AAH46460.1, "Forkhead box J1 [*Homo sapiens*]," dated Jul. 15, 2006, 2 pages.
GenBank Accession No. AAH53850.1, "Forkhead box Q1 [*Homo sapiens*]," dated Jul. 15, 2006, 2 pages.
GenBank Accession No. AAH64698.1, "Transcription factor CP2-like 1 [*Homo sapiens*]," dated Jul. 17, 2006, 2 pages.
GenBank Accession No. AAH80524.1, "E4F transcription factor 1 [*Homo sapiens*]," dated Jul. 15, 2006, 3 pages.
GenBank Accession No. AAH80868.1, "Nkx2-1 protein [synthetic construct]," dated Sep. 2, 2016, 2 pages.
GenBank Accession No. AAH89442.1, "Forkhead box F1 [*Homo sapiens*]," dated Jan. 30, 2008, 2 pages.
GenBank Accession No. AAI43480.1, "GATA4 protein [Homo sapiens], GATA4 protein [*Homo sapiens*]," dated Jan. 8, 2009, 2 pages.
GenBank Accession No. ACA06111.1, "forkhead box A2 [*Homo sapiens*]" dated Feb. 20, 2008, 1 page.
GenBank Accession No. EAW51092.1, "forkhead box N1 [*Homo sapiens*]," dated Mar. 23, 2015, 2 pages.
GenBank Accession No. EAW55070.1, "forkhead box Q1 [*Homo sapiens*]," dated Mar. 23, 2015, 2 pages.
GenBank Accession No. EAW65844.1, "forkhead box A1 [*Homo sapiens*]," dated Mar. 23, 2015, 2 pages.
GenBank Accession No. EAW95250.1, "transcription factor CP2-like 1, isoform CRA_a [*Homo sapiens*]," dated Mar. 23, 2015, 2 pages.
GenBank Accession No. EAW95251.1, "transcription factor CP2-like 1, isoform CRA_b [*Homo sapiens*]," dated Mar. 23, 2015, 2 pages.
GenBank Accession No. EAW95424.1, "forkhead box F1 [*Homo sapiens*], " dated Mar. 23, 2015, 2 pages.
GenBank Accession No. EAX06278.1, "neurogenin 2 [*Homo sapiens*]," dated Mar. 23, 2015, 2 pages.
GenBank Accession No. NM 001308093.1, "*Homo sapiens* GATA binding protein 4 (GATA4), transcript variant 1, mRNA," dated Apr. 28, 2015, 4 pages.
Gen Bank Accession No. NM 001308093.3, "*Homo sapiens* GATA binding protein 4 (GATA4), transcript variant 1 mRNA," Sep. 16, 2022, 5 pages.
GenBank Accession No. NM 002500.4 "*Homo sapiens* neuronal differentiation 1 (NEUROD1), mRNA," dated May 10, 2014, 4 pages.
GenBank Accession No. NM 004316.3, "*Homo sapiens* achaete-scute family bHLH transcription factor 1 (ASCL1), mRNA," dated May 3, 2014,, 4 pages.
Gen Bank Accession No. NM 004316.4, *Homo sapiens* achaete-scute family bHLH transcription factor 1 (ASCL1), mRNA, Jun. 26, 2022, 4 pages.
GenBank Accession No. NM 004405, "*Homo sapiens* distal-less homeobox 2 (DLX2), mRNA," May 10, 2014, 5 pages.
GenBank Accession No. NM 021784.4, "*Homo sapiens* forldtead box A2 (FOXA2), transcript variant 1, mRNA" dated Feb. 2, 2014, 4 pages.
Gen Bank Accession No. NM 021784.5, *Homo sapiens* forkhead box A2 (FOXA2), transcript variant 1, mRNA, Sep. 18, 2022, 4 pages.
Gen Bank Accession No. NM 024019.4, *Homo sapiens* neurogenin 2 (NEUROG2), mRNA, Jun. 1, 2022, 4 pages.
GenBank Accession No. NM 178849.2, "*Homo sapiens* hepatocyte nuclear factor 4, alpha (HNF4A), transcript variant 1, mRNA," Oct. 15, 2014, 4 pages.
Gen Bank Accession No. NM 178849.3, *Homo sapiens* hepatocyte nuclear factor 4 alpha (HNF4A), transcript variant 1 mRNA, Aug. 16, 2022, 6 pages.
GenBank Accession No. NP 000448.3, "hepatocyte nuclear factor 4-alpha isoform HNF4alpha2 [*Homo sapiens*]" dated Oct. 15, 2014, 3 pages.
GenBank Accession No. NP 000449.1, "hepatocyte nuclear factor 1-beta isoform 1 [*Homo sapiens*]," dated Jan. 16, 2015, 3 pages.
GenBank Accession No. NP 001025174.1, "hepatocyte nuclear factor 4-alpha isoform HNElalpha7 [*Fiorito sapiens*]" dated Oct. 15, 2014, 3 pages.
GenBank Accession No. NP 001025175.1, "hepatocyte nuclear factor 4-alpha isoform HNF4alpha9 [*Homo sapiens*]," dated Oct. 15, 2014, 3 pages.
GenBank Accession No. NP 001073136.1, "homeobox protein Nkx-2.1 isofisoform1 [*Homo sapiens*]," dated May 10, 2014, 3 pages.
GenBank Accession No. NP 001108450.1, "tumor protein 63 isoform 2 [*Homo sapiens*]," dated May 4, 2014, 3 pages.
GenBank Accession No. NP 001108451.1, "tumor protein 63 isoform 3 [*Homo sapiens*]," dated May 4, 2014, 3 pages.
GenBank Accession No. NP 001159395.1 "hepatocyte nuclear factor 1-beta isoform 2 [*Homo sapiens*]," dated May 11, 2014, 3 pages.
GenBank Accession No. NP 001230009.1, "ETS-related transcription factor Elf-5 isoform 3 [*Homo sapiens*]," dated Feb. 26, 2014, 3 pages.
GenBank Accession No. NP 001230010.1, "ETS-related transcription factor Elf-5 isoform 4 [*Homo sapiens*]," dated Aug. 9, 2014, 3 pages.
GenBank Accession No. NP 001245284.1, "hepatocyte nuclear factor 4-alpha isoform HNF4alpha4 [*Homo sapiens*]," dated Oct. 15, 2014, 3 pages.
GenBank Accession No. NP 001274111.1, "hepatocyte nuclear factor 4-alpha isoform HNE4alpha10 [*Homo sapiens*]," dated Oct. 15, 2014, 3 pages.
GenBank Accession No. NP 001274112.1, "hepatocyte nuclear factor 4-alpha isoform HNF4alpha11 [*Homo sapiens*]," dated Oct. 15, 2014, 3 pages.
GenBank Accession No. NP 001274113.1, "hepatocyte nuclear factor 4-alpha isoform 1INF4alpha12 [*Homo sapiens*]," dated Jan. 18, 2014, 3 pages.
GenBank Accession No. NP 001291215.1, "hepatocyte nuclear factor 1-beta isoform 3 [*Homo sapiens*]," dated Jan. 15, 2015, 3 pages.
GenBank Accession No. NP 001295022.1, "transcription factor GATA-4 isoform 1 [*Homo sapiens*]," dated Apr. 28, 2015, 3 pages.
GenBank Accession No. NP 001295023.1, "transcription factor GATA-4 isoform 3 [*Homo sapiens*]," dated Apr. 28, 2015, 3 pages.
GenBank Accession No. NP 001316073.1, "tumor protein 63 isoform 7 [*Homo sapiens*]," dated Jul. 2, 2016, 3 pages.
GenBank Accession No. NP 001316893.1, "tumor protein 63 isoform 13 [*Homo sapiens*], " dated Aug. 13, 2016, 3 pages.
GenBank Accession No. NP 001350675.1, "LIM/homeobox protein Lhx3 isoform c [*Homo sapiens*]," dated May 30, 2018, 3 pages.
GenBank Accession No. NP 001350793.1, "B-cell lymphoma/leukemia 11A isoform 4 [*Homo sapiens*]," dated Jun. 3, 2018, 3 pages.
GenBank Accession No. NP 001352538.1, "B-cell lymphoma/leukemia 11A isoform 5 [*Homo sapiens*]," dated Sep. 12, 2018, 3 pages.
GenBank Accession No. NP 001356298.1, forkhead box protein N1 [*Homo sapien*], dated Apr. 8, 2019, 3 pages.
GenBank Accession No. NP 001361203.1, "transcription factor GATA-4 isoform 4 [*Homo sapiens*]," dated Sep. 18, 2019, 3 pages.
GenBank Accession No. NP 001413.1, "ETS-related transcription factor Elf-5 isoform 2 [*Homo sapiens*]," dated May 3, 2014, 3 pages.
GenBank Accession No. NP 001442.2, "forkhead box protein F1 [*Homo sapiens*]," dated May 11, 2014, 3 pages.
GenBank Accession No. NP 001445.2, "forkhead box protein J1 [*Homo sapiens*]," dated May 3, 2014, 3 pages.

(56) References Cited

OTHER PUBLICATIONS

GenBank Accession No. NP 002043.2, "transcription factor GATA-4 [*Homo sapiens*]," dated Sep. 23, 2014, 3 pages.
GenBank Accession No. NP 002193.2, "insulin gene enhancer protein ISL-1 [*Homo sapiens*]," dated Aug. 26, 2018, 3 pages.
GenBank Accession No. NP 002491.2, "neurogenic differentiation factor 1 [*Homo sapiens*]," dated May 10, 2014, 3 pages.
GenBank Accession No. NP 003308.1, "homeobox protein Nkx-2.1 isoisoform2 [*Homo sapiens*]" dated Apr. 19, 2014, 3 pages.
GenBank Accession No. NP 003584.2, "forkhead box protein N1 [*Homo sapiens*]," dated May 3, 2014, 3 pages.
GenBank Accession No. NP 003713.3, tumor protein 63 isoform 1 [*Homo sapien*], May 4, 2014, 2 pages.
GenBank Accession No. NP 004307.2, "achaete-scute homolog 1 [*Homo sapiens*], " dated May 3, 2014,, 2 pages.
GenBank Accession No. NP 004396.1, "homeobox protein DIA-2 [*Homo sapiens*]," May 10, 2014, 3 pages.
GenBank Accession No. NP 004487.2, "hepatocyte nuclear factor 3-alpha [*Homo sapiens*]," dated May 11, 2014, 3 pages.
GenBank Accession No. NP 055368.1, "transcription factor CP2-like protein 1 [*Homo sapiens*]," dated May 14, 2014, 3 pages.
GenBank Accession No. NP 068556.2, "hepatocyte nuclear factor 3-beta isoform 1 [*Homo sapiens*]," dated Feb. 2, 2014, 3 pages.
GenBank Accession No. NP 075044.2, "B-cell lymphoma/leukemia 11A isoform 1 [*Homo sapiens*]," dated May 24, 2014, 4 pages.
GenBank Accession No. NP 076924.1, "neurogenin-2 [*Homo sapiens*], " dated Mar. 16, 2014, 3 pages.
GenBank Accession No. NP 150285.3, "forkhead box protein Q1 [*Homo sapiens*]," dated May 10, 2014,3 pages.
GenBank Accession No. NP 710141.1, "hepatocyte nuclear factor 3-beta isoform 2 [*Homo sapiens*]" dated Feb. 2, 2014, 3 pages.
GenBank Accession No. NP 787110.2, "hepatocyte nuclear factor 4-alpha isoform [*Homo sapiens*]," dated Oct. 15, 2014, 3 pages.
GenBank Accession No. NP 849180.1, "hepatocyte nuclear factor 4-alpha isoform HNF4alphal [*Homo sapiens*]," Oct. 15, 2014, 3 pages.
GenBank Accession No. NP 849181.1, "hepatocyte nuclear factor 4-alpha isoform IINF4alpha3 [*Fiorito sapiens*]," dated Oct. 15, 2014, 3 pages.
GenBank Accession No. NP 938195.1, "ETS-related transcription factor Elf-5 isoform 1 [*Homo sapiens*]," dated Jan. 26, 2014, 3 pages.
GenBank Accession No. P27889.2, "RecName: Full=Hepatocyte nuclear factor 1-beta; Short=1INF-1-beta; Short=FINF-1B; AltName: Full=Homeoprotein LFB3; AltName: Full=Transcription factor 2; Short=TCF-2," dated Feb. 4, 2015, 4 pages.
GenBank Accession No. P35680.1, "RecName: Full=Hepatocyte nuclear factor 1-beta; Short=IINF-1-beta; Short=HNF-1.B; AltName: Full=Homeoprotein LFB3; AltName: Full=Transcription factor 2; Short=TCF-2; AltName: Full=Variant hepatic nuclear factor 1; Short=vHNF1," dated Jan. 7, 2015, 9 pages.
GenBank Accession No. Q12946.2, "RecName: Full=Forkhead box protein F1; AltName: Full=Forkhead-related activator 1; Short= FREAC-1; AltName: Full=Forkhead-related protein FKFIL5: AltName: Full=Forkhead-related transcription factor I," dated Feb. 4, 2015, 6 pages.
GenBank Accession No. Q13562.3, "RecName: Full=Neurogenic differentiation factor 1; Short=NeuroD; Short=NeuroD1; AltName: Full=Class A basic helix-loop-helix protein 3; Short=bHLHa3," dated Feb. 4, 2015, 6 pages.
GenBank Accession No. Q66K89.2, RecName: Full=Transcription factor E4F1; AltName: Full=E4F transcription factor 1; AltName: Full=Putative E3 ubiquitin-protein ligase E4F1; AltName: Full= Transcription factor E4F; AltName: Full=p120E4F; AltName: Full= p50E4F, dated Feb. 4, 2015, 9 pages.
GenBank Accession No. Q9H165.2, "RecName: Full=B-cell lymphoma/leukemia 11A; Short=BCL-1 IA; AltName: Full=B-cell CEEl-lymphoma 11A: AltName: Full=COUP-TF-interacting protein 1; AltName: Full=Ecotropic viral integration site 9 protein homolog; Short=EVI-9; AltName: Full=Zinc finger protein 856," dated Feb. 4, 2015, 7 pages.
GenBank Accession No. Q9Y261.1, "RecName: Full=Hepatocyte nuclear factor 3-beta; Short=IINF-3-beta: Short=IINF-3B; AltName: Full=-Forldiead box protein A2; AltName: Full=Transcription factor 3B: Short=TCF-3B," dated Feb. 4, 2015, 5 pages.
GenBank Accession No. XP 005260464.1, "PREDICTED: hepatocyte nuclear factor 4-alpha isoform X1 [*Homo sapiens*]," Feb. 3, 2014, 2 pages.
Gentet, "Functional diversity of supragranular GABAergic neurons in the barrel cortex," *Frontiers in Neural Circuits*, vol. 6, article 52, pp. 1-13 (Aug. 2012) (electronic publication).
Ginhoux et al., "Fate mapping analysis reveals that adult microglia derive from primitive macrophages," *Science*, 330(6005), pp. 841-845 (Oct. 2010) (electronic publication).
Goldman, "Stem and Progenitor Cell-Based Therapy of the Central Nervous System: Hopes, Hype, and Wishful Thinking," *Cell Stem Cell*, 18(2), pp. 174-188 (Feb. 2016) (electronic publication).
Gómez-Isla et al., "Profound loss of layer II entorhinal cortex neurons occurs in very mild Alzheimer's disease," *Journal of Neuroscience*, 16(14), pp. 4491-4500 (Jul. 1996) (electronic publication).
Gonzalez-Reyes et al., "Involvement of astrocytes in Alzheimer's disease from a neuroinflammatory and oxidative stress perspective," *Frontiers in Molecular Neuroscience*, vol. 10, article 427, pp. 1-20 (Dec. 2017) (electronic publication).
Graham et al., "SOX2 Functions to Maintain Neural Progenitor Identity," *Neuron*, 39(5), pp. 749-765 (Aug. 2003) (electronic publication).
Grande et al., "Environmental impact on direct neuronal reprogramming in vivo in the adult brain," *Nature Communications*, vol. 4, article 2373, pp. 1-12 (Aug. 2013) (electronic publication).
Gresita et al., "Very Low Efficiency of Direct Reprogramming of Astrocytes Into Neurons in the Brains of Young and Aged Mice After Cerebral Ischemia," *Frontiers in Aging Neuroscience*, 11(334), pp. 1-7 (Dec. 2019) (electronic publication).
Gross et al., "Lbx1 specifies somatosensory association interneurons in the dorsal spinal cord," *Neuron*, 34(4), pp. 535-549 (May 2002) (electronic publication).
Gu et al., "R gene expression induced by a type-III effector triggers disease resistance in ice," *Nature*, 435(7045), pp. 1122-1125 (Jul. 2005) (electronic publication).
Guichet et al., "Cell death and neuronal differentiation of glioblastoma stem-like cells induced by neurogenic transcription factors," *Glia*, 61(2), pp. 225-239 (Feb. 2013) (electronic publication).
Guncova et al., "The neurodegenerative process in a neurotoxic rat model and in patients with Huntington's disease: Histopathological parallels and differences," *Acta Histochemica*, 113(8), pp. 783-792 (Dec. 2011) (electronic publication).
Guo et al., "Protein tolerance to random amino acid change," PNAS, vol. 101, No. 25, pp. 9205-9210 (Jun. 2004) (Washington, DC).
Guo et al., "In vivo direct reprogramming of reactive glial cells into functional neurons after brain injury and in an Alzheimer's disease model," *Cell Stem Cell*, 14(2), pp. 188-202 (Feb. 2014) (electronic publication).
Habekost et al., "MicroRNAs and Ascl1 facilitate direct conversion of porcine fibroblasts into induced neurons," *Stem Cell Research*, vol. 48, article: 101984, pp. 1-9 (Oct. 2020) (electronic publication).
Halees et al., "PromoSer: a large-scale mammalian promoter and transcription start site identification service," *Nucleic Acids Research*, 31(13), pp. 3554-3559 (Jul. 2003) (electronic publication).
Hays et al., "The Utility of Cerebral Blood Flow as a Biomarker of Preclinical Alzheimer's Disease," *Cellular and Molecular Neurobiology*, 36(2): 167-179 (Feb. 2016) (electronic publication).
He et al., "Intrinsic control of axon regeneration," *Neuron*, 90(3), pp. 437-451 (May 2016) (electronic publication).
He et al., "Multipotent stem cells from the mouse basal forebrain contribute GABAergic neurons and oligodendrocytes to the cerebral cortex during embryogenesis," *The Journal of Neuroscience*, 21(22), pp. 8854-8862 (Nov. 2001) (electronic publication).

(56) References Cited

OTHER PUBLICATIONS

He et al., "The regulation of microRNA expression by DNA methylation in hepatocellular carcinoma," *Molecular BioSystems*, 11(2), pp. 532-539 (Nov. 2014) (electronic publication).
Heinrich et al., "Directing astroglia from the cerebral cortex into subtype specific functional neurons," *PLoS Biology*, 8(5): e1000373, pp. 1-29 (May 2010) (electronic publication).
Heinrich et al., "Generation of subtype-specific neurons from postnatal astroglia of the mouse cerebral cortex," *Nature Protocols*, 6(2), pp. 214-228 (Feb. 2011) (electronic publication).
Heinrich et al. "Reprogramming of postnatal astroglia of the mouse neocortex into functional, synapse-forming neurons," *Methods in Molecular Biology*, vol. 814, pp. 485-498, 2012 (available online Nov. 2011) (electronic publication).
Heinrich et al., "Sox2-mediated conversion of NG2 glia into induced neurons m the injured adult cerebral cortex," *Stem Cell Reports*, 3(6), pp. 1000-1014 (Dec. 2014) (electronic publication).
Heppner et al., "Immune attack: the role of inflammation in Alzheimer disease," *Nature Reviews Neuroscience*, 16(6), pp. 358-372 (May 2015) (electronic publication).
Herrmann et al., "STAT3 is a critical regulator of astrogliosis and scar formation after spinal cord injury," *Journal of Neuroscience*, 28(28), pp. 7231-7243 (Jul. 2008) (electronic publication).
High et al., "Gene Therapy," *The New England. Journal of Medicine*, 381(5), pp. 455-464 (Aug. 2019) (electronic publication).
Hill et al., "Modulation of oligodendrocyte generation during a critical temporal window after NG2 cell division," *Nature Neuroscience*, vol. 17, pp. 1518-1527 (Nov. 2014) (electronic publication).
Holley et al., "Therapeutic effects of stem cells in rodent models of Huntington's disease: Review and electrophysiological findings," *CNS Neuroscience & Therapeutics*, 24(4), pp. 329-342 (Apr. 2018) (electronic publication).
Hong et al., "Complement and microglia mediate early synapse loss in Alzheimer mouse models," *Science*, 352(6286), pp. 712-716 (Mar. 2016) (electronic publication).
Hong et al., "Functional requirement of dicer1 and miR-17-5p in reactive astrocyte proliferation after spinal cord injury in the mouse," *Glia*, 62(12), pp. 2044-2060 (Dec. 2014) (electronic publication).
Howard et al., "Tropism and toxicity of adeno-associated viral vector serotypes 1, 2, 5, 6, 7, 8, and 9 in rat neurons and glia in vitro," *Virology*, 372(1), pp. 24-34 (Mar. 2008) (electronic publication).
Hu et al., "Region-Restrict Astrocytes Exhibit Heterogeneous Susceptibility to Neuronal Reprogramming," *Stem Cell Reports*, 12(2), pp. 290-304 (Feb. 2019) (electronic publication).
Huang et al., "Alzheimer mechanisms and therapeutic strategies," *Cell*, 148(6), pp. 1204-1222 (Mar. 2012) (electronic publication).
Huang et al., "Ptf1a, Lbx1 and Pax2 coordinate glycinergic and peptidergic transmitter phenotypes in dorsal spinal inhibitory neurons," *Developmental Biology*, 322(2), pp. 394-405 (Oct. 2008) (electronic publication).
Hughes et al., "Focal lesions in the rat central nervous system induced by endothelin-1," *Journal of Neuropathology & Experimental Neurology*, 62(12), pp. 1276-1286 (Dec. 2003) (electronic publication).
Hwang et al., "Efficient genome editing in zebrafish using a CRISPR-Cas system," *Nature Biotechnology*, 31(3), pp. 227-229 (Jan. 2013) (electronic publication).
International Preliminary Report on Patentability in International Application No. PCT/US2018/020251 dated Sep. 3, 2019, 7 pages.
International Preliminary Report on Patentability in International Application No. PCT/US2019/016378 dated Feb. 2, 2018, 10 pages.
International Search Report and Written Opinion in International Application No. PCT/US2017/018398, dated May 8, 2017, 10 pages.
International Search Report and Written Opinion in International Application No. PCT/US2018/020251 dated Jun. 14, 2018, 9 pages.
International Search Report and Written Opinion in International Application No. PCT/US2019/016378 dated Apr. 26, 2019, 14 pages.
International Search Report and Written Opinion in International Application No. PCT/US2020/038050, dated Sep. 17, 2020, 18 pages.
International Search Report and Written Opinion, in International Application No. PCT/US/2020/056059, dated Feb. 25, 2021, 10 pages.
International Search Report and Written Opinion, in International Application No. PCT/US/2020/056064, dated Feb. 25, 2021, 10 pages.
International Search Report and Written Opinion, in International Application No. PCT/US/2020/056108, dated Feb. 12, 2021, 9 pages.
International Search Report and Written Opinion in International Application No. PCT/US2021/052299, dated Mar. 9, 2022, 47 pages.
International Search Report and Written Opinion in International Application No. PCT/US2021/052300, dated Feb. 28, 2022, 7 pages.
International Search Report and Written Opinion in International Application No. PCT/US2021/052302, dated Feb. 18, 2022, 29 pages.
International Search Report and Written Opinion in International Application No. PCT/US2021/052354, dated Mar. 1, 2022, 208 pages.
International Search Report and Written Opinion in International Application No. PCT/US2021/052358, dated Feb. 15, 2022, 31 pages.
International Search Report in International Application No. PCT/US2020/024976, dated Jun. 12, 2020, 5 pages.
International Search Report in International Application No. PCT/US2020/062299, dated Mar. 3, 2021, 4 pages.
International Search Report and Written Opinion issued in International Application No. PCT/US2013/051277, dated Oct. 16, 2013, 12 pages.
Iqbal et al., "Mechanisms of neurofibrillary degeneration and the formation of neurofibrillary tangles," *Journal of Neural Transmission. Supplement*, vol. 53, pp. 169-180 (1998) (electronic publication).
Ivkovic et al. "Expression of the striatal DARPP-32/ARPP-21 phenotype in GABAergic neurons requires neurotrophins in vivo and in vitro. 1," *Neuroscience*, 19(13), pp. 5409-5419 (Jul. 1999) (electronic publication).
Jaunmuktane et al., "Evidence for human transmission of amyloid-(3 pathology and cerebral amyloid angiopathy," *Nature*, 525(7568), pp. 247-250 (Sep. 2015) (electronic publication).
Jessberger et al., "Directed differentiation of hippocampal stem/progenitor cells in the adult brain," *Nature Neuroscience*, 11(8), pp. 888-893 (Aug. 2008) (electronic publication).
Ji et al. Cell "Cell Fate Conversion: Direct Induction of Hepatocyte-Like Cells From Fibroblasts," *Journal of Cellular Biochemistry*, vol. 114, pp. 256-265 (Feb. 2013) (Hoboken, NJ).
Jiang et al., "Motor and behavioral phenotype in conditional mutants with targeted ablation of cortical D1 dopamine receptor-expressing cells," *Neurobiology of Disease*, vol. 76, pp. 137-158 (Apr. 2015) (electronic publication).
Jiang et al., "RNA-guided editing of bacterial genomes using CRISPR-Cas systems," *Nature Biotechnology*, 31(3), pp. 233-239 (Jan. 2013) (electronic publication).
Jinek et al., "A programmable dual-RNA—guided DNA endonuclease in adaptive bacterial immunity," *Science*, 337(6096), pp. 816-821 (Jun. 2012) (electronic publication).
Kang et al., "NO2+ CNS Glial Progenitors Remain Committed to the Oligodendrocyte Lineage in Postnatal Life and following Neurodegeneration," *Neuron*, 68(4), pp. 668-681 (Nov. 2010) (electronic publication).
Karlin et al., "Applications and statistics formultiple high-scoring segments in molecular sequences," *Proceedings of the National Academy of Sciences*, 90(12), pp. 5873-5877 (Jun. 1993) (electronic publication).

(56) References Cited

OTHER PUBLICATIONS

Karlin et al., "Methods for assessing the statistical significance of molecular sequence features by using general scoring schemes," *Proc. Natl. Acad. Sci. U.S.A.*, 87(6), pp. 2264-2268 (Mar. 1990) (electronic publication).
Karow et al., "Reprogramming of pericyte-derived cells of the adult human brain into induced neuronal cells," *Cell Stem Cell*, 11(4), pp. 471-476 (Oct. 2012) (electronic publication).
Kawaguchi et al., "Parvalbumin, somatostatin and cholecystokinin as chemical markers for specific GABAergic interneuron types in the rat frontal cortex," *Journal of Neurocytology*, vol. 31, pp. 277-287 (Mar. 2002) (electronic publication).
Kay et al., "A bacterial effector acts as a plant transcription factor and induces a cell size regulator," Science, 318(5850), pp. 648-651, (Oct. 2007) (electronic publication).
Kepecs et al., "Interneuron Cell Types: Fit to form and formed to fit," *Nature*, vol. 505, pp. 318-326 (Jan. 2014) (electronic publication).
Kim et al., "Functional integration of dopaminergic neurons directly converted from mouse fibroblasts," *Cell Stem Cell*, 9(5), pp. 413-419 (Nov. 2011) (electronic publication).
Kim et al., "Hybrid restriction enzymes: zinc finger fusions to Fok I cleavage domain," *Proc. Natl. Acad. Sci. U.S.A.*, 93(3), pp. 1156-1160 (Feb. 1996) (electronic publication).
Kim et al., "Mitochondrial Aging Defects Emerge in Directly Reprogrammed Human Neurons due to Their Metabolic Profile," *Cell Reports*, 23(9), pp. 2550-2558 (May 2018) (electronic publication).
Kim et al., "Modelling APOE ε3/4 allele-associated sporadic Alzheimer's disease in an induced neuron," *Brain*, 140(8), pp. 2193-2209 (Aug. 2017) (electronic publication).
Kimbrough et al., "Vascular amyloidosis impairs the gliovascular unit in a mouse model of Alzheimer's disease," *Brain*, 138(12), pp. 3716-3373 (Nov. 2015) (electronic publication).
Kitagawa, "Therapeutic application of cell transplantation and increased neurogenesis in cerebral infarction," *Rinsho Shinkeigaku Clinical Neurology*, 44(11), pp. 756-759 (Nov. 2004) (electronic publication).
Kogiso et al. "Transdifferentiation of human fibroblasts into hepatocyte-like cells by defined transcriptional factors," *Hepatology International*, vol. 7, No. 3, pp. 937-944 (Mar. 2013) (New Delhi, India).
Kojima et al., "NeuroD-betacellulin gene therapy induces islet neogenesis in the liver and reverses diabetes in mice," *Nature Medicine*, vol. 9, pp. 596-603 (Apr. 2003) (electronic publication).
Koprivica et al., "EGFR activation mediates inhibition of axon regeneration by myelin and chondroitin sulfate proteoglycans," *Science*, 310(5745), pp. 106-110 (Oct. 2005) (electronic publication).
Kordasiewicz et al., "Sustained therapeutic reversal of Huntington's disease by transient repression of huntingtin synthesis," *Neuron*, 74(6), pp. 1031-1044 (Jun. 2012) (electronic publication).
Kreitzer, "Physiology and pharmacology of striatal neurons," *Annual Review of Neuroscience*, vol. 32, pp. 127-147 (Jul. 2009) (electronic publication).
Kunz et al., "Reduced grid-cell-like representations in adults at genetic risk for Alzheimer's disease," *Science*, 350(6259), pp. 430-433 (Oct. 2015) (electronic publication).
Kuwabara et al., "Win-mediated activation of NeuroD1 and retro-elements during adult neurogenesis," *Nature Neuroscience*, 12(9), pp. 1097-1105 (Aug. 2009) (electronic publication).
LaFerla et al., "Intracellular amyloid-I3 in Alzheimer's disease," *Nature Reviews Neuroscience*, 8(7), pp. 499-509 (Jul. 2007) (electronic publication).
Lambert et al., "Targeting transcription factors for cancer treatment," *Molecules*, 23(6), article 1479, pp. 1-51 (Jun. 2018) (electronic publication).
Lau et al., "Direct neural conversion from human fibroblasts using self-regulating and nonintegrating viral vectors," *Cell Reports*, 9(5), pp. 1673-1680 (Dec. 2014) (electronic publication).
Le Cong et al., "Multiplex genome engineering using CRISPR/Cas systems," *Science*, 339(6121), pp. 819-823 (Jan. 2013) (electronic publication).
Lee et al., "Conversion of Xenopus Ectoderm into Neurons by NeuroD, a Basic Helix-Loop-Helix Protein," *Science*, 268(5212), pp. 836-844 (May 1995) (electronic publication).
Lei et al., "Non-engineered and engineered adult neurogenesis in mammalian brains," *Frontiers in Neuroscience*, vol. 13, article 131, pp. 1-13 (Feb. 2019) (electronic publication).
Lennihan et al., "Effect of Hypervolemic Therapy on Cerebral Blood Flow After Subarachnoid Hemorrhage," *Stroke*, 31(2), pp. 383-391 (Feb. 2000) (electronic publication).
Lethbridge Brainiacs, "Team: Lethbridge/project" (online publication) (screenshot from Wayback Machine dated Jul. 2, 2015), 7 pages, retrieved from the internet: Jul. 13, 2022, <https://web.archive.org/web/20150702194117/http:/2014.igem.org/Team:Lethbridge/project>.
Li et al., "Conversion of Astrocytes and Fibroblasts into Functional Noradrenergic Neuron," *Cell Reports*, 28(3), pp. 682-697 (Jul. 2019) (electronic publication).
Li et al., "In vivo reprogramming for CNS repair: regenerating neurons from endogenous glial cells," *Neuron*, 91(4), pp. 728-738 (Aug. 2016) (electronic publication).
Liang et al., "Myt11 induced direct reprogramming of pericytes into cholinergic neurons," *CNS Neuroscience & Therapeutics*, 24(9):801-809 (Sep. 2018) (electronic publication).
Liddelow et al., "Neurotoxic reactive astrocytes are induced by activated microglia," *Nature*, 541(7638), pp. 481-487 (Jan. 2017) (electronic publication).
Liddelow et al., "Reactive astrocytes: production, function, and therapeutic potential," *Immunity*, 46(6), pp. 957-967 (Jun. 2017) (electronic publication).
Limon et al., "Loss of functional GABAA receptors in the Alzheimer diseased brain," *Proceedings of the National Academy of Sciences*, 109(25), pp. 10071-10076 (Jun. 2012) (electronic publication).
Liu et al., "Ascl 1 converts dorsal midbrain astrocytes into functional neurons in vivo," *Journal of Neuroscience*, 35(25), pp. 9336-9355 (Jun. 2015) (electronic publication).
Liu et al., "Differential neuronal reprogramming induced by NeuroD1 from astrocytes in grey matter versus white matter," *Neural Regeneration Research*, 15(2), pp. 342-351 (Sep. 2020) (electronic publication).
Liu et al., "Direct Lineage Reprogramming Reveals Disease-Specific Phenotypes of Motor Neurons from Human ALS Patients," *Cell Reports*, 14(1), pp. 115-128 (Jan. 2016) (electronic publication).
Liu et al., "Direct reprogramming of human fibroblasts into dopaminergic neuron-like cells," *Cell Research*, 22(2), pp. 321-332 (Feb. 2012) (electronic publication).
Liu et al., "Small molecules enable neurogenin 2 to efficiently convert human fibroblasts into cholinergic neurons," *Nature Communications*, vol. 4, Article: 2183, pp. 1-10 (Jul. 2013) (electronic publication).
Livak et al., "Analysis of Relative Gene Expression Data Using Real-Time Quantitative PCR and the 2—ΔΔCT Method," *Methods*, 25(4), pp. 402-408, (Dec. 2001) (electronic publication).
Livingston et al., "Direct reprogramming of astrocytes to neurons leads to functional recovery after stroke," *bioRxiv*, doi: https://doi.org/10.1101/2020.02.02.92909, pp. 1-15 (Feb. 2020) (electronic publication).
Lollo et al., "Poly-$_L$-Lysine Based Gene Delivery Systems: Synthesis, Purification, and Application," in Gene Therapy Protocols, 2nd Edition, Morgan (ed.), Humana Press, Totowa, NJ, pp. 1-30 (Oct. 2001).
Lu et al., "Molecular and cellular development of spinal cord locomotor circuitry," *Frontiers in Molecular Neuroscience*, vol. 8, article 25, pp. 1-18 (Jun. 2015) (electronic publication).
Lu et al., "Prolonged human neural stem cell maturation supports recovery in injured rodent CNS," *The Journal of Clinical Investigation*, 127(9), pp. 3287-3299 (Aug. 2017) (electronic publication).
Lu et al., "Turning reactive glia into functional neurons in the brain," *Cell Stem Cell*, 14(2), pp. 133-134 (Feb. 2014) (electronic publication).

(56) References Cited

OTHER PUBLICATIONS

Luo et al., "Global DNA methylation remodeling during direct reprogramming of fibroblasts to neurons," *eLife*, vol. 8, article: e40197, pp. 1-19 (Jan. 2019) (electronic publication).
Ma et al., "Distinct Subtypes of Somatostatin-Containing Neocortical Interneurons Revealed in Transgenic Mice," *Journal of Neuroscience*, 26(19), pp. 5069-5082 (May 2006) (electronic publication).
Ma et al., "Human embryonic stem cell-derived GABA neurons correct locomotion deficits in quinolinic acid-lesioned mice," *Cell Stem Cell*, 10(4), pp. 455-464 (Apr. 2012) (electronic publication).
Maas et al., "Traumatic brain injury: integrated approaches to improve prevention, clinical care, and research," *Lancet Neurol.*, 16(12):987-1048 (2017) (electronic publication).
MacDonald et al., "A novel gene containing a trinucleotide repeat that is expanded and unstable on Huntington's disease chromosomes," *Cell*, 72(6), pp. 971-983 (Mar. 1993) (electronic publication).
Makarova. et al., "Evolution and classification of the CRISPR—Cas systems," *Nature Reviews Microbiology*, 9(6), pp. 467-477 (May 2011) (electronic publication).
Mali et al., "RNA-Guided Human Genome Engineering via Cas9," *Science*, 339(6121), pp. 823-826 (Jan. 2013) (electronic publication).
Mangiarini et al., "Exon 1 of the HD Gene with an Expanded CAG Repeat Is Sufficient to Cause a Progressive Neurological Phenotype in Transgenic Mice," *Cell*, 87(3), pp. 493-506 (Nov. 1996) (electronic publication).
Marchesi, "Alzheimer's dementia begins as a disease of small blood vessels, damaged by oxidative-induced inflammation and dysregulated amyloid metabolism: implications for early detection and therapy," *The FASEB Journal*, 25(1), pp. 5-13 (Jan. 2011) (electronic publication).
Marin et al., "Origin and Molecular Specification of Striatal Interneurons," *Journal of Neuroscience*, 20(16), pp. 6063-6076 (Aug. 2000) (electronic publication).
Markakis et al., "Comparative Transduction Efficiency of AAV Vector Serotypes 1-6 in the Substantia Nigra and Striatum of the Primate Brain," *Molecular Therapy*, 18(3), pp. 588-593 (Mar. 2010) (electronic publication).
Markram et al., "Interneurons of the neocortical inhibitory system," *Nature Reviews Neuroscience*, vol. 5, pp. 793-807 (Oct. 2004) (electronic publication).
Marro et al., "Direct lineage conversion of terminally differentiated hepatocytes to functional neurons," *Cell Stem Cell*, 9(4), pp. 374-382 (Oct. 2011) (electronic publication).
Masserdotti et al., "Transcriptional Mechanisms of Proneural Factors and REST in Regulating Neuronal Reprogramming of Astrocytes," *Cell Stem Cell*, 17(1), pp. 74-88 (Jul. 2015) (electronic publication).
Matsuda et al., "Cerebral blood flow and metabolic abnormalities in Alzheimer's disease," *Annals Nuclear Medicine*, 15(2), pp. 85-92 (Apr. 2001) (electronic publication).
Matsuda et al., "Pioneer Factor NeuroD1 Rearranges Transcriptional and Epigenetic Profiles to Execute Microglia-Neuron Conversion," *Neuron*, vol. 101, pp. 472-485 (Feb. 2019) (electronic publication).
Mazzoni et al., "Synergistic binding of transcription factors to cell-specific enhancers programs motor neuron identity," *Nature Neuroscience*, 16(9):1219-27 (Sep. 2013) (electronic publication).
McKinsey et al., "Dlx1&2-Dependent Expression of Zfhx1b (Sip1, Zeb2) Regulates the Fate Switch between Cortical and Striatal Interneurons," *Neuron*, 77(1), pp. 83-98 (Jan. 2013) (electronic publication).
McLendon et al., Comprehensive genomic characterization defines human glioblastoma genes and core pathways, *Nature*, 455(7216), pp. 1061-1068, (Oct. 2008) (electronic publication).
McPhee et al., "Effects of AAV-2-mediated aspartoacylase gene transfer in the tremor rat model of Canavan disease," *Molecular Brain Research*, 135(1-2), pp. 112-121 (Apr. 2005) (electronic publication).
Medeiros et al., "Astrocytes: Conductors of the Alzheimer disease neuroinflammatory symphony," *Experimental Neurology*, vol. 239, pp. 133-138 (Jan. 2013) (electronic publication).
Menalled et al., "Systematic behavioral evaluation of Huntington's disease transgenic and knock-in mouse models," *Neurobiology of Disease*, 35(3), pp. 319-336 (Sep. 2009) (electronic publication).
Mertens et al., "Directly Reprogrammed Human Neurons Retain Aging-Associated Transcriptomic Signatures and Reveal Age-Related Nucleocytoplasmic Defects," *Cell Stem Cell*, 17(6), pp. 705-718 (Dec. 2015) (electronic publication).
Miao et al., "Up-regulation of GBP2 is Associated with Neuronal Apoptosis in Rat Brain Cortex Following Traumatic Brain Injury," *Neurochemical Research*, vol. 42, pp. 1515-1523 (May 2017) (electronic publication).
Miniarikova et al., "AAV5-miHTT gene therapy demonstrates suppression of mutant huntingtin aggregation and neuronal dysfunction in a rat model of Huntington's disease," *Gene Therapy*, vol. 24, pp. 630-639 (Aug. 2017) (electronic publication).
Mitew et al., "Altered synapses and gliotransmission in Alzheimer's disease and AD model mice," *Neurobiology of Aging*, 34(10), pp. 2341-2351 (Oct. 2013) (electronic publication).
Miyata et al., "NeuroD is required for differentiation of the granule cells in the cerebellum and hippocampus," *Genes & Development*, vol. 13, pp. 1647-1652 (May 1999) (electronic publication).
Moghimi et al., "Nanomedicine: current status and future prospects," *The FASEB Journal*, 19(3), pp. 311-330 (Mar. 2005) (electronic publication).
Morrow et al., "NeuroD regulates multiple functions in the developing neural retina in rodent," *Development*, 126(1), pp. 23-36 (Jan. 1999) (electronic publication).
Myers et al., "Optimal alignments in linear space," *Bioinformatics*, 4(1), pp. 11-17 (Mar. 1988) (electronic publication).
Nemoto et al., "Direct Neuronal Reprogramming of Common Marmoset Fibroblasts by ASCL1, microRNA-9/9*, and microRNA-124 Overexpression," *Cells*, 10(6), pp. 1-14 (Dec. 2021) (electronic publication).
Ngo et al., "Computational Complexity, Protein Structure Prediction, and the Levinthal Paradox," *The Protein Folding Problem and Tertiary Structure Prediction*, pp. 433-495 (1994) (electronic publication).
Nicoleau et al., "Human Pluripotent Stem Cell Therapy for Huntington's Disease: Technical, Immunological, and Safety Challenges," *Neurotherapeutics*, vol. 8, pp. 562-576 (Oct. 2011) (electronic publication).
Nishimura et al., "Generation of induced neurons by direct reprogramming in the mammalian cochlea," *Neuroscience*, vol. 275, pp. 125-135 (Sep. 2014) (electronic publication).
Nishiyama et al., "Polydendrocytes (NG2 cells): multifunctional cells with lineage plasticity," *Nature Reviews Neuroscience*, vol. 10, pp. 9-22 (Jan. 2009) (electronic publication).
Niu et al., "In vivo reprogramming of astrocytes to neuroblasts in the adult brain," *Nature Cell Biology*, vol. 15, pp. 1164-1175 (Sep. 2013) (electronic publication).
Niu et al., "SOX2 Reprograms Resident Astrocytes into Neural Progenitors in the Adult Brain," *Stem Cell Reports*, 4(5), pp. 780-794 (May 2015) (electronic publication).
Noda et al., "Direct Reprogramming of Spiral Ganglion Non-neuronal Cells into Neurons: Toward Ameliorating Sensorineural Hearing Loss by Gene Therapy," *Frontiers in Cell and Developmental Biology*, 6(16), pp. 1-14 (Feb. 2018) (electronic publication).
Norenberg, et al., "The Pathology of Human Spinal Cord Injury: Defining the Problems," *The Journal of Neurotrauma*, 21(4), pp. 429-440 (Jul. 2004) (electronic publication).
Nussbaum et al., "Prion-like behaviour and tau-dependent cytotoxicity of pyroglutamylated amyloid-β," *Nature*, vol. 485, pp. 651-655 (May 2012) (electronic publication).
Oakley et al., "Intraneuronal β-Amyloid Aggregates, Neurodegeneration, and Neuron Loss in Transgenic Mice with Five Familial Alzheimer's Disease Mutations: Potential Factors in Amyloid Plaque Formation," *The Journal of Neuroscience*, 26(40), pp. 10129-10140 (Oct. 2006) (electronic publication).

(56) References Cited

OTHER PUBLICATIONS

Obermeier et a., "Development, maintenance and disruption of the blood-brain barrier," *Nature Medicine*, vol. 19, pp. 1584-1596 (Dec. 2013) (electronic publication).
Office Action in Chinese Application No. 201380048924.2, dated Apr. 13, 2018, English Translation, 7 pages.
Office Action in Chinese Application No. 201380048924.2, dated Jun. 17, 2016, Chinese Language, 6 pages.
Office Action in Chinese Application No. 201380048924.2, dated Jun. 17, 2016, English Translation, 5 pages.
Office Action in Chinese Application No. 201380048924.2, dated Mar. 21, 2017, Chinese Language, 5 pages.
Office Action in Chinese Application No. 201380048924.2, dated Mar. 21, 2017, English Translation, 7 pages.
Office Action in Chinese Application No. 201380048924.2, dated Sep. 26, 2017, English Translation, 6 pages.
Ohori et al., "Growth Factor Treatment and Genetic Manipulation Stimulate Neurogenesis and Oligodendrogenesis by Endogenous Neural Progenitors in the Injured Adult Spinal Cord," *Journal of Neuroscience*, 26(46), pp. 11948-11960 (Nov. 2006) (electronic publication).
Ojala et al., "Adeno-Associated Virus Vectors and Neurological Gene Therapy," *Neuroscientist*, 21(1), pp. 84-98 (Feb. 2015) (electronic publication).
Okada et al., "Conditional ablation of Stat3 or Socs3 discloses a dual role for reactive astrocytes after spinal cord injury," *Nature Medicine*, Jul. 2006, vol. 12, pp. 829-834 (Jun. 2006) (electronic publication).
Oproescu et al., "New Insights Into the Intricacies of Proneural Gene Regulation in the Embryonic and Adult Cerebral Cortex," *Frontier in Molecular Neuroscience*, 14(642016), pp. 1-24 (Feb. 2021) (electronic publication).
Ortinski et al., "Selective induction of astrocytic gliosis generates deficits in neuronal inhibition," *Nature Neuroscience*, 13(5), pp. 584-591 (Apr. 2010) (electronic publication).
Osborn et al., "Astrogliosis: An integral player in the pathogenesis of Alzheimer's disease," *Progress in Neurobiology*, vol. 144, pp. 121-141 (Sep. 2016) (electronic publication).
Ostrom et al., "CBTRUS Statistical Report: Primary Brain and Central Nervous System Tumors Diagnosed in the United States in 2008-2012," *Neuro-Oncology*, 17(suppl_4), pp. iv1-iv62 (Oct. 2015) (electronic publication).
Palop et al., "Amyloid-β-induced neuronal dysfunction in Alzheimer's disease: from synapses toward neural networks," *Nature Neuroscience*, 13(7), pp. 812-818 (Jun. 2010) (electronic publication).
Pang et al., "Induction of human neuronal cells by defined transcription factors," *Nature*, vol. 476, pp. 220-223 (May 2011) (electronic publication).
Panganiban et al., "Developmental functions of the Distal-less/Dlx homeobox genes," *Development*, 129(19), pp. 4371-4386 (Oct. 2002) (electronic publication).
Parkhurst et al., "Microglia Promote Learning-Dependent Synapse Formation through Brain-Derived Neurotrophic Factor," *Cell*, 155(7), pp. 1596-1609 (Dec. 2013) (electronic publication).
Paul et al., "Cystathionine γ-lyase deficiency mediates neurodegeneration in Huntington's disease," *Nature*, vol. 509, pp. 96-100 (Mar. 2014) (electronic publication).
Pereira et al., "Direct Reprogramming of Resident NG2 Glia into Neurons with Properties of Fast-Spiking Parvalbumin-Containing Interneurons," *Stem Cell Reports*, 9(3), pp. 742-751 (Sep. 2017) (electronic publication).
Perrin, "Preclinical research: Make mouse studies work," *Nature* vol. 507, pp. 423-425 (Mar. 2014) (electronic publication).
Petryniak et al., "Dlx1 and Dlx2 Control Neuronal versus Oligodendroglial Cell Fate Acquisition in the Developing Forebrain," *Neuron*, 55(3), pp. 417-433 (Aug. 2007) (electronic publication).
Pfisterer et al., "Direct conversion of human fibroblasts to dopaminergic neurons," *PNAS*, 108(25), pp. 10343-10348 (Jun. 2011) (electronic publication).
Pla et al., "Dlx1 and Dlx2 Promote Interneuron GABA Synthesis, Synaptogenesis, and Dendritogenesis," *Cerebral Cortex*, 28(11), pp. 3797-3815 (Nov. 2018) (electronic publication).
Porter et al., "Conditional Survival of All Primary Brain Tumor Patients by Age, Behavior, and Histology," *Neuroepidemiology*, vol. 36, pp. 230-239 (Jun. 2011) (electronic publication).
Pouladi et al., "Choosing an animal model for the study of Huntington's disease," *Nature Reviews Neuroscience*, vol. 14, pp. 708-721 (Sep. 2013) (electronic publication).
Prinz et al., "Microglia and brain macrophages in the molecular age: from origin to neuropsychiatric disease," *Nature Reviews Neuroscience*, vol. 15, pp. 300-312 (Apr. 2014) (electronic publication).
Qin et al., "Chapter 16: ELISA Methodology to Quantify Astrocyte Production of Cytokines/Chemokines In Vitro," in Astrocytes, Methods in Molecular Biology vol. 814, Milner eds, Humana Press, Totowa, NJ pp. 235-249 (online publication, Nov. 2012).
Querfurth et al., "Mechanisms of disease," *The New England Journal of Medicine*, 362(4), pp. 329-344 (Jan. 2010) (electronic publication).
Rangel-Barajas et al., "Dysregulation of corticostriatal connectivity in Huntington's disease: a role for dopamine modulation," *Journal of Huntington's Disease*, 5(4), pp. 303-331 (Dec. 2016) (electronic publication).
Rao et al., "Molecular Mechanisms Underlying Ascl1-Mediated Astrocyte-to-Neuron Conversion," *Stem Cell Reports*, 16(3), pp. 534-547, (Mar. 2021) (electronic publication).
Reidling et al., "Human Neural Stem Cell Transplantation Rescues Functional Deficits in R6/2 and Q140 Huntington's Disease Mice," *Stem Cell Reports*, 10(1), pp. 58-72 (Jan. 2018) (electronic publication).
Reinius et al., "Conditional targeting of medium spiny neurons in the striatal matrix," *Frontiers in Behavioral Neuroscience*, 9(71) pp. 1-14 (Mar. 2015) (electronic publication).
Rexed, "A cytoarchitectonic atlas of the spinal coed in the cat," *Journal of Comparative Neurology*, 100(2), pp. 297-379 (Apr. 1954) (electronic publication).
Richardson et al., "Future applications: gene therapy," *Neurosurgery Clinics*, 20(2), pp. 219-224 (Apr. 2009) (electronic publication).
Richardson et al., "NG2-glia as Multipotent Neural Stem Cells: Fact or Fantasy?," *Neuron*, 70(4), pp. 661-673 (May 2011) (electronic publication).
Rikani et al., "The mechanism of degeneration of striatal neuronal subtypes in Huntington disease," *Annals of Neurosciences*, 21(3), pp. 112-114 (Jul. 2014) (electronic publication).
Römer et al., "Plant Pathogen Recognition Mediated by Promoter Activation of the Pepper Bs3 Resistance Gene," *Science*, 318(5850), pp. 645-648 (Oct. 2007) (electronic publication).
Roome et al., "A reproducible Endothelin-1 model of forelimb motor cortex stroke in the mouse," *Journal of Neuroscience Methods*, vol. 233, pp. 34-44 (Aug. 2014) (electronic publication).
Ross et al., "Huntington's disease: from molecular pathogenesis to clinical treatment," *The Lancet Neurology*, 10(1), pp. 83-98 (Jan. 2011) (electronic publication).
Roybon et al., "GABAergic Differentiation Induced by Mash1 Is Compromised by the bHLH Proteins Neurogenin2, NeuroD1, and NeuroD2," *Cerebral Cortex*, 20(5), pp. 1234-1244 (May 2010) (electronic publication).
Roybon et al., "Neurogenin2 Directs Granule Neuroblast Production and Amplification while NeuroD1 Specifies Neuronal Fate during Hippocampal Neurogenesis," *PLOS One*, 4(3):e4779, pp. 1-19 (Mar. 2009) (electronic publication).
Russo et al., "CRISPR-Mediated Induction of Neuron-Enriched Mitochondrial Proteins Boosts Direct Glia-to-Neuron Conversion," *Cell Stem Cell*, 28(3), pp. 524-534 (Mar. 2021) (electronic publication).
Sadleir et al., "Aβ reduction in BACE1 heterozygous null SXFAD mice is associated with transgenic APP level," *Molecular Neurodegeneration*, 10(1):1 (2015) (electronic publication).
Sandhu et al., "Glutamic acid decarboxylase 67 haplodeficiency impairs social behavior in mice," *Genes, Brain and Behavior*, 13(4), pp. 439-450 (Mar. 2014) (electronic publication).

(56) References Cited

OTHER PUBLICATIONS

Sanjana et al., "Improved vectors and genome-wide libraries for CRISPR screening," *Nature Methods*, vol. 11, pp. 783-784 (Jul. 2014) (electronic publication).
Santos et al., "Excitatory interneurons dominate sensory processing in the spinal substantia gelatinosa of rat," *The Journal of Physiology*, 581(1), pp. 241-254 (May 2007) (electronic publication).
Sassone et al., "Regenerative approaches in Huntington's disease: from mechanistic insights to therapeutic protocols," *Frontiers in Neuroscience*, 12(800), pp. 1-8 (Nov. 2018) (electronic publication).
Schmid et al., "Dysfunction of Somatostatin-Positive Interneurons Associated with Memory Deficits in an Alzheimer's Disease Model," *Neuron*, 92(1), pp. 114-125 (Oct. 2016) (electronic publication).
Schnütgen et al., "A directional strategy for monitoring Cre-mediated recombination at the cellular level in the mouse," *Nature Biotechnology*, 21(5), pp. 562-565 (Mar. 2003) (electronic publication).
Schornack et al., "Gene-for-gene-mediated recognition of nuclear-targeted AvrBs3-like bacterial effector proteins," *Journal of Plant Physiology*, 163(3), 256-272 (Feb. 2006) (electronic publication).
Schuster et al., "Biodistribution of adeno-associated virus serotype 9 (AAV9) vector after intrathecal and intravenous delivery in mouse," *Frontiers in Neuroanatomy*, vol. 8, article 42, pp. 1-14 (Jun. 2014) (electronic publication).
Servick, "Reprogrammed cells could tackle brain damage, Turning astrocytes into neurons improves symptoms in preliminary mouse studies," *Science*, 362 (6416), pp. 736-737 (Nov. 2019) (electronic publication).
Shalem et al., "Genome-Scale CRISPR-Cas9 Knockout Screening in Human Cells," *Science*, 343(6166), pp. 84-87 (Dec. 2014) (electronic publication).
Sheng et al., "Direct reprogramming of Sertoli cells into multipotent neural stem cells by defined factors," *Cell Research*, 22(1), pp. 208-218 (Jan. 2012) (electronic publication).
Sheng et al., "Most Tissue-Resident Macrophages Except Microglia Are Derived from Fetal Hematopoietic Stem Cells," *Immunity*, 43(2), pp. 382-393 (Aug. 2015) (electronic publication).
Shin et al., "GABAergic Neurons from Mouse Embryonic Stem Cells Possess Functional Properties of Striatal Neurons In Vitro, and Develop into Striatal Neurons In Vivo in a Mouse Model of Huntington's Disease," *Stem Cell Reviews and Reports*, vol. 8, pp. 513-531 (Jul. 2012) (electronic publication).
Silver et al., "Regeneration beyond the filial scar," *Nature Reviews Neuroscience*, 5(2), pp. 146-156 (Feb. 2004) (electronic publication).
Sizemore et al., "Viral vector-based tools advance knowledge of basal ganglia anatomy and physiology," *Journal of Neurophysiology*, 115(4), pp. 2124-2146 (Apr. 2016) (electronic publication).
Skolnick et al., "From genes to protein structure and function: novel applications of computational approaches in the genomic era," *Trends in Biotechnology*, 18(1), pp. 34-39, (Jan. 2000) (electronic publication).
Smith et al., "Small Molecules Modulate Chromatin Accessibility to Promote NEUROG2-Mediated Fibroblast-to-Neuron Reprogramming," *Stem Cell Reports*, 7(5), pp. 955-969 (Nov. 2016).
Sofroniew, "Molecular dissection of reactive astrogliosis and glial scar formation," *Trends in Neurosciences*, 32(12), pp. 638-647 (Dec. 2009) (electronic publication).
Son et al., "Conversion of mouse and human fibroblasts into functional spinal motor neurons," *Cell Stem Cell*, 9(3), pp. 205-218, (Sep. 2011) (electronic publication).
Srivastava et al., "In Vivo Cellular Reprogramming: The Next Generation," *Cell*, 166(6), pp. 1386-1396 (Sep. 2016) (electronic publication).
Stamouli et al., "Pro-inflammatory cytokines in Alzheimer's disease," *Psychiatrike = Psychiatriki*, 27(4), pp. 264-275 (Oct. 2016) (electronic publication).
Stawinski et al., "Chapter 6: Di-and Oligonucleotides Synthesis Using H-Phosphonate Chemistry," in Oligonucleotide Synthesis: Methods and Application, vol. 288, Herdewijin (ed.), Humana Press, Totowa, NJ pp. 87-100 (Sep. 2004).
Stoica et al., "AAV-mediated gene transfer to the mouse CNS," *Current Protocols in Microbiology*, vol. 0 14, Unit14D.5, pp. 1-25 (Aug. 2013) (electronic publication).
Stühmer et al., "Ectopic expression of the Dlx genes induces glutamic acid decarboxylase and Dlx expression," *Development*, 129(1), pp. 245-252 (Jan. 2002) (electronic publication).
Su et al., "In vivo conversion of astrocytes to neurons in the injured adult spinal cord," *Nature Communications*, vol. 5, article 3338 pp. 1-5 (Feb. 2014) (electronic publication).
Sugio et al., "Two type III effector genes of *Xanthomonas oryzae* pv. oryzae control the induction of the host genes OsTFIIAγ1 and OsTFX1 during bacterial blight of rice," *Proceedings of the National Academy of Sciences*, 104(25): 10720-10725 (Jun. 2007) (electronic publication).
Takahashi et al., "Induction of Pluripotent Stem Cells from Adult Human Fibroblasts by Defined Factors," *Cell*, 131(5), pp. 861-872 (Nov. 2007) (electronic publication).
Takahashi et al., "Induction of Pluripotent stem cells from mouse embryonic and adult fibroblast cultures by defined factors," *Cell*, 126(4), pp. 663-676 (Aug. 2006) (electronic publication).
Takano et al., "Astrocytes and Ischemic Injury," *Stroke*, 40(3): suppl 1, pp. S8-S12 (Mar. 2009) (electronic publication).
Takashima et al., "Prolonged inhibition of hepatocellular carcinoma cell proliferation by combinatorial expression of defined transcription factors," *Cancer Science*, 109(11), pp. 3543-3553 (Sep. 2018) (electronic publication).
Tamamaki et al., "Green fluorescent protein expression and colocalization with calretinin, parvalbumin, and somatostatin in the GAD67-GFP knock-in mouse," *Journal of Comparative Neurology*, 467(1), pp. 60-79 (Oct. 2003) (electronic publication).
Taniguchi, "Genetic dissection of GABAergic neural circuits in mouse neocortex," *Frontiers in Cell Neuroscience*, 8:8 1-22 (Jan. 2014) (electronic publication).
Tong et al., "Astrocyte Kir4.1 ion channel deficits contribute to neuronal dysfunction in Huntington's disease model mice," *Nature Neuroscience*, vol. 17, pp. 694-703 (Mar. 2014) (electronic publication).
Torper et al., "Generation of induced neurons via direct conversion in vivo," *Proceedings of the National Academy of Sciences*, 110(17), pp. 7038-7043 (Mar. 2013) (electronic publication).
Torper et al., "In vivo reprogramming of striatal NG2 glia into functional neurons that integrate into local host circuitry," *Cell Reports*, 12(3), pp. 474-481 (Jul. 2015) (electronic publication).
Toy et al., "Role of Glial Cells in Axonal Regeneration," *Experimental Neurobiology*, 22(2), pp. 68-76, Jun. 27, 2013 (electronic publication).
Treutlein et al., "Dissecting direct reprogramming from fibroblast to neuron using single-cell RNA-seq," *Nature*, 534(7607), pp. 391-395 (Jun. 2016) (electronic publication).
Tsai et al., "Regional Astrocyte Allocation Regulates CNS Synaptogenesis and Repair," *Science*, 337(6092), pp. 358-362 (Jun. 2012) (electronic publication).
Tsoa et al., "Spatiotemporally different origins of NG2 progenitors produce cortical interneurons versus glia in the mammalian forebrain," *Proceedings of the National Academy of Sciences*, 111(20), pp. 7444-7449 (May 2014) (electronic publication).
Tsunemoto et al., "Diverse reprogramming codes for neuronal identity," *Nature*, vol. 557, pp. 375-380 (May 2018) (electronic publication).
Tuszynski et al., "Neural stem cell dissemination after grafting to CNS injury sites," *Cell*, 156(3), pp. 388-389 (Jan. 2014) (electronic publication).
Van Gijsel-Bonnello et al., "Metabolic changes and inflammation in cultured astrocytes from the 5xFAD mouse model of Alzheimer's disease: Alleviation by pantethine," *PLOS one*, 12(4):e0175369, pp. 1-22 (Apr. 2017) (electronic publication).
Vasan et al., "Direct Neuronal Reprogramming: Bridging the Gap Between Basic Science and Clinical Application," *Frontiers in Cell and Developmental Biology*, 9(68108), pp. 1-29 (Jul. 2021) (electronic publication).

(56) References Cited

OTHER PUBLICATIONS

Velasco et al., "A Multi-step Transcriptional and Chromatin State Cascade Underlies Motor Neuron Programming from Embryonic Stem Cells," *Cell Stem Cell*, 20(2), pp. 205-217 (Feb. 2017) (electronic publication).
Venegas et al., "Microglia-derived ASC specks cross-seed amyloid-β in Alzheimer's disease," *Nature*, vol. 552, pp. 355-361 (Dec. 2017) (electronic publication).
Verret et al., "Inhibitory Interneuron Deficit Links Altered Network Activity and Cognitive Dysfunction in Alzheimer Model," *Cell*, 149(3), pp. 708-721 (Apr. 2012) (electronic publication).
Victor et al., "Generation of Human Striatal Neurons by MicroRNA-Dependent Direct Conversion of Fibroblasts," *Neuron*, 84(2), pp. 311-323 (Oct. 2014) (electronic publication).
Vierbuchen et al., "Direct conversion of fibroblasts to functional neurons by defined factors," *Nature*, vol. 463, pp. 1035-1041 (Jan. 2010) (electronic publication).
Viñals et al., "BMP-2 decreases Mashl stability by increasing Idl expression," *The EMBO Journal*, 23(17), pp. 3527-3537 (Sep. 2004) (electronic publication).
Walker, "Huntington's disease," *Lancet*, 369(9557), pp. 218-228 (Jan. 2007) (electronic publication).
Wang et al., "Dlx5 and Dlx6 Regulate the Development of Parvalbumin-Expressing Cortical Interneurons," *Journal of Neuroscience*, 30(15), pp. 5334-5345 (Apr. 2010) (electronic publication).
Wang et al., "The p53 Pathway Controls SOX2-Mediated Reprogramming in the Adult Mouse Spinal Cord," *Cell Reports*, 17(3), pp. 891-903 (Oct. 2016) (electronic publication).
Wang, "Developing hippocampal delivery of AAV-NeuroD1 as a novel therapy for Alzheimer's disease," *A Thesis in Molecular, Cellular and Integrative Biosciences*, 40 pages (May 2016) (electronic publication).
Wapinski et al., "Hierarchical mechanisms for direct reprogramming of fibroblasts to neurons," *Cell*, 155(3), pp. 621-635 (Oct. 2013) (electronic publication).
Wapinski et al., "Rapid Chromatin Switch in the Direct Reprogramming of Fibroblasts to Neurons," *Cell Reports*, 20(13), pp. 3236-3247 (Sep. 2017) (electronic publication).
Wesson et al., "Olfactory dysfunction correlates with amyloid-fi burden in an Alzheimer's disease mouse model," *Journal of Neuroscience*, 30(2):505-514 (2010) (electronic publication).
Wolfson et al., "Alterations of regional cerebral blood flow and oxygen metabolism in Parkinson's disease," *Neurology*, 35(10), pp. 1399-1405, Abstract only (Oct. 1985) (electronic publication).
Wonders et al., "The origin and specification of cortical interneurons," *Nature Review Neuroscience*, vol. 7, pp. 687-696 (Aug. 2006) (electronic publication).
Wu et al., "A Chemical Recipe for Generation of Clinical-Grade Striatal Neurons from hESCs," *Stem Cell Reports*, 11(3), pp. 635-650 (Sep. 2018) (electronic publication).
Wu et al., "Gene therapy conversion of striatal astrocytes into GABAergic neurons in mouse models of Huntington's disease," *Nature Communications*, vol. 11, article 1105, pp. 1-18 (Feb. 2020) (electronic publication).
Wu et al., "Tonic inhibition in dentate gyrus impairs long-term potentiation and memory in an Alzheimer's disease model," *Nature Communications*, vol. 5, article 4159, pp. 1-13 (Jun. 2014) (electronic publication).
Xuan et al., "Genome-wide promoter extraction and analysis in human, mouse, and rat," *Genome Biology*, 6(8), article R72, pp. R72.1-R72.12 (Aug. 2005) (electronic publication).
Yamashita et al., "In vivo direct reprogramming of glial linage to mature neurons after cerebral ischemia," *Scientific Reports*, vol. 9, article 10956, pp. 1-7 (Jul. 2019) (electronic publication).
Yan et al., "A Huntingtin Knockin Pig Model Recapitulates Features of Selective Neurodegeneration in Huntington's Disease," *Cell*, 173(4), pp. 989-1002 (May 2018) (electronic publication).
Yang et al., "CRISPR/Cas9-mediated gene editing ameliorates neurotoxicity in mouse model of Huntington's disease," *The Journal of Clinical Investigation*, 127(7), pp. 2719-2724 (Jun. 2017) (electronic publication).
Yang et al., "Generation of pure GABAergic neurons by transcription factor programming," *Nature Methods*, 14(6):621-628 (May 2017) (electronic publication).
Yang et al., "Induced Neuronal Cells: How to Make and Define a Neuron," *Cell Stem Cell*, 9(6), pp. 517-525 (Dec. 2011) (electronic publication).
Yang et al., "Os8N3 is a host disease-susceptibility gene for bacterial blight of rice," *Proc. Natl. Acad. Sci. USA*, 103(27), pp. 10503-10508 (Jul. 2006) (electronic publication).
Yang et al., "Towards a transgenic model of Huntington's disease in a non-human primate," *Nature*, 453(7197), pp. 921-924 (May 2008) (electronic publication).
Yiu et al., "Glial inhibition of CNS axon regeneration," *Nature Reviews Neuroscience*, vol. 7, pp. 617-627 (Aug. 2006) (electronic publication).
Yokoyama et al., "Molecular cloning of a human neuroD from a neuroblastoma cell line specifically expressed in the fetal brain and adult cerebellum," *Molecular Brain Research*, 42(1), pp. 135-139 (Nov. 1996) (electronic publication).
Yoo et al., "MicroRNA-mediated conversion of human fibroblasts to neurons," *Nature*, vol. 476, pp. 228-231 (Jul. 2011) (electronic publication).
Yung et al., "Differential modulation of BMP signaling promotes the elaboration of cerebral cortical GABAergic neurons or oligodendrocytes from a common sonic hedgehog-responsive ventral forebrain progenitor species," *PNAS*, 99(25), pp. 16273-16278 (Dec. 2002) (electronic publication).
Zaiss et al., "Differential activation of inmate immune responses by adenovirus and adeno-associated virus vectors," *Journal of Virology*, 76(9), pp. 4580-4590 (May 2002) (electronic publication).
Zernicka-Goetz et al., "Following cell fate in the living mouse embryo," *Development*, 124(6), pp. 1133-1137 (Mar. 1997).
Zetsche et al., "Cpfl is a single RNA-guided endonuclease of a class 2 CRISPR-Cas System," *Cell*, 163(3), pp. 759-771, (Oct. 2015) (electronic publication).
Zhang et al., "Astrocyte heterogeneity: an underappreciated topic in neurobiology," *Current Opinions in Neurobiology*, 20(5), pp. 588-594 (Oct. 2010) (electronic publication).
Zhang et al., "Development of Neuroregenerative Gene Therapy to Reverse Glial Scar Tissue Back to Neuron-Enriched Tissue," *Frontiers in Cell and Developmental Biology*, 14(594170), pp. 1-19 (Nov. 2020) (electronic publication).
Zhang et al., "Modeling the phenotype of spinal muscular atrophy by the direct conversion of human fibroblasts to motor neurons," *Oncotarget*, 8(7), pp. 10945-10953 (Feb. 2017) (electronic publication).
Zhang et al., "Reversing Glial Scar Back To Neural Tissue Through NeuroD1-Mediated Astrocyte-To-Neuron Conversion," *bioRxiv*, article 261438, 36 pages (Feb. 2018) (electronic publication).
Zhang, et al., "Small Molecules Efficiently Reprogram Human Astroglial Cells into Functional Neurons," *Cell Stem Cell*, 17(6), pp. 735-747 (Dec. 2015) (electronic publication).
Zhao et al., "Distinct morphological stages of dentate granule neuron maturation in the adult mouse hippocampus," *The Journal of Neuroscience*, 26(1), pp. 3-11 (Jan. 2006) (electronic publication).
Zhao et al., "Neuronal transcription factors induce conversion of human glioma cells to neurons and inhibit tumorigenesis," *PLoS One*, 7(7):e41506, pp. 1-11 (Jul. 2012) (electronic publication).
Zhao et al., "The ASH1-miR-375-YWHAZ Signaling Axis Regulates Tumor Properties in Hepatocellular Carcinoma," *Molecular Therapy Nucleic Acids*, vol. 11, pp. 538-553 (Jun. 2018) (electronic publication).
Zhao et al., "TRED: a Transcriptional Regulatory Element Database and a platform for in silico gene regulation studies," *Nucleic Acids Research*, 33(suppl_1), pp. D103-S107 (Jan. 2005) (electronic publication).

(56) References Cited

OTHER PUBLICATIONS

Zhong et al., "The Wnt receptor Ryk controls specification of GABAergic neurons versus oligodendrocytes during telencephalon development," *Development*, 138(3), pp. 409-419 (Feb. 2011) (electronic publication).
Zhuo et al., "Live astrocytes visualized by green fluorescent protein in transgenic mice," *Developmental Biology*, 187(1), pp. 36-42 (Jul. 1997) (electronic publication).
Extended European Search Report issued in European Patent Application No. 20777797.0, dated Nov. 25, 2022.
Extended European Search Report issued in European Patent Application No. 20833514.1, dated Mar. 14, 2023.
Hussain et al., "Blood-Brain Barrier Breakdown: An Emerging Biomarker of Cognitive Impairment in Normal Aging and Dementia," *Frontiers in Neuroscience* vol. 15, Article 688090, pp. 1-22; (Aug. 2021) (Lausanne, Switzerland).
Leib et al., "Limited astrocyte-to-neuron conversion in the mouse brain using NeuroD1 overexpression," *Molecular Therapy*, vol. 30, No. 3, pp. 982-986, (Mar. 2022), (Cambridge, MA).
Malankhanova et al., "Modern Genome Editing Technologies in Huntington's Disease Research," *Journal of Huntington's Disease*, vol. 6, pp. 19-31, (Mar. 2017) (Amsterdam, Netherlands).
Margaritsescu et al., "Original Paper: Histopathological changes in acute ischemic stroke," *Romanian Journal of Morphology and Embryology*, vol. 50, No. 3, pp. 327-339 (2009) (online publication).
McPhee, et al. "Immune responses to AAV in a phase I study for Canavan disease," *The Journal of Gene Medicine*, vol. 8, pp. 577-588 (Mar. 2006) (Hoboken, NJ).
Prakash et al., "Blood-brain barrier breakdown and neovascularization processes after stroke and traumatic brain injury," *Curr Opin Neural., Author Manuscript*, 28(6), pp. 556-554, (Dec. 2015) available online, DOI: doi:10.1097/WCO.0000000000000248.
Wannissorn et al., "11 Factors That Disrupt the Blood-Brain Barrier," *SelfDecode* pp. 1-13, (Nov. 2021) available online at https://health.selfdecode.com/blog/factors-and-disease-states-that-disrupt-the-blood-brain-barrier/ (printed Mar. 1, 2023) (electronic publication).
Bloom et al. "Influence of the microenvironment on cell fate determination and migration," *Physiol Genomics* 46(9), pp. 309-314, (May 2014), available online: DOI: 10.1152/physiolgenomics.00170.2013:10.1152/physiolgenomics.00170.2013, accessed Sep. 5, 2023.
Boghdadi et al., "The Neuroprotective Role of Reactive Astrocytes after Central Nervous System Injury," *Journal of Neurotrauma*, 37, pp. 681-691, (Mar. 2020), available online: DOI: https://doi.org/10.1089/neu.2019.6938, accessed and printed Sep. 9, 2023.
Cepparulo et al.,"Hemorrhagic Stroke Induces a Time-Dependent Upregulation of miR-150-5p and miR-181b-5p in the Bloodstream," *Front. Neurol.* vol. 12, Article 736474, pp. 1-12 (Oct. 2021) (electronic publication); available online: DOC: 10.3389/fneur.2021.736474.
Choi et al., "Optimization of AAV expression cassettes to improve packaging capacity and transgene expression in neurons," *Molecular Brain*, vol. 7, pp. 1-10 (Mar. 2014) (electronic publication); available online: https://molecularbrain.biomedcentral.com/articles/10.1186/1756-6606-7-17.
Craig et al. "Evaluation of Gene Therapy as an Intervention Strategy to Treat Brain Injury from Stroke," *Frontiers in Molecular Neuroscience Mini Review Article*, 9(34), pp. 1-9, (May 2016), available online: DOI: https://doi.org/10.3389/fnmol.2016.00034.
Cyr,"Brain & Nervous System—Types of Neurons," Medically reviewed by Nicholas R. Metrus, MD, published Jan. 10, 2022 (accessed Jul. 27, 2023), 18 pages, available online: https://www.verywellhealth.com/types-of-neurons-5201172.
Domenger et al., "Next-generation AAV vectors-do not judge a virus (only) by its cover," *Human Molecular Genetics*, vol. 28, No. R1, pp. R3-R14 (Jul. 2019) available online: doi: 10.1093/hmg/ddz148 (electronic publication).
Extended European Search Report issued in European Patent Application No. 20876711.1, issued Oct. 13, 2023; 8 pages.
Extended European Search Report issued in European Patent Application No. 20875993.6, issued Oct. 13, 2023; 7 pages.
Finkel et al., "Diversity of Adult Neural Stem and Progenitor Cells in Physiology and Disease," *Cells*, vol. 10 (2045), pp. 1-23 (Aug. 2021) (electronic publication) available online: https://doi.org/10.3390/cells10082045.
Gadd et al., "Structural Basis for Partial Redundancy in a Class of Transcription Factors, the LIM Homeodomain Proteins, in Neural Cell Type Specification," *J Biol Chem*, vol. 286, No. 50, pp. 42971-42980 (Dec. 2011) (electronic publication) available online: 10.1074/jbc.M111.248559.
GenBank Accession No. JX912274, submitted Jul. 1, 2014, 3 pages (electronic publication); available online: https://www.ncbi.nlm.nih.gov/nuccore/JX912274.
GenBank Accession No. NM_004316.4, "*Homo sapiens* achaete-scute family bHLH transcription factor 1 (ASCL1), mRNA," updated Nov. 23, 2023, 4 pages (accessed and printed Aug. 15, 2023); available at: https://www.ncbi.nlm.nih.gov/nuccore/NM_004316.4.
Janowska et al., "Directed glial differentiation and transdifferentiation for neural tissue regeneration," *Experimental Neurology*, Vo. 319 (112813), pp. 1-14, (2019) (available online Aug. 2018) available: https://doi.org/10.1016/j.expneurol.2018.08.010.
Jones et al., "Proneural transcription factors Dlx2 and Pax6 are altered in adult SVZ neural precursor cells following striatal cell loss," *Molecular and Cellular Neuroscience*, 47(1), pp. 53-60, (May 2011), available online: https://doi.org/10.1016/j.mcn.2011.03.001.
Liu et al., "Systematic comparison of 2A peptides for cloning multi-genes in a polycistronic vector," *Scientific Reports*, 7(2193), 9 pages, (May 2017) (online publication), available at DOI: 10.1038/s41598-017-02460-2.
Maguire et al., "Gene Therapy for the Nervous System: Challenges and New strategies," *Neurotherapeutics*. 11(4), pp. 817-839, (Oct. 2014), available online: DOI: 10.1007/s13311-014-0299-5.
Mattugini et al., "Inducing Different Neuronal Subtypes from Astrocytes in the Injured Mouse Cerebral Cortex," *Neuron* vol. 103, Issue 6, pp. 1086-1095 (Sep. 2019) (electronic publication); available online: https://doi.org/10.1016/j.neuron.2019.08.009.
Nishiyama et al., "Astrocytes and NG2-glia: what's in a name?" *Journal of Anatomy*, 207(6), pp. 687-693, (Dec. 2005), available online: https://doi.org/10.1111/j.1469-7580.2005.00489.x.
Richetin, "Genetic manipulation of adult-born hippocampal neurons rescues memory in a mouse model of Alzheimer's disease," *Brain*, 138(2), pp. 440-455, (Feb. 2015), available online: https://doi.org/10.1093/brain/awu354.
Sato et al., "Usefulness of Double Gene Construct for Rapid Identification of Transgenic Mice Exhibiting Tissue-Specific Gene Expression," *Molecular Reproduction and Development*, vol. 60(4), pp. 446-456 (Dec. 2001) (electronic publication) available online: 10.1002/mrd. 1109.
Szymczak et al., "Development of 2A peptide-based strategies in the design of multicistronic vectors," *Expert Opin Biol Ther* 5(5), pp. 627-638 (Nov. 2005) (electronic publication); available online: DOI: 10.1517/14712598.5.5.627.
Trotter, et al., "NG2 cells: properties, progeny and origin," *Brain Res. Rev.*, 63(1-2), pp. 72-82, (May 2010), available online: DOI: 10.1016/j.brainresrev.2009.12.006.
"Types of Strokes and Treatment," American Stroke Association, pp. 1-4 (electronic publication). Available online https://www.stroke.org/en/about-stroke/types-of-stroke, accessed Aug. 1, 2023.
Xie et al., "New AAV tools fail to detect Neurod1-mediated neuronal conversion of Muller glia and astrocytes in vivo," *EBioMedicine* 90 (104531), pp. 1-19 (Apr. 2023) (electronic publication); available online: https://doi.org/10.1016/j.ebiom.2023.104531.
AAV phSyn1(S)-FlpO-bGHpA (Plasmid # 51669), *Addgene Blog*, 6 pages, (accessed and printed Jan. 12, 2024) available at: https://www.addgene.org/51669/.
Alliot et al., "Astrocytic cell clones derived from established cultures of 8-day postnatal mouse cerebella," *Brain Res.*, 306(1-2), pp. 283-291, (Jul. 1984) (electronic publication), available online: DOI: 10.1016/0006-8993(84)90377-9.
Bao et al., "Silencing of A20 Aggravates Neuronal Death and Inflammation After Traumatic Brain Injury: A Potential Trigger of

(56) References Cited

OTHER PUBLICATIONS

Necroptosis," *Front. Mol. Neurosci.*, 12(222), 21 pages, (Sep. 2019) (electronic publication), available online, DOI: https://doi.org/10.3389/fnmol.2019.00222.
Boone et al., "Effects of AAV-mediated knockdown of nNOS and GPx-1 gene expression in rat hippocampus after traumatic brain injury," *Plos ONE*, 12(10): e0185943, 22 pages, (Oct. 2017) (electronic publication), available online: https://doi.org/10.1371/journal.pone.0185943.
Extended European Search Report issued in European Patent Application No. 20875773.2, issued Oct. 6, 2023; 10 pages.
Extended European Search Report issued in European Patent Application No. 20894844.8, issued Nov. 17, 2023, 7 pages.
GenBank Accession No. EAW54861.1 "ISL1 transcription factor, LIM/homeodomain, (islet-1) [*Homo sapiens*]," published Mar. 23, 2015, 2 pages (accessed and printed Jan. 9, 2024, available at: https://www.ncbi.nlm.nih.gov/protein/EAW54861.
GenBank Accession No. AAH31213.1, "ISL LIM homeobox 1 [*Homo sapiens*]," published Jul. 17, 2007, 2 pages (accessed and printed Jan. 9, 2024) available online at: https://www.ncbi.nlm.nih.gov/protein/AAH31213.1.
GenBank Accession No. NP_002491.3, "neurogenic differentiation factor 1 [*Homo sapiens*]," published Dec. 4, 2023, 2 pages (accessed and printed Jan. 9, 2024) available online at: https://www.ncbi.nlm.nih.gov/protein/NP_002491.
GenBank Accession No. AC010327.8, "*Homo sapiens* chromosome 19 clone CTD-2587H24, complete sequence," published Aug. 1, 2002, 32 pages (accessed and printed Jan. 12, 2024), available online: https://www.ncbi.nlm.nih.gov/nuccore/AC010327.8.
Lashof-Sullivan et al., "Intravenously administered nanoparticles increase survival following blast trauma," *PNAS*, 111(28), pp. 10293-10298, (Jun. 2014) (electronic publication), available online: https://doi.org/10.1073/pnas.1406979111.
Logsdon et al., "Blast exposure elicits blood-brain barrier disruption and repair mediated by tight junction integrity and nitric oxide dependent processes," *Sci Rep*, 8(11344), (Jul. 2018) (electronic publication), available online: https://doi.org/10.1038/s41598-018-29341-6.
PAAV-FLEX-GFP (Plasmid #28304) Addgene Blog, 5 pages (accessed and printed Jan. 9, 2024) (online publication) available at: https://www.addgene.org/28304/.
PAAV-CaMKII-GFP (Plasmid #64545) Addgene Blog, 4 pages (accessed and printed Jan. 9, 2024) (online publication) available at: https://www.addgene.org/64545/.
PAAV-GFAP-hChR2(H134R)-mCherry (Plasmid #27055) Addgene Blog, 5 pages (accessed and printed Jan. 12, 2024, available at: https://www.addgene.org/27055/.
Rodriguez et al. "Astroglia in dementia and Alzheimer's disease." *Cell Death & Differentiation*, 16(3), pp. 378-385, (Dec. 2009) (electronic publication), available online: DOI: https://doi.org/10.1038/cdd.2008.172.
Search Report issued in Chinese Patent Application No. 202080030149.8, dated Dec. 26, 2023, 8 pages.
Shen et al., "The potential application of gene therapy in the treatment of traumatic brain injury," *Neurosurg Rev*, 30, pp. 291-298 (Aug. 2007) (electronic publication) available online: https://doi.org/10.1007/s10143-007-0094-4.
Smithsonian, "Numbers of Insects (Species and Individuals)," last visited Jan. 4, 2024, available online: https://www.si.edu/spotlight/buginfo/bugnos; 9pages, accessed and printed Apr. 1, 2024.
Stanley et al., "Complementation between mutants of CHO cells resistant to a variety of plant lectins," *Somatic Cell Genet.* 3(4), pp. 391-405, (Jul. 1977) (electronic publication), available online: DOI: 10.1007/BF01542968.
Steele et al., "Reactive astrocytes give neurons less support: implications for Alzheimer's disease," *Neurobiology of Aging*, 33(2), pp. 423-e1-423.e13, (Feb. 2012) (online publication), available online: DOI: https://doi.org/10.1016/j.neurobiolaging.2010.09.018.
Sukumari-Ramesh, et al., "Astrocyte-Specific Expression of Survivin after Intracerebral Hemorrhage in Mice: A Possible Role in Reactive Gliosis?" Journal of Neurotrauma, 29(18), pp. 2798-2804, (Dec. 2012), (electronic publication), available online: https://doi.org/10.1089/neu.2011.2243.
Ting et al. "Acute Brain Slice Methods for Adult and Aging Animals: Application of Targeted Patch Clamp Analysis and Optogenetics," *Methods in Molecular Biology*, 1183, pp. 221-242, (Jan. 2014) (electronic publication), available online: DOI: 10.1007/978-1-4939-1096-0_14.
Weston, "The Potential of Stem Cells in Treatment of Traumatic Brain Injury," *Current Neurology and Neuroscience Reports*, 18(1), pp. 1-10, (Jan. 2018), (electronic publication) available online: https://doi.org/10.1007/s11910-018-0812-z.
Wikipedia, "Mammal," accessed and printed Aug. 31, 2022, available online: en.wikipedia.org/wiki/Mammal, 49 pages.
Wikipedia, "Vertebrate," accessed and printed Jan. 4, 2024, available online: en.wikipedia.org/wiki/Vertebrates, 23 pages.
Windle et al., "An analysis of four different methods of producing focal cerebral ischemia with endothelin-1 in the rat," *Experimental Neurology*, 201(2), pp. 324-334, (Oct. 2006) (electronic publication), available online: https://doi.org/10.1016/j.expneurol.2006.04.012.
Wright et al., "ProTECT: A Randomized Clinical Trial of Progesterone for Acute Traumatic Brain Injury—Neurology/Original Research," *Annals of Emergency Medicine*, 49(4), pp. 391-402, (Apr. 2007) (electronic publication), available online, DOI: 10.1016/j.annemergmed.2006.07.932.
Wu et al., "γ-Aminobutyric Acid Type A (GABAA) Receptor α Subunits Play a Direct Role in Synaptic Versus Extrasynaptic Targeting," *The Journal of Biological Chemistry*, 287(33), pp. 27417-27430, (Aug. 2012) (electronic publication), available online: DOI: https://doi.org/10.1074/jbc.M112.360461.
You et al., "Necrostatin-1 reduces histopathology and improves functional outcome after controlled cortical impact in mice," *Journal of Cerebral Blood Flow & Metabolism*, 28, pp. 1564-1573, (May 2008) (electronic publication), available online: 10.1038/jcbfm.2008.44.
Yoshimura et al., FGF-2 regulates neurogenesis and degeneration in the dentate gyrus after traumatic brain injury in mice, *J Clin Invest.*, 112(8), pp. 1202-1210, (Oct. 2003) (electronic publication), available online: https://doi.org/10.1172/JCI16618.
Zhuo et al., "In vivo reprogramming of adult pancreatic exocrine cells to β-cells," *Nature*, 455(7213), pp. 627-632, (Oct. 2008) (available online), available online: DOI: 10.1038/nature07314.
Extended European Search Report issued in European Patent Application No. 21876283.9, issued Jan. 17, 2025, 8 pages.
International Search Report and Written Opinion, dated Feb. 15, 2022, PCT/US2021/052358.
International Search Report in International Application No. PCT/US2021/052348, dated Feb. 17, 2022, 7 pages.
Altamirano et al., 2019, "Signaling within the pineal gland: A parallelism with the central nervous system," Seminars in Cell and Development Biology, 95:151-159.
Altschul et al., 1990, "Basic local alignment search tool," Journal of Molecular Biology, 215(3):403-410.
Chen et al., "Functional repair after ischemic injury through high efficiency in situ astrocyte-to-neuron conversion," BioRxiv, pp. 1-29, (Apr. 2018) (electronic publication), available online: DOI: http://dx.doi.org/10. 1 101/294967.
Chenna et al., 2003, "Multiple sequence alignment with the Clustal series of programs," Nucleic Acids Research, 31:3497-3500.
Pawson, et al. Assembly of Cell Regulatory Systems Through Protein Interaction Domains, Science, vol. 300, pp. 445-452 (Apr. 2003) (London, UK).
Funato, T., "Gene Delivery using adeno-associated (AAV) vectors," Nippon-rinsho, 56(3):149-152, English Abstract.
GenBank Accession No. NM_002500.5, "*Homo sapiens* neuronal differentiation 1 (NEUROD1), transcript variant 1, mRNA]," published Dec. 4, 2023, 4 pages (accessed and printed Jan. 9, 2024) available online at: https://www.ncbi.nlm.nih.gov/nuccore/NM 002500.
GenBank Accession No. AAH06221.2, "NK.2 homeobox 1 [*Homo sapiens*], " dated Jan. 30, 2008, 2 pages.
GenBank Accession No. NM 024019.3, "*Homo sapiens* neurogenin 2 (NEUROG2), mRNA," dated Mar. 16, 2014, 3 pages.

(56) References Cited

OTHER PUBLICATIONS

Larkin et al., 2007, "Clustal W and Clustal X version 2.0," Bioinformatics, 23(21):2947-48.
Lee et al., 2008, "GFAP promoter elements required for region-specific and astrocyte-specific expression," Glia, vol. 56.
Makarova et al., "An updated evolutionary classification of CRISPR-Cas systems," Nature Reviews Microbiology, 13(11), pp. 722-736, (Sep. 2015) (electronic publication) (electronic publication).
Horie et al., "Mouse model of focal cerebral ischemia using endothelia-1," Journal of Neuroscience Methods, 173(2), pp. 286-290 (Aug. 2008) (electronic publication).
Song et al., 2002, "Astroglia induce neurogenesis from adult neural stem cells," Nature, 417:39-44.
Sun et al., 2016, "Direct Induction and Functional Maturation of Forebrain GABAergic Neurons from Human Pluripotent Stem Cells," Cell Reports, 16:1942-1953.
Thompson et al., 1994, "Clustal W: Improving the sensitivity of progressive mutliple sequence alignment through sequence weighting, position-specific gap penalties and weight matrix choice," Nucleic Acids Research, 22:4673-4680.
Wang et al., "Revisiting astrocyte to neuron conversion with lineage tracing in vivo," Cell vol. 184, pp. 5465-5481 (Oct. 2021) (electronic publication); available online: https://doi.org/10.1016/j.cell.2021.09.005.
GenBank Accession No. Q12946.2, "RecName: Full=Forkhead box protein F1: AltName: Full=Forkhead-related activator 1; Short=FREAC-1: AltName: Full=Forkhead-related protein FKHL5: AltName: Full=Forkhead-related transcription factor 1," dated Feb. 4, 2015, 6 pages.
NCBI listing N M_004316.4, Ascl1 sequence, updates Nov. 23, 2018 (Year: 2018).
NCBI, "Human glial fibrillary acidic protein (GFAP)" Genebank sequence M67446.1, 1991, https://www.ncbi.nlm.nih.gov/nuccore/M67446.1, (Year: 1991).

* cited by examiner

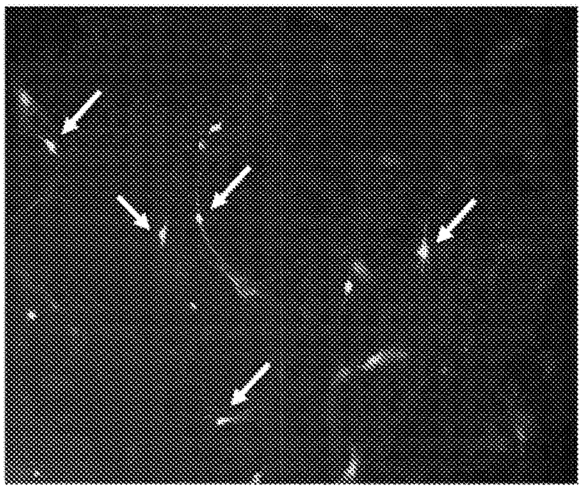
NeuN/MAP2
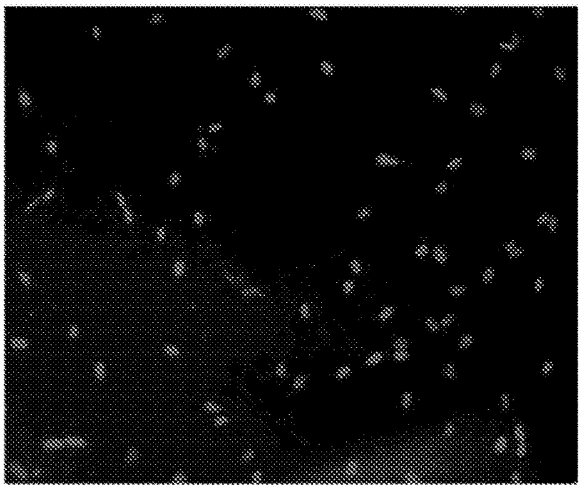
DAPI
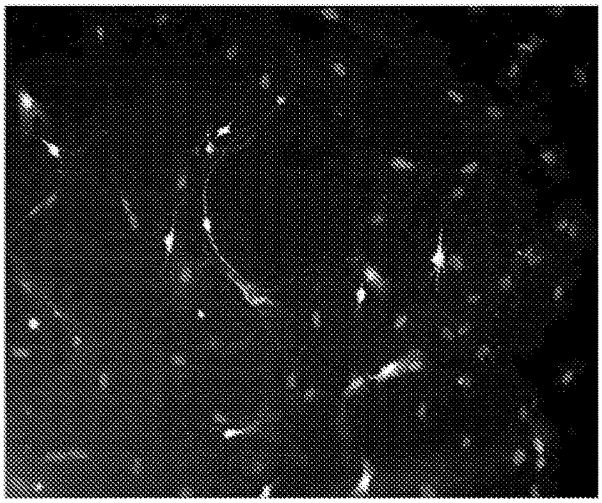
NeuN/MAP2/DAPI
(Merged)
FIGURE 17

ND1
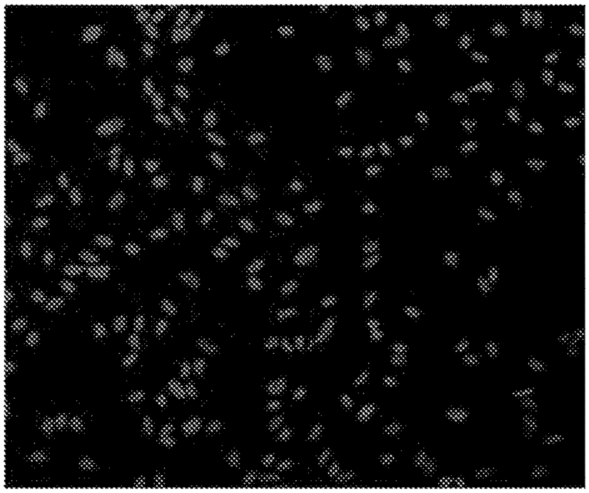
DAPI
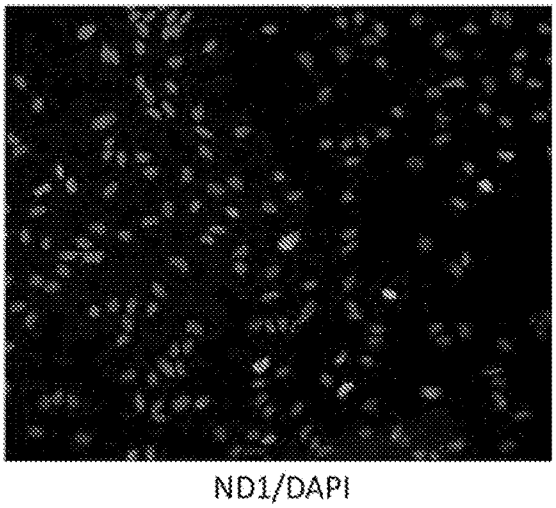
ND1/DAPI
(Merged)
FIGURE 19

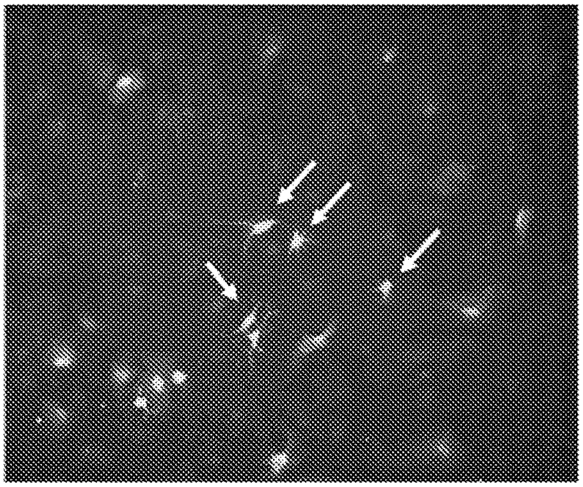
NeuN/MAP2
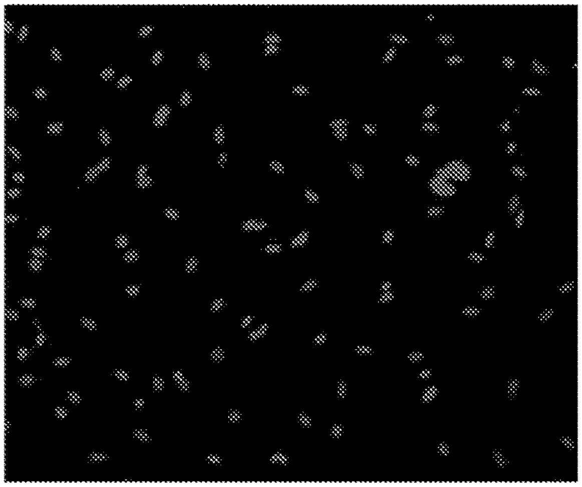
DAPI
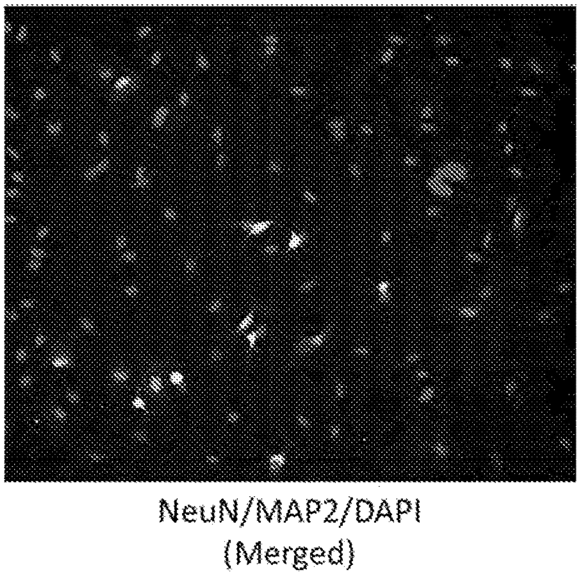
NeuN/MAP2/DAPI
(Merged)
FIGURE 20

NeuN/MAP2

DAPI

NeuN/MAP2/DAPI
(Merged)

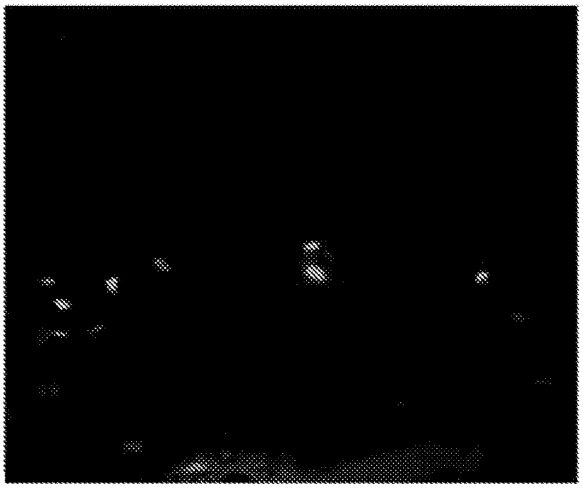
ND1
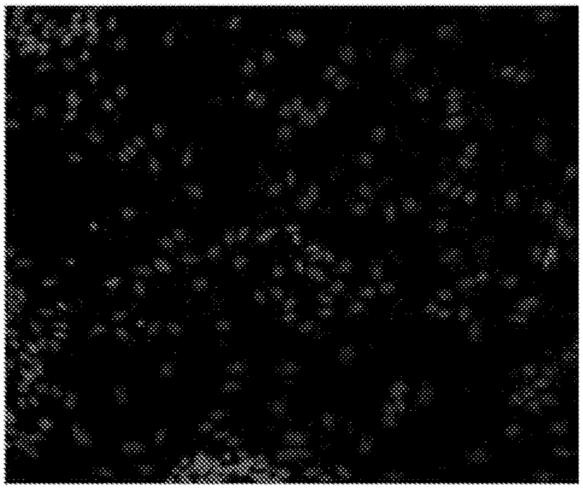
DAPI
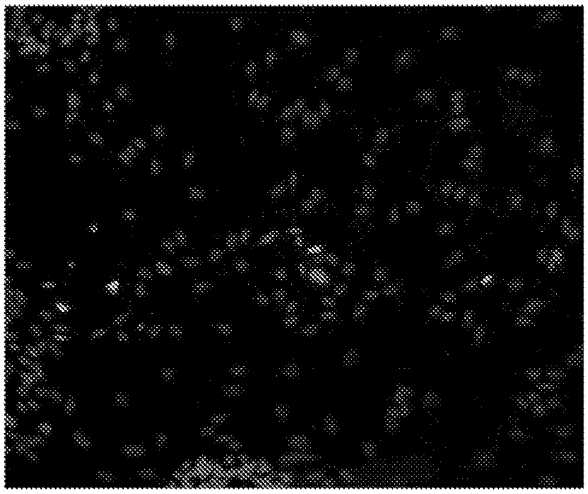
ND1/ DAPI
(Merged)

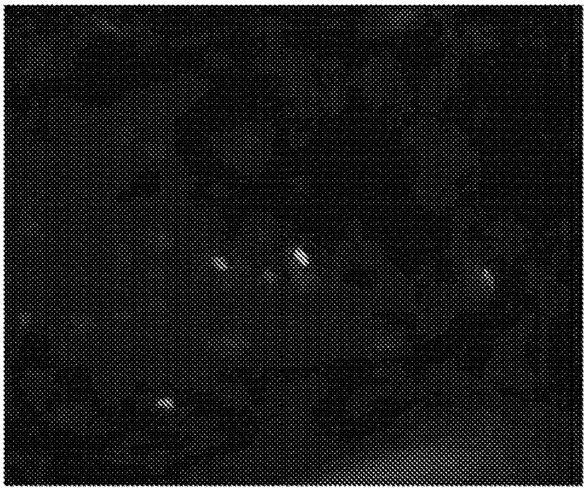
ND1
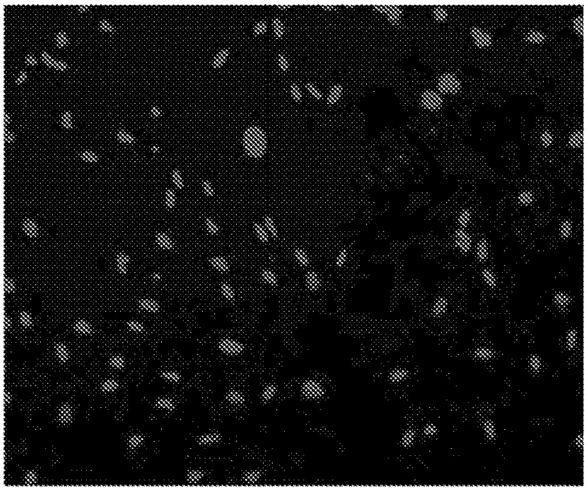
DAPI
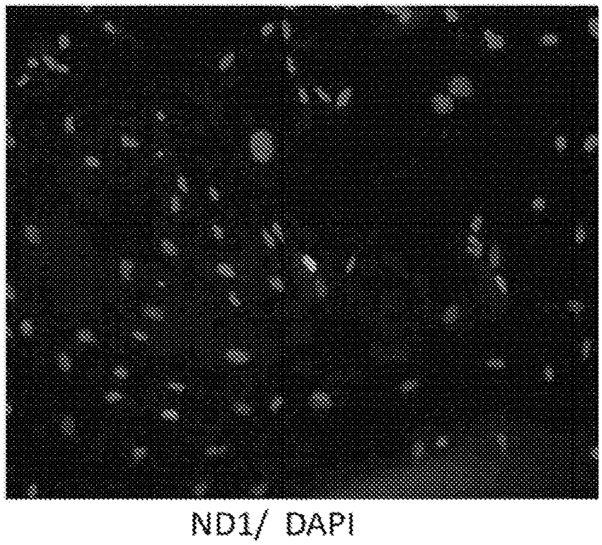
ND1/ DAPI
(Merged)
FIGURE 29

*10 days post infection*
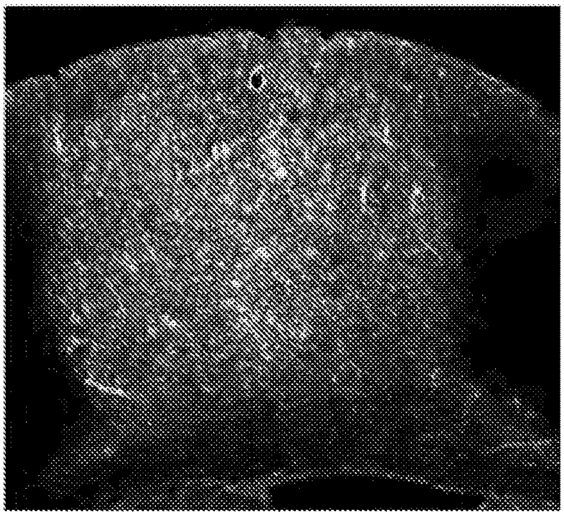
P12 Control Group
Cortex
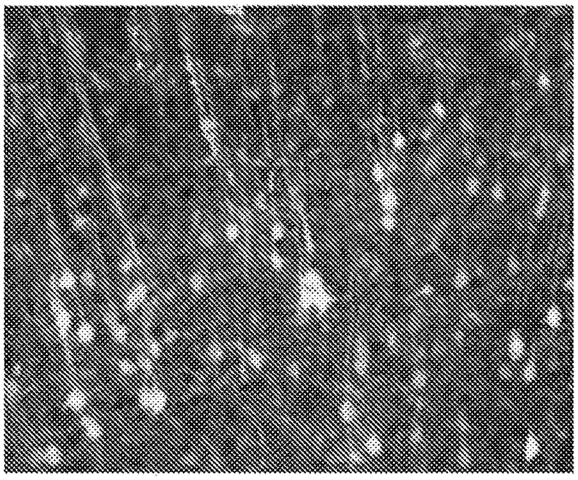
P134 Group
High conversion
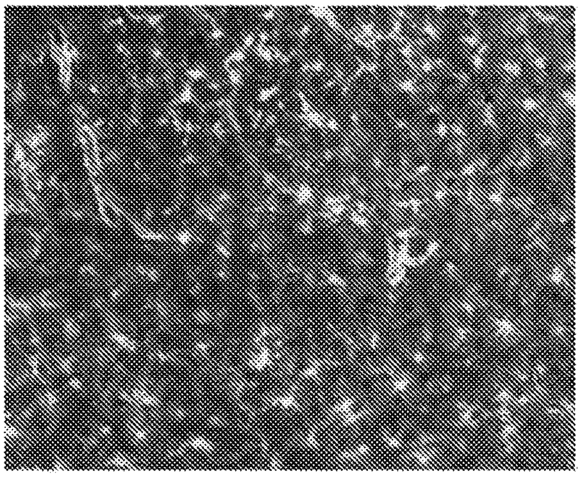
P138 Group
Low conversion
FIGURE 32

*30 days post infection*
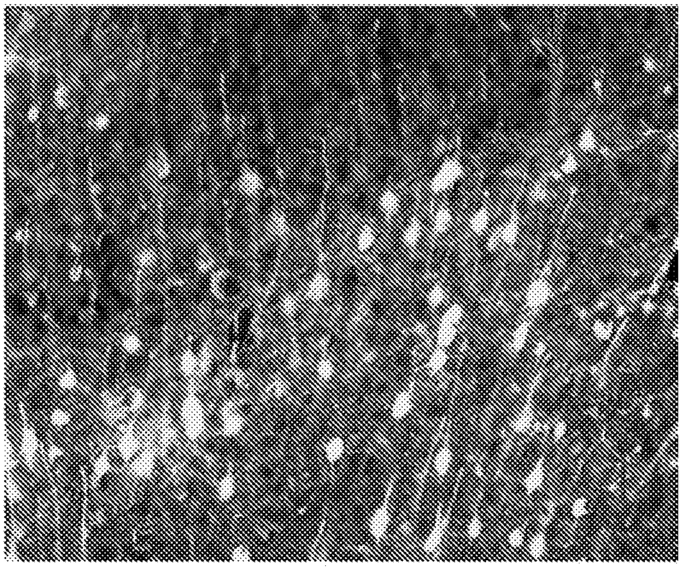
P134 Group
High conversion
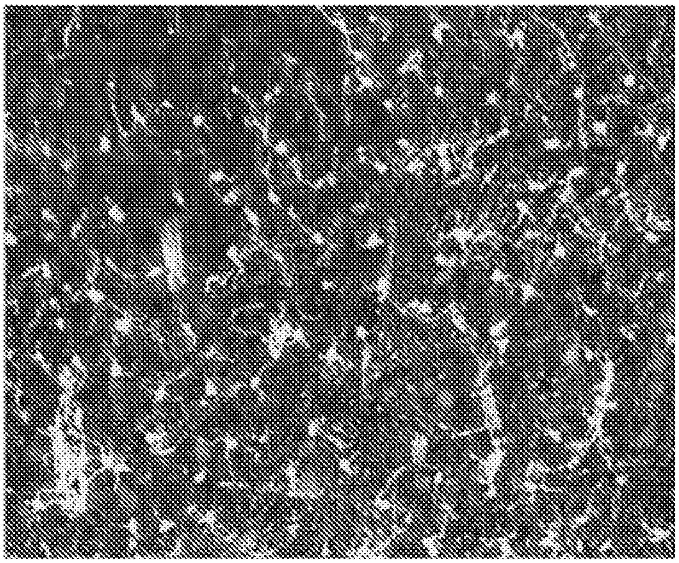
P138 Group
Low conversion
FIGURE 33

NeuN/MAP2 DAPI Merged (NeuN/MAP2/DAPI)

Merged
(GFP/GFAP/NeuN)

SEQUENCE LISTING

```
<160> NUMBER OF SEQ ID NOS: 30

<210> SEQ ID NO 1
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

tgcaggcagc tgcgcgctcg ctcgctcact gaggccgccc gggcgtcggg cgacctttgg     60

tcgcccggcc tcagtgagcg agcgagcgcg cagagaggga gtggccaact ccatcactag    120

gggttcct                                                             128


<210> SEQ ID NO 2
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

tgcaaagatg gataaagttt taaacagaga ggaatctttg cagctaatgg accttctagg     60

tcttgaaagg agtgggaatt ggctccggtg cccgtcagtg ggcagagcgc acatcgccca    120

cagtccccga gaagttgggg ggaggggtcg gca                                 153


<210> SEQ ID NO 3
<211> LENGTH: 553
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

acgttactgg ccgaagccgc ttggaataag gccggtgtgc gtttgtctat atgttatttt     60

ccaccatatt gccgtctttt ggcaatgtga gggcccggaa acctggccct gtcttcttga    120

cgagcattcc taggggtctt tcccctctcg ccaaaggaat gcaaggtctg ttgaatgtcg    180

tgaaggaagc agttcctctg gaagcttctt gaagacaaac aacgtctgta gcgacccttt    240

gcaggcagcg gaacccccca cctggcgaca ggtgcctctg cggccaaaag ccacgtgtat    300

aagatacacc tgcaaaggcg gcacaacccc agtgccacgt tgtgagttgg atagttgtgg    360

aaagagtcaa atggctctcc tcaagcgtat tcaacaaggg gctgaaggat gcccagaagg    420

taccccattg tatgggatct gatctggggc ctcggtgcac atgctttaca tgtgtttagt    480
```

```
cgaggttaaa aaaacgtcta ggccccccga accacgggga cgtggttttc ctttgaaaaa    540

cacgatgata ata                                                       553


<210> SEQ ID NO 4
<211> LENGTH: 1667
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

ctgcaagcag acctggcagc attgggctgg ccgcccccca gggcctcctc ttcatgccca     60

gtgaatgact caccttggca cagacacaat gttcggggtg ggcacagtgc ctgcttcccg    120

ccgcacccca gccccccctca aatgccttcc gagaagccca ttgagtaggg ggcttgcatt    180

gcaccccagc ctgacagcct ggcatcttgg gataaaagca gcacagcccc ctaggggctg    240

cccttgctgt gtggcgccac cggcggtgga gaacaaggct ctattcagcc tgtgcccagg    300

aaaggggatc aggggatgcc caggcatgga cagtgggtgg caggggggga gaggagggct    360

gtctgcttcc cagaagtcca aggacacaaa tgggtgaggg gactgggcag ggttctgacc    420

ctgtgggacc agagtggagg gcgtagatgg acctgaagtc tccagggaca acagggccca    480

ggtctcaggc tcctagttgg gcccagtggc tccagcgttt ccaaacccat ccatccccag    540

aggttcttcc catctctcca ggctgatgtg tgggaactcg aggaaataaa tctccagtgg    600

gagacggagg ggtggccagg gaaacggggc gctgcaggaa taaagacgag ccagcacagc    660

cagctcatgc gtaacggctt tgtggagctg tcaaggcctg gtctctggga gagaggcaca    720

gggaggccag acaaggaagg ggtgacctgg agggacagat ccaggggcta aagtcctgat    780

aaggcaagag agtgccggcc ccctcttgcc ctatcaggac ctccactgcc acatagaggc    840

catgattgac ccttagacaa agggctggtg tccaatccca gcccccagcc ccagaactcc    900

agggaatgaa tgggcagaga gcaggaatgt gggacatctg tgttcaaggg aaggactcca    960

ggagtctgct gggaatgagg cctagtagga aatgaggtgg cccttgaggg tacagaacag   1020

gttcattctt cgccaaattc ccagcacctt gcaggcactt acagctgagt gagataatgc   1080

ctgggttatg aaatcaaaaa gttggaaagc aggtcagagg tcatctggta cagcccttcc   1140

ttcccttttt tttttttttt ttttgtgaga caaggtctct ctctgttgcc caggctggag   1200

tggcgcaaac acagctcact gcagcctcaa cctactgggc tcaagcaatc ctccagcctc   1260

agcctcccaa agtgctggga ttacaagcat gagccacccc actcagccct ttccttcctt   1320

tttaattgat gcataataat tgtaagtatt catcatggtc caaccaaccc tttcttgacc   1380

caccttccta gagagagggt cctcttgatt cagcggtcag ggccccagac ccatggtctg   1440

gctccaggta ccacctgcct catgcaggag ttggcgtgcc caggaagctc tgcctctggg   1500

cacagtgacc tcagtggggt gaggggagct ctccccatag ctgggctgcg gcccaacccc   1560

accccctcag gctatgccag ggggtgttgc caggggcacc cgggcatcgc cagtctagcc   1620

cactccttca taaagccctc gcatcccagg agcgagcaga gccagag                 1667


<210> SEQ ID NO 5
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 5
gtaagtatca aggttacaag acaggtttaa ggagaccaat agaaactggg cttgtcgaga 60
cagagaagac tcttgcgttt ctgataggca cctattggtc ttactgacat ccactttgcc 120
tttctctcca cag 133

<210> SEQ ID NO 6
<211> LENGTH: 1068
<212> TYPE: DNA
<213> ORGANISM: Homo sapiens

<400> SEQUENCE: 6
atgaccaaat cgtacagcga gagtgggctg atgggcgagc ctcagcccca aggtcctcca 60
agctggacag acgagtgtct cagttctcag gacgaggagc acgaggcaga caagaaggag 120
gacgacctcg aagccatgaa cgcagaggag gactcactga ggaacggggg agaggaggag 180
gacgaagatg aggacctgga agaggaggaa gaagaggaag aggaggatga cgatcaaaag 240
cccaagagac gcggccccaa aaagaagaag atgactaagg ctcgcctgga gcgttttaaa 300
ttgagacgca tgaaggctaa cgcccgggag cggaaccgca tgcacggact gaacgcggcg 360
ctagacaacc tgcgcaaggt ggtgccttgc tattctaaga cgcagaagct gtccaaaatc 420
gagactctgc gcttggccaa gaactacatc tgggctctgt cggagatcct gcgctcaggc 480
aaaagcccag acctggtctc cttcgttcag acgctttgca agggcttatc ccaacccacc 540
accaacctgg ttgcgggctg cctgcaactc aatcctcgga cttttctgcc tgagcagaac 600
caggacatgc ccccccacct gccgacggcc agcgcttcct tccctgtaca cccctactcc 660
taccagtcgc ctgggctgcc cagtccgcct tacggtacca tggacagctc ccatgtcttc 720
cacgttaagc ctccgccgca cgcctacagc gcagcgctgg agcccttctt tgaaagccct 780
ctgactgatt gcaccagccc ttcctttgat ggacccctca gcccgccgct cagcatcaat 840
ggcaacttct ctttcaaaca cgaaccgtcc gccgagtttg agaaaaatta tgcctttacc 900
atgcactatc ctgcagcgac actggcaggg gcccaaagcc acggatcaat cttctcaggc 960
accgctgccc ctcgctgcga gatccccata gacaatatta tgtccttcga tagccattca 1020
catcatgagc gagtcatgag tgcccagctc aatgccatat ttcatgat 1068

<210> SEQ ID NO 7
<211> LENGTH: 589
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480

```
aatccagcgg accttccttc ccgcggcctg ctgccggctc tgcggcctct tccgcgtctt    540

cgccttcgcc ctcagacgag tcggatctcc ctttgggccg cctccccgc               589


<210> SEQ ID NO 8
<211> LENGTH: 251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

cgatccaccg gatctagata actgatcata atcagccata ccacatttgt agaggtttta     60

cttgctttaa aaaacctccc acacctcccc ctgaacctga aacataaaat gaatgcaatt    120

gttgttgtta acttgtttat tgcagcttat aatggttaca aataaagcaa tagcatcaca    180

aatttcacaa ataaagcatt tttttcactg cattctagtt gtggtttgtc caaactcatc    240

aatgtatctt a                                                         251


<210> SEQ ID NO 9
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag ctgcctgca                                                 139


<210> SEQ ID NO 10
<211> LENGTH: 356
<212> TYPE: PRT
<213> ORGANISM: Homo sapiens

<400> SEQUENCE: 10

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
```

```
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355
```

<210> SEQ ID NO 11
<211> LENGTH: 380
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
gacattgatt attgactagt tattaatagt aatcaattac ggggtcatta gttcatagcc     60

catatatgga gttccgcgtt acataactta cggtaaatgg cccgcctggc tgaccgccca    120

acgacccccg cccattgacg tcaataatga cgtatgttcc catagtaacg ccaataggga    180

ctttccattg acgtcaatgg gtggactatt tacggtaaac tgcccacttg gcagtacatc    240

aagtgtatca tatgccaagt acgcccccta ttgacgtcaa tgacggtaaa tggcccgcct    300

ggcattatgc ccagtacatg accttatggg actttcctac ttggcagtac atctacgtat    360

tagtcatcgc tattaccatg                                                 380
```

<210> SEQ ID NO 12
<211> LENGTH: 2214
<212> TYPE: DNA
<213> ORGANISM: Homo sapiens

<400> SEQUENCE: 12

```
cgcgtcccac ctccctctct gtgctgggac tcacagaggg agacctcagg aggcagtctg     60

tccatcacat gtccaaatgc agagcatacc ctgggctggg cgcagtggcg cacaactgta    120

attccagcac tttgggaggc tgatgtggaa ggatcacttg agcccagaag ttctagacca    180
```

gcctgggcaa catggcaaga ccctatctct acaaaaaaag ttaaaaaatc agccacgtgt 240
ggtgacacac acctgtagtc ccagctattc aggaggctga ggtgagggga tcacttaagg 300
ctgggaggtt gaggctgcag tgagtcgtgg ttgcgccact gcactccagc ctgggcaaca 360
gtgagaccct gtctcaaaag acaaaaaaaa aaaaaaaaaa aaaaagaaca tatcctggtg 420
tggagtaggg gacgctgctc tgacagaggc tcgggggcct gagctggctc tgtgagctgg 480
ggaggaggca gacagccagg ccttgtctgc aagcagacct ggcagcattg ggctggccgc 540
cccccagggc ctcctcttca tgcccagtga atgactcacc ttggcacaga cacaatgttc 600
ggggtgggca cagtgcctgc ttcccgccgc accccagccc ccctcaaatg ccttccgaga 660
agcccattga gcaggggggct tgcattgcac cccagcctga cagcctggca tcttgggata 720
aaagcagcac agccccctag gggctgccct tgctgtgtgg cgccaccggc ggtggagaac 780
aaggctctat tcagcctgtg cccaggaaag gggatcaggg gatgcccagg catggacagt 840
gggtggcagg gggggagagg agggctgtct gcttcccaga agtccaagga cacaaatggg 900
tgaggggact gggcagggtt ctgaccctgt gggaccagag tggagggcgt agatggacct 960
gaagtctcca gggacaacag ggcccaggtc tcaggctcct agttgggccc agtggctcca 1020
gcgtttccaa acccatccat ccccagaggt tcttcccatc tctccaggct gatgtgtggg 1080
aactcgagga aataaatctc cagtgggaga cggaggggtg gccagggaaa cggggcgctg 1140
caggaataaa gacgagccag cacagccagc tcatgtgtaa cggctttgtg gagctgtcaa 1200
ggcctggtct ctgggagaga ggcacaggga ggccagacaa ggaaggggtg acctggaggg 1260
acagatccag gggctaaagt cctgataagg caagagagtg ccggcccccct cttgccctat 1320 caggacctcc actgccacat agaggccatg attgaccctt agacaaaggg ctggtgtcca 1380
atcccagccc ccagccccag aactccaggg aatgaatggg cagagagcag gaatgtggga 1440
catctgtgtt caagggaagg actccaggag tctgctggga atgaggccta gtaggaaatg 1500
aggtggccct tgagggtaca gaacaggttc attcttcgcc aaattcccag caccttgcag 1560
gcacttacag ctgagtgaga taatgcctgg gttatgaaat caaaaagttg gaaagcaggt 1620
cagaggtcat ctggtacagc ccttccttcc cttttttttt ttttttttt gtgagacaag 1680 gtctctctct gttgcccagg ctggagtggc gcaaacacag ctcactgcag cctcaaccta 1740
ctgggctcaa gcaatcctcc agcctcagcc tcccaaagtg ctgggattac aagcatgagc 1800
caccccactc agccctttcc ttccttttta attgatgcat aataattgta agtattcatc 1860
atggtccaac caaccctttc ttgacccacc ttcctagaga gagggtcctc ttgcttcagc 1920
ggtcagggcc ccagacccat ggtctggctc caggtaccac ctgcctcatg caggagttgg 1980
cgtgcccagg aagctctgcc tctgggcaca gtgacctcag tggggtgagg ggagctctcc 2040
ccatagctgg gctgcggccc aaccccaccc cctcaggcta tgccaggggg tgttgccagg 2100
ggcacccggg catcgccagt ctagcccact ccttcataaa gccctcgcat cccaggagcg 2160
agcagagcca gagcaggttg gagaggagac gcatcacctc cgctgctcgc cggg 2214

<210> SEQ ID NO 13
<211> LENGTH: 987
<212> TYPE: DNA
<213> ORGANISM: Homo sapiens

<400> SEQUENCE: 13
atgactggag tctttgacag tctagtggct gatatgcact cgacccagat cgccgcctcc 60

```
agcacgtacc accagcacca gcagcccccg agcggcggcg gcgccggccc gggtggcaac    120

agcagcagca gcagcagcct ccacaagccc caggagtcgc ccacccttcc ggtgtccacc    180

gccaccgaca gcagctacta caccaaccag cagcacccgg cgggcggcgg cggcggcggg    240

ggctcgccct acgcgcacat gggttcctac cagtaccaag ccagcggcct caacaacgtc    300

ccttactccg ccaagagcag ctatgacctg ggctacaccg ccgcctacac ctcctacgct    360

ccctatggaa ccagttcgtc cccagccaac aacgagcctg agaaggagga ccttgagcct    420

gaaattcgga tagtgaacgg gaagccaaag aaagtccgga aaccccgcac catctactcc    480

agtttccagc tggcggctct tcagcggcgt ttccaaaaga ctcaatactt ggccttgccg    540

gagcgagccg agctggcggc ctctctgggc ctcacccaga ctcaggtcaa aatctggttc    600

cagaaccgcc ggtccaagtt caagaagatg tggaaaagtg gtgagatccc ctcggagcag    660

caccctgggg ccagcgcttc tccaccttgt gcttcgccgc cagtctcagc gccggcctcc    720

tgggactttg gtgtgccgca gcggatggcg ggcggcggtg gtccgggcag tggcggcagc    780

ggcgccggca gctcgggctc cagcccgagc agcgcggcct cggcttttct gggcaactac    840

ccctggtacc accagacctc gggatccgcc tcacacctgc aggccacggc gccgctgctg    900

caccccactc agaccccgca gccgcatcac caccaccacc atcacggcgg cgggggcgcc    960

ccggtgagcg cggggacgat ttctga                                         987
```

```
<210> SEQ ID NO 14
<211> LENGTH: 328
<212> TYPE: PRT
<213> ORGANISM: Homo sapiens

<400> SEQUENCE: 14

Met Thr Gly Val Phe Asp Ser Leu Val Ala Asp Met His Ser Thr Gln
1               5                   10                  15

Ile Ala Ala Ser Ser Thr Tyr His Gln His Gln Gln Pro Pro Ser Gly
            20                  25                  30

Gly Gly Ala Gly Pro Gly Gly Asn Ser Ser Ser Ser Ser Ser Leu His
        35                  40                  45

Lys Pro Gln Glu Ser Pro Thr Leu Pro Val Ser Thr Ala Thr Asp Ser
    50                  55                  60

Ser Tyr Tyr Thr Asn Gln Gln His Pro Ala Gly Gly Gly Gly Gly Gly
65                  70                  75                  80

Gly Ser Pro Tyr Ala His Met Gly Ser Tyr Gln Tyr Gln Ala Ser Gly
                85                  90                  95

Leu Asn Asn Val Pro Tyr Ser Ala Lys Ser Ser Tyr Asp Leu Gly Tyr
            100                 105                 110

Thr Ala Ala Tyr Thr Ser Tyr Ala Pro Tyr Gly Thr Ser Ser Ser Pro
        115                 120                 125

Ala Asn Asn Glu Pro Glu Lys Glu Asp Leu Glu Pro Glu Ile Arg Ile
    130                 135                 140

Val Asn Gly Lys Pro Lys Lys Val Arg Lys Pro Arg Thr Ile Tyr Ser
145                 150                 155                 160

Ser Phe Gln Leu Ala Ala Leu Gln Arg Arg Phe Gln Lys Thr Gln Tyr
                165                 170                 175

Leu Ala Leu Pro Glu Arg Ala Glu Leu Ala Ala Ser Leu Gly Leu Thr
            180                 185                 190

Gln Thr Gln Val Lys Ile Trp Phe Gln Asn Arg Arg Ser Lys Phe Lys
        195                 200                 205
```

```
Lys Met Trp Lys Ser Gly Glu Ile Pro Ser Glu Gln His Pro Gly Ala
    210                 215                 220

Ser Ala Ser Pro Pro Cys Ala Ser Pro Pro Val Ser Ala Pro Ala Ser
225                 230                 235                 240

Trp Asp Phe Gly Val Pro Gln Arg Met Ala Gly Gly Gly Gly Pro Gly
                245                 250                 255

Ser Gly Gly Ser Gly Ala Gly Ser Ser Gly Ser Ser Pro Ser Ser Ala
            260                 265                 270

Ala Ser Ala Phe Leu Gly Asn Tyr Pro Trp Tyr His Gln Thr Ser Gly
        275                 280                 285

Ser Ala Ser His Leu Gln Ala Thr Ala Pro Leu Leu His Pro Thr Gln
    290                 295                 300

Thr Pro Gln Pro His His His His His His His Gly Gly Gly Gly Ala
305                 310                 315                 320

Pro Val Ser Ala Gly Thr Ile Phe
                325


<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

gctactaact tcagcctgct gaagcaggct ggagacgtgg aggagaaccc tggacct        57


<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

gaggggagag gaagtcttct gacctgcgga gacgtcgaag agaatcctgg accc           54


<210> SEQ ID NO 17
<211> LENGTH: 477
<212> TYPE: DNA
<213> ORGANISM: Homo sapiens

<400> SEQUENCE: 17

gggtggcatc cctgtgaccc ctccccagtg cctctcctgg ccctggaagt tgccactcca     60

gtgcccacca gccttgtcct aataaaatta agttgcatca ttttgtctga ctaggtgtcc    120

ttctataata ttatggggtg gaggggggtg gtatggagca aggggcaagt tgggaagaca    180

acctgtaggg cctgcggggt ctattgggaa ccaagctgga gtgcagtggc acaatcttgg    240

ctcactgcaa tctccgcctc ctgggttcaa gcgattctcc tgcctcagcc tcccgagttg    300

ttgggattcc aggcatgcat gaccaggctc agctaatttt tgtttttttg gtagagacgg    360

ggtttcacca tattggccag gctggtctcc aactcctaat ctcaggtgat ctacccacct    420

tggcctccca aattgctggg attacaggcg tgaaccactg ctcccttccc tgtcctt       477


<210> SEQ ID NO 18
<211> LENGTH: 66
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 18
ggaagcggag ctactaactt cagcctgctg aagcaggctg gagacgtgga ggagaaccct 60
ggacct 66

<210> SEQ ID NO 19
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
ggaagcggag ctactaactt cagcctgctg aagcaggctg gagacgtgga ggagaaccct 60
ggacct 66

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Gly Ser Gly Glu Gly Arg Gly Ser Leu Leu Thr Cys Gly Asp Val Glu
1 5 10 15

Glu Asn Pro Gly Pro
20

<210> SEQ ID NO 22
<211> LENGTH: 241
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 22
gtcctttcca caagatatat aaacccaaga aatcgaaata ctttcaagtt acggtaagca 60
tatgatagtc cattttaaaa cataatttta aaactgcaaa ctacccaaga aattattact 120
ttctacgtca cgtattttgt actaatatct ttgtgtttac agtcaaatta attctaatta 180
tctctctaac agccttgtat cgtatatgca aatatgaagg aatcatggga aataggccct 240
c 241

<210> SEQ ID NO 23
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
ccggtggttc agttacgggt taattctcga gaattaaccc gtaactgaac catttttg 58

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
ccggcagtta cgggttaatt aatacctgac ccatattaat taacccgtaa ctgctttttg 60

<210> SEQ ID NO 25
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
ccggtgttgc cgcagcatca ctaatctcga gattagtgat gctgcggcaa cattttg 57

<210> SEQ ID NO 26
<211> LENGTH: 681
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26
aacatatcct ggtgtggagt aggggacgct gctctgacag aggctcgggg gcctgagctg 60
gctctgtgag ctggggagga ggcagacagc caggccttgt ctgcaagcag acctggcagc 120
attgggctgg ccgcccccca gggcctcctc ttcatgccca gtgaatgact caccttggca 180
cagacacaat gttcggggtg ggcacagtgc ctgcttcccg ccgcacccca gccccccctca 240 aatgccttcc gagaagccca ttgagcaggg ggcttgcatt gcaccccagc ctgacagcct 300
ggcatcttgg gataaaagca gcacagcccc ctaggggctg cccttgctgt gtggcgccac 360
cggcggtgga gaacaaggct ctattcagcc tgtgcccagg aaaggggatc aggggatgcc 420
caggcatgga cagtgggtgg caggggggga gaggagggct gtctgcttcc cagaagtcca 480
aggacacaaa tgggtgaggg gagagctctc cccatagctg ggctgcggcc caacccccacc 540 ccctcaggct atgccagggg gtgttgccag gggcacccgg gcatcgccag tctagcccac 600
tccttcataa agccctcgca tcccaggagc gagcagagcc agagcaggtt ggagaggaga 660
cgcatcacct ccgctgctcg c 681

<210> SEQ ID NO 27
<211> LENGTH: 1062
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 27
ggagtcgctg cgttgccttc gccccgtgcc ccgctccgcg ccgcctcgcg ccgcccgccc 60
cggctctgac tgaccgcgtt actcccacag gtgagcgggc gggacggccc ttctccctcc 120
gggctgtaat tagcgcttgg tttaatgacg gctcgtttct tttctgtggc tgcgtgaaag 180
ccttaaaggg ctccgggagg gccctttgtgc gggggggagc ggctcggggg gtgcgtgcgt 240
gtgtgtgtgc gtggggagcg ccgcgtgcgg cccgcgctgc ccggcggctg tgagcgctgc 300
gggcgcggcg cggggctttg tgcgctccgc gtgtgcgcga ggggagcgcg ggccgggggc 360
ggtgccccgc ggtgcggggg ggctgcgagg ggaacaaagg ctgcgtgcgg ggtgtgtgcg 420
tgggggggtg agcagggggt gtgggcgcgg cggtcgggct gtaacccccc cctggcaccc 480
ccctccccga gttgctgagc acggcccggc ttcgggtgcg gggctccgtg cggggcgtgg 540
cgcggggctc gccgtgccgg gcggggggtg gcggcaggtg ggggtgccgg gcggggcggg 600
gccgcctcgg gccggggagg gctcggggga ggggcgcggc ggccccggag cgccggcggc 660
tgtcgaggcg cggcgagccg cagccattgc cttttatggt aatcgtgcga gagggcgcag 720
ggacttcctt tgtcccaaat ctggcggagc cgaaatctgg gaggcgccgc cgcacccccct 780 ctagcgggcg cgggcgaagc ggtgcggcgc cggcaggaag gaaatgggcg gggagggcct 840
tcgtgcgtcg ccgcgccgcc gtccccttct ccatctccag cctcggggct gccgcagggg 900
gacggctgcc ttcggggggg acggggcagg gcggggttcg gcttctggcg tgtgaccggc 960
ggctttagag cctctgctaa ccatgttcat gccttcttct ttttcctaca gctcctgggc 1020
aacgtgctgg ttgttgtgct gtctcatcat tttggcaaag at 1062

<210> SEQ ID NO 28
<211> LENGTH: 978
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28
ggccactgtg aggcagaagt gaggagggga tggggaaggg gggccttgtg agcagaaggg 60
gctgaatccc caagaaggag tgcccgagaa gtctcaggga ggggccgaac ctccctgctc 120
cctgggcctc cctacctctt gatggggcac tatccttgcc ccccaacatg atgggaggga 180
ccagaaacag gcccagggcc ccggggatct gatgcccgca tgccttctgc caggagtcca 240
gggtcccctc agcacctccc tactggggaa agcagtgcag gagcagcggg gcccctgtgt 300
ttcattcatg gctgggcttt gtgactgtgg gcagcgagct cacctattct gagcctgtgt 360
ccatataaag gaggagttgg aagcggagaa ggttgatgtc catgagggag attggattct 420
ggggtgaaga aagtgaggga aagagcaggc aggtctgggc gcaaagcaca ggtgactgcc 480
tgccaccagc ttgtgacccc catcaagtta ctttgacttg cacagctgtg aagcggtggt 540
cataataaaa ttcatttcaa aaggtggtta cctgggatca gaggaatccc caggggcatg 600
gcgcttcact gagctgacag gacatgcatg tgtgccttca agtgcaggag gacatgtgcg 660
tgtgtgtgtg tgtgtgtgca acagtgagtg tatgcttgtg gatgcgcctg tgtgagcaga 720
agcaggtgca ccaaccctga taaggcacct tagtaatgag ttaaggcaaa agcccacatc 780

```
tgctcatcct ccagacaagt cctctgtcta aggcccccca acccttaatc ctcctgctgc    840

tctactggtc ctgggtgggg gtggtctctg tgacagctgc ctcaagggag actgaggcag    900

gtattcaagt gtcctcagaa gagcctggac ccaggaatgt gtccccccac tccaggctcc    960

aggatgaaac caacctga                                                  978


<210> SEQ ID NO 29
<211> LENGTH: 581
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

gagcatctta ccgccattta tacccatatt tgttctgttt ttcttgattt gggtatacat     60

ttaaatgtta ataaaacaaa atggtggggc aatcatttac atttttaggg atatgtaatt    120

actagttcag gtgtattgcc acaagacaaa catgttaaga aactttcccg ttatttacgc    180

tctgttcctg ttaatcaacc tctggattac aaaatttgtg aaagattgac tgatattctt    240

aactatgttg ctccttttac gctgtgtgga tatgctgctt tatagcctct gtatctagct    300

attgcttccc gtacggcttt cgttttctcc tccttgtata aatcctggtt gctgtctctt    360

ttagaggagt tgtggcccgt tgtccgtcaa cgtggcgtgg tgtgctctgt gtttgctgac    420

gcaaccccca ctggctgggg cattgccacc acctgtcaac tcctttctgg gactttcgct    480

ttccccctcc cgatcgccac ggcagaactc atcgccgcct gccttgcccg ctgctggaca    540

ggggctaggt tgctgggcac tgataattcc gtggtgttgt c                        581


<210> SEQ ID NO 30
<211> LENGTH: 208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

ctgtgccttc tagttgccag ccatctgttg tttgcccctc ccccgtgcct tccttgaccc     60

tggaaggtgc cactcccact gtcctttcct aataaaatga ggaaattgca tcgcattgtc    120

tgagtaggtg tcattctatt ctggggggtg gggtggggca ggacagcaag ggggaggatt    180

gggaagagaa tagcaggcat gctgggga                                       208
```

NEUROD1 AND DLX2 VECTOR

CROSS-REFERENCE TO RELATED APPLICATION

This application is a U.S. patent application which claims the benefit and priority to U.S. Provisional Application Nos. 63/084,945 filed Sep. 29, 2020, and 63/247,442 filed Sep. 23, 2021, each of which are incorporated by reference in their entireties herein.

INCORPORATION BY REFERENCE

A sequence listing contained in the file named P34838US2_SL.txt which is 28,311 bytes (measured in MS-Windows®) and created on Sep. 27, 2021, is filed electronically herewith and incorporated by reference in its entirety.

FIELD OF THE INVENTION

The present disclosure includes methods and compositions using an AAV vector comprising a nucleic acid sequence encoding human NeuroD1 and Dlx2 to convert glial cells to neurons.

BACKGROUND OF THE INVENTION

Neurons are often killed or damaged and unable to regenerate in subjects with a neurological condition or following an injury to the central nervous system (CNS) or peripheral nervous system (PNS).

Glial cells become reactive following an injury to the CNS or PNS such as a brain injury or neurological condition.

Currently there are no methods available to regenerate functional new neurons in human subjects having a neurological condition using adeno-associated viruses (AAVs).

SUMMARY OF THE INVENTION

In one aspect, this disclosure provides, and includes, an adeno-associated virus (AAV) vector comprising a human neurogenic differentiation 1 (hNeuroD1) sequence comprising the nucleic acid sequence of SEQ ID NO: 6 and a human distal-less homeobox 2 (hDlx2) sequence comprising the nucleic acid sequence of SEQ ID NO: 13, where the hNeuroD1 sequence and the hDlx2 sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, where the hNeuroD1 sequence and the hDlx2 sequence are operably linked to regulatory elements comprising: (a) glial fibrillary acidic protein (GFAP) promoter comprising a nucleic acid sequence selected from the group consisting of SEQ ID NOs: 4, 12, and 26; (b) an enhancer from a human elongation factor-1 alpha (EF1-α) promoter comprising the nucleic acid sequence of SEQ ID NO: 2 or a cytomegalovirus (CMV) enhancer comprising the nucleic acid sequence of SEQ ID NO: 11; (c) chimeric intron comprising the nucleic acid sequence selected from the group consisting of SEQ ID NOs: 5 and 27; (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

In one aspect, this disclosure provides, and includes, an adeno-associated virus (AAV) vector comprising a nucleic acid sequence encoding a human neurogenic differentiation 1 (hNeuroD1) protein comprising the amino acid coding sequence of SEQ ID NO: 10 and a nucleic acid coding sequence encoding a human distal-less homeobox 2 (hDlx2) protein comprising the amino acid sequence of SEQ ID NO: 14, where the hNeuroD1 coding sequence and the hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, where the hNeuroD1 coding sequence and the hDlx2 coding sequence is operably linked to regulatory elements comprising: (a) a glial fibrillary acidic protein (GFAP) promoter comprising a nucleic acid sequence selected from the group consisting of SEQ ID NOs: 4, 12, and 26; (b) an enhancer from a human elongation factor-1 alpha (EF1-α) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence selected from the group consisting of SEQ ID NOs: 5 and 27; (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

In an aspect, this disclosure provides, and includes, an adeno-associated virus (AAV) vector comprising a neurogenic differentiation 1 (NeuroD1) nucleic acid coding sequence encoding a NeuroD1 protein and a distal-less homeobox 2 (Dlx2) nucleic acid coding sequence encoding a Dlx2 protein, where the NeuroD1 coding sequence and the Dlx2 coding sequence are separated by a linker sequence, where the NeuroD1 coding sequence and the Dlx2 coding sequence are operably linked to regulatory elements comprising: (a) a glial fibrillary acidic protein (GFAP) promoter; (b) an enhancer; (c) a chimeric intron; (d) a woodchuck hepatitis virus posttranscriptional regulatory element (WPRE); and (e) a polyadenylation signal sequence.

In an aspect, this disclosure provides, and includes, a composition comprising an adeno-associated virus (AAV) vector for converting glial cells to functional neurons in a human, where the AAV vector comprises a human neurogenic differentiation 1 (hNeuroD1) sequence having a nucleic acid sequence of SEQ ID NO: 6 and a human distal-less homeobox 2 (hDlx2) sequence having a nucleic acid sequence of SEQ ID NO: 13, where the hNeuroD1 sequence and the hDlx2 sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, where the hNeuroD1 sequence and hDlx2 sequence are operably linked to regulatory elements comprising: (a) a human glial fibrillary acidic protein (GFAP) promoter comprising a nucleic acid sequence selected from the group consisting of SEQ ID NOs: 4, 12, and 26; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence selected from the group consisting of SEQ ID NOs: 5 and 27; (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

In an aspect, this disclosure provides, and includes, a composition comprising an adeno-associated-virus (AAV) vector for converting glial cells to functional neurons in a human, where the AAV vector comprises a nucleic acid coding sequence encoding a human neurogenic differentiation 1 (hNeuroD1) protein comprising the amino acid sequence of SEQ ID NO: 10 and a nucleic acid coding sequence encoding a human distal-less homeobox 2 (hDlx2) protein comprising the amino acid sequence of SEQ ID NO: 14, where the hNeuroD1 coding sequence and the hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, where the hNeuroD1 coding sequence and the hDlx2 coding sequence are operably linked to regulatory elements comprising: (a) a human glial fibrillary acidic protein (GFAP) promoter comprising a nucleic acid sequence selected from the group consisting of SEQ ID NOs: 4, 12, and 26; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence selected from the group consisting of SEQ ID NOs: 5 and 27; (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

In an aspect, this disclosure provides, and includes, a composition comprising an adeno-associated virus (AAV) vector for the treatment of a subject in need thereof, where the AAV vector comprises a neurogenic differentiation 1 (NeuroD1) sequence and a distal-less homeobox 2 (Dlx2) sequence, where the NeuroD1 sequence and the Dlx2 sequence are separated by a linker sequence, where the NeuroD1 sequence and Dlx2 sequence are operably linked to expression control elements comprising: (a) a glial fibrillary acidic protein (GFAP) promoter; (b) an enhancer; (c) a chimeric intron; (d) a woodchuck hepatitis virus posttranscriptional regulatory element (WPRE); and (e) a polyadenylation signal.

In an aspect, this disclosure provides, and includes, a method of converting reactive astrocytes to functional neurons in a brain of a living human comprising: injecting an adeno-associated virus (AAV) into a subject in need thereof, where said AAV comprises a DNA vector construct comprising a human neurogenic differentiation 1 (hNeuroD1) sequence comprising the nucleic acid sequence of SEQ ID NO: 6 and a human distal-less homeobox 2 (hDlx2) sequence comprising the nucleic acid sequence of SEQ ID NO: 13, where said hNeuroD1 sequence and said hDlx2 sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, where said hNeuroD1 sequence and said hDlx2 sequence are operably linked to regulatory elements comprising: (a) a human glial fibrillary acidic protein (GFAP) promoter comprising a nucleic acid sequence selected from the group consisting of SEQ ID NOs: 4, 12, and 26; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence selected from the group consisting of SEQ ID NOs: 5 and 27; (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

In an aspect, this disclosure provides, and includes, a method of converting reactive astrocytes to functional neurons in a brain of a living human comprising: injecting an adeno-associated virus (AAV) into a subject in need thereof, where said AAV comprises a DNA vector construct comprising a nucleic acid coding sequence encoding a human neurogenic differentiation 1 (hNeuroD1) protein comprising the amino acid sequence of SEQ ID NO: 10 and a nucleic acid coding sequence encoding a human distal-less homeobox 2 (hDlx2) protein comprising the amino acid sequence of SEQ ID NO: 14, where said hNeuroD1 coding sequence and said hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, where said hNeuroD1 coding sequence and hDlx2 coding sequence are operably linked to expression control elements comprising: (a) a human glial fibrillary acidic protein (GFAP) promoter comprising a nucleic acid sequence selected from the group consisting of SEQ ID NOs: 4, 12, and 26; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence selected from the group consisting of SEQ ID NOs: 5 and 27; (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

In an aspect, this disclosure provides, and includes, a method of converting glial cells to neurons in a subject in need thereof comprising: delivering an adeno-associated virus (AAV) to said subject in need thereof, where said AAV comprises a DNA vector construct comprising a neurogenic differentiation 1 (NeuroD1) sequence and a distal-less homeobox 2 (Dlx2) sequence, where said NeuroD1 sequence and Dlx2 sequence are separated by a linker sequence, where said NeuroD1 sequence and Dlx2 sequence are operably linked to expression control elements comprising: (a) a glial fibrillary acid protein (GFAP) promoter; (b) an enhancer; (c) a chimeric intron; (d) a woodchuck hepatitis virus posttranscriptional regulatory element (WPRE); and (e) and a polyadenylation signal sequence, where said vector is capable of converting at least one glial cell to a neuron in said subject in need thereof.

In an aspect, this disclosure provides, and includes, a method of treating a neurological condition in a subject in need thereof comprising: delivering an adeno-associated virus (AAV) to said subject, where said AAV comprises a DNA vector construct comprising a neurogenic differentiation 1 (NeuroD1) sequence and distal-less homeobox 2 (Dlx2) sequence, where said NeuroD1 sequence and Dlx2 sequence are separated by a linker sequence, where said NeuroD1 sequence and said Dlx2 sequence are operably linked to expression control elements comprising: (a) a glial fibrillary acid protein (GFAP) promoter; (b) an enhancer; (c) a chimeric intron; (d) a woodchuck hepatitis virus posttranscriptional regulatory element (WPRE); and (e) a polyadenylation signal to said subject in need thereof.

In an aspect, this disclosure provides, and includes, a composition comprising (i) an adeno-associated virus (AAV) vector comprising a human neurogenic differentiation 1 (hNeuroD1) sequence comprising the nucleic acid sequence of SEQ ID NO: 6, and (ii) an adeno-associated virus (AAV) vector comprising a human distal-less homeobox 2 (hDlx2) sequence comprising the nucleic acid sequence of SEQ ID NO: 13; where the hNeuroD1 sequence is operably linked to regulatory elements comprising: (a) a glial fibrillary acidic protein (GFAP) promoter comprising the nucleic acid sequence of SEQ ID NO: 26; (b) an enhancer from a human elongation factor-1 alpha (EF1-α) promoter comprising the nucleic acid sequence of SEQ ID NO: 2; (c) a chimeric intron comprising the nucleic acid sequence of SEQ ID NO: 5 or SEQ ID NO: 27; (d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

In an aspect, this disclosure provides, and includes, a composition comprising (i) an adeno-associated virus (AAV) vector comprising a human neurogenic differentiation 1 (hNeuroD1) sequence comprising the nucleic acid sequence of SEQ ID NO: 6, and (ii) an adeno-associated virus (AAV) vector comprising a human distal-less homeobox 2 (hDlx2) sequence comprising the nucleic acid sequence of SEQ ID NO: 13; where the hNeuroD1 sequence is operably linked to regulatory elements comprising: (a) a glial fibrillary acidic protein (GFAP) promoter comprising the nucleic acid sequence of SEQ ID NO: 26; (b) a cytomegalovirus (CMV) enhancer comprising the nucleic acid sequence of SEQ ID NO: 11; (c) a chimeric intron comprising the nucleic acid sequence of SEQ ID NO: 5 or SEQ ID NO: 27; (d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

In an aspect, this disclosure provides, and includes, a composition comprising (i) an adeno-associated virus (AAV) vector comprising a nucleic acid sequence encoding a human neurogenic differentiation 1 (hNeuroD1) protein comprising the amino acid coding sequence of SEQ ID NO: 10, and (ii) an adeno-associated virus (AAV) vector comprising a nucleic acid coding sequence encoding a human distal-less homeobox 2 (hDlx2) protein comprising the amino acid sequence of SEQ ID NO: 14; where the nucleic acid sequence encoding an hNeuroD1 protein is operably linked to regulatory elements comprising: (a) a glial fibrillary acidic protein (GFAP) promoter comprising the nucleic acid sequence of SEQ ID NO: 26; (b) an enhancer from a human elongation factor-1 alpha (EF1-α) promoter comprising the nucleic acid sequence of SEQ ID NO: 2; (c) a chimeric intron comprising the nucleic acid sequence of SEQ ID NO: 5 or SEQ ID NO: 27; (d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

In an aspect, this disclosure provides, and includes, a composition comprising (i) an adeno-associated virus (AAV) vector comprising a nucleic acid sequence encoding a human neurogenic differentiation 1 (hNeuroD1) protein comprising the amino acid coding sequence of SEQ ID NO: 10, and (ii) an adeno-associated virus (AAV) vector comprising a nucleic acid coding sequence encoding a human distal-less homeobox 2 (hDlx2) protein comprising the amino acid sequence of SEQ ID NO: 14; where the nucleic acid sequence encoding an hNeuroD1 protein is operably linked to regulatory elements comprising: (a) a glial fibrillary acidic protein (GFAP) promoter comprising the nucleic acid sequence of SEQ ID NO: 26; (b) a cytomegalovirus (CMV) enhancer comprising the nucleic acid sequence of SEQ ID NO: 11; (c) a chimeric intron comprising the nucleic acid sequence of SEQ ID NO: 5 or SEQ ID NO: 27; (d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

In an aspect, this disclosure provides, and includes, an adeno-associated virus (AAV) vector comprising a human neurogenic differentiation 1 (hNeuroD1) sequence comprising the nucleic acid sequence of SEQ ID NO: 6 and a human distal-less homeobox 2 (hDlx2) sequence comprising the nucleic acid sequence of SEQ ID NO: 13, where said hNeuroD1 sequence and said hDlx2 sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, where said hNeuroD1 sequence and said hDlx2 sequence are operably linked to regulatory elements comprising: (a) a glial fibrillary acidic protein (GFAP) promoter comprising the nucleic acid sequence of SEQ ID NO: 26; (b) an enhancer from a human elongation factor-1 alpha (EF1-α) promoter comprising the nucleic acid sequence of SEQ ID NO: 2; (c) a chimeric intron comprising the nucleic acid sequence of SEQ ID NO: 5 or SEQ ID NO: 27; (d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

In an aspect, this disclosure provides, and includes, an adeno-associated virus (AAV) vector comprising a human neurogenic differentiation 1 (hNeuroD1) sequence comprising the nucleic acid sequence of SEQ ID NO: 6 and a human distal-less homeobox 2 (hDlx2) sequence comprising the nucleic acid sequence of SEQ ID NO: 13, where said hNeuroD1 sequence and said hDlx2 sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, where said hNeuroD1 sequence and said hDlx2 sequence are operably linked to regulatory elements comprising: (a) a glial fibrillary acidic protein (GFAP) promoter comprising the nucleic acid sequence of SEQ ID NO: 26; (b) a cytomegalovirus (CMV) enhancer comprising the nucleic acid sequence of SEQ ID NO: 11; (c) a chimeric intron comprising the nucleic acid sequence of SEQ ID NO: 5 or SEQ ID NO: 27; (d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

In an aspect, this disclosure provides, and includes, an adeno-associated virus (AAV) vector comprising a nucleic acid sequence encoding a human neurogenic differentiation 1 (hNeuroD1) protein comprising the amino acid coding sequence of SEQ ID NO: 10 and a nucleic acid coding sequence encoding a human distal-less homeobox 2 (hDlx2) protein comprising the amino acid sequence of SEQ ID NO: 14, where said hNeuroD1 coding sequence and said hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, where said hNeuroD1 coding sequence and said hDlx2 coding sequence is operably linked to regulatory elements comprising: (a) a glial fibrillary acidic protein (GFAP) promoter comprising the nucleic acid sequence of SEQ ID NO: 26; (b) an enhancer from a human elongation factor-1 alpha (EF1-α) promoter comprising the nucleic acid sequence of SEQ ID NO: 2; (c) a chimeric intron comprising the nucleic acid sequence of SEQ ID NO: 5 or SEQ ID NO: 27; (d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

In an aspect, this disclosure provides, and includes, an adeno-associated virus (AAV) vector comprising a nucleic acid sequence encoding a human neurogenic differentiation 1 (hNeuroD1) protein comprising the amino acid coding sequence of SEQ ID NO: 10 and a nucleic acid coding sequence encoding a human distal-less homeobox 2 (hDlx2) protein comprising the amino acid sequence of SEQ ID NO: 14, where said hNeuroD1 coding sequence and said hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, where said hNeuroD1 coding sequence and said hDlx2 coding sequence is operably linked to regulatory elements comprising: (a) a glial fibrillary acidic protein (GFAP) promoter comprising the nucleic acid sequence of SEQ ID NO: 26; (b) a cytomegalovirus (CMV) enhancer comprising the nucleic acid sequence of SEQ ID NO: 11; (c) a chimeric intron comprising the nucleic acid sequence of SEQ ID NO: 5 or SEQ ID NO: 27; (d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

In an aspect, this disclosures provides, and includes, an adeno-associated virus (AAV) vector comprising a human neurogenic differentiation 1 (hNeuroD1) sequence comprising the nucleic acid sequence of SEQ ID NO: 6 and a human distal-less homeobox 2 (hDlx2) sequence comprising the nucleic acid sequence of SEQ ID NO: 13, where said hNeuroD1 sequence and said hDlx2 sequence are separated by a P2A linker comprising the nucleic acid sequence selected from the group consisting of SEQ ID NO: 15 and 18 or an internal ribosomal entry site of the encephalomyocarditis virus (IRES) sequence comprising SEQ ID NO: 3, where said hNeuroD1 sequence and said hDlx2 sequence are operably linked to regulatory elements comprising: (a) a glial fibrillary acidic protein (GFAP) promoter comprising the nucleic acid sequence of SEQ ID NO: 26; (b) a cytomegalovirus (CMV) enhancer comprising the nucleic acid sequence of SEQ ID NO: 11; (c) a chimeric intron comprising the nucleic acid sequence of SEQ ID NO: 5 or SEQ ID NO: 27; and (d) a bGH polyadenylation sequence comprising the nucleic acid sequence of SEQ ID NO: 30.

In an aspect, this disclosures provides, and includes, an adeno-associated virus (AAV) vector comprising a nucleic acid sequence encoding a human neurogenic differentiation 1 (hNeuroD1) protein comprising the amino acid coding sequence of SEQ ID NO: 10 and a nucleic acid coding sequence encoding a human distal-less homeobox 2 (hDlx2) protein comprising the amino acid sequence of SEQ ID NO: 14, where said hNeuroD1 coding sequence and said hDlx2 coding sequence are separated by a P2A linker comprising the nucleic acid sequence selected from the group consisting of SEQ ID NO: 15 and 18 or an internal ribosomal entry site of the encephalomyocarditis virus (IRES) sequence comprising SEQ ID NO: 3, where said hNeuroD1 coding sequence and said hDlx2 coding sequence is operably linked to regulatory elements comprising: (a) a glial fibrillary acidic protein (GFAP) promoter comprising the nucleic acid sequence of SEQ ID NO: 26; (b) a cytomegalovirus (CMV) enhancer comprising the nucleic acid sequence of SEQ ID NO: 11; (c) a chimeric intron comprising the nucleic acid sequence of SEQ ID NO: 5 or SEQ ID NO: 27; and (d) a bGH polyadenylation sequence comprising the nucleic acid sequence of SEQ ID NO: 30.

BRIEF DESCRIPTION OF THE DRAWINGS

FIG. 13A presents the percentage transduction rate of AAV9-P12 (pGfaABC1D:GFP) and AAV5-P7 (pEF-1α:GFP) at MOIs of $5\times10^{5}$ vg/cell, $2\times10^{5}$ vg/cell, and $5\times10^{4}$ vg/cell. FIG. 13B presents the percentage transduction rate of AAV9-P12 (pGfaABC1D:GFP) in cells seeded at a series of densities of $2\times10^{4}$ cell/well, $1.5\times10^{4}$ cell/well, $1\times10^{4}$ cell/well, and $5\times10^{3}$ cell/well and infected with virus at a series of amounts of 2 μl, 1 μl, 0.5 μl, 0.25 μl, 0.125 μl of $1\times10^{13}$ vg/ml virus in 100 μl of medium.

FIG. 17 depicts RCAs immunostained with anti-NeuN and anti-MAP2 antibodies and DAPI (nuclear stain) 3 weeks post transduction with AAV9-P134 (CE-pGfa681-CRGI-hND1-oPRE-bGHpA) at $2\times10^{10}$ vg/ml. Transduction with the ND1-containing vector generates neurons (NeuN//MAP2+) from the astrocyte culture.

FIG. 19 depicts RCAs immunostained with an anti-ND1 antibody and DAPI (nuclear stain) 6 days post transduction with AAV9-P138 (EE-pGfa681-CRGI-hND1-oPRE-bGHpA) at $2\times10^{10}$ vg/ml).

FIG. 20 depicts RCAs immunostained with anti-NeuN and anti-MAP2 antibodies and DAPI (nuclear stain) 3 weeks post transduction with AAV9-P138 (EE-pGfa681-CRGI-hND1-oPRE-bGHpA) at $2\times10^{10}$ vg/ml). Transduction with the ND1-containing vector generates neurons (NeuN//MAP2+) from the astrocyte culture.

FIG. 28 depicts RCAs immunostained with an anti-NeuN antibody and DAPI (nuclear stain) 3 weeks post transduction with AAV9-P35 (EE-pGfa681-CI-hND1-WPRE-SV40 pA) at $2\times10^{10}$ vg/ml. Transduction with the ND1-containing vector generates neurons (NeuN+) from the astrocyte culture.

FIG. 29 depicts RCAs immunostained with an anti-ND1 antibody and DAPI (nuclear stain) 24 hours post transfection with NXL-P107 (CE-pGfa681-CI-hND1-bGHpA).

FIG. 32 depicts the brain cortex tissue of mice infected with AAV9-P12 (P12 control group), AAV9-P12+AAV9-P134 (P134 group), and AAV9-P12+AAV9-P138 (P138 group) at 10 days post infection (dpi).

FIG. 33 depicts the brain cortex tissue of mice infected with AAV9-P12+AAV9-P134 (P134 group), and AAV9-P12+AAV9-P138 (P138 group) at 30 days post infection (dpi).

FIG. 39A depicts the cells that are immunostained with antibodies against NeuroD1, GFAP, NeuN, and with DAPI (nuclear stain). GFP fluorescence indicates the presence of cells infected with the control virus. FIG. 39B is a quantification of the glial cell-to-neuron conversion rate at 30 dpi.

24 hours post transfection with NXL-P20 (CE-pGfa681-CI-hND1-P2A-hDlx2-WPRE-SV40 pA).

Figure 51:
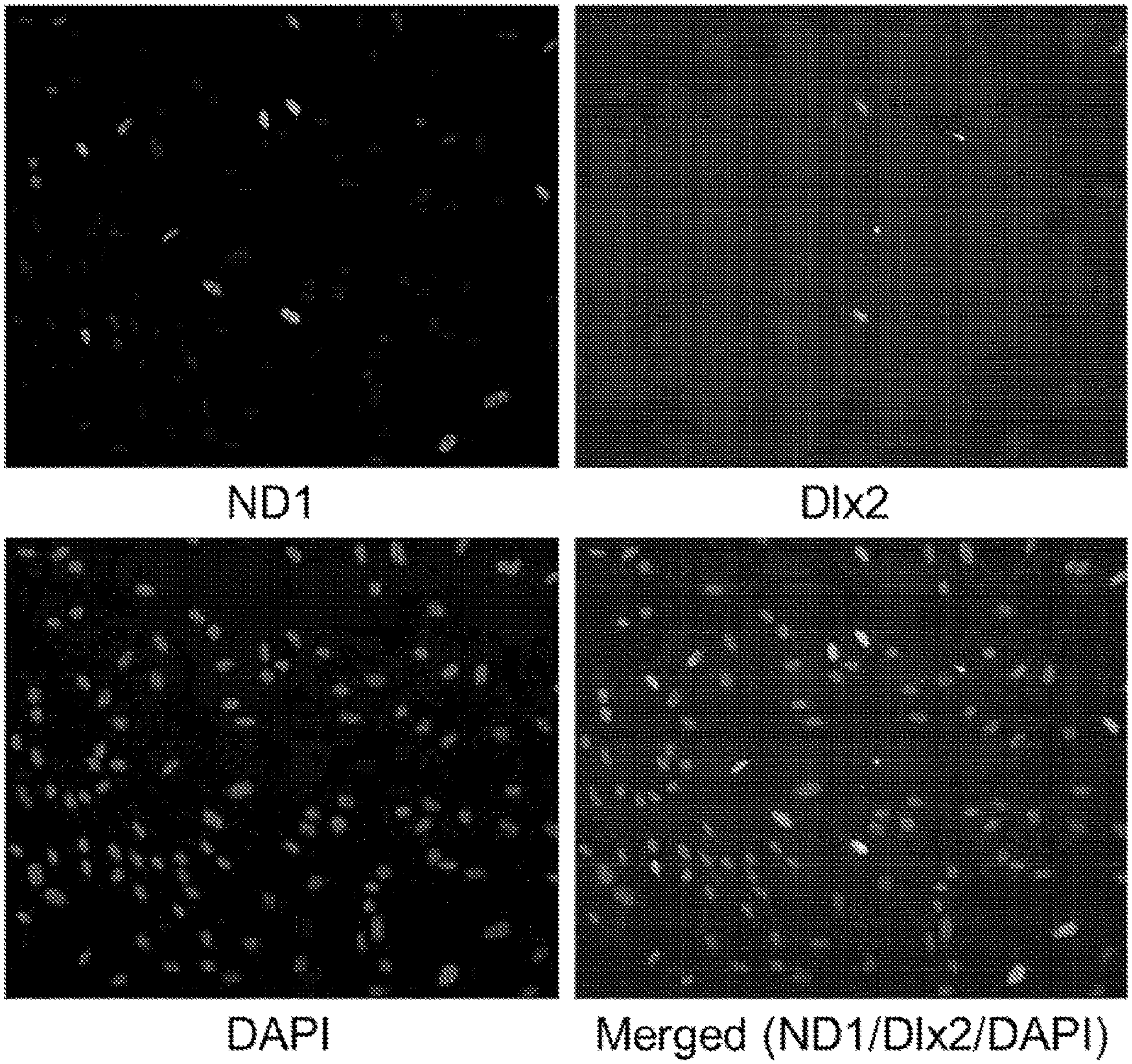

FIG. 51 depicts RCAs immunostained with an anti-ND1 antibody, an anti-Dlx2 antibody, and DAPI (nuclear stain) 6 days post transduction with AAV9-P20 (CE-pGfa681-CI-hDND1-p2A-hDlx2-WPRE-SV40 pA) at $2\times10^{10}$ vg/ml.

Figure 52:
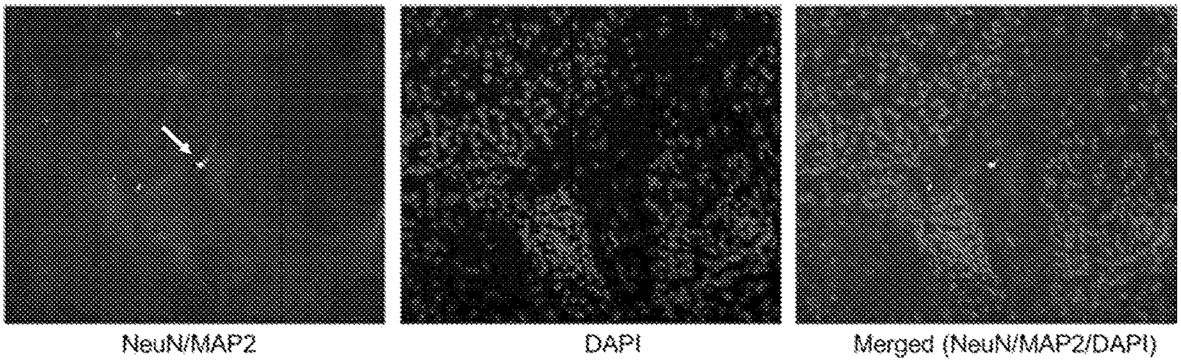

FIG. 52 depicts RCAs immunostained with an anti-NeuN antibody, an anti-MAP2 antibody, and DAPI (nuclear stain) 3 weeks post transduction with AAV9-P20 (CE-pGfa681-CI-hND1-P2A-hDlx2-bSV40 pA) at $2\times10^{10}$ vg/ml.

Figure 53:
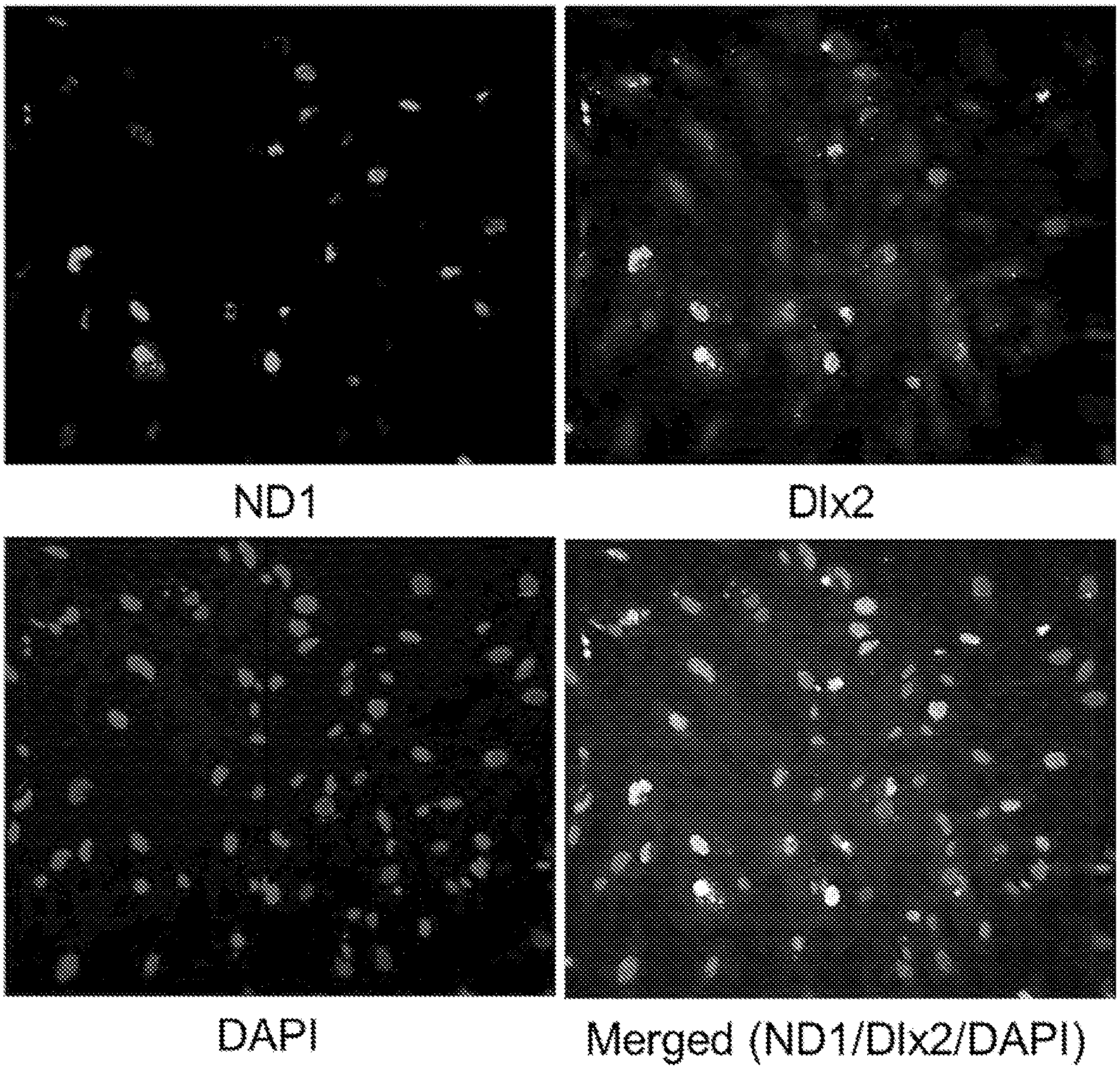

FIG. 53 depicts RCAs immunostained with an anti-ND1 antibody, an anti-Dlx2 antibody, and DAPI (nuclear stain) 24 hours post transfection with NXL-P31 (EE-pGfa681-CI-hND1-P2A-hDlx2-WPRE-SV40 pA).

Figure 54:
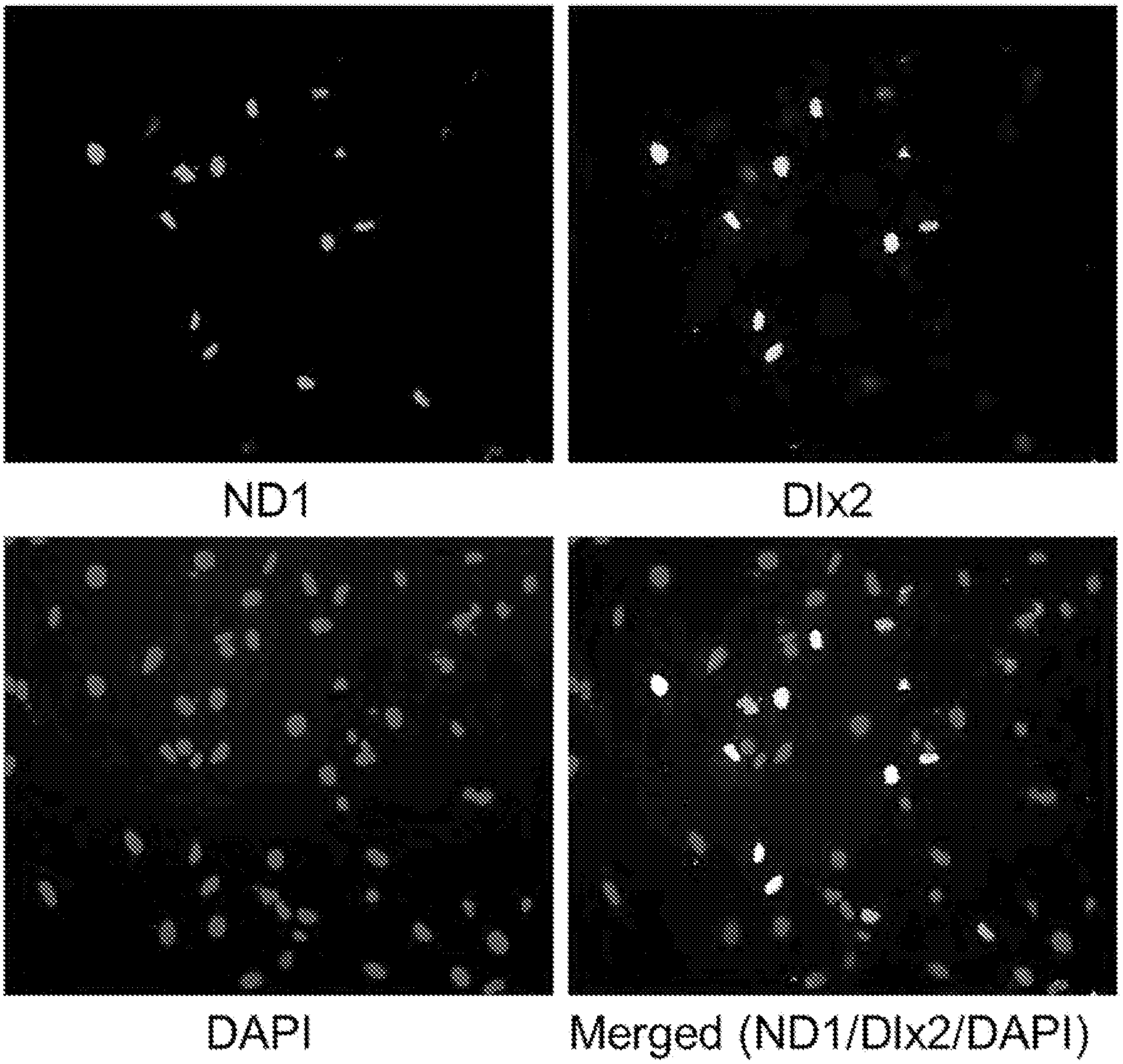

FIG. 54 depicts RCAs immunostained with an anti-ND1 antibody, an anti-Dlx2 antibody, and DAPI (nuclear stain) 24 hours post transfection with NXL-P123 (EE-pGfa681-CI-hDlx2-p2A-hND1-bGHpA).

Figure 55:
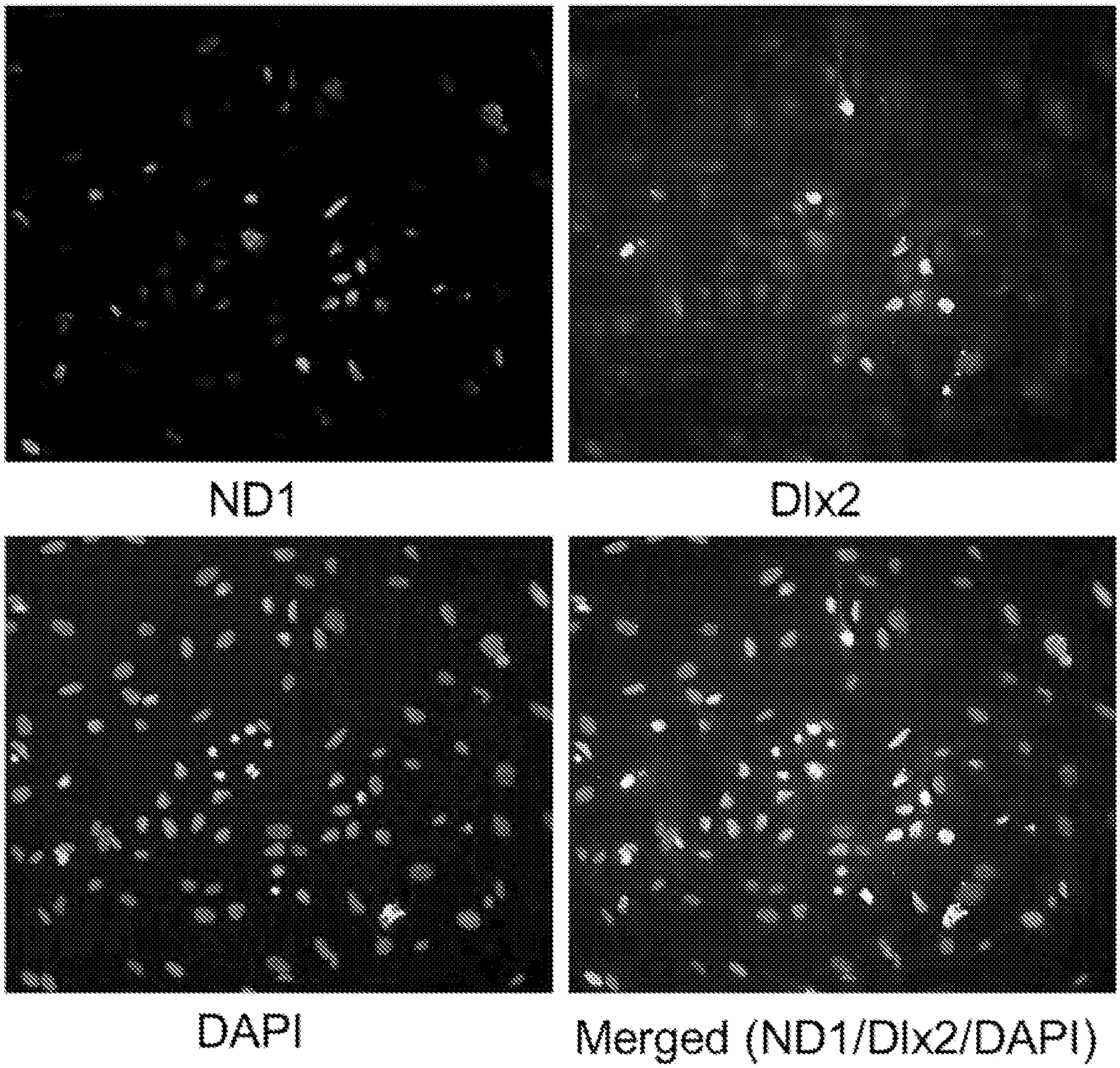

FIG. 55 depicts RCAs immunostained with an anti-ND1 antibody, an anti-Dlx2 antibody, and DAPI (nuclear stain) 24 hours post transfection with NXL-P113 (EE-pGfa681-CI-hDlx2-IRES-hND1-bGHpA).

Figure 56:
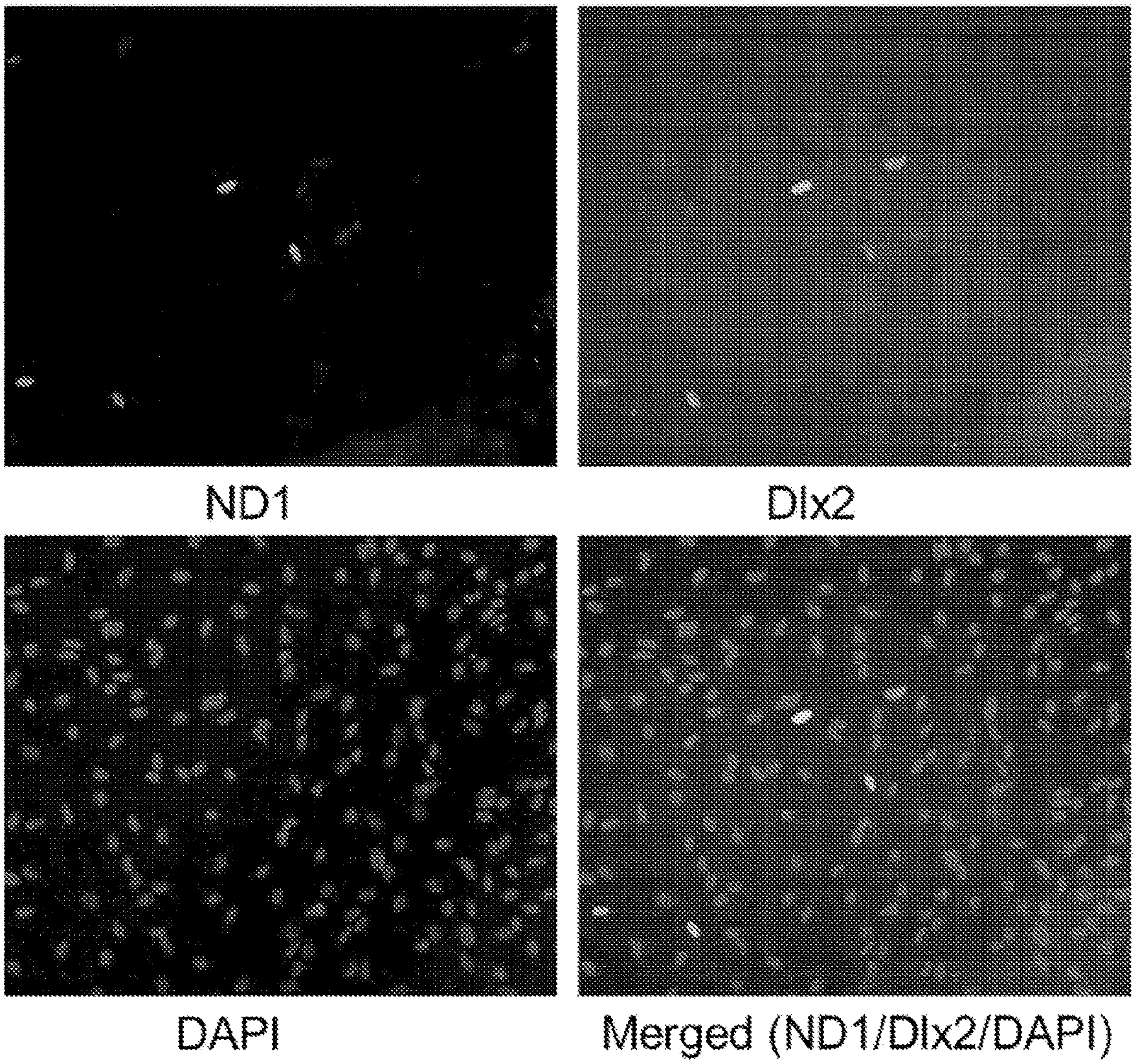

FIG. 56 depicts RCAs immunostained with an anti-ND1 antibody, an anti-Dlx2 antibody, and DAPI (nuclear stain) 24 hours post transfection with NXL-P111 (CE-pGfa681-CI-hDlx2-p2A-hND1-SV40 pA).

Figure 57A:
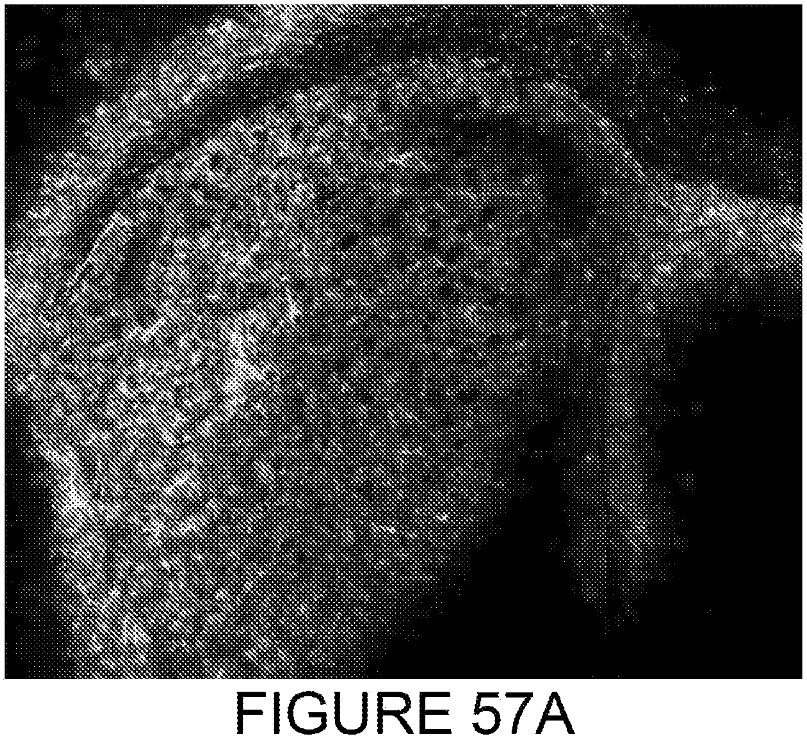
Figure 57B:
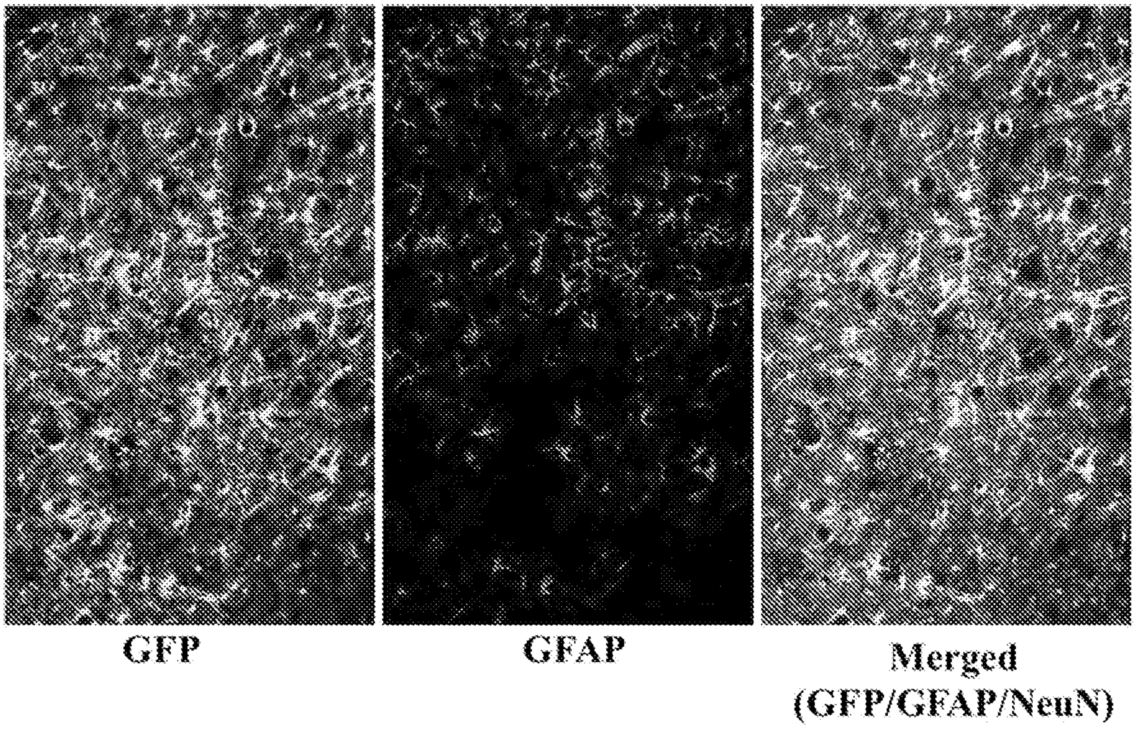

FIGS. 57A and 57B depict the brain striatum tissue of mice infected with AAV9-P12 (virus) at 10 dpi and 30 dpi. FIG. 57A shows wide infection of mouse striatum by AAV-P12 at 10 dpi as demonstrated by the GFP fluorescence. FIG. 57B shows infection of the mouse by AAV9-P12 at 30 dpi. The cells are immunostained with antibodies against GFAP and NeuN.

Figure 58:
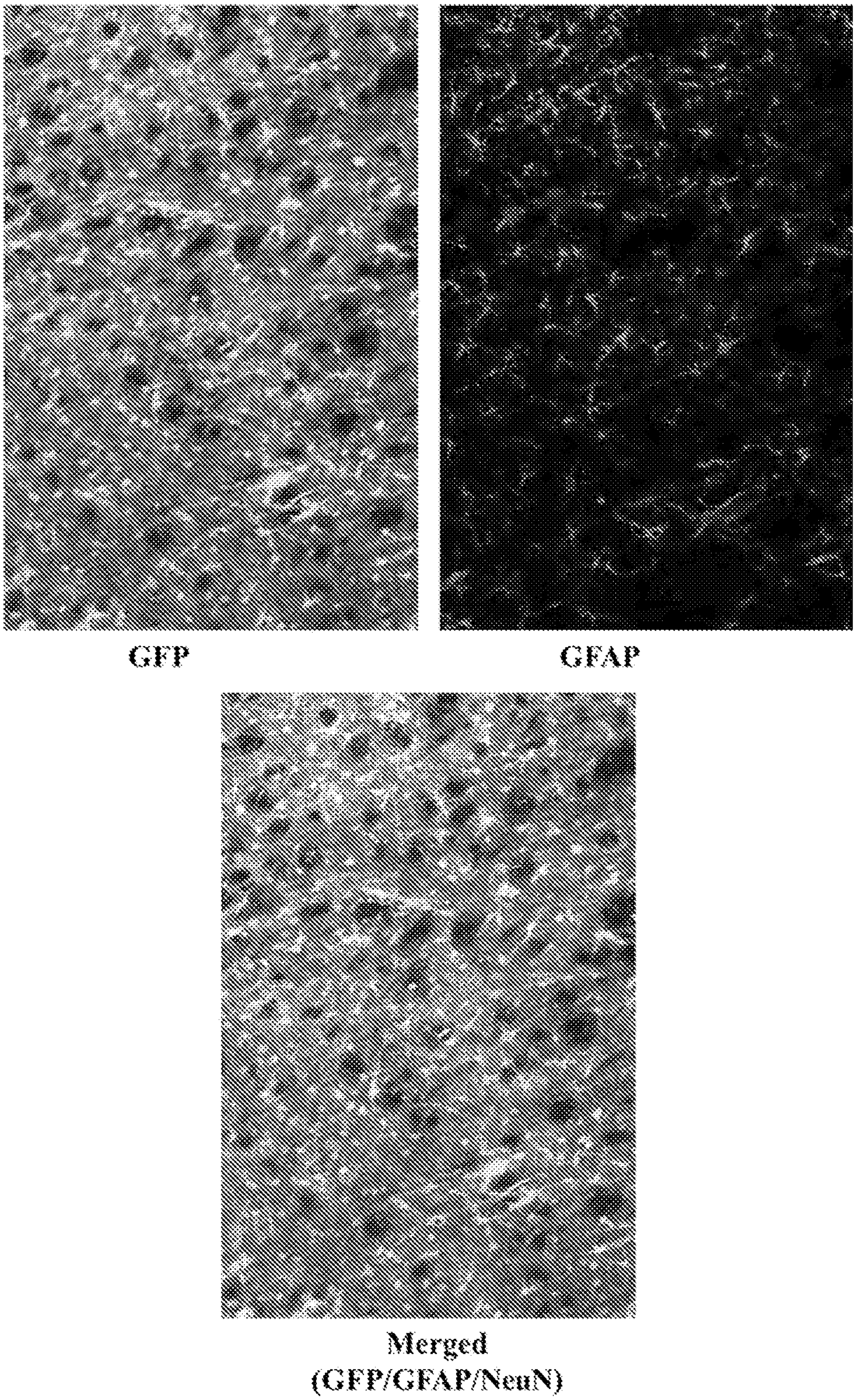

FIG. 58 depicts the brain striatum tissue of mice co-infected with AAV9-P12 and AAV9-P112 (the P112 group) at 10 dpi. GFP fluorescence identifies the AAV9-P112-infected cells. The cells are immunostained with antibodies against GFAP and NeuN.

Figure 59:
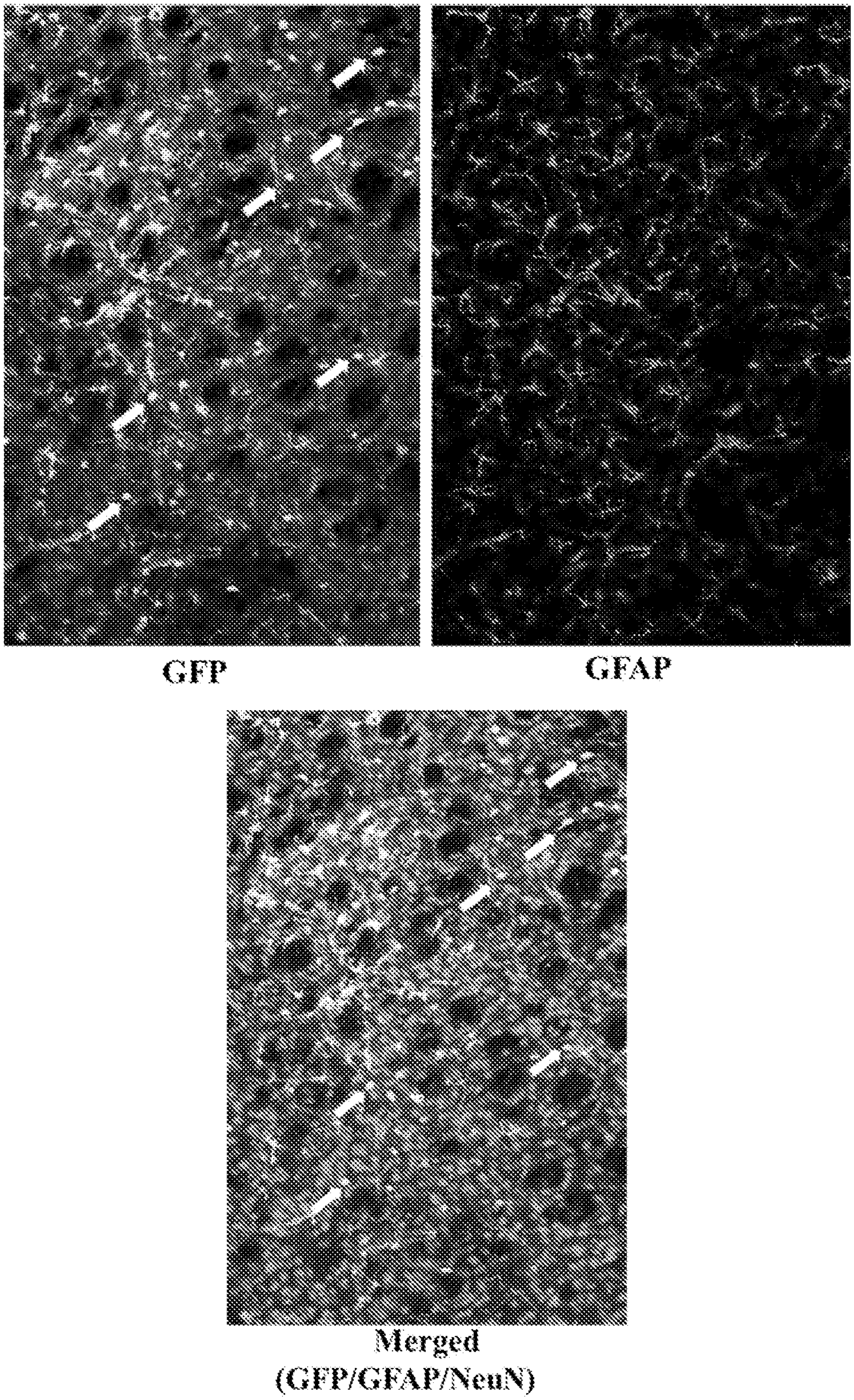

FIG. 59 depicts the brain striatum tissue of mice co-infected with AAV9-P12 and AAV9-P112 (the P112 group) at 30 dpi. GFP fluorescence identifies the AAV9-P112-infected cells. The cells are immunostained with antibodies against GFAP and NeuN. The white arrows indicate cells co-infected with AAV9-P12 and AAV9-P112 which became NeuN-positive neurons.

Figure 60:
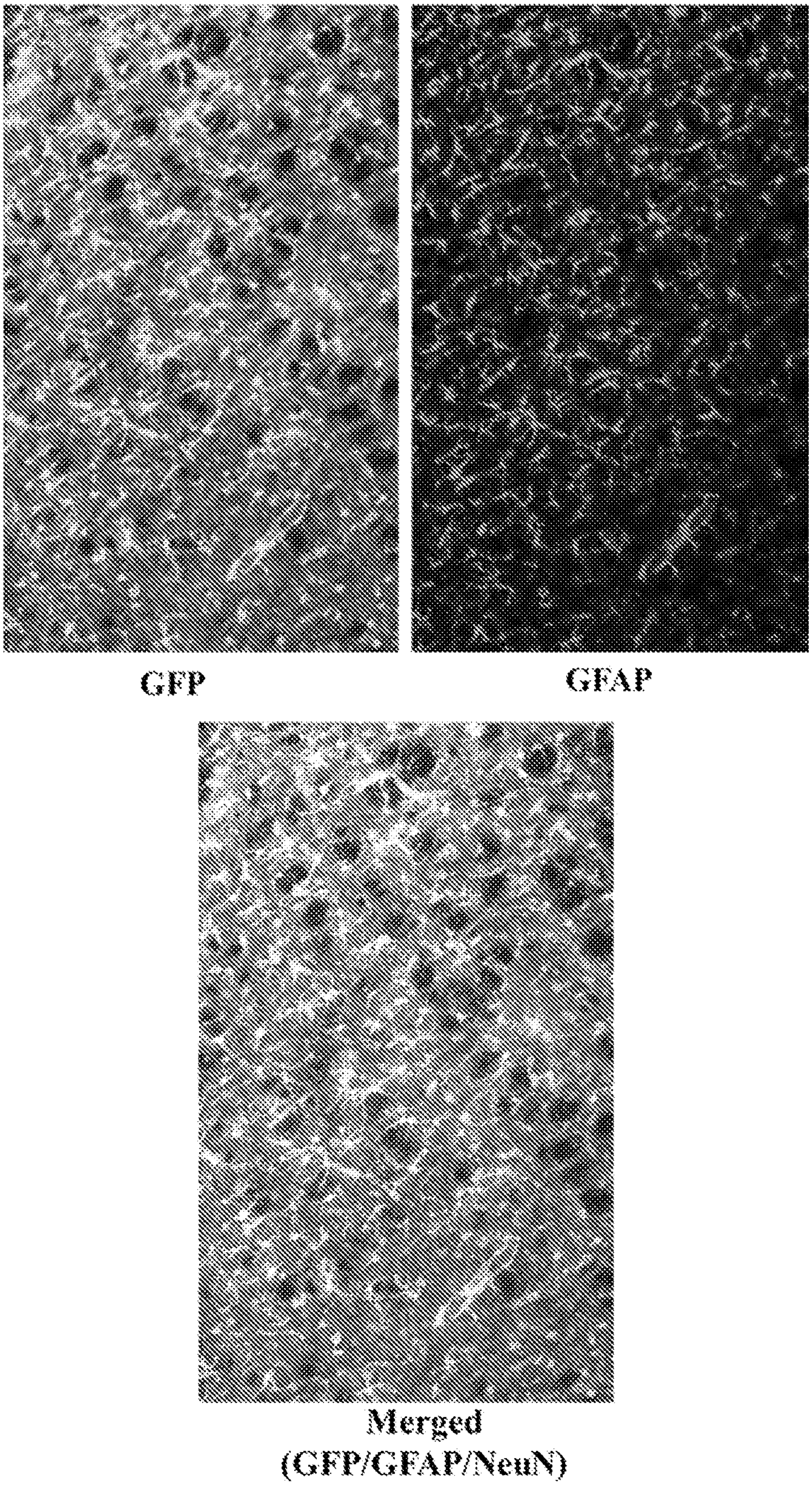

FIG. 60 depicts the brain striatum tissue of mice co-infected with AAV9-P12 and AAV9-P122 (the P122 group) at 10 dpi. GFP fluorescence identifies the AAV9-P112-infected cells. The cells are immunostained with antibodies against GFAP and NeuN.

Figure 61:
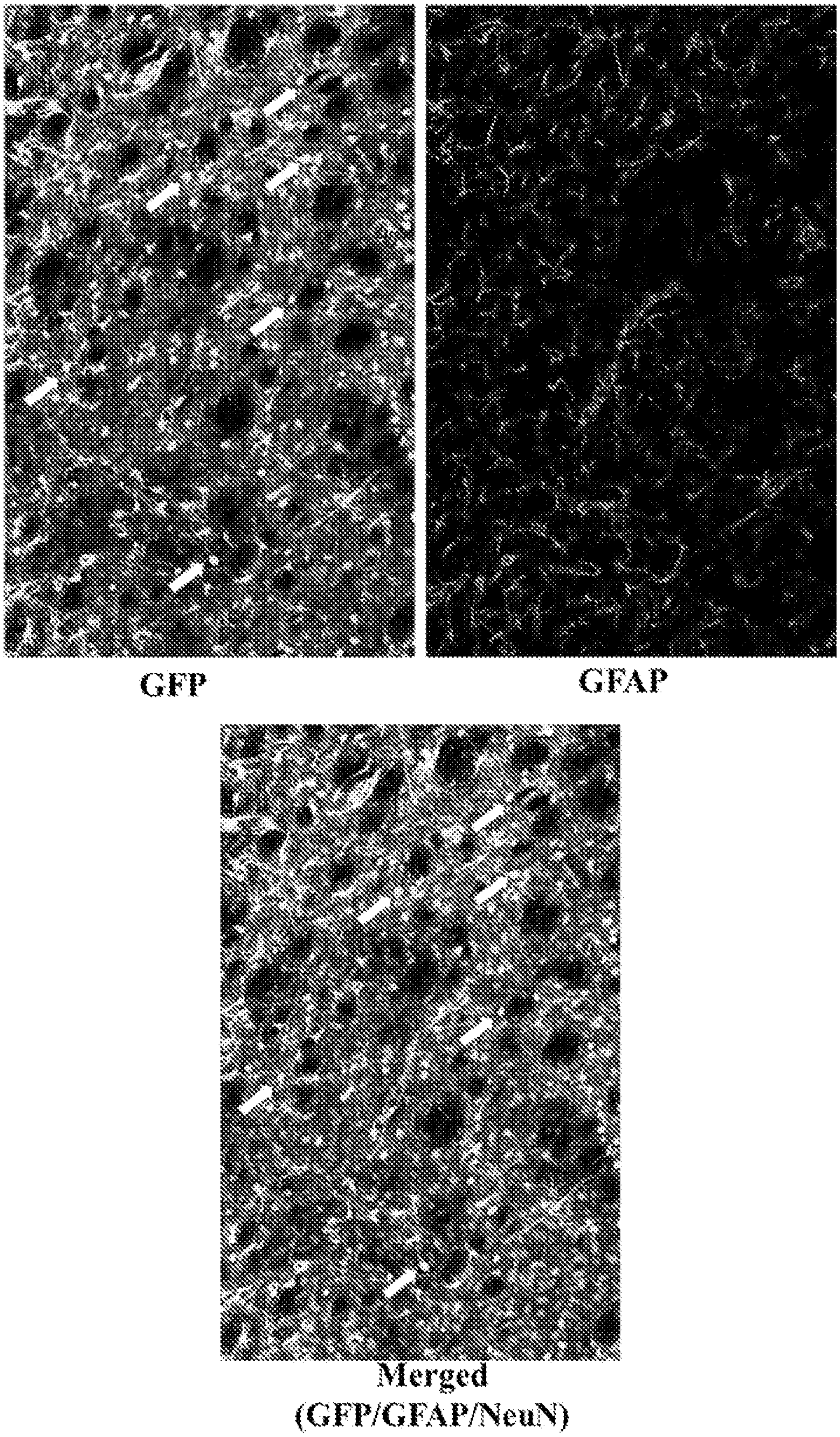

FIG. 61 depicts the brain striatum tissue of mice co-infected with AAV9-P12 and AAV9-P122 (the P122 group) at 30 dpi. GFP fluorescence identifies the AAV9-P112-infected cells. The cells are immunostained with antibodies against GFAP and NeuN.

Figure 62:
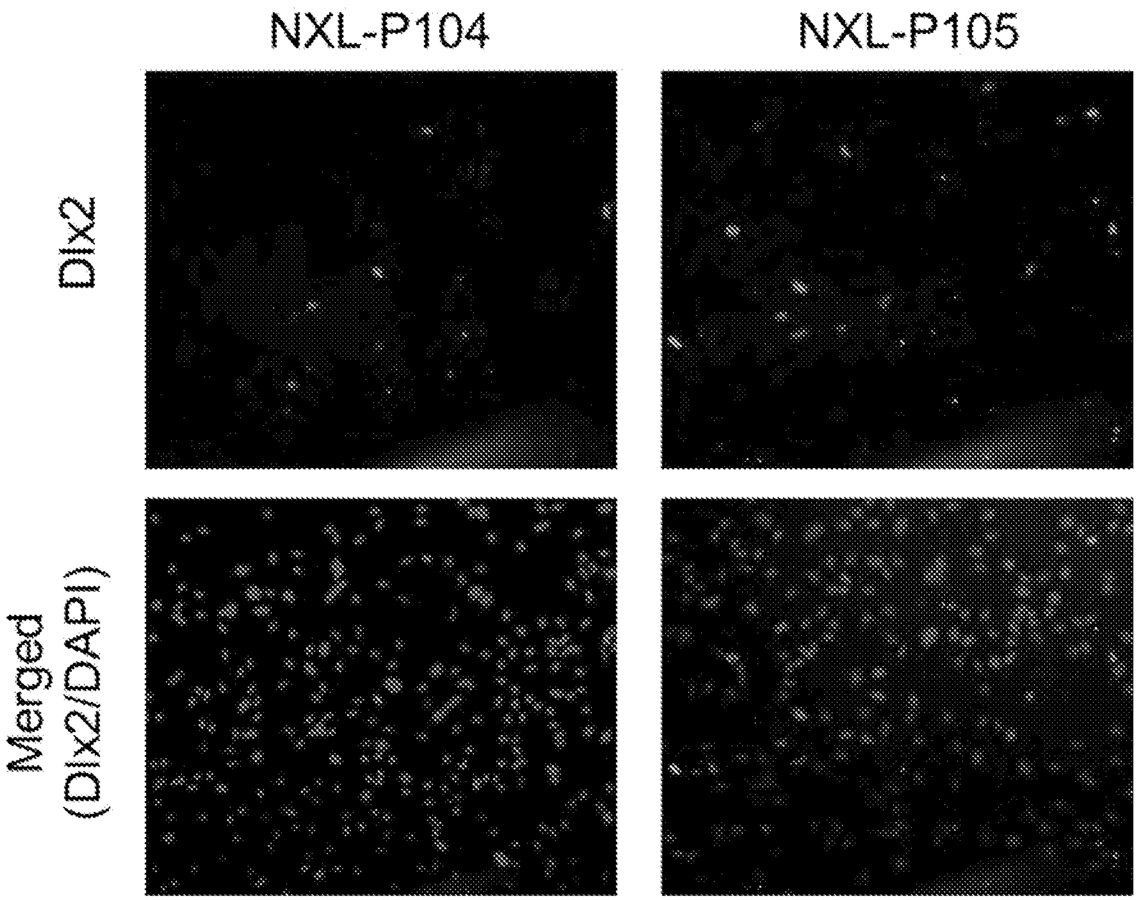

FIG. 62 depicts rat cortical astrocytes (RCAs) immunostained with an anti-Dlx2 antibody and DAPI (nuclear stain) 24 hours post transfection with NXL-P104 (CE-pGfa681-CGRI-Dlx2-bGHpA) or NXL-P105 (CE-pGfa681-CI-Dlx2-oPRE-bGHpA).

Figure 63:
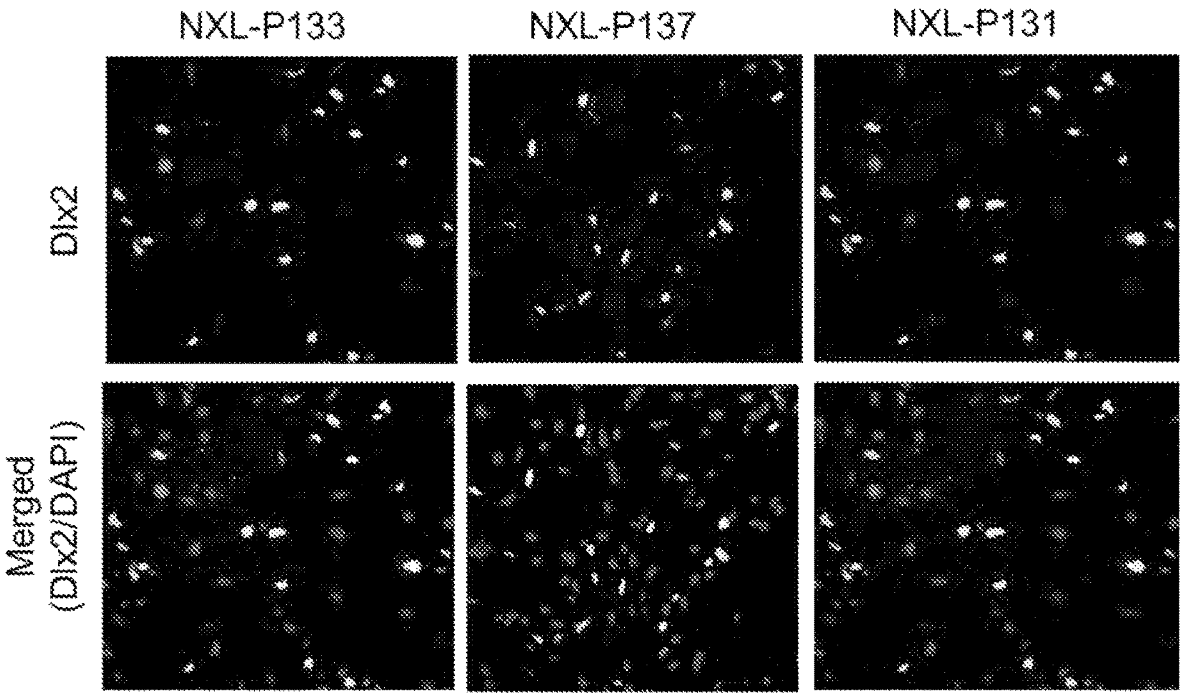

FIG. 63 depicts rat cortical astrocytes (RCAs) immunostained with an anti-Dlx2 antibody and DAPI (nuclear stain) 24 hours post transfection with NXL-P133 (EE-pGfa681-CGRI-Dlx2-oPRE-bGHpA), NXL-P137 (EE-pGfa681-CGRI-Dlx2-oPRE-bGHpA), or NXL-P131 (EE-pGfa681-CI-Dlx2-oPRE-bGHpA).

Figure 64:
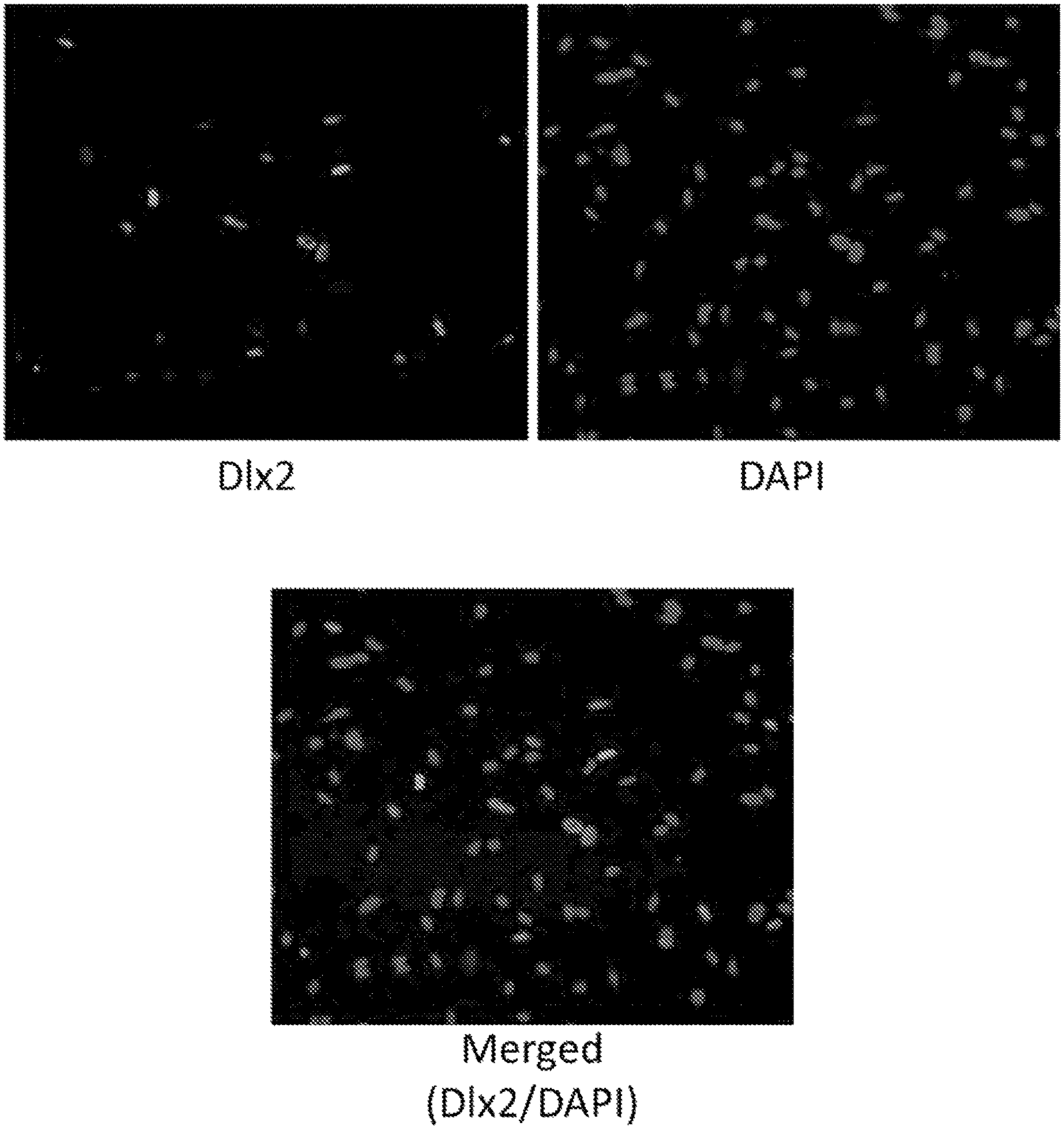

FIG. 64 depicts rat cortical astrocytes (RCAs) immunostained with an anti-Dlx2 antibody and DAPI (nuclear stain) after transduction with AAV9-P133 (CE-pGfa681-CGRI-Dlx2-oPRE-bGHpA).

BRIEF DESCRIPTION OF SEQUENCES

A listing of nucleic acid sequences and amino acid sequences is provided in Table 1.

TABLE 1

| Nucleic acid sequences | | | |
|---|---|---|---|
| SEQ ID NO | Sequence Description | Sequence Type | Sequence |
| 1 | Upstream AAV2 ITR | Nucleic acid | TGCAGGCAGCTGCGCGCTCGCTCGCTCACTGAGGCCGCCCGGGCGTCGGGCGACCTTTGGTCGCCCGGCCTCAGTGAGCGAGCGAGCGCGCAGAGAGGGAGTGGCCAACTCCATCACTAGGGGTTCCT |
| 2 | Ef1a enhancer | Nucleic acid | TGCAAAGATGGATAAAGTTTTAAACAGAGAGGAATCTTTGCAGCTAATGGACCTTCTAGGTCTTGAAAGGAGTGGGAATTGGCTCCGGTGCCCGTCAGTGGGCAGAGCGCACATCGCCCACAGTCCCCGAGAAGTTGGGGGGAGGGGTCGGCA |
| 3 | Internal Ribosomal Entry Sequence (IRES) | Nucleic acid | ACGTTACTGGCCGAAGCCGCTTGGAATAAGGCCGGTGTGCGTTTGTCTATATGTTATTTTCCACCATATTGCCGTCTTTTGGCAATGTGAGGGCCCGGAAACCTGGCCCTGTCTTCTTGACGAGCATTCCTAGGGGTCTTTCCCCTCTCGCCAAAGGAATGCAAGGTCTGTTGAATGTCGTGAAGGAAGCAGTTCCTCTGGAAGCTTCTTGAAGACAAACAACGTCTGTAGCGACCCTTTGCAGGCAGCGGAACCCCCCACCTGGCGACAGGTGCCTCTGCGGCCAAAAGCCACGTGTATAAGATACACCTGCAAAGGCGGCACAACCCCAGTGCCACGTTGTGAGTTGGATAGTTGTGGAAAGAGTCAAATGGCTCTCCTCAAGCGTATTCAACAAGGGGCTGAAGGATGCCCAGAAGGTACCCCATTGTATGGGATCTGATCTGGGGCCTCGGTGCACATGCTTTACATGTGTTTAGTCGAGGTTAAAAAAACGTCTAGGCCCCCCGAACCACGGGGACGTGGTTTTCCTTTGAAAAACACGATGATAATA |

TABLE 1-continued

| Nucleic acid sequences | | | |
|---|---|---|---|
| SEQ ID NO | Sequence Description | Sequence Type | Sequence |
| 4 | Gfa1.6 promoter | Nucleic acid | CTGCAAGCAGACCTGGCAGCATTGGGCTGGCCGCCCCC<br>CAGGGCCTCCTCTTCATGCCCAGTGAATGACTCACCTT<br>GGCACAGACACAATGTTCGGGGTGGGCACAGTGCCTGC<br>TTCCCGCCGCACCCCAGCCCCCCTCAAATGCCTTCCGA<br>GAAGCCCATTGAGTAGGGGGCTTGCATTGCACCCCAGC<br>CTGACAGCCTGGCATCTTGGGATAAAAGCAGCACAGCC<br>CCCTAGGGGCTGCCCTTGCTGTGTGGCGCCACCGGCGG<br>TGGAGAACAAGGCTCTATTCAGCCTGTGCCCAGGAAAG<br>GGGATCAGGGGATGCCCAGGCATGGACAGTGGGTGGCA<br>GGGGGGGAGAGGAGGGCTGTCTGCTTCCCAGAAGTCCA<br>AGGACACAAATGGGTGAGGGGACTGGGCAGGGTTCTGA<br>CCCTGTGGGACCAGAGTGGAGGGCGTAGATGGACCTGA<br>AGTCTCCAGGGACAACAGGGCCCAGGTCTCAGGCTCCT<br>AGTTGGGCCCAGTGGCTCCAGCGTTTCCAAACCCATCC<br>ATCCCCAGAGGTTCTTCCCATCTCTCCAGGCTGATGTG<br>TGGGAACTCGAGGAAATAAATCTCCAGTGGGAGACGGA<br>GGGGTGGCCAGGGAAACGGGGCGCTGCAGGAATAAAGA<br>CGAGCCAGCACAGCCAGCTCATGCGTAACGGCTTTGTG<br>GAGCTGTCAAGGCCTGGTCTCTGGGAGAGAGGCACAGG<br>GAGGCCAGACAAGGAAGGGGTGACCTGGAGGGACAGAT<br>CCAGGGGCTAAAGTCCTGATAAGGCAAGAGAGTGCCGG<br>CCCCCTCTTGCCCTATCAGGACCTCCACTGCCACATAG<br>AGGCCATGATTGACCCTTAGACAAAGGGCTGGTGTCCA<br>ATCCCAGCCCCCAGCCCCAGAACTCCAGGGAATGAATG<br>GGCAGAGAGCAGGAATGTGGGACATCTGTGTTCAAGGG<br>AAGGACTCCAGGAGTCTGCTGGGAATGAGGCCTAGTAG<br>GAAATGAGGTGGCCCTTGAGGGTACAGAACAGGTTCAT<br>TCTTCGCCAAATTCCCAGCACCTTGCAGGCACTTACAG<br>CTGAGTGAGATAATGCCTGGGTTATGAAATCAAAAAGT<br>TGGAAAGCAGGTCAGAGGTCATCTGGTACAGCCCTTCC<br>TTCCCTTTTTTTTTTTTTTTTTTTTTGTGAGACAAGGTCT<br>CTCTCTGTTGCCCAGGCTGGAGTGGCGCAAACACAGCT<br>CACTGCAGCCTCAACCTACTGGGCTCAAGCAATCCTCC<br>AGCCTCAGCCTCCCAAAGTGCTGGGATTACAAGCATGA<br>GCCACCCCACTCAGCCCTTTCCTTCCTTTTTAATTGAT<br>GCATAATAATTGTAAGTATTCATCATGGTCCAACCAAC<br>CCTTTCTTGACCCACCTTCCTAGAGAGAGGGTCCTCTT<br>GATTCAGCGGTCAGGGCCCCAGACCCATGGTCTGGCTC<br>CAGGTACCACCTGCCTCATGCAGGAGTTGGCGTGCCCA<br>GGAAGCTCTGCCTCTGGGCACAGTGACCTCAGTGGGGT<br>GAGGGGAGCTCTCCCCATAGCTGGGCTGCGGCCCAACC<br>CCACCCCCTCAGGCTATGCCAGGGGGTGTTGCCAGGGG<br>CACCCGGGCATCGCCAGTCTAGCCCACTCCTTCATAAA<br>GCCCTCGCATCCCAGGAGCGAGCAGAGCCAGAG |
| 5 | Chimeric Intron | Nucleic acid | GTAAGTATCAAGGTTACAAGACAGGTTTAAGGAGACCA<br>ATAGAAACTGGGCTTGTCGAGACAGAGAAGACTCTTGC<br>GTTTCTGATAGGCACCTATTGGTCTTACTGACATCCAC<br>TTTGCCTTTCTCTCCACAG |
| 6 | hND1 (human NeuroD1) | Nucleic acid | ATGACCAAATCGTACAGCGAGAGTGGGCTGATGGGCGA<br>GCCTCAGCCCCAAGGTCCTCCAAGCTGGACAGACGAGT<br>GTCTCAGTTCTCAGGACGAGGAGCACGAGGCAGACAAG<br>AAGGAGGACGACCTCGAAGCCATGAACGCAGAGGAGGA<br>CTCACTGAGGAACGGGGGAGAGGAGGAGGACGAAGATG<br>AGGACCTGGAAGAGGAGGAAGAAGAGGAAGAGGAGGAT<br>GACGATCAAAAGCCCAAGAGACGCGGCCCCAAAAAGAA<br>GAAGATGACTAAGGCTCGCCTGGAGCGTTTTAAATTGA<br>GACGCATGAAGGCTAACGCCCGGGAGCGGAACCGCATG<br>CACGGACTGAACGCGGCGCTAGACAACCTGCGCAAGGT<br>GGTGCCTTGCTATTCTAAGACGCAGAAGCTGTCCAAAA<br>TCGAGACTCTGCGCTTGGCCAAGAACTACATCTGGGCT<br>CTGTCGGAGATCCTGCGCTCAGGCAAAAGCCCAGACCT<br>GGTCTCCTTCGTTCAGACGCTTTGCAAGGGCTTATCCC<br>AACCCACCACCAACCTGGTTGCGGGCTGCCTGCAACTC<br>AATCCTCGGACTTTTCTGCCTGAGCAGAACCAGGACAT<br>GCCCCCCCACCTGCCGACGGCCAGCGCTTCCTTCCCTG<br>TACACCCCTACTCCTACCAGTCGCCTGGGCTGCCCAGT<br>CCGCCTTACGGTACCATGGACAGCTCCCATGTCTTCCA<br>CGTTAAGCCTCCGCCGCACGCCTACAGCGCAGCGCTGG<br>AGCCCTTCTTTGAAAGCCCTCTGACTGATTGCACCAGC<br>CCTTCCTTTGATGGACCCCTCAGCCCGCCGCTCAGCAT<br>CAATGGCAACTTCTCTTTCAAACACGAACCGTCCGCCG<br>AGTTTGAGAAAAATTATGCCTTTACCATGCACTATCCT<br>GCAGCGACACTGGCAGGGGCCCAAAGCCACGGATCAAT |

TABLE 1-continued

| Nucleic acid sequences | | | |
|---|---|---|---|
| SEQ ID NO | Sequence Description | Sequence Type | Sequence |
| | | | CTTCTCAGGCACCGCTGCCCCTCGCTGCGAGATCCCCA<br>TAGACAATATTATGTCCTTCGATAGCCATTCACATCAT<br>GAGCGAGTCATGAGTGCCCAGCTCAATGCCATATTTCA<br>TGAT |
| 7 | WPRE (Woodchuck Hepatitis Virus Posttran-scriptional Regulatory Element) | Nucleic acid | AATCAACCTCTGGATTACAAAATTTGTGAAAGATTGAC<br>TGGTATTCTTAACTATGTTGCTCCTTTTACGCTATGTG<br>GATACGCTGCTTTAATGCCTTTGTATCATGCTATTGCT<br>TCCCGTATGGCTTTCATTTTCTCCTCCTTGTATAAATC<br>CTGGTTGCTGTCTCTTTATGAGGAGTTGTGGCCCGTTG<br>TCAGGCAACGTGGCGTGGTGTGCACTGTGTTTGCTGAC<br>GCAACCCCCACTGGTTGGGGCATTGCCACCACCTGTCA<br>GCTCCTTTCCGGGACTTTCGCTTTCCCCCTCCCTATTG<br>CCACGGCGGAACTCATCGCCGCCTGCCTTGCCCGCTGC<br>TGGACAGGGGCTCGGCTGTTGGGCACTGACAATTCCGT<br>GGTGTTGTCGGGGAAATCATCGTCCTTTCCTTGGCTGC<br>TCGCCTGTGTTGCCACCTGGATTCTGCGCGGGACGTCC<br>TTCTGCTACGTCCCTTCGGCCCTCAATCCAGCGGACCT<br>TCCTTCCCGCGGCCTGCTGCCGGCTCTGCGGCCTCTTC<br>CGCGTCTTCGCCTTCGCCCTCAGACGAGTCGGATCTCC<br>CTTTGGGCCGCCTCCCCGC |
| 8 | SV40 poly(A) signal | Nucleic acid | CGATCCACCGGATCTAGATAACTGATCATAATCAGCCA<br>TACCACATTTGTAGAGGTTTTACTTGCTTTAAAAAACC<br>TCCCACACCTCCCCCTGAACCTGAAACATAAAATGAAT<br>GCAATTGTTGTTGTTAACTTGTTTATTGCAGCTTATAA<br>TGGTTACAAATAAAGCAATAGCATCACAAATTTCACAA<br>ATAAAGCATTTTTTTCACTGCATTCTAGTTGTGGTTTG<br>TCCAAACTCATCAATGTATCTTA |
| 9 | Downstream AAV2 ITR | Nucleic acid | AGGAACCCCTAGTGATGGAGTTGGCCACTCCCTCTCTG<br>CGCGCTCGCTCGCTCACTGAGGCCGGGCGACCAAAGGT<br>CGCCCGACGCCCGGGCTTTGCCCGGGCGGCCTCAGTGA<br>GCGAGCGAGCGCGCAGCTGCCTGCA |
| 10 | hND1 (human NeuroD1) | Amino Acid | MTKSYSESGLMGEPQPQGPPSWTDECLSSQDEEHEADK<br>KEDDLEAMNAEEDSLRNGGEEEDEDEDLEEEEEEEEED<br>DDQKPKRRGPKKKKMTKARLERFKLRRMKANARERNRM<br>HGLNAALDNLRKVVPCYSKTQKLSKIETLRLAKNYIWA<br>LSEILRSGKSPDLVSFVQTLCKGLSQPTTNLVAGCLQL<br>NPRTFLPEQNQDMPPHLPTASASFPVHPYSYQSPGLPS<br>PPYGTMDSSHVFHVKPPPHAYSAALEPFFESPLTDCTS<br>PSFDGPLSPPLSINGNFSFKHEPSAEFEKNYAFTMHYP<br>AATLAGAQSHGSIFSGTAAPRCEIPIDNIIVISFDSHS<br>HHERVMSAQLNAIFHD |
| 11 | CMV enhancer ("CE") | Nucleic Acid | GACATTGATTATTGACTAGTTATTAATAGTAATCAATT<br>ACGGGGTCATTAGTTCATAGCCCATATATGGAGTTCCG<br>CGTTACATAACTTACGGTAAATGGCCCGCCTGGCTGAC<br>CGCCCAACGACCCCCGCCCATTGACGTCAATAATGACG<br>TATGTTCCCATAGTAACGCCAATAGGGACTTTCCATTG<br>ACGTCAATGGGTGGACTATTTACGGTAAACTGCCCACT<br>TGGCAGTACATCAAGTGTATCATATGCCAAGTACGCCC<br>CCTATTGACGTCAATGACGGTAAATGGCCCGCCTGGCA<br>TTATGCCCAGTACATGACCTTATGGGACTTTCCTACTT<br>GGCAGTACATCTACGTATTAGTCATCGCTATTACCATG |
| 12 | hGFA2.2 promoter | Nucleic Acid | CGCGTCCCACCTCCCTCTCTGTGCTGGGACTCACAGAG<br>GGAGACCTCAGGAGGCAGTCTGTCCATCACATGTCCAA<br>ATGCAGAGCATACCCTGGGCTGGGCGCAGTGGCGCACA<br>ACTGTAATTCCAGCACTTTGGGAGGCTGATGTGGAAGG<br>ATCACTTGAGCCCAGAAGTTCTAGACCAGCCTGGGCAA<br>CATGGCAAGACCCTATCTCTACAAAAAAAGTTAAAAAA<br>TCAGCCACGTGTGGTGACACACACCTGTAGTCCCAGCT<br>ATTCAGGAGGCTGAGGTGAGGGGATCACTTAAGGCTGG<br>GAGGTTGAGGCTGCAGTGAGTCGTGGTTGCGCCACTGC<br>ACTCCAGCCTGGGCAACAGTGAGACCCTGTCTCAAAAG<br>ACAAAAAAAAAAAAAAAAAAAAAAAAAGAACATATCCTGG<br>TGTGGAGTAGGGGACGCTGCTCTGACAGAGGCTCGGGG<br>GCCTGAGCTGGCTCTGTGAGCTGGGGAGGAGGCAGACA<br>GCCAGGCCTTGTCTGCAAGCAGACCTGGCAGCATTGGG<br>CTGGCCGCCCCCCAGGGCCTCCTCTTCATGCCCAGTGA<br>ATGACTCACCTTGGCACAGACACAATGTTCGGGGTGGG<br>CACAGTGCCTGCTTCCCGCCGCACCCCAGCCCCCCTCA<br>AATGCCTTCCGAGAAGCCCATTGAGCAGGGGGCTTGCA |

TABLE 1-continued

Nucleic acid sequences

| SEQ ID NO | Sequence Description | Sequence Type | Sequence |
|---|---|---|---|
| | | | TTGCACCCCAGCCTGACAGCCTGGCATCTTGGGATAAA<br>AGCAGCACAGCCCCCTAGGGGCTGCCCTTGCTGTGTGG<br>CGCCACCGGCGGTGGAGAACAAGGCTCTATTCAGCCTG<br>TGCCCAGGAAAGGGGATCAGGGGATGCCCAGGCATGGA<br>CAGTGGGTGGCAGGGGGGGAGAGGAGGGCTGTCTGCTT<br>CCCAGAAGTCCAAGGACACAAATGGGTGAGGGGACTGG<br>GCAGGGTTCTGACCCTGTGGGACCAGAGTGGAGGGCGT<br>AGATGGACCTGAAGTCTCCAGGGACAACAGGGCCCAGG<br>TCTCAGGCTCCTAGTTGGGCCCAGTGGCTCCAGCGTTT<br>CCAAACCCATCCATCCCCAGAGGTTCTTCCCATCTCTC<br>CAGGCTGATGTGTGGGAACTCGAGGAAATAAATCTCCA<br>GTGGGAGACGGAGGGGTGGCCAGGGAAACGGGGCGCTG<br>CAGGAATAAAGACGAGCCAGCACAGCCAGCTCATGTGT<br>AACGGCTTTGTGGAGCTGTCAAGGCCTGGTCTCTGGGA<br>GAGAGGCACAGGGAGGCCAGACAAGGAAGGGGTGACCT<br>GGAGGGACAGATCCAGGGGCTAAAGTCCTGATAAGGCA<br>AGAGAGTGCCGGCCCCCTCTTGCCCTATCAGGACCTCC<br>ACTGCCACATAGAGGCCATGATTGACCCTTAGACAAAG<br>GGCTGGTGTCCAATCCCAGCCCCCAGCCCCAGAACTCC<br>AGGGAATGAATGGGCAGAGAGCAGGAATGTGGGACATC<br>TGTGTTCAAGGGAAGGACTCCAGGAGTCTGCTGGGAAT<br>GAGGCCTAGTAGGAAATGAGGTGGCCCTTGAGGGTACA<br>GAACAGGTTCATTCTTCGCCAAATTCCCAGCACCTTGC<br>AGGCACTTACAGCTGAGTGAGATAATGCCTGGGTTATG<br>AAATCAAAAAGTTGGAAAGCAGGTCAGAGGTCATCTGG<br>TACAGCCCTTCCTTCCCTTTTTTTTTTTTTTTTTTTGT<br>GAGACAAGGTCTCTCTCTGTTGCCCAGGCTGGAGTGGC<br>GCAAACACAGCTCACTGCAGCCTCAACCTACTGGGCTC<br>AAGCAATCCTCCAGCCTCAGCCTCCCAAAGTGCTGGGA<br>TTACAAGCATGAGCCACCCCACTCAGCCCTTTCCTTCC<br>TTTTTAATTGATGCATAATAATTGTAAGTATTCATCAT<br>GGTCCAACCAACCCTTTCTTGACCCACCTTCCTAGAGA<br>GAGGGTCCTCTTGCTTCAGCGGTCAGGGCCCCAGACCC<br>ATGGTCTGGCTCCAGGTACCACCTGCCTCATGCAGGAG<br>TTGGCGTGCCCAGGAAGCTCTGCCTCTGGGCACAGTGA<br>CCTCAGTGGGGTGAGGGGAGCTCTCCCCATAGCTGGGC<br>TGCGGCCCAACCCCACCCCCTCAGGCTATGCCAGGGGG<br>TGTTGCCAGGGGCACCCGGGCATCGCCAGTCTAGCCCA<br>CTCCTTCATAAAGCCCTCGCATCCCAGGAGCGAGCAGA<br>GCCAGAGCAGGTTGGAGAGGAGACGCATCACCTCCGCT<br>GCTCGCCGGG |
| 13 | Human Dlx2 | Nucleic Acid | ATGACTGGAGTCTTTGACAGTCTAGTGGCTGATATGCA<br>CTCGACCCAGATCGCCGCCTCCAGCACGTACCACCAGC<br>ACCAGCAGCCCCCGAGCGGCGGCGGCGCCGGCCCGGGT<br>GGCAACAGCAGCAGCAGCAGCAGCCTCCACAAGCCCCA<br>GGAGTCGCCCACCCTTCCGGTGTCCACCGCCACCGACA<br>GCAGCTACTACACCAACCAGCAGCACCCGGCGGGCGGC<br>GGCGGCGGCGGGGGCTCGCCCTACGCGCACATGGGTTC<br>CTACCAGTACCAAGCCAGCGGCCTCAACAACGTCCCTT<br>ACTCCGCCAAGAGCAGCTATGACCTGGGCTACACCGCC<br>GCCTACACCTCCTACGCTCCCTATGGAACCAGTTCGTC<br>CCCAGCCAACAACGAGCCTGAGAAGGAGGACCTTGAGC<br>CTGAAATTCGGATAGTGAACGGGAAGCCAAAGAAAGTC<br>CGGAAACCCCGCACCATCTACTCCAGTTTCCAGCTGGC<br>GGCTCTTCAGCGGCGTTTCCAAAAGACTCAATACTTGG<br>CCTTGCCGGAGCGAGCCGAGCTGGCGGCCTCTCTGGGC<br>CTCACCCAGACTCAGGTCAAAATCTGGTTCCAGAACCG<br>CCGGTCCAAGTTCAAGAAGATGTGGAAAAGTGGTGAGA<br>TCCCCTCGGAGCAGCACCCTGGGGCCAGCGCTTCTCCA<br>CCTTGTGCTTCGCCGCCAGTCTCAGCGCCGGCCTCCTG<br>GGACTTTGGTGTGCCGCAGCGGATGGCGGGCGGCGGTG<br>GTCCGGGCAGTGGCGGCAGCGGCGCCGGCAGCTCGGGC<br>TCCAGCCCGAGCAGCGCGGCCTCGGCTTTTCTGGGCAA<br>CTACCCCTGGTACCACCAGACCTCGGGATCCGCCTCAC<br>ACCTGCAGGCCACGGCGCCGCTGCTGCACCCCACTCAG<br>ACCCCGCAGCCGCATCACCACCACCACCATCACGGCGG<br>CGGGGGCGCCCCGGTGAGCGCGGGGACGATTTTCTGA |
| 14 | Human Dlx2 | Amino Acid | MTGVFDSLVADMHSTQIAASSTYHQHQQPPSGGGAGPG<br>GNSSSSSSLHKPQESPTLPVSTATDSSYYTNQQHPAGG<br>GGGGGSPYAHMGSYQYQASGLNNVPYSAKSSYDLGYTA<br>AYTSYAPYGTSSSPANNEPEKEDLEPEIRIVNGKPKKV<br>RKPRTIYSSFQLAALQRRFQKTQYLALPERAELAASLG<br>LTQTQVKIWFQNRRSKFKKMWKSGEIPSEQHPGASASP |

TABLE 1-continued

| Nucleic acid sequences | | | |
|---|---|---|---|
| SEQ ID NO | Sequence Description | Sequence Type | Sequence |
| | | | PCASPPVSAPASWDFGVPQRMAGGGGPGSGGSGAGSSG SSPSSAASAFLGNYPWYHQTSGSASHLQATAPLLHPTQ TPQPHEIHEIHHHGGGGAPVSAGTIF |
| 15 | P2A | Nucleic Acid | GCTACTAACTTCAGCCTGCTGAAGCAGGCTGGAGACGT GGAGGAGAACCCTGGACCT |
| 16 | T2A | Nucleic Acid | GAGGGGAGAGGAAGTCTTCTGACCTGCGGAGACGTCGA AGAGAATCCTGGACCC |
| 17 | hGH poly(A) signal | Nucleic Acid | GGGTGGCATCCCTGTGACCCCTCCCCAGTGCCTCTCCT GGCCCTGGAAGTTGCCACTCCAGTGCCCACCAGCCTTG TCCTAATAAAATTAAGTTGCATCATTTTGTCTGACTAG GTGTCCTTCTATAATATTATGGGGTGGAGGGGGGTGGT ATGGAGCAAGGGGCAAGTTGGGAAGACAACCTGTAGGG CCTGCGGGGTCTATTGGGAACCAAGCTGGAGTGCAGTG GCACAATCTTGGCTCACTGCAATCTCCGCCTCCTGGGT TCAAGCGATTCTCCTGCCTCAGCCTCCCGAGTTGTTGG GATTCCAGGCATGCATGACCAGGCTCAGCTAATTTTTG TTTTTTTGGTAGAGACGGGGTTTCACCATATTGGCCAG GCTGGTCTCCAACTCCTAATCTCAGGTGATCTACCCAC CTTGGCCTCCCAAATTGCTGGGATTACAGGCGTGAACC ACTGCTCCCTTCCCTGTCCTT |
| 18 | GSG P2A | Nucleic Acid | GGAAGCGGAGCTACTAACTTCAGCCTGCTGAAGCAGGC TGGAGACGTGGAGGAGAACCCTGGACCT |
| 19 | GSG-T2A | Nucleic Acid | GGAAGCGGAGCTACTAACTTCAGCCTGCTGAAGCAGGC TGGAGACGTGGAGGAGAACCCTGGACCT |
| 20 | GSG-P2A | Amino Acid | GSGATNFSLLKQAGDVEENPGP |
| 21 | GSG-T2A | Amino Acid | GSGEGRGSLLTCGDVEENPGP |
| 22 | U6 promoter | Nucleic Acid | GTCCTTTCCACAAGATATATAAACCCAAGAAATCGAAA TACTTTCAAGTTACGGTAAGCATATGATAGTCCATTTT AAAACATAATTTTAAAACTGCAAACTACCCAAGAAATT ATTACTTTCTACGTCACGTATTTTGTACTAATATCTTT GTGTTTACAGTCAAATTAATTCTAATTATCTCTCTAAC AGCCTTGTATCGTATATGCAAATATGAAGGAATCATGG GAAATAGGCCCTC |
| 23 | Htt shRNA 1 | Nucleic Acid | CCGGTGGTTCAGTTACGGGTTAATTCTCGAGAATTAAC CCGTAACTGAACCATTTTTG |
| 24 | Htt shRNA 2 | Nucleic Acid | CCGGCAGTTACGGGTTAATTAATACCTGACCCATATTA ATTAACCCGTAACTGCTTTTTG |
| 25 | Htt shRNA 3 | Nucleic Acid | CCGGTGTTGCCGCAGCATCACTAATCTCGAGATTAGTG ATGCTGCGGCAACATTTTTG |
| 26 | pGfa681 promoter (also called "GfaABC1D" promoter) | | AACATATCCTGGTGTGGAGTAGGGGACGCTGCTCTGAC AGAGGCTCGGGGGCCTGAGCTGGCTCTGTGAGCTGGGG AGGAGGCAGACAGCCAGGCCTTGTCTGCAAGCAGACCT GGCAGCATTGGGCTGGCCGCCCCCCAGGGCCTCCTCTT CATGCCCAGTGAATGACTCACCTTGGCACAGACACAAT GTTCGGGGTGGGCACAGTGCCTGCTTCCCGCCGCACCC CAGCCCCCCTCAAATGCCTTCCGAGAAGCCCATTGAGC AGGGGGCTTGCATTGCACCCCAGCCTGACAGCCTGGCA TCTTGGGATAAAAGCAGCACAGCCCCCTAGGGGCTGCC CTTGCTGTGTGGCGCCACCGGCGGTGGAGAACAAGGCT CTATTCAGCCTGTGCCCAGGAAAGGGGATCAGGGGATG CCCAGGCATGGACAGTGGGTGGCAGGGGGGGAGAGGAG GGCTGTCTGCTTCCCAGAAGTCCAAGGACACAAATGGG TGAGGGGAGAGCTCTCCCCATAGCTGGGCTGCGGCCCA ACCCCACCCCCTCAGGCTATGCCAGGGGGTGTTGCCAG GGGCACCCGGGCATCGCCAGTCTAGCCCACTCCTTCAT AAAGCCCTCGCATCCCAGGAGCGAGCAGAGCCAGAGCA GGTTGGAGAGGAGACGCATCACCTCCGCTGCTCGC |

TABLE 1-continued

| Nucleic acid sequences | | | |
|---|---|---|---|
| SEQ ID NO | Sequence Description | Sequence Type | Sequence |
| 27 | CRGI Chimeric Intron | | GGAGTCGCTGCGTTGCCTTCGCCCCGTGCCCCGCTCCG CGCCGCCTCGCGCCGCCCGCCCCGGCTCTGACTGACCG CGTTACTCCCACAGGTGAGCGGGCGGGACGGCCCTTCT CCCTCCGGGCTGTAATTAGCGCTTGGTTTAATGACGGC TCGTTTCTTTTCTGTGGCTGCGTGAAAGCCTTAAAGGG CTCCGGGAGGGCCTTTGTGCGGGGGGGAGCGGCTCGGG GGGTGCGTGCGTGTGTGTGTGCGTGGGGAGCGCCGCGT GCGGCCCGCGCTGCCCGGCGGCTGTGAGCGCTGCGGGC GCGGCGCGGGGCTTTGTGCGCTCCGCGTGTGCGCGAGG GGAGCGCGGGCCGGGGGCGGTGCCCCGCGGTGCGGGGG GGCTGCGAGGGGAACAAAGGCTGCGTGCGGGGTGTGTG CGTGGGGGGGTGAGCAGGGGGTGTGGGCGCGGCGGTCG GGCTGTAACCCCCCCCTGGCACCCCCCTCCCCGAGTTG CTGAGCACGGCCCGGCTTCGGGTGCGGGGCTCCGTGCG GGGCGTGGCGCGGGGCTCGCCGTGCCGGGCGGGGGGTG GCGGCAGGTGGGGGTGCCGGGCGGGGCGGGGCCGCCTC GGGCCGGGGAGGGCTCGGGGGAGGGGCGCGGCGGCCCC GGAGCGCCGGCGGCTGTCGAGGCGCGGCGAGCCGCAGC CATTGCCTTTTATGGTAATCGTGCGAGAGGGCGCAGGG ACTTCCTTTGTCCCAAATCTGGCGGAGCCGAAATCTGG GAGGCGCCGCCGCACCCCCTCTAGCGGGCGCGGGCGAA GCGGTGCGGCGCCGGCAGGAAGGAAATGGGCGGGGAGG GCCTTCGTGCGTCGCCGCGCCGCCGTCCCCTTCTCCAT CTCCAGCCTCGGGGCTGCCGCAGGGGGACGGCTGCCTT CGGGGGGGACGGGGCAGGGCGGGGTTCGGCTTCTGGCG TGTGACCGGCGGCTTTAGAGCCTCTGCTAACCATGTTC ATGCCTTCTTCTTTTTCCTACAGCTCCTGGGCAACGTG CTGGTTGTTGTGCTGTCTCATCATTTTGGCAAAGAT |
| 28 | GFAP first intron (GI) | | GGCCACTGTGAGGCAGAAGTGAGGAGGGGATGGGGAAG GGGGGCCTTGTGAGCAGAAGGGGCTGAATCCCCAAGAA GGAGTGCCCGAGAAGTCTCAGGGAGGGGCCGAACCTCC CTGCTCCCTGGGCCTCCCTACCTCTTGATGGGGCACTA TCCTTGCCCCCCAACATGATGGGAGGGACCAGAAACAG GCCCAGGGCCCCGGGGATCTGATGCCCGCATGCCTTCT GCCAGGAGTCCAGGGTCCCCTCAGCACCTCCCTACTGG GGAAAGCAGTGCAGGAGCAGCGGGGCCCCTGTGTTTCA TTCATGGCTGGGCTTTGTGACTGTGGGCAGCGAGCTCA CCTATTCTGAGCCTGTGTCCATATAAAGGAGGAGTTGG AAGCGGAGAAGGTTGATGTCCATGAGGGAGATTGGATT CTGGGGTGAAGAAAGTGAGGGAAAGAGCAGGCAGGTCT GGGCGCAAAGCACAGGTGACTGCCTGCCACCAGCTTGT GACCCCCATCAAGTTACTTTGACTTGCACAGCTGTGAA GCGGTGGTCATAATAAAATTCATTTCAAAAGGTGGTTA CCTGGGATCAGAGGAATCCCCAGGGGCATGGCGCTTCA CTGAGCTGACAGGACATGCATGTGTGCCTTCAAGTGCA GGAGGACATGTGCGTGTGTGTGTGTGTGTGTGCAACAG TGAGTGTATGCTTGTGGATGCGCCTGTGTGAGCAGAAG CAGGTGCACCAACCCTGATAAGGCACCTTAGTAATGAG TTAAGGCAAAAGCCCACATCTGCTCATCCTCCAGACAA GTCCTCTGTCTAAGGCCCCCCAACCCTTAATCCTCCTG CTGCTCTACTGGTCCTGGGTGGGGGTGGTCTCTGTGAC AGCTGCCTCAAGGGAGACTGAGGCAGGTATTCAAGTGT CCTCAGAAGAGCCTGGACCCAGGAATGTGTCCCCCCAC TCCAGGCTCCAGGATGAAACCAACCTGA |
| 29 | Optimized version of WPRE (oPRE), | | GAGCATCTTACCGCCATTTATACCCATATTTGTTCTGT TTTTCTTGATTTGGGTATACATTTAAATGTTAATAAAA CAAAATGGTGGGGCAATCATTTACATTTTTAGGGATAT GTAATTACTAGTTCAGGTGTATTGCCACAAGACAAACA TGTTAAGAAACTTTCCCGTTATTTACGCTCTGTTCCTG TTAATCAACCTCTGGATTACAAAATTTGTGAAAGATTG ACTGATATTCTTAACTATGTTGCTCCTTTTACGCTGTG TGGATATGCTGCTTTATAGCCTCTGTATCTAGCTATTG CTTCCCGTACGGCTTTCGTTTTCTCCTCCTTGTATAAA TCCTGGTTGCTGTCTCTTTTAGAGGAGTTGTGGCCCGT TGTCCGTCAACGTGGCGTGGTGTGCTCTGTGTTTGCTG ACGCAACCCCCACTGGCTGGGGCATTGCCACCACCTGT CAACTCCTTTCTGGGACTTTCGCTTTCCCCCTCCCGAT CGCCACGGCAGAACTCATCGCCGCCTGCCTTGCCCGCT GCTGGACAGGGGCTAGGTTGCTGGGCACTGATAATTCC GTGGTGTTGTC |

TABLE 1-continued

Nucleic acid sequences

| SEQ ID NO | Sequence Description | Sequence Type | Sequence |
|---|---|---|---|
| 30 | bGH poly (A) signal (bGHpA) | | CTGTGCCTTCTAGTTGCCAGCCATCTGTTGTTTGCCCC TCCCCCGTGCCTTCCTTGACCCTGGAAGGTGCCACTCC CACTGTCCTTTCCTAATAAAATGAGGAAATTGCATCGC ATTGTCTGAGTAGGTGTCATTCTATTCTGGGGGGTGGG GTGGGGCAGGACAGCAAGGGGGAGGATTGGGAAGAGAA TAGCAGGCATGCTGGGGA |

DETAILED DESCRIPTION

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

When a range of numbers is provided herein, the range is understood to be inclusive of the edges of the range as well as any number between the defined edges of the range. For example, "between 1 and 10" includes any number between 1 and 10, as well as the number 1 and the number 10.

When the term "about" is used in reference to a number, it is understood to mean plus or minus 10%. For example, "about 100" would include from 90 to 110.

As used herein "hND1" refers to a human neuronal differentiation (NeuroD1) gene or protein.

As used herein "CE" refers to a cytomegalovirus (CMV) promoter enhancer sequence.

As used herein "EE" refers to an Ef1 alpha promoter enhancer sequence.

As used herein "pGfa681" refers to a human glial fibrillary acid protein (GFAP) promoter truncated sequence of 681 bp size. As used herein "pGfa681," "Gfa681," "GfaABC1D," and "pGfaABC1D" are used interchangeably.

As used herein "CI" refers to a chimeric intron composed of the 5'-donor site from the first intron of the human β-globin gene and the branch and 3'-acceptor site from the intron of an immunoglobulin gene heavy chain variable region.

As used herein "CRGI" refers to a chimeric intron of rabbit beta-globing and chicken beta actin similar in CAG promoter.

As used herein "GI" refers to a human glial fibrillary acid protein (GFAP) first intron.

As used herein "WPRE" refers to a Woodchuck Hepatitis Virus (WHV) Posttranscriptional Regulatory Element.

As used herein "oPRE" refers to an optimized version of WPRE.

As used herein "SV40 pA" refers to a poly A signal of SV40 virus.

As used herein "bGHpA" refers to a poly A signal of bovine growth hormone.

As used herein "vg" refers to a viral genome.

As used herein "hDlx2" refers to a human distal-less homeobox 2 gene or protein.

Any composition or vector provided herein is specifically envisioned for use with any method provided herein.

In an aspect, methods and compositions provided herein comprise a vector. As used herein, the term "vector" refers to a circular, double-stranded DNA molecule that is physically separate from chromosomal DNA. It should be noted that the term "vector" can be used interchangeably with the term "plasmid."

In an aspect, a vector provided herein is a recombinant vector. As used herein, the term "recombinant vector" refers to a vector that comprises a recombinant nucleic acid. As used herein, a "recombinant nucleic acid" refers to a nucleic acid molecule formed by laboratory methods of genetic recombination, such as, without being limiting, molecular cloning. A recombinant vector can be formed by laboratory methods of genetic recombination, such as, without being limiting, molecular cloning. Also, without being limiting, one skilled in the art can create a recombinant vector de novo via synthesizing a plasmid by individual nucleotides, or by splicing together nucleic acid molecules from different pre-existing vectors.

Adeno-associated viruses (AAVs) are replication-defective, non-enveloped Dependoparvovirus viruses that infect humans and additional primate species. AAVs are not known to cause disease in any species, although they can cause mild immune responses. AAVs can infect dividing and quiescent cells. AAVs are stably integrate into the human genome at a specific site in chromosome 19 termed the AAVS1 locus (nucleotides 7774-11429 of GenBank Accession No. AC010327.8), although random integrations at other loci in the human genome are possible.

AAVs comprise a linear genome with a single-stranded DNA of about 4700 nucleotides in length. The genome of AAVs also includes a 145 nucleotide-long inverted terminal repeat (ITR) at each end of the genome. The ITRs flank two viral genes rep (for replication, encoding non-structural proteins) and cap (for capsid, encoding structural proteins). The ITRs contain all of the cis-acting elements need for genome rescue, replication, and packaging of the AAV.

When used in gene therapy approaches, the rep and cap genes of the AAV genome sequence are removed and replaced with DNA of interest positioned between two AAV ITRs. As used herein, an "AAV vector construct" refers to a DNA molecule comprising a desired sequence inserted between two AAV ITR sequences. As used herein, an "AAV vector" refers to an AAV packaged with a DNA vector construct.

As used herein, the term "AAV vector serotype" mainly refers to a variation within the capsid proteins of an AAV vector.

In an aspect, an AAV vector is selected from the group consisting of AAV vector serotype 1, AAV vector serotype 2, AAV vector serotype 3, AAV vector serotype 4, AAV vector serotype 5, AAV vector serotype 6, AAV vector serotype 7, AAV vector serotype 8, AAV vector serotype 9, AAV vector serotype 10, AAV vector serotype 11, and AAV vector serotype 12. In one aspect, an AAV vector is selected from the group consisting AAV serotype 2, AAV serotype 5, and AAV serotype 9. In one aspect, an AAV vector is AAV serotype 1. In one aspect, an AAV vector is AAV serotype 2. In one aspect, an AAV vector is AAV serotype 3. In one aspect, an AAV vector is AAV serotype 4. In one aspect, an AAV vector is AAV serotype 5. In one aspect, an AAV vector is AAV serotype 6. In one aspect, an AAV vector is AAV serotype 7. In one aspect, an AAV vector is AAV serotype 8. In one aspect, an AAV vector is AAV serotype 9. In one aspect, an AAV vector is AAV serotype 10. In one aspect, an AAV vector is AAV serotype 11. In one aspect, an AAV vector is AAV serotype 12.

In an aspect, an AAV vector ITR is selected from the group consisting of an AAV serotype 1 ITR, an AAV serotype 2 ITR, an AAV serotype 3 ITR, an AAV serotype 4 ITR, an AAV serotype 5 ITR, an AAV serotype 6 ITR, an AAV serotype 7 ITR, an AAV serotype 8 ITR, an AAV serotype 9 ITR, an AAV serotype 10 ITR, an AAV serotype 11 ITR, and an AAV serotype 12 ITR. In one aspect, an AAV vector ITR is an AAV serotype 1 ITR. In one aspect, an AAV vector ITR is an AAV serotype 2 ITR. In one aspect, an AAV vector ITR is an AAV serotype 3 ITR. In one aspect, an AAV vector ITR is an AAV serotype 4 ITR. In one aspect, an AAV vector ITR is an AAV serotype 5 ITR. In one aspect, an AAV vector ITR is an AAV serotype 6 ITR. In one aspect, an AAV vector ITR is an AAV serotype 7 ITR. In one aspect, an AAV vector ITR is an AAV serotype 8 ITR. In one aspect, an AAV vector ITR is an AAV serotype 9 ITR. In one aspect, an AAV vector ITR is an AAV serotype 10 ITR. In one aspect, an AAV vector ITR is an AAV serotype 11 ITR. In one aspect, an AAV vector ITR is an AAV serotype 12 ITR.

In an aspect, at least one AAV vector ITR nucleic acid sequence is selected from the group consisting of SEQ ID NO: 1 and 9. In one aspect, at least one AAV vector ITR nucleic acid sequence is SEQ ID NO 1. In one aspect, at least one AAV vector ITR nucleic acid sequence is SEQ ID NO 9.

In an aspect, an AAV ITR nucleic acid sequence comprises a sequence at least 70% identical to SEQ ID NO: 1, or the complement thereof. In one aspect, an AAV ITR nucleic acid sequence comprises a sequence at least 75% identical to SEQ ID NO: 1, or the complement thereof. In one aspect, an AAV ITR nucleic acid sequence comprises a sequence at least 80% identical to SEQ ID NO: 1, or the complement thereof. In one aspect, an AAV ITR nucleic acid sequence comprises a sequence at least 85% identical to SEQ ID NO: 1, or the complement thereof. In one aspect, an AAV ITR nucleic acid sequence comprises a sequence at least 90% identical to SEQ ID NO: 1, or the complement thereof. In one aspect, an AAV ITR nucleic acid sequence comprises a sequence at least 91% identical to SEQ ID NO: 1, or the complement thereof. In one aspect, an AAV ITR nucleic acid sequence comprises a sequence at least 92% identical to SEQ ID NO: 1, or the complement thereof. In one aspect, an AAV ITR nucleic acid sequence comprises a sequence at least 93% identical to SEQ ID NO: 1, or the complement thereof. In one aspect, an AAV ITR nucleic acid sequence comprises a sequence at least 94% identical to SEQ ID NO: 1, or the complement thereof. In one aspect, an AAV ITR nucleic acid sequence comprises a sequence at least 95% identical to SEQ ID NO: 1, or the complement thereof. In one aspect, an AAV ITR nucleic acid sequence comprises a sequence at least 96% identical to SEQ ID NO: 1, or the complement thereof. In one aspect, an AAV ITR nucleic acid sequence comprises a sequence at least 97% identical to SEQ ID NO: 1, or the complement thereof. In one aspect, an AAV ITR nucleic acid sequence comprises a sequence at least 98% identical to SEQ ID NO: 1, or the complement thereof. In one aspect, an AAV ITR nucleic acid sequence comprises a sequence at least 99% identical to SEQ ID NO: 1, or the complement thereof. In one aspect, an AAV ITR nucleic acid sequence comprises a sequence at least 99.5% identical to SEQ ID NO: 1, or the complement thereof. In one aspect, an AAV ITR nucleic acid sequence comprises a sequence at least 99.8% identical to SEQ ID NO: 1, or the complement thereof. In one aspect, an AAV ITR nucleic acid sequence comprises a sequence at least 99.9% identical to SEQ ID NO: 1, or the complement thereof. In one aspect, an AAV ITR nucleic acid sequence comprises a sequence 100% identical to SEQ ID NO: 1, or the complement thereof.

In an aspect, an AAV ITR nucleic acid sequence comprises a sequence at least 70% identical to SEQ ID NO: 9, or the complement thereof. In one aspect, an AAV ITR nucleic acid sequence comprises a sequence at least 75% identical to SEQ ID NO: 9, or the complement thereof. In one aspect, an AAV ITR nucleic acid sequence comprises a sequence at least 80% identical to SEQ ID NO: 9, or the complement thereof. In one aspect, an AAV ITR nucleic acid sequence comprises a sequence at least 85% identical to SEQ ID NO: 9, or the complement thereof. In one aspect, an AAV ITR nucleic acid sequence comprises a sequence at least 90% identical to SEQ ID NO: 9, or the complement thereof. In one aspect, an AAV ITR nucleic acid sequence comprises a sequence at least 91% identical to SEQ ID NO: 9, or the complement thereof. In one aspect, an AAV ITR nucleic acid sequence comprises a sequence at least 92% identical to SEQ ID NO: 9, or the complement thereof. In one aspect, an AAV ITR nucleic acid sequence comprises a sequence at least 93% identical to SEQ ID NO: 9, or the complement thereof. In one aspect, an AAV ITR nucleic acid sequence comprises a sequence at least 94% identical to SEQ ID NO: 9, or the complement thereof. In one aspect, an AAV ITR nucleic acid sequence comprises a sequence at least 95% identical to SEQ ID NO: 9, or the complement thereof. In one aspect, an AAV ITR nucleic acid sequence comprises a sequence at least 96% identical to SEQ ID NO: 9, or the complement thereof. In one aspect, an AAV ITR nucleic acid sequence comprises a sequence at least 97% identical to SEQ ID NO: 9, or the complement thereof. In one aspect, an AAV ITR nucleic acid sequence comprises a sequence at least 98% identical to SEQ ID NO: 9, or the complement thereof. In one aspect, an AAV ITR nucleic acid sequence comprises a sequence at least 99% identical to SEQ ID NO: 9, or the complement thereof. In one aspect, an AAV ITR nucleic acid sequence comprises a sequence at least 99.5% identical to SEQ ID NO: 9, or the complement thereof. In one aspect, an AAV ITR nucleic acid sequence comprises a sequence at least 99.8% identical to SEQ ID NO: 9, or the complement thereof. In one aspect, an AAV ITR nucleic acid sequence comprises a sequence at least 99.9% identical to SEQ ID NO: 9, or the complement thereof. In one aspect, an AAV ITR nucleic acid sequence comprises a sequence 100% identical to SEQ ID NO: 9, or the complement thereof.

The terms "percent identity" or "percent identical" as used herein in reference to two or more nucleotide or amino acid sequences is calculated by (i) comparing two optimally aligned sequences (nucleotide or amino acid) over a window of comparison (the "alignable" region or regions), (ii) determining the number of positions at which the identical nucleic acid base (for nucleotide sequences) or amino acid residue (for proteins and polypeptides) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

When percentage of sequence identity is used in reference to amino acids it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

For optimal alignment of sequences to calculate their percent identity, various pair-wise or multiple sequence alignment algorithms and programs are known in the art, such as ClustalW or Basic Local Alignment Search Tool® (BLAST™), etc., that can be used to compare the sequence identity or similarity between two or more nucleotide or amino acid sequences. Although other alignment and comparison methods are known in the art, the alignment and percent identity between two sequences (including the percent identity ranges described above) can be as determined by the ClustalW algorithm, see, e.g., Chenna et al., "Multiple sequence alignment with the Clustal series of programs," *Nucleic Acids Research* 31: 3497-3500 (2003); Thompson et al., "Clustal W: Improving the sensitivity of progressive multiple sequence alignment through sequence weighting, position-specific gap penalties and weight matrix choice," *Nucleic Acids Research* 22: 4673-4680 (1994); Larkin M A et al., "Clustal W and Clustal X version 2.0," *Bioinformatics* 23: 2947-48 (2007); and Altschul et al. "Basic local alignment search tool." *J. Mol. Biol.* 215:403-410 (1990), the entire contents and disclosures of which are incorporated herein by reference.

The terms "percent complementarity" or "percent complementary" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

The use of the term "polynucleotide," "nucleic acid sequence," or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In one aspect, a nucleic acid molecule provided herein is an RNA molecule. In one aspect, a nucleic acid molecule provided herein is single-stranded. In one aspect, a nucleic acid molecule provided herein is double-stranded. A nucleic acid molecule can encode a polypeptide or a small RNA.

As used herein, the term "polypeptide" refers to a chain of at least two covalently linked amino acids. Polypeptides can be encoded by polynucleotides provided herein. Proteins provided herein can be encoded by nucleic acid molecules provided herein. Proteins can comprise polypeptides provided herein. As used herein, a "protein" refers to a chain of amino acid residues that is capable of providing structure or enzymatic activity to a cell. As used herein, a "coding sequence" refers to a nucleic acid sequence that encodes a protein.

As used herein, the term "CpG site" or "CG site" refers to a region of DNA sequence where a cytosine and guanine is separated by only one phosphate group.

As used herein, the term "CpG island" of "CG island" refers to CpG sites that occur with a high frequency.

As used herein, the term "codon" refers to a sequence of three nucleotides.

As used herein, the term "codon optimized" refers to a code that is modified for enhanced expression in a host cell of interest by replacing at least one codon of a sequence with codons that are more frequently or most frequently used in the genes of the host cell while maintaining the original amino acid sequence.

As used herein, the term "enhancer" refers to a region of DNA sequence that operates to initiate, assist, affect, cause, and/or promote the transcription and expression of the associated transcribable DNA sequence or coding sequence, at least in certain tissue(s), developmental stage(s) and/or condition(s). In an aspect, an enhancer is a cis enhancer. In one aspect, an enhancer is a trans enhancer.

Enhancer sequences can be identified by utilizing genomic techniques well known in the art. Non-limiting examples include use of a reporter gene and next-generation sequencing methods such as chromatin immunoprecipitation sequencing (ChIP-seq), DNase I hypersensitivity sequencing (DNase-seq), micrococcal nuclease sequencing (MNase-seq), formaldehyde-assisted isolation of regulatory elements sequencing (FAIRE-seq), and assay for transposase accessible chromatin sequencing (ATAC-seq).

As used herein, the term "operably linked" refers to a functional linkage between a promoter or other regulatory element and an associated transcribable DNA sequence or coding sequence of a gene (or transgene), such that the promoter, etc., operates to initiate, assist, affect, cause, and/or promote the transcription and expression of the associated transcribable DNA sequence or coding sequence, at least in certain tissue(s), developmental stage(s) and/or condition(s). As used herein, "regulatory elements" refer to any sequence elements that regulate, positively or negatively, the expression of an operably linked sequence. "Regulatory elements" include, without being limiting, a promoter, an enhancer, a leader, a transcription start site (TSS), a linker, 5' and 3' untranslated regions (UTRs), an intron, a polyadenylation signal, and a termination region or sequence, etc., that are suitable, necessary or preferred for regulating or allowing expression of the gene or transcribable DNA sequence in a cell. Such additional regulatory element(s) can be optional and used to enhance or optimize expression of the gene or transcribable DNA sequence.

As used herein, the term "promoter" refers to a DNA sequence that contains an RNA polymerase binding site, a transcription start site, and/or a TATA box and assists or promotes the transcription and expression of an associated transcribable polynucleotide sequence and/or gene (or transgene). A promoter can be synthetically produced, varied, or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein.

As used herein, an "intron" refers to a nucleotide sequence that is removed by RNA splicing as a messenger RNA (mRNA) matures from a mRNA precursor.

As used herein, "mRNA" or "messenger RNA" refers to a single stranded RNA that corresponds to the genetic sequence of a gene.

Expression of mRNA can be measured using any suitable method known in the art. Non-limiting examples of measuring mRNA expression include quantitative reverse transcriptase polymerase chain reaction (qRT-PCR), RNA blot (e.g., a Northern blot), and RNA sequencing. Differences in expression can be described as an absolute quantification or a relative quantification. See, for example, Livak and Schmittgen, *Methods,* 25:402-408 (2001).

As used herein, "genome editing" or "gene editing" refers to targeted mutagenesis, insertion, deletion, inversion, substitution, or translocation of a nucleotide sequence of interest in a genome using a targeted editing technique. A nucleotide sequence of interest can be of any length, for example, at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides. Non-limiting examples of gene editing techniques are small interference RNA (siRNA) technology, small hairpin RNA (shRNA) technology, microRNA (miRNA) technology, antisense oligonucleotides (ASO) technology, or CRISPR/CAS technology.

As used herein, a "ASO" or "antisense oligonucleotide" is a small, single stranded nucleic acid that bind to their target RNA sequence inside the cells and silence genes.

As used herein, a "coding region," a "gene region," or a "gene" refers to a polynucleotide that can produce a functional unit. Non-limiting examples include a protein, or a non-coding RNA molecule. A "coding region," "gene," or "gene region" can comprise a promoter, an enhancer sequence, a leader sequence, a transcriptional start site, a transcriptional stop site, a polyadenylation site, one or more exons, one or more introns, a 5'-UTR, a 3'-UTR, or any combination thereof.

In an aspect, gene editing targets mutant Huntingtin (Htt) aggregates. In one aspect gene editing is by non-coding RNA molecules. Non-limiting examples of a non-coding RNA molecule include a microRNA (miRNA), a miRNA precursor (pre-miRNA), a small interfering RNA (siRNA), a small RNA (18-26 nucleotides in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single-guide RNA (sgRNA). In one aspect, a shRNA targets a Htt gene. In one aspect, a siRNA targets a Htt gene. In one aspect, an ASO targets a Htt gene. In one aspect, miRNA targets a Htt gene. In one aspect, a gRNA targets a Htt gene. In one aspect, a pre-miRNA targets a Htt gene. In one aspect, a small RNA targets a Htt gene.

In one aspect, a hc-siRNA targets a Htt gene. In one aspect, a piRNA targets a Htt gene. In one aspect, a hairpin dsRNA targets a Htt gene. In one aspect, a ta-siRNA targets a Htt gene. In one aspect, a nat-siRNA targets a Htt gene. In one aspect, a crRNA targets a Htt gene. In one aspect, a tracrRNA targets a Htt gene. In one aspect, a sgRNA targets a Htt gene. In one aspect, a shRNA comprises a nucleic acid sequence selected from the group consisting of SEQ ID NOs: 23 to 25. In one aspect, a shRNA comprises a nucleic acid sequence SEQ ID NO: 23. In one aspect, a shRNA comprises a nucleic acid sequence SEQ ID NO: 24. In one aspect, a shRNA comprises a nucleic acid sequence SEQ ID NO: 25.

As used herein a "donor molecule" or "donor sequence" is defined as a nucleic acid sequence that has been selected for site directed, targeted insertion into a genome. In an aspect, a donor molecule comprises a "donor sequence." In one aspect, a targeted editing technique provided herein comprises the use of one or more, two or more, three or more, four or more, or five or more donor molecules or donor sequences. A donor molecule or donor sequence provided herein can be of any length. For example, a donor molecule or donor sequence provided herein is between 2 and 50,000, between 2 and 10,000, between 2 and 5000, between 2 and 1000, between 2 and 500, between 2 and 250, between 2 and 100, between 2 and 50, between 2 and 30, between and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000 or between 20 and 10,000 nucleotides in length.

As used here "HTT" refers to an Htt specific guide RNA (gRNA) and/or a donor sequence.

In an aspect, this disclosure provides, and includes, a composition comprising an adeno-associated virus (AAV) vector where the AAV vector comprises a Cas9 nuclease gene, an Htt specific gRNA, and a donor sequence. In an aspect, this disclosure provides, and includes, a composition comprising an adeno-associated virus (AAV) vector where the AAV vector comprises a Cas9 nuclease gene, an Htt specific gRNA, a donor sequence, and a Dlx2 gene sequence. In an aspect, this disclosure provides, and includes, a composition comprising an adeno-associated virus (AAV) vector where the AAV vector comprises a Cas9 nuclease gene, an Htt specific shRNA, and a donor sequence. In an aspect, this disclosure provides, and includes, a composition comprising an adeno-associated virus (AAV) vector where the AAV vector comprises a Cas9 nuclease gene, an Htt specific shRNA, a donor sequence, and a Dlx2 gene sequence.

Site-specific nucleases provided herein can be used as part of a targeted editing technique. Non-limiting examples of site-specific nucleases include meganucleases, zinc finger nucleases (ZFNs), transcription activator-like effector nucleases (TALENs), RNA-guided nucleases (e.g., Cas9 and Cpf1), a recombinase (without being limiting, for example, a serine recombinase attached to a DNA recognition motif, a tyrosine recombinase attached to a DNA recognition motif), a transposase (without being limiting, for example, a DNA transposase attached to a DNA binding domain), or any combination thereof.

Site-specific nucleases, such as meganucleases, ZFNs, TALENs, Argonaute proteins (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, or modified versions thereof), Cas9 nucleases (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof), induce a double-strand DNA break at the target site of a genomic sequence that is then repaired by the natural processes. Sequence modifications then occur at the cleaved sites, which can include inversions, deletions, or insertions that result in gene disruption or integration of nucleic acid sequences. In an aspect, an RNA-guided nuclease provided herein is selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof In an aspect, a targeted editing technique described herein comprises the use of a RNA-guided nuclease.

While not being limited by any particular scientific theory, CRISPR/CAS nucleases are part of the adaptive immune system of bacteria and archaea, protecting them against invading nucleic acids such as viruses by cleaving target DNA in a sequence-dependent manner. The immunity is acquired by the integration of short fragments of the invading DNA, known as spacers, between ~20 nucleotide long CRISPR repeats at the proximal end of a CRISPR locus (a CRISPR array). A well described Cas protein is the Cas9 nuclease (also known as Csn1), which is part of the Class 2, type II CRISPR/Cas system in *Streptococcus pyogenes*. See Makarova et al. Nature Reviews Microbiology (2015) doi: 10.1038/nrmicro3569. Cas9 comprises an RuvC-like nuclease domain at its amino terminus and an HNH-like nuclease domain positioned in the middle of the protein. Cas9 proteins also contain a PAM-interacting (PI) domain, a recognition lobe (REC), and a BH domain. The Cpf1 nuclease, another type II system, acts in a similar manner to Cas9, but Cpf1 does not require a tracrRNA. See Cong et al. *Science* (2013) 339: 819-823; Zetsche et al., *Cell* (2015) doi: 10.1016/j.cell.2015.09.038; U.S. Patent Publication No. 2014/0068797; U.S. Patent Publication No. 2014/0273235; U.S. Patent Publication No. 2015/0067922; U.S. Pat. Nos. 8,697,359; 8,771,945; 8,795,965; 8,865,406; 8,871,445; 8,889,356; 8,889,418; 8,895,308; and 8,906,616, each of which is herein incorporated by reference in its entirety.

As used herein, the term "glial" or "glial cell" refers to a non-neuronal cell in the CNS or the PNS. In an aspect, at least one glial cell is selected from the group consisting of at least one oligodendrocyte, at least one astrocyte, at least one NG2 cell, at least one ependymal cell, and at least one microglia. In one aspect, at least one glial cell is at least one oligodendrocyte. In one aspect, at least one glial cell is at least one NG2 cell. In one aspect, at least one glial cell is at least one ependymal cell. In one aspect, at least one glial cell is at least one microglia. In one aspect, at least one glial cell is at least one reactive astrocyte. In one aspect, at least one astrocyte is at least one reactive astrocyte.

As used herein, the term "astrocyte" refers to a glial cell that is an important component of the brain. An astrocyte is involved in supporting neuronal functions such as synapse formation and plasticity, potassium buffering, nutrient supply, the secretion and absorption of neural or glial transmitters, and maintenance of the blood-brain barrier. As used herein, the term “reactive astrocytes” refers to an abnormal status of astrocytes after injury or disease.

As used herein, the term “NG2 cell” or “polydendrocyte” refers to a glial cell that expresses chondroitin sulfate proteoglycan (CSPG4) and the alpha receptor for platelet-derived growth factor (PDGFRA).

As used herein, the term “neuron” or “neuronal cell” refers to an electrically excitable cell that communicates with other neurons via synapses. In an aspect, a neuron is selected from the group consisting of an unipolar neuron, a bipolar neuron, a pseudounipolar neuron, and a multipolar neuron. In one aspect, a neuron is an unipolar neuron. In one aspect, a neuron is a bipolar neuron. In one aspect, a neuron is a pseudounipolar neuron. In one aspect, a neuron is a bipolar neuron. In one aspect, a neuron is selected from the group consisting of a sensory neuron, a motor neuron, and an interneuron. In one aspect, a neuron is a sensory neuron. In one aspect, a neuron is a motor neuron. In one aspect, a neuron is an interneuron.

As used herein, the term “functional neuron” refers to a neuron that can perform biological process. Without being limiting, examples of biological processes include processing and transmission of information and communication via chemical and electrical synapses.

As used herein, the term “glutamatergic neurons” refers to a subclass of neurons that produce glutamate and establish excitatory synapses. As used herein, the term “excitatory synapse” refers to a synapse in which an action potential in a presynaptic neuron increases the probability of an action potential occurring in a postsynaptic cell. As used herein, the term “action potential” or “nerve impulse” refers to an electrical impulse across the membrane of an axon. As used herein, the term “axon” or “nerve fiber” refers to a neuron that conducts action potentials. As used herein, the term “GABAergic neurons” refers to a subset of neurons that produce GABA and establish inhibitory synapses. As used herein, the term “GABA” or “gamma-Aminobutyric acid” refers to a compound that opens ion channels to allow the flow of negatively charged chloride ions into the cell or positively charged potassium ions out of the cell. As used herein, the term “inhibitory synapse” refers to a synapse that moves the membrane potential of a postsynaptic neuron away from the threshold for generating action potentials. As used herein, the term “dopaminergic neuron” refers to a subset of neurons that produce dopamine. As used herein, the term “dopamine” refers to a neurotransmitter. As used herein, the term “neurotransmitter” refers to endogenous chemicals that activate neurotransmissions. As used herein, the term “neurotransmission” refers to a process where neurotransmitters are released by the axon terminal of a neuron. As used herein, the term “acetyl cholinergic neuron” or “cholinergic neuron” refers to a subset of neurons that secrete acetylcholine. As used herein, the term “acetylcholine” refers to neurotransmitter. As used herein, the term “seratonergic neuron” refers to a subset of neurons that synthesizes serotonin. As used herein, the term “serotonin” refers to a neurotransmitter. As used herein, a “epinephrinergic neuron” refers to refers to a neuron that releases epinephrine as the neurotransmitter. As used herein, the term “motor neuron” refers to a subset of neurons where the cell body is located in the motor cortex, brainstem, or the spinal cord and the axon projects to the spinal cord or outside the spinal cord and directly or indirectly controls muscles and glands. As used herein, the term peptidergic neuron refers to a subset of neurons that utilize small peptide molecules as their neurotransmitter.

In an aspect, a neuron is a functional neuron. In one aspect, a functional neuron is selected from the group consisting of glutamatergic neurons, GABAergic neurons, dopaminergic neurons, cholinergic neurons, seratonergic neurons, epinephrinergic neurons, motor neurons, and peptidergic neurons. In one aspect, a functional neuron is a glutamatergic neuron. In one aspect, a functional neuron is a GABAergic neuron. In one aspect, a functional neuron is a dopaminergic neuron. In one aspect, a functional neuron is a cholinergic neuron. In one aspect, a functional neuron is a seratonergic neuron. In one aspect, a functional neuron is an epinephrinergic neuron. In one aspect, a functional neuron is a motor neuron. In one aspect, a functional neuron is a peptidergic neuron.

As used herein, the term “converting” or “converted” refers to a cell type changing its physical morphology and/or biological function into a different physical morphology and/or different biological function. In an aspect, this disclosure provides the conversion of at least one glial cell into at least one neuron. In one aspect, conversion of at least one glial cell to at least one neuron occurs in the CNS or PNS. In one aspect, conversion of at least one glial cell to at least one neuron occurs in the CNS. In one aspect, conversion of at least one glial cell to at least one neuron occurs in the PNS.

In one aspect, this disclosure provides, and includes, an adeno-associated virus (AAV) vector comprising a human neurogenic differentiation 1 (hNeuroD1) sequence comprising the nucleic acid sequence of SEQ ID NO: 6 and a human distal-less homeobox 2 (hDlx2) sequence comprising the nucleic acid sequence of SEQ ID NO: 13, where the hNeuroD1 sequence and the hDlx2 sequence are separated by (i) a P2A linker comprising the nucleic acid sequence selected from the group consisting of SEQ ID NO: 15 and 18 (ii) a T2A linker comprising the nucleic acid sequence selected from the group consisting of SEQ ID NO: 16 and 19, (iii) or an internal ribosomal entry site of the encephalomyocarditis virus (IRES) sequence comprising SEQ ID NO: 3, where the hNeuroD1 sequence and the hDlx2 sequence are operably linked to regulatory elements comprising: (a) glial fibrillary acidic protein (GFAP) promoter comprising a nucleic acid sequence selected from the group consisting of SEQ ID NOs: 4, 12, and 26; (b) an enhancer from a human elongation factor-1 alpha (EF1-α) promoter comprising the nucleic acid sequence of SEQ ID NO: 2 or a cytomegalovirus (CMV) enhancer comprising the nucleic acid sequence of SEQ ID NO: 11; (c) chimeric intron comprising the nucleic acid sequence selected from the group consisting of SEQ ID NOs: 5 and 27; (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

In one aspect, this disclosure provides, and includes, an adeno-associated virus (AAV) vector comprising a nucleic acid sequence encoding a human neurogenic differentiation 1 (hNeuroD1) protein comprising the amino acid coding sequence of SEQ ID NO: 10 and a nucleic acid coding sequence encoding a human distal-less homeobox 2 (hDlx2) protein comprising the amino acid sequence of SEQ ID NO:

14, where the hNeuroD1 coding sequence and the hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, where the hNeuroD1 coding sequence and the hDlx2 coding sequence is operably linked to regulatory elements comprising: (a) a glial fibrillary acidic protein (GFAP) promoter comprising a nucleic acid sequence selected from the group consisting of SEQ ID NOs: 4, 12, and 28; (b) an enhancer from a human elongation factor-1 alpha (EF1-α) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence selected from the group consisting of SEQ ID NOs: 5 and 27; (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

In an aspect, this disclosure provides, and includes, an adeno-associated virus (AAV) vector comprising a neurogenic differentiation 1 (NeuroD1) nucleic acid coding sequence encoding a NeuroD1 protein and a distal-less homeobox 2 (Dlx2) nucleic acid coding sequence encoding a Dlx2 protein, where the NeuroD1 coding sequence and the Dlx2 coding sequence are separated by a linker sequence, where the NeuroD1 coding sequence and the Dlx2 coding sequence are operably linked to regulatory elements comprising: (a) a glial fibrillary acidic protein (GFAP) promoter; (b) an enhancer; (c) a chimeric intron; (d) a woodchuck hepatitis virus posttranscriptional regulatory element (WPRE); and (e) a polyadenylation signal sequence.

In an aspect, this disclosure provides, and includes, a composition comprising an adeno-associated virus (AAV) vector for converting glial cells to functional neurons in a human, where the AAV vector comprises a human neurogenic differentiation 1 (hNeuroD1) sequence having a nucleic acid sequence of SEQ ID NO: 6 and a human distal-less homeobox 2 (hDlx2) sequence having a nucleic acid sequence of SEQ ID NO: 13, where the hNeuroD1 sequence and the hDlx2 sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, (iii) or an internal ribosomal entry site of the encephalomyocarditis virus (IRES) sequence comprising SEQ ID NO: 3, where the hNeuroD1 sequence and hDlx2 sequence are operably linked to regulatory elements comprising: (a) a human glial fibrillary acidic protein (GFAP) promoter comprising a nucleic acid sequence selected from the group consisting of SEQ ID NOs: 4, 12, and 26; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence selected from the group consisting of SEQ ID NOs: 5 and 27; (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

In an aspect, this disclosure provides, and includes, a composition comprising an adeno-associated-virus (AAV) vector for converting glial cells to functional neurons in a human, where the AAV vector comprises a nucleic acid coding sequence encoding a human neurogenic differentiation 1 (hNeuroD1) protein comprising the amino acid sequence of SEQ ID NO: 10 and a nucleic acid coding sequence encoding a human distal-less homeobox 2 (hDlx2) protein comprising the amino acid sequence of SEQ ID NO: 14, where the hNeuroD1 coding sequence and the hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, (iii) or an internal ribosomal entry site of the encephalomyocarditis virus (IRES) sequence comprising SEQ ID NO: 3, where the hNeuroD1 coding sequence and the hDlx2 coding sequence are operably linked to regulatory elements comprising: (a) a human glial fibrillary acidic protein (GFAP) promoter comprising a nucleic acid sequence selected from the group consisting of SEQ ID NOs: 4, 12, and 26; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence selected from the group consisting of SEQ ID NOs: 5 and 27; (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

In an aspect, this disclosure provides, and includes, a composition comprising an adeno-associated virus (AAV) vector for the treatment of a subject in need thereof, where the AAV vector comprises a neurogenic differentiation 1 (NeuroD1) sequence and a distal-less homeobox 2 (Dlx2) sequence, where the NeuroD1 sequence and the Dlx2 sequence are separated by a linker sequence, where the NeuroD1 sequence and Dlx2 sequence are operably linked to expression control elements comprising: (a) a glial fibrillary acidic protein (GFAP) promoter; (b) an enhancer; (c) a chimeric intron; (d) a woodchuck hepatitis virus posttranscriptional regulatory element (WPRE); and (e) a polyadenylation signal.

In an aspect, an AAV vector comprises a nucleic acid sequence encoding an AAV protein. In one aspect, an AAV vector comprises a nucleic acid sequence encoding a viral protein. Non-limiting examples of AAV proteins and viral proteins include rep and cap proteins.

Neurogenic differentiation 1 (NeuroD1; also referred to as 02) is a basic helix-loop-helix (bHLH) transcription factor that forms heterodimers with other bHLH proteins to activate transcription of genes that contain a DNA sequence known as an E-box.

In an aspect, a NeuroD1 sequence is a human NeuroD1 (hNeuroD1) sequence. In one aspect, a NeuroD1 sequence is selected from the group consisting of a chimpanzee NeuroD1 sequence, a bonobo NeuroD1 sequence, an orangutan NeuroD1 sequence, a gorilla NeuroD1 sequence, a macaque NeuroD1 sequence, a marmoset NeuroD1 sequence, a capuchin NeuroD1 sequence, a baboon NeuroD1 sequence, a gibbon NeuroD1 sequence, and a lemur NeuroD1 sequence. In one aspect, a NeuroD1 sequence is a chimpanzee NeuroD1 sequence. In one aspect, a NeuroD1 sequence is a bonobo NeuroD1 sequence. In one aspect, a NeuroD1 sequence is an orangutan NeuroD1 sequence. In one aspect, a NeuroD1 sequence is a gorilla NeuroD1 sequence. In one aspect, a NeuroD1 sequence is a macaque NeuroD1 sequence. In one aspect, a NeuroD1 sequence is a marmoset NeuroD1 sequence. In one aspect, a NeuroD1 sequence is a capuchin NeuroD1 sequence. In one aspect, a NeuroD1 sequence is a baboon NeuroD1 sequence. In one aspect, a NeuroD1 sequence is a gibbon NeuroD1 sequence. In one aspect, a NeuroD1 sequence is a lemur NeuroD1 sequence.

In an aspect, a NeuroD1 nucleic acid sequence comprises a sequence at least 70% identical to SEQ ID NO: 6, or the complement thereof. In one aspect, a NeuroD1 nucleic acid sequence comprises a sequence at least 75% identical to SEQ ID NO: 6, or the complement thereof. In one aspect, a NeuroD1 nucleic acid sequence comprises a sequence at least 80% identical to SEQ ID NO: 6, or the complement thereof. In one aspect, a NeuroD1 nucleic acid sequence comprises a sequence at least 85% identical to SEQ ID NO: 6, or the complement thereof. In one aspect, a NeuroD1 nucleic acid sequence comprises a sequence at least 90% identical to SEQ ID NO: 6, or the complement thereof. In one aspect, a NeuroD1 nucleic acid sequence comprises a sequence at least 91% identical to SEQ ID NO: 6, or the complement thereof. In one aspect, a NeuroD1 nucleic acid sequence comprises a sequence at least 92% identical to SEQ ID NO: 6, or the complement thereof. In one aspect, a NeuroD1 nucleic acid sequence comprises a sequence at least 93% identical to SEQ ID NO: 6, or the complement thereof. In one aspect, a NeuroD1 nucleic acid sequence comprises a sequence at least 94% identical to SEQ ID NO: 6, or the complement thereof. In one aspect, a NeuroD1 nucleic acid sequence comprises a sequence at least 95% identical to SEQ ID NO: 6, or the complement thereof. In one aspect, a NeuroD1 nucleic acid sequence comprises a sequence at least 96% identical to SEQ ID NO: 6, or the complement thereof. In one aspect, a NeuroD1 nucleic acid sequence comprises a sequence at least 97% identical to SEQ ID NO: 6, or the complement thereof. In one aspect, a NeuroD1 nucleic acid sequence comprises a sequence at least 98% identical to SEQ ID NO: 6, or the complement thereof. In one aspect, a NeuroD1 nucleic acid sequence comprises a sequence at least 99% identical to SEQ ID NO: 6, or the complement thereof. In one aspect, a NeuroD1 nucleic acid sequence comprises a sequence at least 99.5% identical to SEQ ID NO: 6, or the complement thereof. In one aspect, a NeuroD1 nucleic acid sequence comprises a sequence at least 99.8% identical to SEQ ID NO: 6, or the complement thereof. In one aspect, a NeuroD1 nucleic acid sequence comprises a sequence at least 99.9% identical to SEQ ID NO: 6, or the complement thereof. In one aspect, a NeuroD1 nucleic acid sequence comprises a sequence 100% identical to SEQ ID NO: 6, or the complement thereof.

In an aspect, a nucleic acid coding sequence encodes a NeuroD1 protein comprising an amino acid sequence at least 70% identical or similar to SEQ ID NO: 10. In one aspect, a nucleic acid coding sequence encodes a NeuroD1 protein comprising an amino acid sequence at least 75% identical or similar to SEQ ID NO: 10. In one aspect, a nucleic acid coding sequence encodes a NeuroD1 protein comprising an amino acid sequence at least 80% identical or similar to SEQ ID NO: 10. In one aspect, a nucleic acid coding sequence encodes a NeuroD1 protein comprising an amino acid sequence at least 85% identical or similar to SEQ ID NO: 10. In one aspect, a nucleic acid coding sequence encodes a NeuroD1 protein comprising an amino acid sequence at least 90% identical or similar to SEQ ID NO: 10. In one aspect, a nucleic acid coding sequence encodes a NeuroD1 protein comprising an amino acid sequence at least 91% identical or similar to SEQ ID NO: 10. In one aspect, a nucleic acid coding sequence encodes a NeuroD1 protein comprising an amino acid sequence at least 92% identical or similar to SEQ ID NO: 10. In one aspect, a nucleic acid coding sequence encodes a NeuroD1 protein comprising an amino acid sequence at least 93% identical or similar to SEQ ID NO: 10. In one aspect, a nucleic acid coding sequence encodes a NeuroD1 protein comprising an amino acid sequence at least 94% identical or similar to SEQ ID NO: 10. In one aspect, a nucleic acid coding sequence encodes a NeuroD1 protein comprising an amino acid sequence at least 95% identical or similar to SEQ ID NO: 10. In one aspect, a nucleic acid coding sequence encodes a NeuroD1 protein comprising an amino acid sequence at least 96% identical or similar to SEQ ID NO: 10. In one aspect, a nucleic acid coding sequence encodes a NeuroD1 protein comprising an amino acid sequence at least 97% identical or similar to SEQ ID NO: 10. In one aspect, a nucleic acid coding sequence encodes a NeuroD1 protein comprising an amino acid sequence at least 98% identical or similar to SEQ ID NO: 10. In one aspect, a nucleic acid coding sequence encodes a NeuroD1 protein comprising an amino acid sequence at least 99% identical or similar to SEQ ID NO: 10. In one aspect, a nucleic acid coding sequence encodes a NeuroD1 protein comprising an amino acid sequence at least 99.5% identical or similar to SEQ ID NO: 10. In one aspect, a nucleic acid coding sequence encodes a NeuroD1 protein comprising an amino acid sequence at least 99.8% identical or similar to SEQ ID NO: 10. In one aspect, a nucleic acid coding sequence encodes a NeuroD1 protein comprising an amino acid sequence at least 99.9% identical or similar to SEQ ID NO: 10. In one aspect, a nucleic acid coding sequence encodes a NeuroD1 protein comprising an amino acid sequence 100% identical or similar to SEQ ID NO: 10.

Distal-less homeobox 2 (Dlx2; also referred to as TES1) is a member of the Dlx gene family and is a homeobox containing gene that plays a role in forebrain and craniofacial development.

In an aspect, a Dlx2 sequence is a human Dlx2 (hDlx2) sequence. In one aspect, a Dlx2 sequence is selected from the group consisting of a chimpanzee Dlx2 sequence, a bonobo Dlx2 sequence, an orangutan Dlx2 sequence, a gorilla Dlx2 sequence, a macaque Dlx2 sequence, a marmoset Dlx2 sequence, a capuchin Dlx2 sequence, a baboon Dlx2 sequence, a gibbon Dlx2 sequence, and a lemur Dlx2 sequence. In one aspect, a Dlx2 sequence is a chimpanzee Dlx2 sequence. In one aspect, a Dlx2 sequence is a bonobo Dlx2 sequence. In one aspect, a Dlx2 sequence is an orangutan Dlx2 sequence. In one aspect, a Dlx2 sequence is a gorilla Dlx2 sequence. In one aspect, a Dlx2 sequence is a macaque Dlx2 sequence. In one aspect, a Dlx2 sequence is a marmoset Dlx2 sequence. In one aspect, a Dlx2 sequence is a capuchin Dlx2 sequence. In one aspect, a Dlx2 sequence is a baboon Dlx2 sequence. In one aspect, a Dlx2 sequence is a gibbon Dlx2 sequence. In one aspect, a Dlx2 sequence is a lemur Dlx2 sequence.

In an aspect, a Dlx2 nucleic acid sequence comprises a sequence at least 70% identical to SEQ ID NO: 13, or the complement thereof. In one aspect, a Dlx2 nucleic acid sequence comprises a sequence at least 75% identical to SEQ ID NO: 13, or the complement thereof. In one aspect, a Dlx2 nucleic acid sequence comprises a sequence at least 80% identical to SEQ ID NO: 13, or the complement thereof. In one aspect, a Dlx2 nucleic acid sequence comprises a sequence at least 85% identical to SEQ ID NO: 13, or the complement thereof. In one aspect, a Dlx2 nucleic acid sequence comprises a sequence at least 90% identical to SEQ ID NO: 13, or the complement thereof. In one aspect, a Dlx2 nucleic acid sequence comprises a sequence at least 91% identical to SEQ ID NO: 13, or the complement thereof. In one aspect, a Dlx2 nucleic acid sequence comprises a sequence at least 92% identical to SEQ ID NO: 13, or the complement thereof. In one aspect, a Dlx2 nucleic acid sequence comprises a sequence at least 93% identical to SEQ ID NO: 13, or the complement thereof. In one aspect, a Dlx2 nucleic acid sequence comprises a sequence at least 94% identical to SEQ ID NO: 13, or the complement thereof. In one aspect, a Dlx2 nucleic acid sequence comprises a sequence at least 95% identical to SEQ ID NO: 13, or the complement thereof. In one aspect, a Dlx2 nucleic acid sequence comprises a sequence at least 913% identical to SEQ ID NO: 13, or the complement thereof. In one aspect, a Dlx2 nucleic acid sequence comprises a sequence at least 97% identical to SEQ ID NO: 13, or the complement thereof. In one aspect, a Dlx2 nucleic acid sequence comprises a sequence at least 98% identical to SEQ ID NO: 13, or the complement thereof. In one aspect, a Dlx2 nucleic acid sequence comprises a sequence at least 99% identical to SEQ ID NO: 13, or the complement thereof. In one aspect, a Dlx2 nucleic acid sequence comprises a sequence at least 99.5% identical to SEQ ID NO: 13, or the complement thereof. In one aspect, a Dlx2 nucleic acid sequence comprises a sequence at least 99.8% identical to SEQ ID NO: 13, or the complement thereof. In one aspect, a Dlx2 nucleic acid sequence comprises a sequence at least 99.9% identical to SEQ ID NO: 13, or the complement thereof. In one aspect, a Dlx2 nucleic acid sequence comprises a sequence 100% identical to SEQ ID NO: 13, or the complement thereof.

In an aspect, a nucleic acid coding sequence encodes a Dlx2 protein comprising an amino acid sequence at least 70% identical or similar to SEQ ID NO: 14. In one aspect, a nucleic acid coding sequence encodes a Dlx2 protein comprising an amino acid sequence at least 75% identical or similar to SEQ ID NO: 14. In one aspect, a nucleic acid coding sequence encodes a Dlx2 protein comprising an amino acid sequence at least 80% identical or similar to SEQ ID NO: 14. In one aspect, a nucleic acid coding sequence encodes a Dlx2 protein comprising an amino acid sequence at least 85% identical or similar to SEQ ID NO: 14. In one aspect, a nucleic acid coding sequence encodes a Dlx2 protein comprising an amino acid sequence at least 90% identical or similar to SEQ ID NO: 14. In one aspect, a nucleic acid coding sequence encodes a Dlx2 protein comprising an amino acid sequence at least 91% identical or similar to SEQ ID NO: 14. In one aspect, a nucleic acid coding sequence encodes a Dlx2 protein comprising an amino acid sequence at least 92% identical or similar to SEQ ID NO: 14. In one aspect, a nucleic acid coding sequence encodes a Dlx2 protein comprising an amino acid sequence at least 93% identical or similar to SEQ ID NO: 14. In one aspect, a nucleic acid coding sequence encodes a Dlx2 protein comprising an amino acid sequence at least 94% identical or similar to SEQ ID NO: 14. In one aspect, a nucleic acid coding sequence encodes a Dlx2 protein comprising an amino acid sequence at least 95% identical or similar to SEQ ID NO: 14. In one aspect, a nucleic acid coding sequence encodes a Dlx2 protein comprising an amino acid sequence at least 96% identical or similar to SEQ ID NO: 14. In one aspect, a nucleic acid coding sequence encodes a Dlx2 protein comprising an amino acid sequence at least 97% identical or similar to SEQ ID NO: 14. In one aspect, a nucleic acid coding sequence encodes a Dlx2 protein comprising an amino acid sequence at least 98% identical or similar to SEQ ID NO: 14. In one aspect, a nucleic acid coding sequence encodes a Dlx2 protein comprising an amino acid sequence at least 99% identical or similar to SEQ ID NO: 14. In one aspect, a nucleic acid coding sequence encodes a Dlx2 protein comprising an amino acid sequence at least 99.5% identical or similar to SEQ ID NO: 14. In one aspect, a nucleic acid coding sequence encodes a Dlx2 protein comprising an amino acid sequence at least 99.8% identical or similar to SEQ ID NO: 14. In one aspect, a nucleic acid coding sequence encodes a Dlx2 protein comprising an amino acid sequence at least 99.9% identical or similar to SEQ ID NO: 14. In one aspect, a nucleic acid coding sequence encodes a Dlx2 protein comprising an amino acid sequence 100% identical or similar to SEQ ID NO: 14.

In an aspect, an AAV vector comprises a NeuroD1 sequence and a Dlx2 sequence. In one aspect, an AAV vector comprises a NeuroD1 sequence. In one aspect, an AAV comprises a Dlx2 sequence.

As used herein, "linkers" or "spacers" are short sequences that separate multiple protein and coding domains. Linkers can be cleavable or non-cleavable and facilitate multigene co-expression in single vectors.

As used herein, "2A self-cleaving peptides" or "2A peptides" are a class of linkers that can induce the cleaving of recombinant protein in a cell.

As used herein, "P2A linker," "p2A," or "P2A" refer to the porcine teschovirus-1 (P2A) linker, which is a member of the 2A self-cleaving peptides.

In one aspect a P2A linker has a nucleic acid sequence selected from the group consisting of SEQ ID NO: 15 and 18. In one aspect, a P2A linker has a nucleic acid sequence of SEQ ID NO: 15. In one aspect, a P2A linker has a nucleic acid sequence of SEQ ID NO: 18. In one aspect, a P2A is SEQ ID NO: 15. In one aspect, a GSG-P2A is SEQ ID NO: 18. In one aspect, a P2A linker has a nucleic acid sequence of SEQ ID NO: 18. In one aspect, a P2A linker protein has a nucleic acid coding sequence of SEQ ID NO: 20.

As used herein, "T2A linker" refers to those asigna virus 2A (T2A) linker, which is a member of the 2A self-cleaving peptides.

In one aspect, a T2A linker has a nucleic acid sequence selected from the group consisting of SEQ ID NO: 16 and 19. In one aspect, a T2A linker has a nucleic acid sequence of SEQ ID NO: 16. In one aspect, a T2A linker has a nucleic acid sequence of SEQ ID NO: 19. In one aspect, a T2A linker protein has a nucleic acid coding sequence of SEQ ID NO: 21

As used herein, "E2A linker" refers to equine rhinitis A virus (E2A) linker, which is a member of the 2A self-cleaving peptides.

As used herein, "F2A linker" refers to foot and mouse disease virus (F2A) linker, which is a member of the 2A self-cleaving peptides.

In an aspect, a linker is selected from the group consisting of a P2A linker, a T2A linker, a E2A linker, and a F2A linker. In one aspect, a linker is a P2A linker. In one aspect, a linker is a T2A linker. In one aspect, a linker is a E2A linker. In one aspect, a linker is a F2A linker.

In an aspect, a linker sequence comprises a P2A linker. In one aspect, a P2A linker nucleic acid sequence comprises a sequence at least 70% identical to SEQ ID NO: 15, or the complement thereof. In one aspect, a P2A linker nucleic acid sequence comprises a sequence at least 75% identical to SEQ ID NO: 15, or the complement thereof. In one aspect, a P2A linker nucleic acid sequence comprises a sequence at least 80% identical to SEQ ID NO: 15, or the complement thereof. In one aspect, a P2A linker nucleic acid sequence comprises a sequence at least 85% identical to SEQ ID NO: 15, or the complement thereof. In one aspect, a P2A linker nucleic acid sequence comprises a sequence at least 90% identical to SEQ ID NO: 15, or the complement thereof. In one aspect, a P2A linker nucleic acid sequence comprises a sequence at least 91% identical to SEQ ID NO: 15, or the complement thereof. In one aspect, a P2A linker nucleic acid sequence comprises a sequence at least 92% identical to SEQ ID NO: 15, or the complement thereof. In one aspect, a P2A linker nucleic acid sequence comprises a sequence at least 93% identical to SEQ ID NO: 15, or the complement thereof. In one aspect, a P2A linker nucleic acid sequence comprises a sequence at least 94% identical to SEQ ID NO: 15, or the complement thereof. In one aspect, a P2A linker nucleic acid sequence comprises a sequence at least 95% identical to SEQ ID NO: 15, or the complement thereof. In one aspect, a P2A linker nucleic acid sequence comprises a sequence at least 96% identical to SEQ ID NO: 15, or the complement thereof. In one aspect, a P2A linker nucleic acid sequence comprises a sequence at least 97% identical to SEQ ID NO: 15, or the complement thereof. In one aspect, a P2A linker nucleic acid sequence comprises a sequence at least 98% identical to SEQ ID NO: 15, or the complement thereof. In one aspect, a P2A linker nucleic acid sequence comprises a sequence at least 99% identical to SEQ ID NO: 15, or the complement thereof. In one aspect, a P2A linker nucleic acid sequence comprises a sequence at least 99.5% identical to SEQ ID NO: 15, or the complement thereof. In one aspect, a P2A linker nucleic acid sequence comprises a sequence at least 99.8% identical to SEQ ID NO: 15, or the complement thereof. In one aspect, a P2A linker nucleic acid sequence comprises a sequence at least 99.9% identical to SEQ ID NO: 15, or the complement thereof. In one aspect, a P2A linker nucleic acid sequence comprises a sequence 100% identical to SEQ ID NO: 15, or the complement thereof.

In an aspect, a linker sequence comprises a P2A linker. In one aspect, a P2A linker nucleic acid sequence comprises a sequence at least 70% identical to SEQ ID NO: 18, or the complement thereof. In one aspect, a P2A linker nucleic acid sequence comprises a sequence at least 75% identical to SEQ ID NO: 18, or the complement thereof. In one aspect, a P2A linker nucleic acid sequence comprises a sequence at least 80% identical to SEQ ID NO: 18, or the complement thereof. In one aspect, a P2A linker nucleic acid sequence comprises a sequence at least 85% identical to SEQ ID NO: 18, or the complement thereof. In one aspect, a P2A linker nucleic acid sequence comprises a sequence at least 90% identical to SEQ ID NO: 18, or the complement thereof. In one aspect, a P2A linker nucleic acid sequence comprises a sequence at least 91% identical to SEQ ID NO: 18, or the complement thereof. In one aspect, a P2A linker nucleic acid sequence comprises a sequence at least 92% identical to SEQ ID NO: 18, or the complement thereof. In one aspect, a P2A linker nucleic acid sequence comprises a sequence at least 93% identical to SEQ ID NO: 18, or the complement thereof. In one aspect, a P2A linker nucleic acid sequence comprises a sequence at least 94% identical to SEQ ID NO: 18, or the complement thereof. In one aspect, a P2A linker nucleic acid sequence comprises a sequence at least 95% identical to SEQ ID NO: 18, or the complement thereof. In one aspect, a P2A linker nucleic acid sequence comprises a sequence at least 96% identical to SEQ ID NO: 18, or the complement thereof. In one aspect, a P2A linker nucleic acid sequence comprises a sequence at least 97% identical to SEQ ID NO: 18, or the complement thereof. In one aspect, a P2A linker nucleic acid sequence comprises a sequence at least 98% identical to SEQ ID NO: 18, or the complement thereof. In one aspect, a P2A linker nucleic acid sequence comprises a sequence at least 99% identical to SEQ ID NO: 18, or the complement thereof. In one aspect, a P2A linker nucleic acid sequence comprises a sequence at least 99.5% identical to SEQ ID NO: 18, or the complement thereof. In one aspect, a P2A linker nucleic acid sequence comprises a sequence at least 99.8% identical to SEQ ID NO: 18, or the complement thereof. In one aspect, a P2A linker nucleic acid sequence comprises a sequence at least 99.9% identical to SEQ ID NO: 18, or the complement thereof. In one aspect, a P2A linker nucleic acid sequence comprises a sequence 100% identical to SEQ ID NO: 18, or the complement thereof.

In an aspect, a nucleic acid coding sequence encodes a P2A protein comprising an amino acid sequence at least 70% identical or similar to SEQ ID NO: 20. In one aspect, a nucleic acid coding sequence encodes a P2A protein comprising an amino acid sequence at least 75% identical or similar to SEQ ID NO: 20. In one aspect, a nucleic acid coding sequence encodes a P2A protein comprising an amino acid sequence at least 80% identical or similar to SEQ ID NO: 20. In one aspect, a nucleic acid coding sequence encodes a P2A protein comprising an amino acid sequence at least 85% identical or similar to SEQ ID NO: 20. In one aspect, a nucleic acid coding sequence encodes a P2A protein comprising an amino acid sequence at least 90% identical or similar to SEQ ID NO: 20. In one aspect, a nucleic acid coding sequence encodes a P2A protein comprising an amino acid sequence at least 91% identical or similar to SEQ ID NO: 20. In one aspect, a nucleic acid coding sequence encodes a P2A protein comprising an amino acid sequence at least 92% identical or similar to SEQ ID NO: 20. In one aspect, a nucleic acid coding sequence encodes a P2A protein comprising an amino acid sequence at least 93% identical or similar to SEQ ID NO: 20. In one aspect, a nucleic acid coding sequence encodes a P2A protein comprising an amino acid sequence at least 94% identical or similar to SEQ ID NO: 20. In one aspect, a nucleic acid coding sequence encodes a P2A protein comprising an amino acid sequence at least 95% identical or similar to SEQ ID NO: 20. In one aspect, a nucleic acid coding sequence encodes a P2A protein comprising an amino acid sequence at least 96% identical or similar to SEQ ID NO: 20. In one aspect, a nucleic acid coding sequence encodes a P2A protein comprising an amino acid sequence at least 97% identical or similar to SEQ ID NO: 20. In one aspect, a nucleic acid coding sequence encodes a P2A protein comprising an amino acid sequence at least 98% identical or similar to SEQ ID NO: 20. In one aspect, a nucleic acid coding sequence encodes a P2A protein comprising an amino acid sequence at least 99% identical or similar to SEQ ID NO: 20. In one aspect, a nucleic acid coding sequence encodes a P2A protein comprising an amino acid sequence at least 99.5% identical or similar to SEQ ID NO: 20. In one aspect, a nucleic acid coding sequence encodes a P2A protein comprising an amino acid sequence at least 99.8% identical or similar to SEQ ID NO: 20. In one aspect, a nucleic acid coding sequence encodes a P2A protein comprising an amino acid sequence at least 99.9% identical or similar to SEQ ID NO: 20. In one aspect, a nucleic acid coding sequence encodes a P2A protein comprising an amino acid sequence 100% identical or similar to SEQ ID NO: 20.

In an aspect, a linker sequence comprises a T2A linker. In one aspect, a T2A linker nucleic acid sequence comprises a sequence at least 70% identical to SEQ ID NO: 16, or the complement thereof. In one aspect, a T2A linker nucleic acid sequence comprises a sequence at least 75% identical to SEQ ID NO: 16, or the complement thereof. In one aspect, a T2A linker nucleic acid sequence comprises a sequence at least 80% identical to SEQ ID NO: 16, or the complement thereof. In one aspect, a T2A linker nucleic acid sequence comprises a sequence at least 85% identical to SEQ ID NO: 16, or the complement thereof. In one aspect, a T2A linker nucleic acid sequence comprises a sequence at least 90% identical to SEQ ID NO: 16, or the complement thereof. In one aspect, a T2A linker nucleic acid sequence comprises a sequence at least 91% identical to SEQ ID NO: 16, or the complement thereof. In one aspect, a T2A linker nucleic acid sequence comprises a sequence at least 92% identical to SEQ ID NO: 16, or the complement thereof. In one aspect, a T2A linker nucleic acid sequence comprises a sequence at least 93% identical to SEQ ID NO: 16, or the complement thereof. In one aspect, a T2A linker nucleic acid sequence comprises a sequence at least 94% identical to SEQ ID NO: 16, or the complement thereof. In one aspect, a T2A linker nucleic acid sequence comprises a sequence at least 95% identical to SEQ ID NO: 16, or the complement thereof. In one aspect, a T2A linker nucleic acid sequence comprises a sequence at least 96% identical to SEQ ID NO: 16, or the complement thereof. In one aspect, a T2A linker nucleic acid sequence comprises a sequence at least 97% identical to SEQ ID NO: 16, or the complement thereof. In one aspect, a T2A linker nucleic acid sequence comprises a sequence at least 98% identical to SEQ ID NO: 16, or the complement thereof. In one aspect, a T2A linker nucleic acid sequence comprises a sequence at least 99% identical to SEQ ID NO: 16, or the complement thereof. In one aspect, a T2A linker nucleic acid sequence comprises a sequence at least 99.5% identical to SEQ ID NO: 16, or the complement thereof. In one aspect, a T2A linker nucleic acid sequence comprises a sequence at least 99.8% identical to SEQ ID NO: 16, or the complement thereof. In one aspect, a T2A linker nucleic acid sequence comprises a sequence at least 99.9% identical to SEQ ID NO: 16, or the complement thereof. In one aspect, a T2A linker nucleic acid sequence comprises a sequence 100% identical to SEQ ID NO: 16, or the complement thereof.

In an aspect, a linker sequence comprises a T2A linker. In one aspect, a T2A linker nucleic acid sequence comprises a sequence at least 70% identical to SEQ ID NO: 19, or the complement thereof. In one aspect, a T2A linker nucleic acid sequence comprises a sequence at least 75% identical to SEQ ID NO: 19, or the complement thereof. In one aspect, a T2A linker nucleic acid sequence comprises a sequence at least 80% identical to SEQ ID NO: 19, or the complement thereof. In one aspect, a T2A linker nucleic acid sequence comprises a sequence at least 85% identical to SEQ ID NO: 19, or the complement thereof. In one aspect, a T2A linker nucleic acid sequence comprises a sequence at least 90% identical to SEQ ID NO: 19, or the complement thereof. In one aspect, a T2A linker nucleic acid sequence comprises a sequence at least 91% identical to SEQ ID NO: 19, or the complement thereof. In one aspect, a T2A linker nucleic acid sequence comprises a sequence at least 92% identical to SEQ ID NO: 19, or the complement thereof. In one aspect, a T2A linker nucleic acid sequence comprises a sequence at least 93% identical to SEQ ID NO: 19, or the complement thereof. In one aspect, a T2A linker nucleic acid sequence comprises a sequence at least 94% identical to SEQ ID NO: 19, or the complement thereof. In one aspect, a T2A linker nucleic acid sequence comprises a sequence at least 95% identical to SEQ ID NO: 19, or the complement thereof. In one aspect, a T2A linker nucleic acid sequence comprises a sequence at least 96% identical to SEQ ID NO: 19, or the complement thereof. In one aspect, a T2A linker nucleic acid sequence comprises a sequence at least 97% identical to SEQ ID NO: 19, or the complement thereof. In one aspect, a T2A linker nucleic acid sequence comprises a sequence at least 98% identical to SEQ ID NO: 19, or the complement thereof. In one aspect, a T2A linker nucleic acid sequence comprises a sequence at least 99% identical to SEQ ID NO: 19, or the complement thereof. In one aspect, a T2A linker nucleic acid sequence comprises a sequence at least 99.5% identical to SEQ ID NO: 19, or the complement thereof. In one aspect, a T2A linker nucleic acid sequence comprises a sequence at least 99.8% identical to SEQ ID NO: 19, or the complement thereof. In one aspect, a T2A linker nucleic acid sequence comprises a sequence at least 99.9% identical to SEQ ID NO: 19, or the complement thereof. In one aspect, a T2A linker nucleic acid sequence comprises a sequence 100% identical to SEQ ID NO: 19, or the complement thereof.

In an aspect, a nucleic acid coding sequence encodes a T2A protein comprising an amino acid sequence at least 70% identical or similar to SEQ ID NO: 21. In one aspect, a nucleic acid coding sequence encodes a T2A protein comprising an amino acid sequence at least 75% identical or similar to SEQ ID NO: 21. In one aspect, a nucleic acid coding sequence encodes a T2A protein comprising an amino acid sequence at least 80% identical or similar to SEQ ID NO: 21. In one aspect, a nucleic acid coding sequence encodes a T2A protein comprising an amino acid sequence at least 85% identical or similar to SEQ ID NO: 21. In one aspect, a nucleic acid coding sequence encodes a T2A protein comprising an amino acid sequence at least 90% identical or similar to SEQ ID NO: 21. In one aspect, a nucleic acid coding sequence encodes a T2A protein comprising an amino acid sequence at least 91% identical or similar to SEQ ID NO: 21. In one aspect, a nucleic acid coding sequence encodes a T2A protein comprising an amino acid sequence at least 92% identical or similar to SEQ ID NO: 21. In one aspect, a nucleic acid coding sequence encodes a T2A protein comprising an amino acid sequence at least 93% identical or similar to SEQ ID NO: 21. In one aspect, a nucleic acid coding sequence encodes a T2A protein comprising an amino acid sequence at least 94% identical or similar to SEQ ID NO: 21. In one aspect, a nucleic acid coding sequence encodes a T2A protein comprising an amino acid sequence at least 95% identical or similar to SEQ ID NO: 21. In one aspect, a nucleic acid coding sequence encodes a T2A protein comprising an amino acid sequence at least 96% identical or similar to SEQ ID NO: 21. In one aspect, a nucleic acid coding sequence encodes a T2A protein comprising an amino acid sequence at least 97% identical or similar to SEQ ID NO: 21. In one aspect, a nucleic acid coding sequence encodes a T2A protein comprising an amino acid sequence at least 98% identical or similar to SEQ ID NO: 21. In one aspect, a nucleic acid coding sequence encodes a T2A protein comprising an amino acid sequence at least 99% identical or similar to SEQ ID NO: 21. In one aspect, a nucleic acid coding sequence encodes a T2A protein comprising an amino acid sequence at least 99.5% identical or similar to SEQ ID NO: 21. In one aspect, a nucleic acid coding sequence encodes a T2A protein comprising an amino acid sequence at least 99.8% identical or similar to SEQ ID NO: 21. In one aspect, a nucleic acid coding sequence encodes a T2A protein comprising an amino acid sequence at least 99.9% identical or similar to SEQ ID NO: 21. In one aspect, a nucleic acid coding sequence encodes a T2A protein comprising an amino acid sequence 100% identical or similar to SEQ ID NO: 21.

As used herein “IRES” refers to an internal ribosomal entry site of the encephalomyocarditis virus (EMCV).

In one aspect, an AAV or vector of the present disclosure comprises an internal ribosomal entry site of the encephalomyocarditis virus (IRES) sequence. In one aspect, the IRES sequence comprises SEQ ID NO: 3. In one aspect, the IRES sequence comprises a sequence at least 70% identical to SEQ ID NO: 3, or the complement thereof. In one aspect, the IRES sequence comprises a sequence at least 75% identical to SEQ ID NO: 3, or the complement thereof. In one aspect, the IRES sequence comprises a sequence at least 80% identical to SEQ ID NO: 3, or the complement thereof. In one aspect, the IRES sequence comprises a sequence at least 85% identical to SEQ ID NO: 3, or the complement thereof. In one aspect, the IRES sequence comprises a sequence at least 90% identical to SEQ ID NO: 3, or the complement thereof. In one aspect, the IRES sequence comprises a sequence at least 91% identical to SEQ ID NO: 3, or the complement thereof. In one aspect, the IRES sequence comprises a sequence at least 92% identical to SEQ ID NO: 3, or the complement thereof. In one aspect, the IRES sequence comprises a sequence at least 93% identical to SEQ ID NO: 3, or the complement thereof. In one aspect, the IRES sequence comprises a sequence at least 94% identical to SEQ ID NO: 3, or the complement thereof. In one aspect, the IRES sequence comprises a sequence at least 95% identical to SEQ ID NO: 3, or the complement thereof. In one aspect, the IRES sequence comprises a sequence at least 96% identical to SEQ ID NO: 3, or the complement thereof. In one aspect, the IRES sequence comprises a sequence at least 97% identical to SEQ ID NO: 3, or the complement thereof. In one aspect, the IRES sequence comprises a sequence at least 98% identical to SEQ ID NO: 3, or the complement thereof. In one aspect, the IRES sequence comprises a sequence at least 99% identical to SEQ ID NO: 3, or the complement thereof. In one aspect, the IRES sequence comprises a sequence at least 99.5% identical to SEQ ID NO: 3, or the complement thereof. In one aspect, the IRES sequence comprises a sequence at least 99.8% identical to SEQ ID NO: 3, or the complement thereof. In one aspect, the IRES sequence comprises a sequence at least 99.9% identical to SEQ ID NO: 3, or the complement thereof. In one aspect, the IRES sequence comprises a sequence 100% identical to SEQ ID NO: 3, or the complement thereof.

Glial fibrillary acid protein (GFAP); also referred to as glial fibrillary acidic protein is a member of the type III intermediate filament family of proteins that is expressed in the central nervous system and plays a role in cell communication and the functioning of the blood-brain barrier.

In an aspect, the promoter is selected from the group consisting of GFAP promoter, Sox9 promoter, S100b promoter, Aldh1l1 promoter, Lipocalin 2 (Lcn2) promoter, glutamine synthetase promoter, Aquaporin-4 (AQP4) promoter, oligodendrocyte transcription factor (Olig2) promoter, and synapsin promoter, NG2 promoter, ionized calcium binding adaptor molecule 1 (Iba1) promoter, cluster of differentiation 86 (CD86) promoter, platelet-derived growth factor receptor alpha (PDGFRA) promoter, platelet-derived growth factor receptor beta (PDGFRB) promoter, elongation factor 1-alpha (EF1a) promoter, CAG promoter, cytomegalovirus (CMV) promoter, ubiquitin promoter. In one aspect, the promoter is GFAP promoter. In one aspect, the promoter is a truncated GFAP promoter. In one aspect, the promoter is Sox9 promoter. In one aspect, the promoter is S100b promoter. In one aspect, the promoter is Aldh1l1 promoter. In one aspect, the promoter is Lcn2 promoter. In one aspect, the promoter is glutamine synthetase promoter. In one aspect, the promoter is AQP4 promoter. In one aspect, the promoter is Olig2 promoter. In one aspect, the promoter is synapsin promoter. In one aspect, the promoter is Iba1 promoter. In one aspect, the promoter is CD86 promoter. In one aspect, the promoter is PDGFRA promoter. In one aspect, the promoter is PDGFRB promoter. In one aspect, the promoter is EF1a promoter. In one aspect, the promoter is CAG promoter. In one aspect, the promoter is CMV promoter. In one aspect, the promoter is ubiquitin promoter.

In an aspect, an ubiquitin promoter is selected from the group consisting of U6, H1, 7SK, and U1. In one aspect, an ubiquitin promoter is U6. In one aspect, an ubiquitin promoter is H1. In one aspect, an ubiquitin promoter is H1. In one aspect, an ubiquitin promoter is 7SK. In one aspect, an ubiquitin promoter is U1. In one aspect, U6 comprises the nucleic acid sequence of SEQ ID NO: 22.

In an aspect, a GFAP promoter is a promoter directing astrocyte-specific expression of a protein called glial fibrillary acidic protein (GFAP) in cells. In one aspect, a GFAP promoter sequence is a human GFAP (hGFAP) promoter sequence. In one aspect, a GFAP promoter is selected from the group consisting of GfaABC1D (also called “pGfa681”), Gfa1.6, and hGFA2.2. In one aspect, a GFAP promoter is GfaABC1D (also called “pGfa681”). In one aspect, a GFAP promoter is Gfa1.6. In one aspect, a GFAP promoter is hGFA2.2. In one aspect, pGfa681 is SEQ ID NO: 26. In one aspect, GFAP Gfa1.6 is SEQ ID NO: 4. In one aspect, hGFa2.2 is SEQ ID NO: 12. In one aspect, a GFAP promoter is selected from the group consisting of SEQ ID NOs: 4, 12, and 26. In one aspect, a GFAP promoter is SEQ ID NO: 4. In one aspect, a GFAP promoter is SEQ ID NO: 12. In one aspect, a GFAP promoter is SEQ ID NO: 26.

In one aspect, a GFAP promoter sequence is selected from the group consisting of a chimpanzee GFAP promoter sequence, a bonobo GFAP promoter sequence, an orangutan GFAP promoter sequence, a gorilla GFAP promoter sequence, a macaque GFAP promoter sequence, a marmoset GFAP promoter sequence, a capuchin GFAP promoter sequence, a baboon GFAP promoter sequence, a gibbon GFAP promoter sequence, and a lemur GFAP promoter sequence. In one aspect, a GFAP promoter sequence is a chimpanzee GFAP promoter sequence. In one aspect, a GFAP promoter sequence is a bonobo GFAP promoter sequence. In one aspect, a GFAP promoter sequence is an orangutan GFAP promoter sequence. In one aspect, a GFAP promoter sequence is a gorilla GFAP promoter sequence. In one aspect, a GFAP promoter sequence is a macaque GFAP promoter sequence. In one aspect, a GFAP promoter sequence is a marmoset GFAP promoter sequence. In one aspect, a GFAP promoter sequence is a capuchin GFAP promoter sequence. In one aspect, a GFAP promoter sequence is a baboon GFAP promoter sequence. In one aspect, a GFAP promoter sequence is a gibbon GFAP promoter sequence. In one aspect, a GFAP promoter sequence is a lemur GFAP promoter sequence.

In an aspect, a GFAP promoter sequence comprises at least 100 nucleotides. In one aspect, a GFAP promoter comprises at least 500 nucleotides. In a further aspect, a GFAP promoter comprises at least 1000 nucleotides. In still another aspect, a GFAP promoter comprises at least 1400 nucleotides.

It is appreciated in the art that a fragment of a promoter sequence can function to drive transcription of an operably linked nucleic acid molecule. For example, without being limiting, if a 1000 nucleotides promoter is truncated to 500 nucleotides, and the 500 nucleotides fragment is capable of driving transcription, the 500 nucleotides fragment is referred to as a "functional fragment."

In an aspect, a promoter comprises at least 10 nucleotides. In one aspect, a promoter comprises at least 50 nucleotides. In one aspect, a promoter comprises at least 100 nucleotides. In one aspect, an intron comprises at least 140 nucleotides. In one aspect, a promoter comprises at least 200 nucleotides. In one aspect, a promoter comprises at least 250 nucleotides. In one aspect, a promoter comprises at least 300 nucleotides. In one aspect, a promoter comprises at least 350 nucleotides. In one aspect, a promoter comprises at least 400 nucleotides. In one aspect, a promoter comprises at least 450 nucleotides. In one aspect, a promoter comprises at least 500 nucleotides. In one aspect, a promoter comprises between 50 nucleotides and 7500 nucleotides. In one aspect, a promoter comprises between 50 nucleotides and 5000 nucleotides. In one aspect, a promoter comprises between 50 nucleotides and 2500 nucleotides. In one aspect, a promoter comprises between 50 nucleotides and 1000 nucleotides. In one aspect, a promoter comprises between 50 nucleotides and 500 nucleotides. In one aspect, a promoter comprises between 10 nucleotides and 7500 nucleotides. In one aspect, a promoter comprises between 10 nucleotides and 5000 nucleotides. In one aspect, a promoter comprises between 10 nucleotides and 2500 nucleotides. In one aspect, a promoter comprises between 10 nucleotides and 1000 nucleotides. In one aspect, a promoter comprises between 10 nucleotides and 500 nucleotides In an aspect, a GFAP promoter nucleic acid sequence comprises a sequence at least 70% identical to a sequence selected from the group consisting of SEQ ID NO: 4, 12, 26, and functional fragment thereof. In one aspect, a GFAP promoter nucleic acid sequence comprises a sequence at least 75% identical to a sequence selected from the group consisting of SEQ ID NO: 4, 12, 26, and functional fragment thereof. In one aspect, a GFAP promoter nucleic acid sequence comprises a sequence at least 80% identical to a sequence selected from the group consisting of SEQ ID NO: 4, 12, 26, and functional fragment thereof. In one aspect, a GFAP promoter nucleic acid sequence comprises a sequence at least 85% identical to a sequence selected from the group consisting of SEQ ID NO: 4, 12, 26, and functional fragment thereof. In one aspect, a GFAP promoter nucleic acid sequence comprises a sequence at least 90% identical to a sequence selected from the group consisting of SEQ ID NO: 4, 12, 26, and functional fragment thereof. In one aspect, a GFAP promoter nucleic acid sequence comprises a sequence at least 91% identical to a sequence selected from the group consisting of SEQ ID NO: 4, 12, 26, and functional fragment thereof. In one aspect, a GFAP promoter nucleic acid sequence comprises a sequence at least 92% identical to a sequence selected from the group consisting of SEQ ID NO: 4, 12, 26, and functional fragment thereof. In one aspect, a GFAP promoter nucleic acid sequence comprises a sequence at least 93% identical to a sequence selected from the group consisting of SEQ ID NO: 4, 12, 26, and functional fragment thereof. In one aspect, a GFAP promoter nucleic acid sequence comprises a sequence at least 94% identical to a sequence selected from the group consisting of SEQ ID NO: 4, 12, 26, and functional fragment thereof. In one aspect, a GFAP promoter nucleic acid sequence comprises a sequence at least 95% identical to a sequence selected from the group consisting of SEQ ID NO: 4, 12, 26, and functional fragment thereof. In one aspect, a GFAP promoter nucleic acid sequence comprises a sequence at least 96% identical to a sequence selected from the group consisting of SEQ ID NO: 4, 12, 26, and functional fragment thereof. In one aspect, a GFAP promoter nucleic acid sequence comprises a sequence at least 97% identical to a sequence selected from the group consisting of SEQ ID NO: 4, 12, 26, and functional fragment thereof. In one aspect, a GFAP promoter nucleic acid sequence comprises a sequence at least 98% identical to a sequence selected from the group consisting of SEQ ID NO: 4, 12, 26, and functional fragment thereof. In one aspect, a GFAP promoter nucleic acid sequence comprises a sequence at least 99% identical to a sequence selected from the group consisting of SEQ ID NO: 4, 12, 26, and functional fragment thereof. In one aspect, a GFAP promoter nucleic acid sequence comprises a sequence at least 99.5% identical to a sequence selected from the group consisting of SEQ ID NO: 4, 12, 26, and functional fragment thereof. In one aspect, a GFAP promoter nucleic acid sequence comprises a sequence at least 99.8% identical to a sequence selected from the group consisting of SEQ ID NO: 4, 12, 26, and functional fragment thereof. In one aspect, a GFAP promoter nucleic acid sequence comprises a sequence at least 99.9% identical to a sequence selected from the group consisting of SEQ ID NO: 4, 12, 26, and functional fragment thereof. In one aspect, a GFAP promoter nucleic acid sequence comprises a sequence 100% identical to a sequence selected from the group consisting of SEQ ID NO: 4, 12, 26, and functional fragment thereof.

In an aspect, a nucleic acid sequence as provided herein is codon optimized.

In an aspect, a nucleic acid sequence as provided herein is CpG site depleted.

As used herein, the term "brain" refers to an organ that functions as the center of the nervous system. In an aspect, a brain comprises a cerebrum, a cerebral cortex, a cerebellum, and/or a brain stem.

As used herein, the term "cerebral cortex" refers to the outer layer of neural tissue of the cerebrum.

As used herein, the term "striatum" or "corpus striatum" refers to a cluster of neurons in the subcortical basal ganglia of the forebrain and comprises the ventral striatum and dorsal striatum.

As used herein, the term "substantia nigra" refers to a cluster of neurons in the subcortical basal ganglia of the midbrain and comprises the pars *compacta* and the pars *reticulata*.

As used herein, the term "forebrain" refers to the forward-most portion of the brain.

As used herein, the term "putamen" refers to a round structure at the base of the forebrain and is a component of the dorsal striatum.

As used herein, the term "caudate nucleus" refers to a structure at the base of the forebrain and is a component of the dorsal striatum.

As used herein, the term "subcortical basal ganglia" refers to a cluster of neurons in the deep cerebral hemispheres of the brain.

As used herein, the term "spinal cord" refers to a structure that functions in the transmission of nerve signals from the motor cortex to the body.

As used herein, the term "motor cortex" refers to a region in the frontal lobe of the cerebral cortex that is involved in the planning, control, and execution of voluntary movements.

In an aspect, a method provided herein converts reactive astrocytes to functional neurons in the brain. In one aspect, a method provided herein converts reactive astrocytes to functional neurons in a cerebral cortex of the brain. In one aspect, a method provided herein coverts reactive astrocytes to functional neurons in a striatum of the brain. In one aspect, a method provided herein converts reactive astrocytes to functional neurons in a dorsal striatum of the brain. In one aspect, a method provided herein converts reactive astrocytes to functional neurons in a spinal cord of the brain. In one aspect, a method provided herein converts reactive astrocytes to functional neurons in a putamen of the brain. In one aspect, a method provided herein converts reactive astrocytes to functional neurons in a caudate nucleus of the brain. In one aspect, a method provided herein converts reactive astrocytes to functional neurons in a substantia nigra of the brain.

Elongation factor-1 alpha (EF-1 alpha; also referred to as eEF1a1) is an isoform of the alpha subunit of the elongation factor 1 complex. The complex is involved in the enzymatic delivery of aminoacyl tRNAs to the ribosome. The EF-1 alpha isoform is expressed in the brain, placenta, lung, liver, kidney, and pancreas.

In an aspect, an enhancer sequence from the EF-1 alpha promoter is a human enhancer sequence from the EF-1 alpha promoter. In one aspect, an enhancer sequence from the EF-1 alpha promoter is selected form the group consisting of a chimpanzee enhancer sequence from the EF-1 alpha promoter, a bonobo enhancer sequence from the EF-1 alpha promoter, an orangutan enhancer sequence from the EF-1 alpha promoter, a gorilla enhancer sequence from the EF-1 alpha promoter, a macaque enhancer sequence from the EF-1 alpha promoter, a marmoset enhancer sequence from the EF-1 alpha promoter, a capuchin enhancer sequence from the EF-1 alpha promoter, a baboon enhancer sequence from the EF-1 alpha promoter, a gibbon enhancer sequence from the EF-1 alpha promoter, and a lemur enhancer sequence from the EF-1 alpha promoter. In one aspect, an enhancer sequence from the EF-1 alpha promoter is a chimpanzee an enhancer sequence from the EF-1 alpha promoter. In one aspect, an enhancer sequence from the EF-1 alpha promoter is a bonobo enhancer sequence from the EF-1 alpha promoter. In one aspect, an enhancer sequence from the EF-1 alpha promoter is an orangutan enhancer sequence from the EF-1 alpha promoter. In one aspect, an enhancer sequence from the EF-1 alpha promoter is a gorilla enhancer sequence from the EF-1 alpha promoter. In one aspect, an enhancer sequence from the EF-1 alpha promoter is a macaque enhancer sequence from the EF-1 alpha promoter. In one aspect, enhancer sequence from the EF-1 alpha promoter is a marmoset enhancer sequence from the EF-1 alpha promoter. In one aspect, enhancer sequence from the EF-1 alpha promoter is a capuchin enhancer sequence from the EF-1 alpha promoter. In one aspect, enhancer sequence from the EF-1 alpha promoter is a baboon enhancer sequence from the EF-1 alpha promoter. In one aspect, enhancer sequence from the EF-1 alpha promoter is a gibbon enhancer sequence from the EF-1 alpha promoter. In one aspect, enhancer sequence from the EF-1 alpha promoter is a lemur enhancer sequence from the EF-1 alpha promoter.

In an aspect, an enhancer from the EF-1 alpha promoter nucleic acid sequence comprises a sequence at least 70% identical to SEQ ID NO: 2, or the complement thereof. In one aspect, an enhancer from the EF-1 alpha promoter nucleic acid sequence comprises a sequence at least 75% identical to SEQ ID NO: 2, or the complement thereof. In one aspect, an enhancer from the EF-1 alpha promoter nucleic acid sequence comprises a sequence at least 80% identical to SEQ ID NO: 2, or the complement thereof. In one aspect, an enhancer from the EF-1 alpha promoter nucleic acid sequence comprises a sequence at least 85% identical to SEQ ID NO: 2, or the complement thereof. In one aspect, an enhancer from the EF-1 alpha promoter nucleic acid sequence comprises a sequence at least 90% identical to SEQ ID NO: 2, or the complement thereof. In one aspect, an enhancer from the EF-1 alpha promoter nucleic acid sequence comprises a sequence at least 91% identical to SEQ ID NO: 2, or the complement thereof. In one aspect, an enhancer from the EF-1 alpha promoter nucleic acid sequence comprises a sequence at least 92% identical to SEQ ID NO: 2, or the complement thereof. In one aspect, an enhancer from the EF-1 alpha promoter nucleic acid sequence comprises a sequence at least 93% identical to SEQ ID NO: 2, or the complement thereof. In one aspect, an enhancer from the EF-1 alpha promoter nucleic acid sequence comprises a sequence at least 94% identical to SEQ ID NO: 2, or the complement thereof. In one aspect, an enhancer from the EF-1 alpha promoter nucleic acid sequence comprises a sequence at least 95% identical to SEQ ID NO: 2, or the complement thereof. In one aspect, an enhancer from the EF-1 alpha promoter nucleic acid sequence comprises a sequence at least 96% identical to SEQ ID NO: 2, or the complement thereof. In one aspect, an enhancer from the EF-1 alpha promoter nucleic acid sequence comprises a sequence at least 97% identical to SEQ ID NO: 2, or the complement thereof. In one aspect, an enhancer from the EF-1 alpha promoter nucleic acid sequence comprises a sequence at least 98% identical to SEQ ID NO: 2, or the complement thereof. In one aspect, an enhancer from the EF-1 alpha promoter nucleic acid sequence comprises a sequence at least 99% identical to SEQ ID NO: 2, or the complement thereof. In one aspect, an enhancer from the EF-1 alpha promoter nucleic acid sequence comprises a sequence at least 99.5% identical to SEQ ID NO: 2, or the complement thereof. In one aspect, an enhancer from the EF-1 alpha promoter nucleic acid sequence comprises a sequence at least 99.8% identical to SEQ ID NO: 2, or the complement thereof. In one aspect, an enhancer from the EF-1 alpha promoter nucleic acid sequence comprises a sequence at least 99.9% identical to SEQ ID NO: 2, or the complement thereof. In one aspect, an enhancer from the EF-1 alpha promoter nucleic acid sequence comprises a sequence 100% identical to SEQ ID NO: 2, or the complement thereof.

Cytomegalovirus (CMV) is a genus of viruses in the order Herpesvirale.

In an aspect, an enhancer sequence from the CMV is a human enhancer sequence from the CMV. In one aspect, an enhancer sequence from the CMV is selected form the group consisting of a chimpanzee enhancer sequence from the CMV, a bonobo enhancer sequence from the CMV, an orangutan enhancer sequence from the CMV, a gorilla enhancer sequence from the CMV, a macaque enhancer sequence from the CMV, a marmoset enhancer sequence from the CMV, a capuchin enhancer sequence from the CMV, a baboon enhancer sequence from the CMV, a gibbon enhancer sequence from the CMV, and a lemur enhancer sequence from the CMV. In one aspect, an enhancer sequence from the CMV is a chimpanzee an enhancer sequence from the CMV. In one aspect, an enhancer sequence from the CMV is a bonobo enhancer sequence from the CMV. In one aspect, an enhancer sequence from the CMV is an orangutan enhancer sequence from the CMV. In one aspect, an enhancer sequence from the CMV is a gorilla enhancer sequence from the CMV. In one aspect, an enhancer sequence from the CMV is a macaque enhancer sequence from the CMV. In one aspect, enhancer sequence from the CMV is a marmoset enhancer sequence from the CMV. In one aspect, enhancer sequence from the CMV is a capuchin enhancer sequence from the CMV. In one aspect, enhancer sequence from the CMV is a baboon enhancer sequence from the CMV. In one aspect, enhancer sequence from the CMV is a gibbon enhancer sequence from the CMV. In one aspect, enhancer sequence from the CMV is a lemur enhancer sequence from the CMV.

In an aspect, an enhancer from the CMV nucleic acid sequence comprises a sequence at least 70% identical to SEQ ID NO: 11, or the complement thereof. In one aspect, an enhancer from the CMV nucleic acid sequence comprises a sequence at least 75% identical to SEQ ID NO: 11, or the complement thereof. In one aspect, an enhancer from the CMV nucleic acid sequence comprises a sequence at least 80% identical to SEQ ID NO: 11, or the complement thereof. In one aspect, an enhancer from the CMV nucleic acid sequence comprises a sequence at least 85% identical to SEQ ID NO: 11, or the complement thereof. In one aspect, an enhancer from the CMV nucleic acid sequence comprises a sequence at least 90% identical to SEQ ID NO: 11, or the complement thereof. In one aspect, an enhancer from the CMV nucleic acid sequence comprises a sequence at least 91% identical to SEQ ID NO: 11, or the complement thereof. In one aspect, an enhancer from the CMV nucleic acid sequence comprises a sequence at least 911% identical to SEQ ID NO: 11, or the complement thereof. In one aspect, an enhancer from the CMV nucleic acid sequence comprises a sequence at least 93% identical to SEQ ID NO: 11, or the complement thereof. In one aspect, an enhancer from the CMV nucleic acid sequence comprises a sequence at least 94% identical to SEQ ID NO: 11, or the complement thereof. In one aspect, an enhancer from the CMV nucleic acid sequence comprises a sequence at least 95% identical to SEQ ID NO: 11, or the complement thereof. In one aspect, an enhancer from the CMV nucleic acid sequence comprises a sequence at least 96% identical to SEQ ID NO: 11, or the complement thereof. In one aspect, an enhancer from the CMV nucleic acid sequence comprises a sequence at least 97% identical to SEQ ID NO: 11, or the complement thereof. In one aspect, an enhancer from the CMV nucleic acid sequence comprises a sequence at least 98% identical to SEQ ID NO: 11, or the complement thereof. In one aspect, an enhancer from the CMV nucleic acid sequence comprises a sequence at least 99% identical to SEQ ID NO: 11, or the complement thereof. In one aspect, an enhancer from the CMV nucleic acid sequence comprises a sequence at least 99.5% identical to SEQ ID NO: 11, or the complement thereof. In one aspect, an enhancer from the CMV nucleic acid sequence comprises a sequence at least 99.8% identical to SEQ ID NO: 11, or the complement thereof. In one aspect, an enhancer from the CMV nucleic acid sequence comprises a sequence at least 99.9% identical to SEQ ID NO: 11, or the complement thereof. In one aspect, an enhancer from the CMV nucleic acid sequence comprises a sequence 100% identical to SEQ ID NO: 11, or the complement thereof.

In an aspect, an enhancer is selected from the group consisting of an enhancer from EF1-α promoter and CMV enhancer. In one aspect, an enhancer is from EF1-α promoter. In one aspect, an enhancer is an CMV enhancer.

In an aspect, a vector of the present disclosures comprises a chimeric intron. In an aspect the chimeric intron is composed of the 5'-donor site from the first intron of the human β-globin gene and the branch and 3'-acceptor site from the intron of an immunoglobulin gene heavy chain variable region. In an aspect, the chimeric intron is a chimeric intron of a rabbit beta-globing and a chicken beta actin similar in CAG promoter. In an aspect, a vector of the present disclosure comprises a glial fibrillary acid protein (GFAP) intron. In an aspect, a vector of the present disclosure comprises a glial fibrillary acid protein (GFAP) first intron.

Introns can be grouped into at least five classes, including: spliceosomal introns; transfer RNA introns; group I introns; group II introns; and group III introns. An intron can be synthetically produced, varied, or derived from a known or naturally occurring intron sequence or other intron sequence. An intron can also include a chimeric intron comprising a combination of two or more heterologous sequences. An intron of the present application can thus include variants of intron sequences that are similar in composition, but not identical to, other intron sequence(s) known or provided herein. In an aspect, an intron comprises at least 10 nucleotides. In one aspect, an intron comprises at least 50 nucleotides. In one aspect, an intron comprises at least 100 nucleotides. In one aspect, an intron comprises at least 140 nucleotides. In one aspect, an intron comprises at least 200 nucleotides. In one aspect, an intron comprises at least 250 nucleotides. In one aspect, an intron comprises at least 300 nucleotides. In one aspect, an intron comprises at least 350 nucleotides. In one aspect, an intron comprises at least 400 nucleotides. In one aspect, an intron comprises at least 450 nucleotides. In one aspect, an intron comprises at least 500 nucleotides. In one aspect, an intron comprises between 50 nucleotides and 7500 nucleotides. In one aspect, an intron comprises between 50 nucleotides and 5000 nucleotides. In one aspect, an intron comprises between 50 nucleotides and 2500 nucleotides. In one aspect, an intron comprises between 50 nucleotides and 1000 nucleotides. In one aspect, an intron comprises between 50 nucleotides and 500 nucleotides. In one aspect, an intron comprises between 10 nucleotides and 7500 nucleotides. In one aspect, an intron comprises between 10 nucleotides and 5000 nucleotides. In one aspect, an intron comprises between 10 nucleotides and 2500 nucleotides. In one aspect, an intron comprises between 10 nucleotides and 1000 nucleotides. In one aspect, an intron comprises between 10 nucleotides and 500 nucleotides.

In an aspect, a chimeric intron nucleic acid sequence is selected from the group consisting of SEQ ID NOs: 5 and 27. In one aspect, a chimeric intron nucleic acid sequence is SEQ ID NO: 5. In one aspect, a chimeric intron nucleic acid sequence is SEQ ID NO: 27.

In an aspect, a chimeric intron nucleic acid sequence comprises a sequence at least 70% identical to SEQ ID NO: 5, or the complement thereof. In one aspect, a chimeric intron nucleic acid sequence comprises a sequence at least 75% identical to SEQ ID NO: 5, or the complement thereof. In one aspect, a chimeric intron nucleic acid sequence comprises a sequence at least 80% identical to SEQ ID NO:

5, or the complement thereof. In one aspect, a chimeric intron nucleic acid sequence comprises a sequence at least 85% identical to SEQ ID NO: 5, or the complement thereof. In one aspect, a chimeric intron nucleic acid sequence comprises a sequence at least 90% identical to SEQ ID NO: 5, or the complement thereof. In one aspect, a chimeric intron nucleic acid sequence comprises a sequence at least 91% identical to SEQ ID NO: 5, or the complement thereof. In one aspect, a chimeric intron nucleic acid sequence comprises a sequence at least 92% identical to SEQ ID NO: 5, or the complement thereof. In one aspect, a chimeric intron nucleic acid sequence comprises a sequence at least 93% identical to SEQ ID NO: 5, or the complement thereof. In one aspect, a chimeric intron nucleic acid sequence comprises a sequence at least 94% identical to SEQ ID NO: 5, or the complement thereof. In one aspect, a chimeric intron nucleic acid sequence comprises a sequence at least 95% identical to SEQ ID NO: 5, or the complement thereof. In one aspect, a chimeric intron nucleic acid sequence comprises a sequence at least 96% identical to SEQ ID NO: 5, or the complement thereof. In one aspect, a chimeric intron nucleic acid sequence comprises a sequence at least 97% identical to SEQ ID NO: 5, or the complement thereof. In one aspect, a chimeric intron nucleic acid sequence comprises a sequence at least 98% identical to SEQ ID NO: 5, or the complement thereof. In one aspect, a chimeric intron nucleic acid sequence comprises a sequence at least 99% identical to SEQ ID NO: 5, or the complement thereof. In one aspect, a chimeric intron nucleic acid sequence comprises a sequence at least 99.5% identical to SEQ ID NO: 5, or the complement thereof. In one aspect, a chimeric intron nucleic acid sequence comprises a sequence at least 99.8% identical to SEQ ID NO: 5, or the complement thereof. In one aspect, a chimeric intron nucleic acid sequence comprises a sequence at least 99.9% identical to SEQ ID NO: 5, or the complement thereof. In one aspect, a chimeric intron nucleic acid sequence comprises a sequence 100% identical to SEQ ID NO: 5, or the complement thereof.

In an aspect, a chimeric intron nucleic acid sequence comprises a sequence at least 70% identical to SEQ ID NO: 27, or the complement thereof. In one aspect, a chimeric intron nucleic acid sequence comprises a sequence at least 75% identical to SEQ ID NO: 27, or the complement thereof. In one aspect, a chimeric intron nucleic acid sequence comprises a sequence at least 80% identical to SEQ ID NO: 27, or the complement thereof. In one aspect, a chimeric intron nucleic acid sequence comprises a sequence at least 85% identical to SEQ ID NO: 27, or the complement thereof. In one aspect, a chimeric intron nucleic acid sequence comprises a sequence at least 90% identical to SEQ ID NO: 27, or the complement thereof. In one aspect, a chimeric intron nucleic acid sequence comprises a sequence at least 91% identical to SEQ ID NO: 27, or the complement thereof. In one aspect, a chimeric intron nucleic acid sequence comprises a sequence at least 92% identical to SEQ ID NO: 27, or the complement thereof. In one aspect, a chimeric intron nucleic acid sequence comprises a sequence at least 93% identical to SEQ ID NO: 27, or the complement thereof. In one aspect, a chimeric intron nucleic acid sequence comprises a sequence at least 94% identical to SEQ ID NO: 27, or the complement thereof. In one aspect, a chimeric intron nucleic acid sequence comprises a sequence at least 95% identical to SEQ ID NO: 27, or the complement thereof. In one aspect, a chimeric intron nucleic acid sequence comprises a sequence at least 96% identical to SEQ ID NO: 27, or the complement thereof. In one aspect, a chimeric intron nucleic acid sequence comprises a sequence at least 97% identical to SEQ ID NO: 27, or the complement thereof. In one aspect, a chimeric intron nucleic acid sequence comprises a sequence at least 98% identical to SEQ ID NO: 27, or the complement thereof. In one aspect, a chimeric intron nucleic acid sequence comprises a sequence at least 99% identical to SEQ ID NO: 27, or the complement thereof. In one aspect, a chimeric intron nucleic acid sequence comprises a sequence at least 99.5% identical to SEQ ID NO: 27, or the complement thereof. In one aspect, a chimeric intron nucleic acid sequence comprises a sequence at least 99.8% identical to SEQ ID NO: 27, or the complement thereof. In one aspect, a chimeric intron nucleic acid sequence comprises a sequence at least 99.9% identical to SEQ ID NO: 27, or the complement thereof. In one aspect, a chimeric intron nucleic acid sequence comprises a sequence 100% identical to SEQ ID NO: 27, or the complement thereof.

The woodchuck hepatitis virus posttranscriptional regulatory element (WPRE) is a DNA sequence that creates a tertiary structure enhancing expression of genes that are delivered in viral vectors.

In an aspect, a WPRE nucleic acid sequence is an optimized version of WPRE.

In an aspect, a WPRE nucleic acid sequence is selected from the group consisting of SEQ ID NOs: 7 and 29. In one aspect, a WPRE nucleic acid sequence is SEQ ID NO: 7. In one aspect, a WPRE nucleic acid sequence is SEQ ID NO: 29.

In an aspect, a WPRE nucleic acid sequence comprises a sequence at least 70% identical to SEQ ID NO: 7, or the complement thereof. In one aspect, a WPRE nucleic acid sequence comprises a sequence at least 75% identical to SEQ ID NO: 7, or the complement thereof. In one aspect, a WPRE nucleic acid sequence comprises a sequence at least 80% identical to SEQ ID NO: 7, or the complement thereof. In one aspect, a WPRE nucleic acid sequence comprises a sequence at least 85% identical to SEQ ID NO: 7, or the complement thereof. In one aspect, a WPRE nucleic acid sequence comprises a sequence at least 90% identical to SEQ ID NO: 7, or the complement thereof. In one aspect, a WPRE nucleic acid sequence comprises a sequence at least 91% identical to SEQ ID NO: 7, or the complement thereof. In one aspect, a WPRE nucleic acid sequence comprises a sequence at least 92% identical to SEQ ID NO: 7, or the complement thereof. In one aspect, a WPRE nucleic acid sequence comprises a sequence at least 93% identical to SEQ ID NO: 7, or the complement thereof. In one aspect, a WPRE nucleic acid sequence comprises a sequence at least 94% identical to SEQ ID NO: 7, or the complement thereof. In one aspect, a WPRE nucleic acid sequence comprises a sequence at least 95% identical to SEQ ID NO: 7, or the complement thereof. In one aspect, a WPRE nucleic acid sequence comprises a sequence at least 96% identical to SEQ ID NO: 7, or the complement thereof. In one aspect, a WPRE nucleic acid sequence comprises a sequence at least 97% identical to SEQ ID NO: 7, or the complement thereof. In one aspect, a WPRE nucleic acid sequence comprises a sequence at least 98% identical to SEQ ID NO: 7, or the complement thereof. In one aspect, a WPRE nucleic acid sequence comprises a sequence at least 99% identical to SEQ ID NO: 7, or the complement thereof. In one aspect, a WPRE nucleic acid sequence comprises a sequence at least 99.5% identical to SEQ ID NO: 7, or the complement thereof. In one aspect, a WPRE nucleic acid sequence comprises a sequence at least 99.8% identical to SEQ ID NO: 7, or the complement thereof. In one aspect, a WPRE nucleic acid sequence comprises a sequence at least 99.9% identical to SEQ ID NO: 7, or the complement thereof. In one aspect, a WPRE nucleic acid sequence comprises a sequence 100% identical to SEQ ID NO: 7, or the complement thereof.

In an aspect, a WPRE nucleic acid sequence comprises a sequence at least 70% identical to SEQ ID NO: 29, or the complement thereof. In one aspect, a WPRE nucleic acid sequence comprises a sequence at least 75% identical to SEQ ID NO: 29, or the complement thereof. In one aspect, a WPRE nucleic acid sequence comprises a sequence at least 80% identical to SEQ ID NO: 29, or the complement thereof. In one aspect, a WPRE nucleic acid sequence comprises a sequence at least 85% identical to SEQ ID NO: 29, or the complement thereof. In one aspect, a WPRE nucleic acid sequence comprises a sequence at least 90% identical to SEQ ID NO: 29, or the complement thereof. In one aspect, a WPRE nucleic acid sequence comprises a sequence at least 91% identical to SEQ ID NO: 29, or the complement thereof. In one aspect, a WPRE nucleic acid sequence comprises a sequence at least 92% identical to SEQ ID NO: 29, or the complement thereof. In one aspect, a WPRE nucleic acid sequence comprises a sequence at least 93% identical to SEQ ID NO: 29, or the complement thereof. In one aspect, a WPRE nucleic acid sequence comprises a sequence at least 94% identical to SEQ ID NO: 29, or the complement thereof. In one aspect, a WPRE nucleic acid sequence comprises a sequence at least 95% identical to SEQ ID NO: 29, or the complement thereof. In one aspect, a WPRE nucleic acid sequence comprises a sequence at least 96% identical to SEQ ID NO: 29, or the complement thereof. In one aspect, a WPRE nucleic acid sequence comprises a sequence at least 97% identical to SEQ ID NO: 29, or the complement thereof. In one aspect, a WPRE nucleic acid sequence comprises a sequence at least 98% identical to SEQ ID NO: 29, or the complement thereof. In one aspect, a WPRE nucleic acid sequence comprises a sequence at least 99% identical to SEQ ID NO: 29, or the complement thereof. In one aspect, a WPRE nucleic acid sequence comprises a sequence at least 99.5% identical to SEQ ID NO: 29, or the complement thereof. In one aspect, a WPRE nucleic acid sequence comprises a sequence at least 99.8% identical to SEQ ID NO: 29, or the complement thereof. In one aspect, a WPRE nucleic acid sequence comprises a sequence at least 99.9% identical to SEQ ID NO: 29, or the complement thereof. In one aspect, a WPRE nucleic acid sequence comprises a sequence 100% identical to SEQ ID NO: 29, or the complement thereof.

SV40 polyadenylation signal sequence (also refer as SV40 PolyA; Simian virus 40 PolyA; and PolyA) is a DNA sequence that can terminate transcription and add a PolyA tail to the 3' end of a messenger RNA (mRNA).

hGH polyadenylation signal sequence (also refer as hGH PolyA) is a DNA sequence that can terminate transcription and add a PolyA tail to the 3' end of a messenger RNA (mRNA).

bGH polyadenylation signal sequence (also refer as bGH PolyA or bGHpA) refers to a PolyA signal or PolyA tail of a bovine growth hormone.

As used herein, a “PolyA tail” refers to a stretch of RNA that only contains the nucleobase adenine. In an aspect, an RNA molecule transcribed from an AAV vector construct provided herein comprises a PolyA tail. In one aspect, a PolyA tail comprises at least two adenines. In one aspect, a PolyA tail comprises at least ten adenines. In one aspect, a PolyA tail comprises at least 50 adenines. In one aspect, a PolyA tail comprises at least 100 adenines. In one aspect, a PolyA tail comprises at least 140 adenines. In one aspect, a PolyA tail comprises at least 200 adenines. In one aspect, a PolyA tail comprises at least 250 adenines. In one aspect, a PolyA tail comprises between 50 adenines and 300 adenines.

In an aspect, a SV40 polyadenylation signal nucleic acid sequence comprises a sequence at least 70% identical to SEQ ID NO: 8, or the complement thereof. In one aspect, a SV40 polyadenylation signal nucleic acid sequence comprises a sequence at least 75% identical to SEQ ID NO: 8, or the complement thereof. In one aspect, a SV40 polyadenylation signal nucleic acid sequence comprises a sequence at least 80% identical to SEQ ID NO: 8, or the complement thereof. In one aspect, a SV40 polyadenylation signal nucleic acid sequence comprises a sequence at least 85% identical to SEQ ID NO: 8, or the complement thereof. In one aspect, a SV40 polyadenylation signal nucleic acid sequence comprises a sequence at least 90% identical to SEQ ID NO: 8, or the complement thereof. In one aspect, a SV40 polyadenylation signal nucleic acid sequence comprises a sequence at least 91% identical to SEQ ID NO: 8, or the complement thereof. In one aspect, a SV40 polyadenylation signal nucleic acid sequence comprises a sequence at least 92% identical to SEQ ID NO: 8, or the complement thereof. In one aspect, a SV40 polyadenylation signal nucleic acid sequence comprises a sequence at least 93% identical to SEQ ID NO: 8, or the complement thereof. In one aspect, a SV40 polyadenylation signal nucleic acid sequence comprises a sequence at least 94% identical to SEQ ID NO: 8, or the complement thereof. In one aspect, a SV40 polyadenylation signal nucleic acid sequence comprises a sequence at least 95% identical to SEQ ID NO: 8, or the complement thereof. In one aspect, a SV40 polyadenylation signal nucleic acid sequence comprises a sequence at least 96% identical to SEQ ID NO: 8, or the complement thereof. In one aspect, a SV40 polyadenylation signal nucleic acid sequence comprises a sequence at least 97% identical to SEQ ID NO: 8, or the complement thereof. In one aspect, a SV40 polyadenylation signal nucleic acid sequence comprises a sequence at least 98% identical to SEQ ID NO: 8, or the complement thereof. In one aspect, a SV40 polyadenylation signal nucleic acid sequence comprises a sequence at least 99% identical to SEQ ID NO: 8, or the complement thereof. In one aspect, a SV40 polyadenylation signal nucleic acid sequence comprises a sequence at least 99.5% identical to SEQ ID NO: 8, or the complement thereof. In one aspect, a SV40 polyadenylation signal nucleic acid sequence comprises a sequence at least 99.8% identical to SEQ ID NO: 8, or the complement thereof. In one aspect, a SV40 polyadenylation signal nucleic acid sequence comprises a sequence at least 99.9% identical to SEQ ID NO: 8, or the complement thereof. In one aspect, a SV40 polyadenylation signal nucleic acid sequence comprises a sequence 100% identical to SEQ ID NO: 8, or the complement thereof.

In an aspect, a hGH polyadenylation signal nucleic acid sequence comprises a sequence at least 70% identical to SEQ ID NO: 17, or the complement thereof. In one aspect, a hGH polyadenylation signal nucleic acid sequence comprises a sequence at least 75% identical to SEQ ID NO: 17, or the complement thereof. In one aspect, a hGH polyadenylation signal nucleic acid sequence comprises a sequence at least 80% identical to SEQ ID NO: 17, or the complement thereof. In one aspect, a hGH polyadenylation signal nucleic acid sequence comprises a sequence at least 85% identical to SEQ ID NO: 17, or the complement thereof. In one aspect, a hGH polyadenylation signal nucleic acid sequence comprises a sequence at least 90% identical to SEQ ID NO: 17, or the complement thereof. In one aspect, a hGH polyadenylation signal nucleic acid sequence comprises a sequence at least 91% identical to SEQ ID NO: 17, or the complement thereof. In one aspect, a hGH polyadenylation signal nucleic acid sequence comprises a sequence at least 92% identical to SEQ ID NO: 17, or the complement thereof. In one aspect, a hGH polyadenylation signal nucleic acid sequence comprises a sequence at least 93% identical to SEQ ID NO: 17, or the complement thereof. In one aspect, a hGH polyadenylation signal nucleic acid sequence comprises a sequence at least 94% identical to SEQ ID NO: 17, or the complement thereof. In one aspect, a hGH polyadenylation signal nucleic acid sequence comprises a sequence at least 95% identical to SEQ ID NO: 17, or the complement thereof. In one aspect, a hGH polyadenylation signal nucleic acid sequence comprises a sequence at least 96% identical to SEQ ID NO: 17, or the complement thereof. In one aspect, a hGH polyadenylation signal nucleic acid sequence comprises a sequence at least 97% identical to SEQ ID NO: 17, or the complement thereof. In one aspect, a hGH polyadenylation signal nucleic acid sequence comprises a sequence at least 917% identical to SEQ ID NO: 17, or the complement thereof. In one aspect, a hGH polyadenylation signal nucleic acid sequence comprises a sequence at least 99% identical to SEQ ID NO: 17, or the complement thereof. In one aspect, a hGH polyadenylation signal nucleic acid sequence comprises a sequence at least 99.5% identical to SEQ ID NO: 17, or the complement thereof. In one aspect, a hGH polyadenylation signal nucleic acid sequence comprises a sequence at least 99.17% identical to SEQ ID NO: 17, or the complement thereof. In one aspect, a hGH polyadenylation signal nucleic acid sequence comprises a sequence at least 99.9% identical to SEQ ID NO: 17, or the complement thereof. In one aspect, a hGH polyadenylation signal nucleic acid sequence comprises a sequence 100% identical to SEQ ID NO: 17, or the complement thereof In an aspect, a bGH polyadenylation signal nucleic acid sequence comprises a sequence at least 70% identical to SEQ ID NO: 30, or the complement thereof. In one aspect, a bGH polyadenylation signal nucleic acid sequence comprises a sequence at least 75% identical to SEQ ID NO: 30, or the complement thereof. In one aspect, a bGH polyadenylation signal nucleic acid sequence comprises a sequence at least 80% identical to SEQ ID NO: 30, or the complement thereof. In one aspect, a bGH polyadenylation signal nucleic acid sequence comprises a sequence at least 85% identical to SEQ ID NO: 30, or the complement thereof. In one aspect, a bGH polyadenylation signal nucleic acid sequence comprises a sequence at least 90% identical to SEQ ID NO: 30, or the complement thereof. In one aspect, a bGH polyadenylation signal nucleic acid sequence comprises a sequence at least 91% identical to SEQ ID NO: 30, or the complement thereof. In one aspect, a bGH polyadenylation signal nucleic acid sequence comprises a sequence at least 92% identical to SEQ ID NO: 30, or the complement thereof. In one aspect, a bGH polyadenylation signal nucleic acid sequence comprises a sequence at least 93% identical to SEQ ID NO: 30, or the complement thereof. In one aspect, a bGH polyadenylation signal nucleic acid sequence comprises a sequence at least 94% identical to SEQ ID NO: 30, or the complement thereof. In one aspect, a bGH polyadenylation signal nucleic acid sequence comprises a sequence at least 95% identical to SEQ ID NO: 30, or the complement thereof. In one aspect, a bGH polyadenylation signal nucleic acid sequence comprises a sequence at least 96% identical to SEQ ID NO: 30, or the complement thereof. In one aspect, a bGH polyadenylation signal nucleic acid sequence comprises a sequence at least 97% identical to SEQ ID NO: 30, or the complement thereof. In one aspect, a bGH polyadenylation signal nucleic acid sequence comprises a sequence at least 917% identical to SEQ ID NO: 30, or the complement thereof. In one aspect, a bGH polyadenylation signal nucleic acid sequence comprises a sequence at least 99% identical to SEQ ID NO: 30, or the complement thereof. In one aspect, a bGH polyadenylation signal nucleic acid sequence comprises a sequence at least 99.5% identical to SEQ ID NO: 30, or the complement thereof. In one aspect, a bGH polyadenylation signal nucleic acid sequence comprises a sequence at least 99.17% identical to SEQ ID NO: 30, or the complement thereof. In one aspect, a bGH polyadenylation signal nucleic acid sequence comprises a sequence at least 99.9% identical to SEQ ID NO: 30, or the complement thereof. In one aspect, a bGH polyadenylation signal nucleic acid sequence comprises a sequence 100% identical to SEQ ID NO: 30, or the complement thereof As used herein, the term "central nervous system" or "CNS" refers to the brain and spinal cord of a bilaterally symmetric animal. The CNS also includes the retina, the optic nerve, olfactory nerves, and olfactory epithelium.

As used herein, the term "peripheral nervous system" or "PNS" refers to nerves and ganglia outside of the brain and spinal cord, excluding the retina, the optic nerve, olfactory nerves, and olfactory epithelium. In an aspect, the peripheral nervous system is divided into the somatic nervous system and the autonomic nervous system.

As used herein, the term "somatic nervous system" refers to the parts of the PNS that are associated with voluntary control of body movements.

As used herein, the term "autonomic nervous system" refers to the parts of the PNS that regulate the function of internal organs As used herein, the term "GFAP positive" refers to a cell having detectable protein accumulation of human glial fibrillary acid protein (GFAP) or detectable accumulation of GFAP mRNA expression using techniques standard in the art. In one aspect, a glial cell is GFAP positive.

As used herein, the term "detectable" refers to protein or mRNA accumulation that is identifiable.

Protein accumulation can be identified using antibodies. Non limiting examples of measuring protein accumulation include Western blots, enzyme linked immunosorbent assays (ELISAs), immunoprecipitations and immunofluorescence. An antibody provided herein can be a polyclonal antibody or a monoclonal antibody. An antibody having specific binding affinity for a protein provided herein can be generated using methods well known in the art. An antibody provided herein can be attached to a solid support such as a microtiter plate using methods known in the art.

As used herein, the term "multiplicity of infection" and "MOI" refers to a the number of virions that are added per cell during infection.

As used herein, the term "virion" refers to the infective form of a virus outside a host cell.

As used herein, the term "neurological condition" refers to a disorder, illness, sickness, injury, or disease, in the central nervous system or the peripheral nervous system. Non-limiting examples of neurological conditions can be found in Neurological Disorders: course and treatment, 2$^{nd}$ Edition (2002) (Academic Press Inc.) and Christopher Goetz, Textbook of Clinical Neurology, 3$^{rd}$ Edition (2007) (Saunders).

As used herein, the term "injury" refers to damage to the central nervous system or peripheral nervous system.

In one aspect, a neurological condition is selected from the group consisting of Alzheimer's Disease, Parkinson's Disease, amyotrophic lateral sclerosis (ALS), Huntington's Disease, epilepsy, physical injury, stroke, cerebral aneurysm, traumatic brain injury, concussion, a tumor, inflammation, infection, ataxia, brain atrophy, spinal cord atrophy, multiple sclerosis, traumatic spinal cord injury, ischemic or hemorrhagic myelopathy (myelopathy), global ischemia, hypoxic ischemic encephalopathy, embolism, fibrocartilage embolism myelopathy, thrombosis, nephropathy, chronic inflammatory disease, meningitis, and cerebral venous sinus thrombosis. In one aspect, a neurological condition is Alzheimer's Disease. In one aspect, a neurological condition is Parkinson's Disease. In one aspect, a neurological condition is ALS. In one aspect, a neurological condition is Huntington's Disease. In one aspect, a neurological condition is epilepsy. In one aspect, a neurological condition is a physical injury. In one aspect, a neurological condition is stroke. In one aspect, a neurological condition is ischemic stroke. In one aspect, a neurological condition is hemorrhagic stroke. In one aspect, a neurological condition is cerebral aneurysm. In one aspect, a neurological condition is traumatic brain injury. In one aspect, a neurological condition is concussion. In one aspect, a neurological condition is a tumor. In one aspect, a neurological condition is inflammation. In one aspect, a neurological condition is infection. In one aspect, a neurological condition is ataxia. In, one aspect, a neurological condition is brain atrophy. In, one aspect, a neurological condition is spinal cord atrophy. In one aspect, a neurological condition is multiple sclerosis. In one aspect, a neurological condition is traumatic spinal cord injury. In one aspect, a neurological condition is ischemic or hemorrhagic myelopathy (myelopathy). In one aspect, a neurological condition is global ischemia. In one aspect, a neurological condition is hypoxic ischemic encephalopathy. In one aspect, a neurological condition is embolism. In one aspect, a neurological condition is fibrocartilage embolism myelopathy. In one aspect, a neurological condition is thrombosis. In one aspect, a neurological condition is nephropathy. In one aspect, a neurological condition is chronic inflammatory disease. In one aspect, a neurological condition is meningitis. In one aspect, a neurological condition is cerebral venous sinus thrombosis.

In an aspect, a neurological condition comprises an injury to the CNS or to the PNS. In one aspect, a neurological condition comprises an injury to the CNS. In one aspect, a neurological condition comprises an injury to the PNS.

In an aspect, this disclosure provides, and includes, a method of converting reactive astrocytes to functional neurons in a brain of a living human comprising: injecting an adeno-associated virus (AAV) into a subject in need thereof, wherein said AAV comprises a DNA vector construct comprising a human neurogenic differentiation 1 (hNeuroD1) sequence comprising the nucleic acid sequence of SEQ ID NO: 6 and a human distal-less homeobox 2 (hDlx2) sequence comprising the nucleic acid sequence of SEQ ID NO: 13, wherein said hNeuroD1 sequence and said hDlx2 sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, wherein said hNeuroD1 sequence and said hDlx2 sequence are operably linked to regulatory elements comprising: (a) a human glial fibrillary acidic protein (GFAP) promoter comprising a nucleic acid sequence selected from the group consisting of SEQ ID NOs: 4, 12, and 26; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence selected from the group consisting of SEQ ID NOs: 5 and 27; (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

In an aspect, this disclosure provides, and includes, a method of converting reactive astrocytes to functional neurons in a brain of a living human comprising: injecting an adeno-associated virus (AAV) into a subject in need thereof, wherein said AAV comprises a DNA vector construct comprising a nucleic acid coding sequence encoding a human neurogenic differentiation 1 (hNeuroD1) protein comprising the amino acid sequence of SEQ ID NO: 10 and a nucleic acid coding sequence encoding a human distal-less homeobox 2 (hDlx2) protein comprising the amino acid sequence of SEQ ID NO: 14, wherein said hNeuroD1 coding sequence and said hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, (iii) or an internal ribosomal entry site of the encephalomyocarditis virus (IRES) sequence comprising SEQ ID NO: 3, wherein said hNeuroD1 coding sequence and hDlx2 coding sequence are operably linked to expression control elements comprising: (a) a human glial fibrillary acidic protein (GFAP) promoter comprising a nucleic acid sequence selected from the group consisting of SEQ ID NOs: 4, 12, and 26; (b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11; (c) a chimeric intron comprising the nucleic acid sequence selected from the group consisting of SEQ ID NOs: 5 and 27; (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

In an aspect, this disclosure provides, and includes, a method of converting glial cells to neurons in a subject in need thereof comprising: delivering an adeno-associated virus (AAV) to said subject in need thereof, wherein said AAV comprises a DNA vector construct comprising a neurogenic differentiation 1 (NeuroD1) sequence and a distal-less homeobox 2 (Dlx2) sequence, wherein said NeuroD1 sequence and Dlx2 sequence are separated by a linker sequence, wherein said NeuroD1 sequence and Dlx2 sequence are operably linked to expression control elements comprising: (a) a glial fibrillary acid protein (GFAP) promoter; (b) an enhancer; (c) a chimeric intron; (d) a woodchuck hepatitis virus posttranscriptional regulatory element (WPRE); and (e) and a polyadenylation signal sequence, wherein said AAV vector is capable of converting at least one glial cell to a neuron in said subject in need thereof.

In an aspect, this disclosure provides, and includes, a method of treating a neurological condition in a subject in need thereof comprising: delivering an adeno-associated virus (AAV) to said subject, wherein said AAV comprises a DNA vector comprising a neurogenic differentiation 1 (NeuroD1) sequence and distal-less homeobox 2 (Dlx2) sequence, wherein said NeuroD1 sequence and Dlx2 sequence are separated by a linker sequence, wherein said NeuroD1 sequence and said Dlx2 sequence are operably linked to expression control elements comprising: (a) a glial fibrillary acid protein (GFAP) promoter; (b) an enhancer; (c) a chimeric intron; (d) a woodchuck hepatitis virus posttranscriptional regulatory element (WPRE); and (e) a polyadenylation signal to said subject in need thereof.

In an aspect, a method as provided herein, is capable of converting at least one glial cell to a neuron. In one aspect, a method as provided herein converts at least one glial cell to a neuron.

Achaete-scute family BHLH transcription factor 1 (Ascl1; also referred to as ASH1, HASH1, MASH-1, and bHLHa46) encodes a member of the basic helix-loop-helix family of transcription factors and is a gene that plays a role in neuronal commitment and differentiation.

Insulin gene enhancer protein (ISL1; also known as ISL LIM homeobox-1 and ISLET1) is a gene that encodes a transcription factor containing two N-terminal LIM domains and one C-terminal homeodomain. The encoded protein plays a role in the embryogenesis of pancreatic islets of Langerhans.

LIM-homeobox 3 (LHX3; also known as LIM3 and CPHD3) gene encodes for a protein from a family of proteins with a unique cysteine-rich zinc-binding domain (LIM domain).

Huntingtin (Htt; also known as Huntington Disease gene) gene encodes for the huntingtin protein The wild type contains 6-35 glutamine residues and the mutated Htt contains more than 36 glutamine residue.

In an aspect, a method as provided herein uses an AAV vector comprising a NeuroD1 coding sequence and a Dlx2 coding sequence in accordance with the present disclosure. In one aspect, a method as provided herein uses an AAV vector comprising a NeuroD1 coding sequence in combination with a second AAV vector comprising a Dlx2 coding sequence. In one aspect, a method as provided herein uses an AAV vector comprising a NeuroD1 or a Dlx2 coding sequence in combination with a second AAV vector comprising a third transcription factor coding sequence. In one aspect, a third transcription factor is selected from the group consisting of Ascl1, ISL1, and LHX3. In one aspect, a third transcription factor is Ascl1. In one aspect, a second transcription factor is ISL1. In one aspect, a third transcription factor is LHX3. In one aspect, a method as provided herein uses an AAV vector comprising a NeuroD1 coding sequence, a Dlx2 coding sequence, a second NeuroD1 coding sequence, and a second Dlx2 coding sequence. In one aspect, a method as provided herein uses an AAV vector comprising a NeuroD1 and a Dlx2 coding sequence in combination with a second AAV vector comprising a NeuroD1 and a Dlx2 coding sequence.

In one aspect, a method as provided herein uses an AAV vector comprising a NeuroD1 and a Dlx2 coding sequence in combination with an AAV vector comprising a shRNA sequence targeting Htt. In an aspect, a method as provided herein uses an AAV vector comprising a NeuroD1 and a Dlx2 coding sequence in combination with an AAV vector comprising an shRNA sequence targeting Htt and a second shRNA sequence targeting Htt. In an aspect, a method as provided herein uses an AAV vector comprising a NeuroD1 and a Dlx2 coding sequence in combination with an AAV vector comprising a shRNA sequence targeting Htt, a second shRNA sequence targeting Htt, and a third shRNA targeting Htt. In an aspect, a method as provided herein uses an AAV vector comprising a NeuroD1 and a Dlx2 coding sequence and a shRNA sequence targeting Htt. In an aspect, a method as provided herein uses an AAV vector comprising a NeuroD1 and a Dlx2 coding sequence and a shRNA sequence targeting Htt and a second shRNA sequence targeting Htt. In an aspect, a method as provided herein uses an AAV vector comprising a NeuroD1 and a Dlx2 coding sequence and a shRNA sequence targeting Htt, a second shRNA sequence targeting Htt and a third shRNA targeting Htt.

In one aspect, a method as provided herein uses an AAV vector comprising a NeuroD1 and a Dlx2 coding sequence in combination with an ASO sequence targeting Htt. In an aspect, a method as provided herein uses an AAV vector comprising a NeuroD1 and a Dlx2 coding sequence in combination with an ASO sequence targeting Htt and a second ASO sequence targeting Htt. In an aspect, a method as provided herein uses an AAV vector comprising a NeuroD1 and a Dlx2 coding sequence in combination with an ASO sequence targeting Htt, a second ASO sequence targeting Htt, and a third ASO targeting Htt.

In one aspect, a method as provided herein uses an AAV vector comprising a NeuroD1 and a Dlx2 coding sequence in combination with an siRNA sequence targeting Htt. In an aspect, a method as provided herein uses an AAV vector comprising a NeuroD1 and a Dlx2 coding sequence in combination with an siRNA sequence targeting Htt and a second siRNA sequence targeting Htt. In an aspect, a method as provided herein uses an AAV vector comprising a NeuroD1 and a Dlx2 coding sequence in combination with an siRNA sequence targeting Htt, a second siRNA sequence targeting Htt, and a third siRNA targeting Htt.

In one aspect, a method as provided herein uses an AAV vector comprising a NeuroD1 and a Dlx2 coding sequence in combination with an AAV vector comprising a miRNA sequence targeting Htt. In an aspect, a method as provided herein uses an AAV vector comprising a NeuroD1 and a Dlx2 coding sequence in combination with an AAV vector comprising an miRNA sequence targeting Htt and a second miRNA sequence targeting Htt. In an aspect, a method as provided herein uses an AAV vector comprising a NeuroD1 and a Dlx2 coding sequence in combination with an AAV vector comprising a miRNA sequence targeting Htt, a second miRNA sequence targeting Htt, and a third miRNA targeting Htt. In an aspect, a method as provided herein uses an AAV vector comprising a NeuroD1 and a Dlx2 coding sequence and a miRNA sequence targeting Htt. In an aspect, a method as provided herein uses an AAV vector comprising a NeuroD1 and a Dlx2 coding sequence and a miRNA sequence targeting Htt and a second miRNA sequence targeting Htt. In an aspect, a method as provided herein uses an AAV vector comprising a NeuroD1 and a Dlx2 coding sequence and a miRNA sequence targeting Htt, a second miRNA sequence targeting Htt and a third MIRNA targeting Htt.

In one aspect, a method as provided herein uses an AAV vector comprising a NeuroD1 and a Dlx2 coding sequence in combination with an AAV vector comprising a gRNA sequence targeting Htt and a CAS nuclease. In an aspect, a method as provided herein uses an AAV vector comprising a NeuroD1 and a Dlx2 coding sequence and a gRNA sequence targeting Htt and a CAS nuclease.

In an aspect, an AAV vector as provided herein, is measured for functionality by assessing transcription levels and protein levels of NeuN, doublecortin (DCX), β3-tubulin, (neurofilament 200) NF-200, (microtubule-associated protein 2) MAP2, ionized calcium binding adaptor molecule (Iba1).

As used herein, the term "NeuN" or "Fox-3" or "Rbfox2" or "Hexaribonucleotide Binding Protein-3" refers to a protein which is a homologue to the protein product of a sex-determining gene in *Caenorhabditis elegans* and is a neuronal nuclear antigen.

As used herein, the term "DCX" or "doubling" or "lissencephalin-X" refers to a microtubule-associated protein expressed by neuronal precursor cells and immature neurons in embryonic and adult cortical structures.

As used herein, the term "β-tubulin" or "Class III β-tubulin" or "β-tubulin III" refers to a microtubule element of the tubulin family found in neurons.

As used herein, the term "NF-200" refers to a class of protein that is a type IV intermediate filaments found in the cytoplasm of neurons.

As used herein, the term "MAP2" refers to a protein that belongs to the microtubule-associated protein family and play a role in determining and stabilizing neuronal morphology during neuron development.

As used herein, the term "Iba1" refers to a microglia macrophage-specific calcium binding protein.

In an aspect a method provided herein converts glial cells to neurons in combination with gene editing techniques. In one aspect, a gene editing technique targets the mutant Htt. In one aspect, a gene editing technique is selected from the group consisting of siRNA, miRNA, ASO, and CRISPR/CAS. In one aspect, a gene editing technique is siRNA. In one aspect, a gene editing technique is miRNA. In one aspect, a gene editing technique is ASO. In one aspect, a gene editing technique is CRISPR/CAS.

In an aspect, a composition as provided herein, is capable of converting at least one glial cell to a neuron. In one aspect, a composition as provided herein converts at least one glial cell to a neuron As used herein, the term "mammal" refers to any species classified in the class Mammalia.

As used herein, the term "human" refers to a *Homo sapiens*. In an aspect, a human has a neurological disorder.

As used herein, the term "living human" refers to a human that has heart, respiration and brain activity.

As used herein, the term "non-human primate" refers to any species or subspecies classified in the order Primates that are not *Homo sapiens*. Non-limiting examples of non-human primates include chimpanzee, bonobo, orangutan, gorilla, macaque, marmoset, capuchin, baboon, gibbon, and lemur.

As used herein, the term "delivering" or "delivery" refers to treating a mammal with an AAV vector or composition as provided herein. In an aspect, an AAV vector or composition as provided herein is delivered to a subject in need thereof. In one aspect, an AAV vector or composition as provided herein is formulated to be delivered to a subject in need thereof. In one aspect, delivering comprises local delivery. In one aspect, an AAV vector or composition as provided herein is formulated for local delivery. In one aspect, delivering comprises systemic delivery. In one aspect, an AAV vector or composition as provided herein is formulated for systemic delivery. In one aspect, delivery comprises injecting an AAV vector or composition as provided herein into a subject in need thereof. In one aspect, delivering is selected from the group consisting of intraperitoneal, intramuscular, intravenous, intrathecal, intracerebral, intracranial, intra lateral ventricle of the brain, intra cisterna magna, intra vitreous, intra-subretina, intraparenchymal, intranasal, or oral administration. In one aspect, delivery comprises intraperitoneal delivery. In one aspect, delivery comprises intramuscular delivery. In one aspect, delivery comprises intravenous delivery. In one aspect, delivery comprises intrathecal delivery. In one aspect, delivery comprises intracerebral delivery. In one aspect, delivery comprises intracranial delivery. In one aspect, delivery comprises intra lateral ventricle of the brain delivery. In one aspect, delivery comprises intra cisterna magna delivery. In one aspect, delivery comprises intra vitreous delivery. In one aspect, delivery comprises intra-subretina delivery. In one aspect, delivery comprises intraparenchymal delivery. In one aspect, delivery comprises intranasal delivery. In one aspect, delivery comprises oral administration.

As used herein, the term "injecting" refers to delivering an AAV vector or composition as provided herein under pressure and with force. As a non-limiting example, injecting can comprise the use of a syringe and needle.

In an aspect, an AAV vector or composition as provided herein is injected into a brain of a subject. In one aspect, an AAV vector or composition is injected into a cerebral cortex of a subject. In one aspect, and AAV vector or composition as provided herein is injected in the striatum of a subject. In one aspect, an AAV vector or composition as provided herein is injected in to a spinal cord or a subject. In one aspect, an AAV vector or composition is injected in the striatum of a subject. In one aspect, an AAV vector or composition is injected in the dorsal striatum of a subject. In one aspect, an AAV vector or composition is injected in the putamen of a subject. In one aspect, an AAV vector or composition is injected in the caudate nucleus of a subject. In one aspect, an AAV vector or composition is injected in the substantia nigra of a subject In an aspect, an AAV vector or composition as provided herein has spread in the brain between about 1% and about 100%. In one aspect, an AAV vector or composition as provided herein has spread in the brain between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the cerebral cortex between about 1% and about 100%. In one aspect, an AAV vector or composition as provided herein has spread in the cerebral cortex between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the spinal cord between about 1% and about 100%. In one aspect, an AAV vector or composition as provided herein has spread in the spinal cord between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the striatum between about 1% and about 100%. In one aspect, an AAV vector or composition as provided herein has spread in the striatum between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the dorsal striatum between about 1% and about 100%. In one aspect, an AAV vector or composition as provided herein has spread in the dorsal striatum between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the putamen between about 1% and about 100%. In one aspect, an AAV vector or composition as provided herein has spread in the putamen between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the caudate nucleus between about 1% and about 100%. In one aspect, an AAV vector or composition as provided herein has spread in the caudate nucleus between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In and aspect, an AAV vector or composition as provided herein has a spread at from injection site between about 1% and about 100%. In one aspect, an AAV vector or composition as provided herein has a spread from injection site between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

In an aspect, an AAV vector or composition as provided herein has spread in the substantia nigra between about 1% and about 100%. In one aspect, an AAV vector or composition as provided herein has spread in the putamen between about 1% and about 10%, between 1% and about 20%, between 1% and about 30%, between 10% and about 20%, between 10% and about 30%, between about 10% and about 40%, between about 20% and about 30%, between about 20% and about 40%, between about 20% and about 50%, between about 30% and about 40%, between about 30% and about 50%, between about 30% and about 60%, between about 40% and about 50%, between about 40% and about 60%, between about 40% and about 70%, between about 50% and about 60%, between about 50% and about 70%, between about 50% and about 80%, between about 60% and about 70%, between about 60% and about 80%, between about 60% and about 90%, between about 70% and about 80%, between about 70% and about 90%, between about 70% and about 100%, between about 80% and about 90%, between about 80% and about 100%, or between about 90% and about 100%.

As used herein, the term "AAV particle" refers to packaged capsid forms of the AAV virus that transmits its nucleic acid genome to cells.

In an aspect, a composition comprising an AAV particle encoded by an AAV vector as provided herein is injected at a concentration between $10^{10}$ AAV particles/mL and $10^{14}$ AAV particles/mL. In one aspect, a composition comprising an AAV particle encoded by an AAV vector as provided herein is injected at a concentration between $10^{10}$ AAV particles/mL and $10^{11}$ AAV particles/mL, between $10^{10}$ AAV particles/mL and $10^{12}$ AAV particles/mL, between $10^{10}$ AAV particles/mL and $10^{13}$ AAV particles/mL, between $10^{11}$ AAV particles/mL and $10^{12}$ AAV particles/mL, between $10^{11}$ AAV particles/mL and $10^{3}$ AAV particles/mL, between $10^{11}$ AAV particles/mL and $10^{14}$ AAV particles/mL, between $10^{12}$ AAV particles/mL and $10^{3}$ AAV particles/mL, between $10^{12}$ AAV particles/mL and $10^{14}$ AAV particles/mL, or between $10^{3}$ AAV particles/mL and $10^{14}$ AAV particles/mL.

In an aspect, a composition comprising an AAV particle encoded by an AAV vector as provided herein is injected at volume between 10 μL and 1000 μL. In one aspect, a composition comprising an AAV particle encoded by an AAV vector as provided herein is injected at volume between 10 μL and 100 μL, between 10 μL and 200 μL, between 10 μL and 300 μL, between 100 μL and 200 μL, between 100 μL and 300 μL, between 100 μL and 400 μL, between 200 μL and 300 μL, between 200 μL and 400 μL, between 200 μL and 500 μL, between 300 μL and 400 μL, between 300 μL and 500 μL, between 300 μL and 600 μL, between 400 μL and 500 μL, between 400 μL and 600 μL, between 400 uL and 700 μL, between 500 μL and 600 μL, between 500 μL and 700 μL, between 500 μL and 800 μL, between 600 μL and 700 μL, between 600 μL and 800 μL, between 600 μL and 900 μL, between 700 μL and 800 μL, between 700 μL and 900 μL, between 700 μL and 1000 μL, between 800 μL and 900 μL, between 800 μL and 1000 μL, or between 900 μL and 1000 μL.

As used herein, the term "subject" refers to any animal subject. Non-limiting examples of animal subjects include humans, laboratory animals (e.g., primates, rats, mice), livestock (e.g., cows, sheep, goats, pigs, turkeys, chickens), and household pets (e.g., dogs, cats, rodents, etc.).

As used herein, "a subject in need thereof" refers to a subject with a neurological condition. In an aspect, a subject in need thereof has a neurological condition selected from the group consisting of Alzheimer's Disease, Parkinson's Disease, amyotrophic lateral sclerosis (ALS), Huntington's Disease, epilepsy, physical injury, stroke, cerebral aneurysm, traumatic brain injury, concussion, a tumor, inflammation, infection, ataxia, brain atrophy, spinal cord atrophy, multiple sclerosis, traumatic spinal cord injury, ischemic or hemorrhagic myelopathy (myelopathy), global ischemia, hypoxic ischemic encephalopathy, embolism, fibrocartilage embolism myelopathy, thrombosis, nephropathy, chronic inflammatory disease, meningitis, and cerebral venous sinus thrombosis. In one aspect, a subject in need thereof has Alzheimer's Disease. In one aspect, a subject in need thereof has Parkinson's Disease. In one aspect, a subject in need thereof has ALS. In one aspect, a subject in need thereof has Huntington's Disease. In one aspect, a subject in need thereof has epilepsy. In one aspect, a subject in need thereof has a physical injury. In one aspect, a subject in need thereof has a stroke. In one aspect, a subject in need thereof has ischemic stroke. In one aspect, a subject in need thereof has hemorrhagic stroke. In one aspect, a subject in need thereof has a cerebral aneurysm. In one aspect, a subject in need thereof has traumatic brain injury. In one aspect, a subject in need thereof has concussion. In one aspect, a subject in need thereof has a tumor. In one aspect, a subject in need thereof has inflammation. In one aspect, a subject in need thereof has an infection. In, one aspect, a subject in need thereof has ataxia. In, one aspect, a subject in need thereof has brain atrophy. In one aspect, a subject in need thereof has spinal cord atrophy. In one aspect, a subject in need thereof has multiple sclerosis. In one aspect, a subject in need thereof has a traumatic spinal cord injury. In one aspect, a subject in need thereof has ischemic or hemorrhagic myelopathy (myelopathy). In one aspect, a subject in need thereof has global ischemia. In one aspect, a subject in need thereof has hypoxic ischemic encephalopathy. In one aspect, a subject in need thereof has an embolism. In one aspect, a subject in need thereof has fibrocartilage embolism myelopathy. In one aspect, a subject in need thereof has thrombosis. In one aspect, a subject in need thereof has nephropathy. In one aspect, a subject in need thereof has chronic inflammatory disease. In one aspect, a subject in need thereof has meningitis. In one aspect, a subject in need thereof has cerebral venous sinus thrombosis.

In an aspect, a subject in need thereof is a mammal. In one aspect, a subject in need thereof is a human. In one aspect, a subject in need thereof is a non-human primate. In one aspect, a subject in need thereof is selected from the group consisting of chimpanzee, bonobo, orangutan, gorilla, macaque, marmoset, capuchin, baboon, gibbon, and lemur. In one aspect, a subject in need thereof is a chimpanzee. In one aspect, a subject in need thereof is a bonobo. In one aspect, a subject in need thereof is orangutan. In one aspect, a subject in need thereof is gorilla. In one aspect, a subject in need thereof is a macaque. In one aspect, a subject in need thereof is marmoset. In one aspect, a subject in need thereof is a capuchin. In one aspect, a subject in need thereof is a baboon. In one aspect, a subject in need thereof is a gibbon. In one aspect, a subject in need thereof is lemur.

In one aspect, a subject in need thereof is a male. In one aspect, a subject in need thereof is a female. In one aspect, a subject in need thereof is gender neutral. In one aspect, a subject in need thereof is a premature newborn. In one aspect, a premature newborn is born before 36 weeks gestation. In one aspect, a subject in need thereof is a term newborn. In one aspect, a term newborn is below about 2 months old. In one aspect, a subject in need thereof is a neonate. In one aspect, a neonate is below about 1 month old. In one aspect, a subject in need thereof is an infant. In one aspect, an infant is between 2 months and 24 months old. In one aspect, an infant is between 2 months and 3 months, between 2 months and 4 months, between 2 months and 5 months, between 3 months and 4 months, between 3 months and 5 months, between 3 months and 6 months, between 4 months and 5 months, between 4 months and 6 months, between 4 months and 7 months, between 5 months and 6 months, between 5 months and 7 months, between 5 months and 8 months, between 6 months and 7 months, between 6 months and 8 months, between 6 months and 9 months, between 7 months and 8 months, between 7 months and 9 months, between 7 months and 10 months, between 8 months and 9 months, between 8 months and 10 months, between 8 months and 11 months, between 9 months and 10 months, between 9 months and 11 months, between 9 months and 12 months, between 10 months and 11 months, between 10 months and 12 months, between 10 months and 13 months, between 11 months and 12 months, between 11 months and 13 months, between 11 months and 14 months, between 12 months and 13 months, between 12 months and 14 months, between 12 months and 14 months, between 13 months and 14 months, between 13 months and 14 months, between 13 months and 16 months, between 14 months and 14 months, between 14 months and 16 months, between 14 months and 17 months, between 14 months and 16 months, between 14 months and 17 months, between 14 months and 18 months, between 16 months and 17 months, between 16 months and 18 months, between 16 months and 19 months, between 17 months and 18 months, between 17 months and 19 months, between 17 months and 20 months, between 18 months and 19 months, between 18 months and months, between 18 months and 21 months, between 19 months and 20 months, between 19 months and 21 months, between 19 months and 22 months, between 20 months and 21 months, between 20 months and 22 months, between 20 months and 23 months, between 21 months and 22 months, between 21 months and 23 months, between 21 months and 24 months, between 22 months and 23 months, between 22 months and 24 months, and between 23 months and 24 months old. In one aspect, a subject in need thereof is a toddler. In one aspect, a toddler is between 1 year and 4 years old. In one aspect, a toddler is between 1 year and 2 years, between 1 year and 3 years, between 1 year and 4 years, between 2 years and 3 years, between 2 years and 4 years, and between 3 years and 4 years old. In one aspect, a subject in need thereof is a young child. In one aspect, a young child is between 2 years and 5 years old. In one aspect, a young child is between 2 years and 3 years, between 2 years and 4 years, between 2 years and 5 years, between 3 years and 4 years, between 3 years and 5 years, and between 4 years and 5 years old. In one aspect, a subject in need thereof is a child. In one aspect, a child is between 6 years and 12 years old. In one aspect, a child is between 6 years and 7 years, between 6 years and 8 years, between 6 years and 9 years, between 7 years and 8 years, between 7 years and 9 years, between 7 years and 10 years, between 8 years and 9 years, between 8 years and 10 years, between 8 years and 11 years, between 9 years and 10 years, between 9 years and 11 years, between 9 years and 12 years, between 10 years and 11 years, between 10 years and 12 years, and between 11 years and 12 years old. In one aspect, a subject in need thereof is an adolescent. In one aspect, an adolescent is between 13 years and 19 years old. In one aspect, an adolescent is between 13 years and 14 years, between 13 years and 14 years, between 13 years and 16 years, between 14 years and 14 years, between 14 years and 16 years, between 14 years and 17 years, between 14 years and 16 years, between 14 years and 17 years, between 14 years and 18 years, between 16 years and 17 years, between 16 years and 18 years, between 16 years and 19 years, between 17 years and 18 years, between 17 years and 19 years, and between 18 years and 19 years old. In one aspect, a subject in need thereof is a pediatric subject. In one aspect, a pediatric subject between 1 day and 18 years old. In one aspect, a pediatric subject is between 1 day and 1 year, between 1 day and 2 years, between 1 day and 3 years, between 1 year and 2 years, between 1 year and 3 years, between 1 year and 4 years, between 2 years and 3 years, between 2 years and 4 years, between 2 years and 5 years, between 3 years and 4 years, between 3 years and 5 years, between 3 years and 6 years, between 4 years and 5 years, between 4 years and 6 years, between 4 years and 7 years, between 5 years and 6 years, between 5 years and 7 years, between 5 years and 8 years, between 6 years and 7 years, between 6 years and 8 years, between 6 years and 9 years, between 7 years and 8 years, between 7 years and 9 years, between 7 years and 10 years, between 8 years and 9 years, between 8 years and 10 years, between 8 years and 11 years, between 9 years and 10 years, between 9 years and 11 years, between 9 years and 12 years, between 10 years and 11 years, between 10 years and 12 years, between 10 years and 13 years, between 11 years and 12 years, between 11 years and 13 years, between 11 years and 14 years, between 12 years and 13 years, between 12 years and 14 years, between 12 years and 14 years, between 13 years and 14 years, between 13 years and 14 years, between 13 years and 16 years, between 14 years and 14 years, between 14 years and 16 years, between 14 years and 17 years, between 14 years and 16 years, between 14 years and 17 years, between 14 years and 18 years, between 16 years and 17 years, between 16 years and 18 years, and between 17 years and 18 years old. In one aspect, a subject in need thereof is a geriatric subject. In one aspect, a geriatric subject is between 65 years and 95 or more years old. In one aspect, a geriatric subject is between 65 years and 70 years, between 65 years and 75 years, between 65 years and 80 years, between 70 years and 75 years, between 70 years and 80 years, between 70 years and 85 years, between 75 years and 80 years, between 75 years and 85 years, between 75 years and 90 years, between 80 years and 85 years, between 80 years and 90 years, between 80 years and 95 years, between 85 years and 90 years, and between 85 years and 95 years old. In one aspect, a subject in need thereof is an adult. In one aspect, an adult subject is between 20 years and 95 or more years old. In one aspect, an adult subject is between 20 years and 25 years, between 20 years and 30 years, between 20 years and 35 years, between 25 years and 30 years, between 25 years and 35 years, between 25 years and 40 years, between 30 years and 35 years, between 30 years and 40 years, between 30 years and 45 years, between 35 years and 40 years, between 35 years and 45 years, between 35 years and 50 years, between 40 years and 45 years, between 40 years and 50 years, between 40 years and 55 years, between 45 years and 50 years, between 45 years and 55 years, between 45 years and 60 years, between 50 years and 55 years, between 50 years and 60 years, between 50 years and 65 years, between 55 years and 60 years, between 55 years and 65 years, between 55 years and 70 years, between 60 years and 65 years, between 60 years and 70 years, between 60 years and 75 years, between 65 years and 70 years, between 65 years and 75 years, between 65 years and 80 years, between 70 years and 75 years, between 70 years and 80 years, between 70 years and 85 years, between 75 years and 80 years, between 75 years and 85 years, between 75 years and 90 years, between 80 years and 85 years, between 80 years and 90 years, between 80 years and 95 years, between 85 years and 90 years, and between 85 years and 95 years old. In one aspect, a subject in need thereof is between 1 year and 5 years, between 2 years and 10 years, between 3 years and 18 years, between 21 years and 50 years, between 21 years and 40 years, between 21 years and 30 years, between 50 years and 90 years, between 60 years and 90 years, between 70 years and 90 years, between 60 years and 80 years, or between 65 years and 75 years old. In one aspect, a subject in need thereof is a young old subject (65 to 74 years old). In one aspect, a subject in need thereof is a middle old subject (75 to 84 years old). In one aspect, a subject in need thereof is an old subject (>85 years old).

As used herein, the term "flow rate" refers to the rate of delivery of an AAV vector or composition. In an aspect, the flow rate is between 0.1 μL/minute and 5.0 μL/minute. In one aspect, the flow rate is between 0.1 μL/minute and 0.2 μL/minute, between 0.1 μL/minute and 0.3 μL/minute, between 0.1 μL/minute and 0.4 μL/minute, between 0.2 μL/minute and 0.3 μL/minute, between 0.2 μL/minute and 0.4 μL/minute, between 0.2 μL/minute and 0.5 μL/minute, between 0.3 L/minute and 0.4 μL/minute, between 0.3 μL/minute and 0.5 μL/minute, between 0.3 μL/minute and 0.6 μL/minute, between 0.4 μL/minute and 0.5 μL/minute, between 0.4 L/minute and 0.6 μL/minute, between 0.4 μL/minute and 0.7 μL/minute, between 0.5 μL/minute and 0.6 μL/minute, between 0.5 μL/minute and 0.7 μL/minute, between 0.5 μL/minute and 0.8 μL/minute, between 0.6 μL/minute and 0.7 μL/minute, between 0.6 μL/minute and 0.8 μL/minute, between 0.6 L/minute and 0.9 μL/minute, between 0.7 μL/minute and 0.8 μL/minute, between 0.7 μL/minute and 0.9 μL/minute, between 0.7 μL/minute and 1.0 μL/minute, between 0.8 L/minute and 0.9 μL/minute, between 0.8 μL/minute and 1.0 μL/minute, between 0.8 μL/minute and 1.1 μL/minute, between 0.9 μL/minute and 1.0 μL/minute, between 0.9 μL/minute and 1.1 μL/minute, between 0.9 μL/minute and 1.2 μL/minute, between 1.0 μL/minute and 1.1 μL/minute, between 1.0 L/minute and 1.2 μL/minute, between 1.0 μL/minute and 1.3 μL/minute, between 1.1 μL/minute and 1.2 μL/minute, between 1.1 μL/minute and 1.3 μL/minute, between 1.1 L/minute and 1.4 μL/minute, between 1.2 μL/minute and 1.3 μL/minute, between 1.2 μL/minute and 1.4 μL/minute, between 1.2 μL/minute and 1.5 μL/minute, between 1.3 μL/minute and 1.4 μL/minute, between 1.3 μL/minute and 1.5 μL/minute, between 1.3 μL/minute and 1.6 μL/minute, between 1.4 L/minute and 1.5 μL/minute, between 1.4 μL/minute and 1.6 μL/minute, between 1.4 μL/minute and 1.7 μL/minute, between 1.5 μL/minute and 1.6 μL/minute, between 1.5 L/minute and 1.7 μL/minute, between 1.5 μL/minute and 1.8 μL/minute, between 1.6 μL/minute and 1.7 μL/minute, between 1.6 μL/minute and 1.8 μL/minute, between 1.6 μL/minute and 1.9 μL/minute, between 1.7 μL/minute and 1.8 μL/minute, between 1.7 μL/minute and 1.9 μL/minute, between 1.7 L/minute and 2.0 μL/minute, between 1.8 μL/minute and 1.9 μL/minute, between 1.8 μL/minute and 2.0 μL/minute, between 1.8 μL/minute and 2.1 μL/minute, between 1.9 L/minute and 2.0 μL/minute, between 1.9 μL/minute and 2.1 μL/minute, between 1.9 μL/minute and 2.2 L/minute, between 2.0 μL/minute and 2.1 μL/minute, between 2.0 L/minute and 2.2 μL/minute, between 2.0 L/minute and 2.3 L/minute, between 2.1 L/minute and 2.2 L/minute, between 2.1 L/minute and 2.3 L/minute, between 2.1 L/minute and 2.4 μL/minute, between 2.2 L/minute and 2.3 L/minute, between 2.2 L/minute and 2.4 μL/minute, between 2.2 L/minute and 2.5 L/minute, between 2.3 L/minute and 2.4 μL/minute, between 2.3 μL/minute and 2.5 L/minute, between 2.3 μL/minute and 2.6 μL/minute, between 2.4 L/minute and 2.5 μL/minute, between 2.4 L/minute and 2.6 L/minute, between 2.4 L/minute and 2.7 L/minute, between 2.5 L/minute and 2.6 L/minute, between 2.5 L/minute and 2.7 μL/minute, between 2.5 L/minute and 2.8 L/minute, between 2.6 L/minute and 2.7 μL/minute, between 2.6 L/minute and 2.8 L/minute, between 2.6 L/minute and 2.9 μL/minute, between 2.7 μL/minute and 2.8 L/minute, between 2.7 μL/minute and 2.9 μL/minute, between 2.7 L/minute and 3.0 μL/minute, between 2.8 L/minute and 2.9 L/minute, between 2.8 L/minute and 3.0 L/minute, between 2.8 L/minute and 3.1 L/minute, between 2.9 L/minute and 3.0 μL/minute, between 2.9 L/minute and 3.1 L/minute, between 2.9 L/minute and 3.2 μL/minute, between 3.0 L/minute and 3.1 L/minute, between 3.0 L/minute and 3.2 μL/minute, between 3.0 μL/minute and 3.3 L/minute, between 3.1 μL/minute and 3.2 μL/minute, between 3.1 L/minute and 3.3 μL/minute, between 3.1 L/minute and 3.4 L/minute, between 3.2 L/minute and 3.3 L/minute, between 3.2 L/minute and 3.4 L/minute, between 3.2 L/minute and 3.5 μL/minute, between 3.3 L/minute and 3.4 L/minute, between 3.3 L/minute and 3.5 μL/minute, between 3.3 L/minute and 3.6 L/minute, between 3.4 L/minute and 3.5 μL/minute, between 3.4 μL/minute and 3.6 L/minute, between 3.4 μL/minute and 3.7 μL/minute, between 3.5 L/minute and 3.6 μL/minute, between 3.5 L/minute and 3.7 L/minute, between 3.5 L/minute and 3.8 L/minute, between 3.6 L/minute and 3.7 L/minute, between 3.6 L/minute and 3.8 μL/minute, between 3.6 L/minute and 3.9 L/minute, between 3.7 L/minute and 3.8 μL/minute, between 3.7 L/minute and 3.9 L/minute, between 3.7 L/minute and 4.0 μL/minute, between 3.8 μL/minute and 3.9 L/minute, between 3.8 μL/minute and 4.0 μL/minute, between 3.8 L/minute and 4.1 μL/minute, between 3.9 L/minute and 4.0 L/minute, between 3.9 L/minute and 4.1 L/minute, between 3.9 L/minute and 4.2 L/minute, between 4.0 L/minute and 4.1 μL/minute, between 4.0 L/minute and 4.2 L/minute, between 4.0 L/minute and 4.3 μL/minute, between 4.1 L/minute and 4.2 L/minute, between 4.1 L/minute and 4.3 μL/minute, between 4.1 μL/minute and 4.4 L/minute, between 4.2 μL/minute and 4.3 μL/minute, between 4.2 L/minute and 4.4 μL/minute, between 4.2 μL/minute and 4.5 μL/minute, between 4.3 μL/minute and 4.4 μL/minute, between 4.3 L/minute and 4.5 μL/minute, between 4.3 μL/minute and 4.6 μL/minute, between 4.4 μL/minute and 4.5 μL/minute, between 4.4 μL/minute and 4.6 μL/minute, between 4.4 L/minute and 4.7 μL/minute, between 4.5 μL/minute and 4.6 μL/minute, between 4.5 μL/minute and 4.7 μL/minute, between 4.5 μL/minute and 4.8 μL/minute, between 4.6 L/minute and 4.7 μL/minute, between 4.6 μL/minute and 4.8 μL/minute, between 4.6 μL/minute and 4.9 μL/minute, between 4.7 L/minute and 4.8 μL/minute, between 4.7 μL/minute and 4.9 μL/minute, between 4.7 μL/minute and 5.0 μL/minute, 4.8 μL/minute and 4.9 μL/minute, between 4.8 μL/minute and 5.0 μL/minute, or between 4.9 μL/minute and 5.0 μL/minute.

As used herein, the term "therapeutically effective dose" or "pharmaceutically active dose" refers to an amount of AAV particles or composition as provided herein which is effective in treating a neurological condition. In an aspect, an AAV particle or composition as provided herein can be provided together with a pharmaceutically acceptable carrier. As used herein, a "pharmaceutically acceptable carrier" refers to a non-toxic solvent, dispersant, excipient, adjuvant, or other material which is mixed with an AAV particles or composition as provided herein.

Non-limiting examples of a pharmaceutically acceptable carrier include a liquid (e.g., saline), gel, nanoparticles, exosomes, lipid vesicles, or solid form of diluents, adjuvant, excipients or an acid resistant encapsulated ingredient. Non-limiting examples of suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof. In an aspect, a therapeutic effective dose contains auxiliary substances such as wetting or emulsifying agents, stabilizing or pH buffering agents. In one aspect, a therapeutically effective dose of an AAV particle or composition as provided herein is injected to a subject. In one aspect, a therapeutically effective dose of an AAV particle or composition as provided herein is delivered into a subject. In one aspect, a therapeutically effective dose is administered with at least one pharmaceutically acceptable carrier. In one aspect, a therapeutic effective dose contains between about 1% and about 5%, between about 5% and about 10%, between about 10% and about 14%, between about 14% and about 20%, between about 20% and about 25%, between about 25% and about 30%, between about 30% and about 35%, between about 40 and about 45%, between about 50% and about 55%, between about 1% and about 95%, between about 2% and about 95%, between about 5% and about 95%, between about 10% and about 95%, between about 14% and about 95%, between about 20% and about 95%, between about 25% and about 95%, between about 30% and about 95%, between about 35% and about 95%, between about 40% and about 95%, between about 45% and about 95%, between about 50% and about 95%, between about 55% and about 95%, between about 60% and about 95%, between about 65% and about 95%, between about 70% and about 95%, between about 45% and about 95%, between about 80% and about 95%, or between about 85% and about 95% of AAV particle or composition as provided herein.

In an aspect, a therapeutically effective dose is delivered to subject in need thereof at least once daily or at least once weekly for at least two consecutive days or weeks. In one aspect, a therapeutically effective dose is delivered to subject in need thereof at least once daily or at least once weekly for at least 3, 4, 5, 6, 7, 8, 9, 10, 11, 12, 13, 14, or 14 consecutive days or weeks. In one aspect, a therapeutically effective dose is delivered to subject in need thereof at least once daily or at least once weekly for at least 1, 2, 3, 4, 5, 6, 7, 8, 9, 10, 11, or 12 consecutive weeks. In one aspect, a therapeutically effective dose is delivered to subject in need thereof at least once daily or at least once weekly for at most 4, 5, 6, 7, 8, 9, 10, 11, 12, 13, 14, 14, 16, 17, 18, 19, or 20 consecutive days or weeks. In one aspect, a therapeutically effective dose is delivered to subject in need thereof at least once daily or at least once weekly for at most 1, 2, 3, 4, 5, 6, 7, 8, 9, 10, 11, or 12 consecutive weeks or months. In one aspect, a therapeutically effective dose is delivered to subject in need thereof is administered at least once for at least 1, 2, 3, 4, 5, 6, 7, 8, 9, 10, 11, or 12 consecutive months or years, chronically for a subject's entire life span, or an indefinite period of time. In one aspect, a therapeutically effective dose is delivered to subject in need thereof once a year for 2 consecutive years, 3 consecutive years, or 5 consecutive years. In one aspect, a therapeutically effective dose is delivered to subject in need thereof once a year for 2 consecutive years. In one aspect, a therapeutically effective dose is delivered to subject in need thereof once a year for 3 consecutive years. In one aspect, a therapeutically effective dose is delivered to subject in need thereof once a year for 5 consecutive years.

As used herein, the term "remission", "cure," or "resolution rate" refers to the percentage of subjects in need thereof that are cured or obtain remission or complete resolution of a neurological condition in response to a therapeutically effective dose.

As used herein, the term "response rate" refers to the percentage of subjects in need thereof that respond positively (e.g., reduced severity or frequency of one or more symptoms) to a therapeutically effective dose.

In one aspect, a therapeutically effective dose achieves a remission, cure, response rate, or resolution rate of a neurological condition of at least about 50%. In one aspect, a therapeutically effective dose eliminates, reduces, slows, or delays, one or more neurological condition symptoms. Non-limiting examples of neurological condition symptoms include tremor, slowed movement (bradykinesia), rigid muscles, impaired posture and balance, loss of automatic movements, uncoordinated movement, uncontrolled movement, spontaneous jerking movement, speech changes, numbness, writing changes, involuntary movement such as chorea movement, uncontrolled posture, mood change, and sleep disorder. In an aspect, a neurological condition symptom is a movement symptom. Non-limiting examples of movement symptoms include impairment of an involuntary movement or an impairment of a voluntary movement. In one aspect, a neurological condition symptom is a cognitive symptom. Non-limiting examples of cognitive symptoms include fine motor skills, tremors, seizures, chorea, dystonia, dyskinesia, slow or abnormal eye movements, impaired gait, impaired posture, impaired balance, difficulty with speech, difficulty with swallowing, difficulty organizing, difficulty prioritizing, difficulty focusing on tasks, lack of flexibility, lack of impulse control, outbursts, lack of awareness of one's own behaviors and/or abilities, slowness in processing thoughts, difficulty in learning new information, difficulty in remember things, difficulty in communications, difficulty in following orders, difficulty in executing tasks.

In an aspect, neurological condition symptom is a psychiatric symptom. Non-limiting examples of psychiatric symptoms include depression, irritability, sadness or apathy, social withdrawal, insomnia, fatigue, lack of energy, obsessive-compulsive disorder, mania, bipolar disorder, and weight loss. In one aspect, a neurological condition symptom is at least one damaged blood vessel. In one aspect, a neurological condition symptom, is a damaged blood brain barrier. In one aspect, a neurological condition symptom is damaged blood flow. Non-limiting examples of tests to evaluate the elimination, reduction, slow, or delay, of neurological condition symptoms include the unified Huntington's disease rating scale (UHDRS) score, UHDRS Total Functional Capacity (TFC), UHDRS Functional Assessment, UHDRS Gait score, UHDRS Total Motor Score (TMS), Hamilton depression scale (HAM-D), Columbia-suicide severity rating scale (C-SSRS), Montreal cognitive assessment (MoCA), modified Rankin Scale (mRS), National Institutes of Health Stroke Scale (NIHSS), and Barthel Index (BI), Timed Up and Go Test (TUG), Chedoke Arm and Hand Activity Inventory (CAHAI), Symbol Digit Modalities Test, Controlled Oral Word Association tasks, magnetic resonance imaging (MRI), functional magnetic resonance imaging (fMRI), and positron emission tomography (PET) scanning.

In an aspect, a therapeutically effective dose achieves remission, cure, response rate, or resolution rate of a neurological condition of between about 10% and about 99% or more. In one aspect, a therapeutically effective dose achieves remission, cure, response rate, or resolution rate of a neurological condition between 10% and 100%, such as between 10% and 14%, between 10% and 20%, between 10% and 25%, between 14% and 20%, between 14% and 25%, between 14% and 30%, between 20% and 25%, between 20% and 30%, between 20% and 35%, between 25% and 30%, between 25% and 35%, between 25% and 40%, between 30% and 35%, between 30% and 40%, between 35% and 45%, between 35% and 50%, between 40% and 45%, between 40% and 50%, between 40% and 55%, between 45% and 50%, between 45% and 55%, between 45% and 60%, between 50% and 55%, between 50% and 60%, between 50% and 65%, between 55% and 60%, between 55% and 65%, between 55% and 70%, between 60% and 65%, between 60% and 70%, between 60% and 75%, between 65% and 70%, between 65% and 75%, between 65% and 80%, between 70% and 75%, between 70% and 80%, between 70% and 85%, between 75% and 80%, between 75% and 85%, between 75% and 90%, between 80% and 85%, between 80% and 90%, between 80% and 95%, between 85% and 90%, between 85% and 95%, between 85% and 100%, between 90% and 95%, between 90% and 100%, or between 95% and 100%.

In and aspect, a therapeutically effective dose eliminates, reduces, slows, or delays, one or more neurological condition symptoms between 10% and 100%, such as between 10% to about 14%, between 10% and 20%, between 10% and 25%, between 14% and 20%, between 14% and 25%, between 14% and 30%, between 20% and 25%, between 20% and 30%, between 20% and 35%, between 25 and 30%, between 25% and 35%, between 25% and 40%, between 30% and 35%, between 30% and 40%, between 35% and 45%, between 35% and 50%, between 40% and 45%, between 40% and 50%, between 40% and 55%, between 45% and 50%, between 45% and 55%, between 45% and 60%, between 50% and 55%, between 50% and 60%, between 50% and 65%, between 55% and 60%, between 55% and 65%, between 55% and 70%, between 60% and 65%, between 60% and 70%, between 60% and 75%, between 65% and 70%, between 65% and 75%, between 65% and 80%, between 70% and 75%, between 70% and 80%, between 70% and 85%, between 75% and 80%, between 75% and 85%, between 75% and 90%, between 80% and 85%, between 80% and 90%, between 80% and 95%, between 85% and 90%, between 85% and 95%, between 85% and 100%, between 90% and 95%, between 90% and 100%, or between 95% and 100%.

In an aspect, a neurological condition symptom is assessed on the day of treatment, 1 day post treatment, 3 months post treatment, 6 months post treatment, 1 year post treatment and every year thereafter post treatment.

In an aspect, a neurological condition symptom is assessed between 1 day post treatment and 7 days post treatment. In one aspect, symptoms can be assessed between 1 day post treatment and 2 days post treatment, between 1 day post treatment and 3 days post treatment, between 1 day post treatment and 4 days post treatment, between 2 days post treatment and 3 days post treatment, between 2 days post treatment and 4 days post treatment, between 2 days post treatment and 5 days post treatment, between 3 days post treatment and 4 days post treatment, between 3 days post treatment and 5 days post treatment, 3 days post treatment and 6 days post treatment, between 4 days post treatment and 5 days post treatment, between 4 days post treatment and 6 days post treatment, between 4 days post treatment and 7 days post treatment, between 5 days post treatment and 6 days post treatment, between 5 days post treatment and 7 days post treatment, or between 6 days post treatment and 7 days post treatment. In one aspect, symptoms can be assessed between 1 week post treatment and 4 weeks post treatment. In one aspect, symptoms can be assessed between 1 week post treatment and 2 weeks post treatment, between 1 week post treatment and 3 weeks post treatment, between 1 week post treatment and 4 weeks post treatment, between 2 weeks post treatment and 3 weeks post treatment, between 2 weeks post treatment and 4 weeks post treatment, or between 3 weeks post treatment and 4 weeks post treatment. In one aspect, symptoms can be assessed between 1 month post treatment and 12 months post treatment. In one aspect, symptoms can be assessed between 1 month post treatment and 2 months post treatment, between 1 month post treatment and 3 months post treatment, between 1 month post treatment and 4 months post treatment, between 2 months post treatment and 3 months post treatment, between 2 months post treatment and 4 months post treatment, between 2 months post treatment and 5 months post treatment, between 3 months post treatment and 4 months post treatment, between 3 months post treatment and 5 months post treatment, between 3 months post treatment and 6 months post treatment, between 4 months post treatment and 5 months post treatment, between 4 months post treatment and 6 months post treatment, between 4 months post treatment and 7 months post treatment, between 5 months post treatment and 6 months post treatment, between 5 months post treatment and 7 months post treatment, between 5 months post treatment and 8 months post treatment, between 6 months post treatment and 7 months post treatment, between 6 months post treatment and 8 months post treatment, between 6 months post treatment and 9 months post treatment, between 7 months post treatment and 8 months post treatment, between 7 months post treatment and 9 months post treatment, between 7 months post treatment and 10 months post treatment, between 8 months post treatment and 9 months post treatment, between 8 months post treatment and 10 months post treatment, between 8 months post treatment and 11 months post treatment, between 9 months post treatment and 10 months post treatment, between 9 months post treatment and 11 months post treatment, between 9 months post treatment and 12 months post treatment, between 10 months post treatment and 11 months post treatment, between 10 months post treatment and 12 months post treatment, or between 11 months post treatment and 12 months post treatment. In one aspect, symptoms can be assessed between 1 year post treatment and about 20 years post treatment. In one aspect symptoms can be assessed between 1 year post treatment and 5 years post treatment, between 1 year post treatment and 10 years post treatment, between 1 year post treatment and 14 years post treatment, between 5 years post treatment and 10 years post treatment, between 5 years post treatment and 14 years post treatment, between 5 years post treatment and 20 years post treatment, between 10 years post treatment and 14 years post treatment, between 10 years post treatment and years post treatment, or between 14 years post treatment and 20 years post treatment.

As used herein, the term "survival rate" refers to a cohort of subjects in a treatment group still alive after a given period of time after diagnosis of a neurological condition.

In an aspect, a therapeutically effective dose achieves increase survival rate of between about 10% and 99% or more. In one aspect, a therapeutically effective dose achieves an increase in survival rate of between 10% and 100%, such as between 10% and 14%, between 10% and 20%, between 10% and 25%, between 14% and 20%, between 14% and 25%, between 14% and 30%, between 20% and 25%, between 20% and 30%, between 20% and 35%, between 25% and 30%, between 25% and 35%, between 25% and 40%, between 30% and 35%, between 30% and 40%, between 35% and 45%, between 35% and 50%, between 40% and 45%, between 40% and 50%, between 40% and 55%, between 45% and 50%, between 45% and 55%, between 45% and 60%, between 50% and 55%, between 50% and 60%, between 50% and 65%, between 55% and 60%, between 55% and 65%, between 55% and 70%, between 60% and 65%, between 60% and 70%, between 60% and 75%, between 65% and 70%, between 65% and 75%, between 65% and 80%, between 70% and 75%, between 70% and 80%, between 70% and 85%, between 75% and 80%, between 75% and 85%, between 75% and 90%, between 80% and 85%, between 80% and 90%, between 80% and 95%, between 85% and 90%, between 85% and 95%, between 85% and 100%, between 90% and 95%, between 90% and 100%, or between 95% and 100%.

As used herein, the term "life expectancy" refers to a period of time a subject is expected to live.

In an aspect, a therapeutically effective dose increases life expectancy of between about 10% and 99% or more. In one aspect, a therapeutically effective dose increases life expectancy of between 10% and 100%, such as between 10% and 14%, between 10% and 20%, between 10% and 25%, between 14% and 20%, between 14% and 25%, between 14% and 30%, between 20% and 25%, between 20% and 30%, between 20% and 35%, between 25% and 30%, between 25% and 35%, between 25% and 40%, between 30% and 35%, between 30% and 40%, between 35% and 45%, between 35% and 50%, between 40% and 45%, between 40% and 50%, between 40% and 55%, between 45% and 50%, between 45% and 55%, between 45% and 60%, between 50% and 55%, between 50% and 60%, between 50% and 65%, between 55% and 60%, between 55% and 65%, between 55% and 70%, between 60% and 65%, between 60% and 70%, between 60% and 75%, between 65% and 70%, between 65% and 75%, between 65% and 80%, between 70% and 75%, between 70% and 80%, between 70% and 85%, between 75% and 80%, between 75% and 85%, between 75% and 90%, between 80% and 85%, between 80% and 90%, between 80% and 95%, between 85% and 90%, between 85% and 95%, between 85/cand 100%, between 90% and 95%, between 90% and 100%, or between 95% and 100%.

In an aspect, a therapeutically effective dose reduces the amount of atrophy within the brain of a subject in need thereof between about 10% and 99% or more. In one aspect, a therapeutically effective dose reduces the amount of atrophy within the brain of a subject in need thereof between 10% and 100%, such as between 10% and 14%, between 10% and 20%, between 10% and 25%, between 14% and 20%, between 14% and 25%, between 14% and 30%, between 20% and 25%, between 20% and 30%, between 20% and 35%, between 25% and 30%, between 25% and 35%, between 25% and 40%, between 30% and 35%, between 30% and 40%, between 35% and 45%, between 35% and 50%, between 40% and 45%, between 40% and 50%, between 40% and 55%, between 45% and 50%, between 45% and 55%, between 45% and 60%, between 50% and 55%, between 50% and 60%, between 50% and 65%, between 55% and 60%, between 55% and 65%, between 55% and 70%, between 60% and 65%, between 60% and 70%, between 60% and 75%, between 65% and 70%, between 65% and 75%, between 65% and 80%, between 70% and 75%, between 70% and 80%, between 70% and 85%, between 75% and 80%, between 75% and 85%, between 75% and 90%, between 80% and 85%, between 80% and 90%, between 80% and 95%, between 85% and 90%, between 85% and 95%, between 85% and 100%, between 90% and 95%, between 90% and 100%, or between 95% and 100%.

In an aspect, the amount of atrophy within the brain of a subject in need thereof is assessed on the day of treatment, 1 day post treatment, 3 months post treatment, 6 months post treatment, 1 year post treatment and every year thereafter post treatment.

In an aspect, the amount of atrophy within the brain of a subject in need thereof is assessed between 1 day post treatment and 7 days post treatment. In one aspect, symptoms can be assessed between 1 day post treatment and 2 days post treatment, between 1 day post treatment and 3 days post treatment, between 1 day post treatment and 4 days post treatment, between 2 days post treatment and 3 days post treatment, between 2 days post treatment and 4 days post treatment, between 2 days post treatment and 5 days post treatment, between 3 days post treatment and 4 days post treatment, between 3 days post treatment and 5 days post treatment, 3 days post treatment and 6 days post treatment, between 4 days post treatment and 5 days post treatment, between 4 days post treatment and 6 days post treatment, between 4 days post treatment and 7 days post treatment, between 5 days post treatment and 6 days post treatment, between 5 days post treatment and 7 days post treatment, or between 6 days post treatment and 7 days post treatment. In one aspect, symptoms can be assessed between 1 week post treatment and 4 weeks post treatment. In one aspect, symptoms can be assessed between 1 week post treatment and 2 weeks post treatment, between 1 week post treatment and 3 weeks post treatment, between 1 week post treatment and 4 weeks post treatment, between 2 weeks post treatment and 3 weeks post treatment, between 2 weeks post treatment and 4 weeks post treatment, or between 3 weeks post treatment and 4 weeks post treatment. In one aspect, symptoms can be assessed between 1 month post treatment and 12 months post treatment. In one aspect, symptoms can be assessed between 1 month post treatment and 2 months post treatment, between 1 month post treatment and 3 months post treatment, between 1 month post treatment and 4 months post treatment, between 2 months post treatment and 3 months post treatment, between 2 months post treatment and 4 months post treatment, between 2 months post treatment and 5 months post treatment, between 3 months post treatment and 4 months post treatment, between 3 months post treatment and 5 months post treatment, between 3 months post treatment and 6 months post treatment, between 4 months post treatment and 5 months post treatment, between 4 months post treatment and 6 months post treatment, between 4 months post treatment and 7 months post treatment, between 5 months post treatment and 6 months post treatment, between 5 months post treatment and 7 months post treatment, between 5 months post treatment and 8 months post treatment, between 6 months post treatment and 7 months post treatment, between 6 months post treatment and 8 months post treatment, between 6 months post treatment and 9 months post treatment, between 7 months post treatment and 8 months post treatment, between 7 months post treatment and 9 months post treatment, between 7 months post treatment and 10 months post treatment, between 8 months post treatment and 9 months post treatment, between 8 months post treatment and 10 months post treatment, between 8 months post treatment and 11 months post treatment, between 9 months post treatment and 10 months post treatment, between 9 months post treatment and 11 months post treatment, between 9 months post treatment and 12 months post treatment, between 10 months post treatment and 11 months post treatment, between 10 months post treatment and 12 months post treatment, or between 11 months post treatment and 12 months post treatment. In one aspect, symptoms can be assessed between 1 year post treatment and about 20 years post treatment. In one aspect symptoms can be assessed between 1 year post treatment and 5 years post treatment, between 1 year post treatment and 10 years post treatment, between 1 year post treatment and 14 years post treatment, between 5 years post treatment and 10 years post treatment, between 5 years post treatment and 14 years post treatment, between 5 years post treatment and 20 years post treatment, between 10 years post treatment and 14 years post treatment, between 10 years post treatment and years post treatment, or between 14 years post treatment and 20 years post treatment.

Non-limiting examples of tests to evaluate the amount of atrophy within the brain of a subject in need thereof include Nissle staining, MRI, functional magnetic resonance fMRI, and PET scanning While the present disclosure has been described with reference to preferred embodiments, it will be understood by those skilled in the art that various changes may be made and equivalents may be substituted for elements thereof to adapt to particular situations without departing from the scope of the present disclosure. Therefore, it is intended that the present disclosure not be limited to the particular embodiments disclosed as the best mode contemplated for carrying out the present disclosure, but that the present disclosure will include all embodiments falling within the scope and spirit of the appended claims.

The examples set out herein illustrate several embodiments of the present disclosure but should not be construed as limiting the scope of the present disclosure in any manner.

EXAMPLES

Example 1. AAV Vector Constructs

Figure 1A:
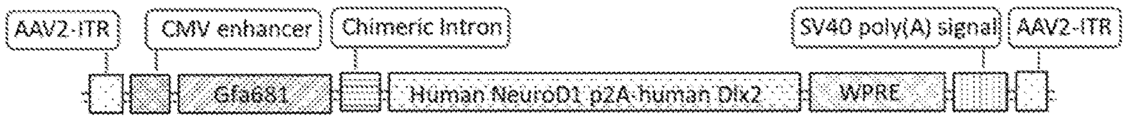
FIG. 1A depicts a map of aCE:Gfa681:NeuroD1:P2A:Dlx2:WPRE:SV40.
Figure 1B:
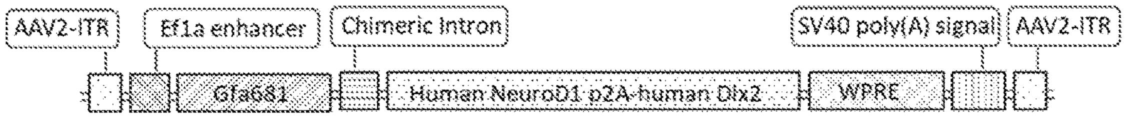
FIG. 1B depicts a map of a EF-1α: Gfa681:NeuroD1:P2A:Dlx2:WPRE:SV40.
Figure 1C:
FIG. 1C depicts a map of a CE:Gfa681:NeuroD1:P2A:Dlx2:WPRE:hGH
Figure 1D:
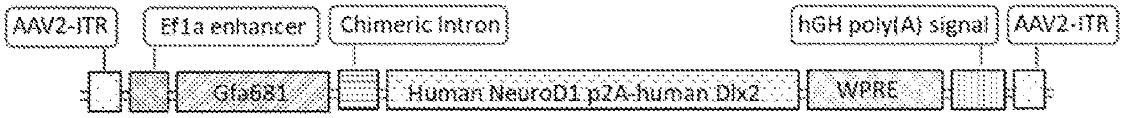
FIG. 1D depicts a map of EF-1α: Gfa681:NeuroD1:P2A:Dlx2:WPRE:hGH.
Figure 2A:
FIG. 2A depicts a map of a CE: Gfa681 NeuroD1:GSG-P2A:Dlx2:WPRE:SV40.
Figure 2B:
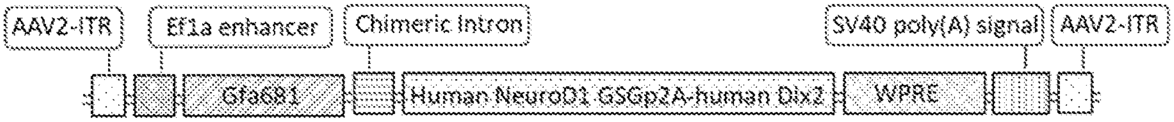
FIG. 2B depicts a map of a EF-1α: Gfa681 NeuroD1:GSG-P2A:Dlx2:WPRE:SV40.
Figure 2C:
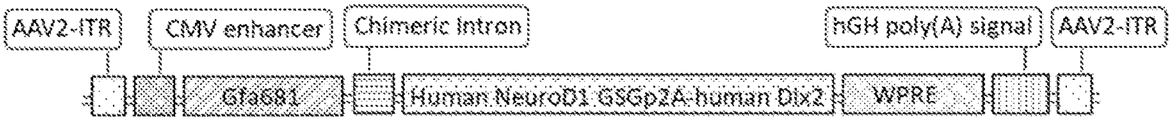
FIG. 2C depicts a map of a CE: Gfa681 NeuroD1:GSG-P2A:Dlx2:WPRE:hGH.
Figure 2D:
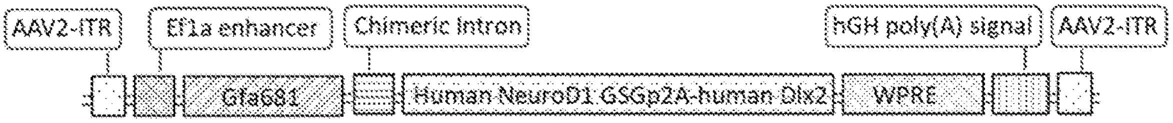
FIG. 2D depicts a map of a EF-1α: Gfa681 NeuroD1:GSG-P2A:Dlx2:WPRE:hGH.
Figure 3A:
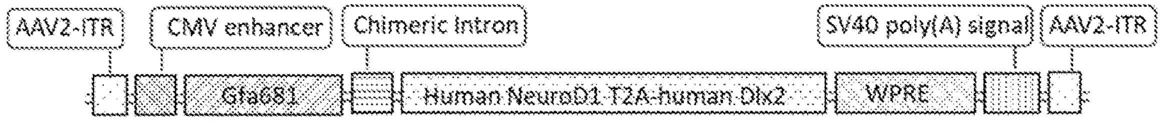
FIG. 3A depicts a map of a CE: Gfa681 NeuroD1:T2A:Dlx2:WPRE:SV40
Figure 3B:
FIG. 3B depicts a map of a EF-1α: Gfa681 NeuroD1:T2A:Dlx2:WPRE:SV40.
Figure 3C:
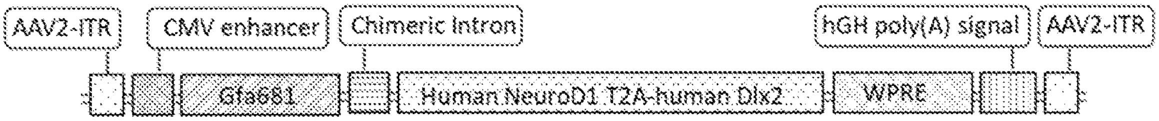
FIG. 3C depicts a map of a CE: Gfa681 NeuroD1:T2A:Dlx2:WPRE:hGH.
Figure 3D:
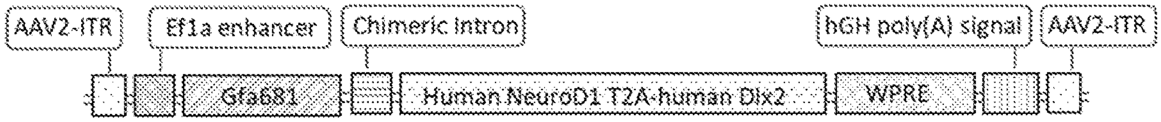
FIG. 3D depicts a map of a EF-1α: Gfa681 NeuroD1:T2A:Dlx2:WPRE:hGH.
Figure 4A:
FIG. 4A depicts a map of a CE: Gfa681 NeuroD1:GSG-T2A:Dlx2:WPRE:SV40
Figure 4B:
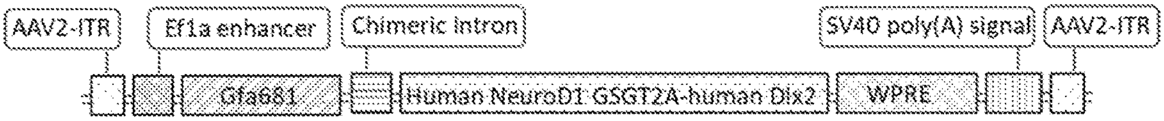
FIG. 4B depicts a map of a EF-1α: Gfa681 NeuroD1:GSG-T2A:Dlx2:WPRE:SV40.
Figure 4C:
FIG. 4C depicts a map of a CE: Gfa681 NeuroD1:GSG-T2A:Dlx2:WPRE:hGH.
Figure 4D:
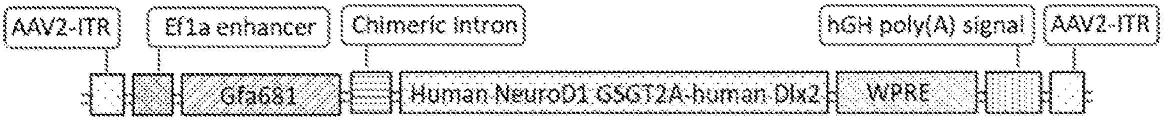
FIG. 4D depicts a map of a EF-1α: Gfa681 NeuroD1:GSG-T2A:Dlx2:WPRE:hGH.
Figure 5A:
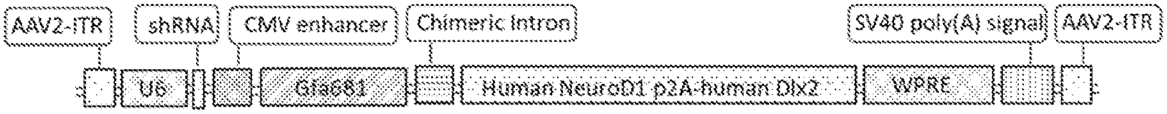
FIG. 5A depicts a map of a U6:shRNA:CE:Gfa681:NeuroD1:P2A:Dlx2:SV40.
Figure 5B:
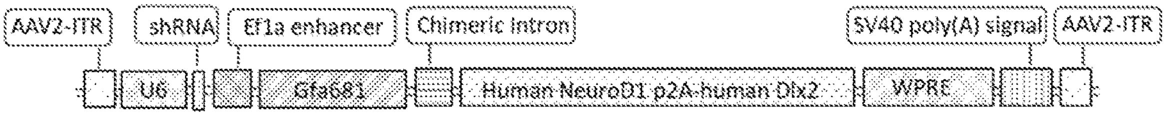
FIG. 5B depicts a map of a U6:shRNA:EF-1α:Gfa681:NeuroD1:P2A:Dlx2:SV40.
Figure 5C:
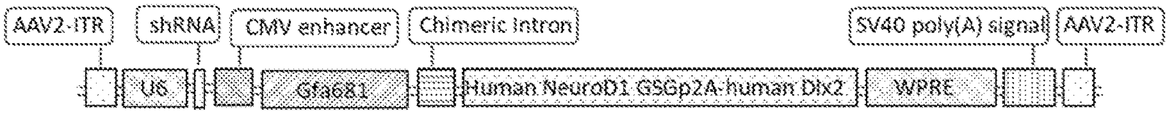
FIG. 5C depicts a map of a U6:shRNA:CE:Gfa681:NeuroD1:GSG-P2A:Dlx2:SV40.
Figure 5D:
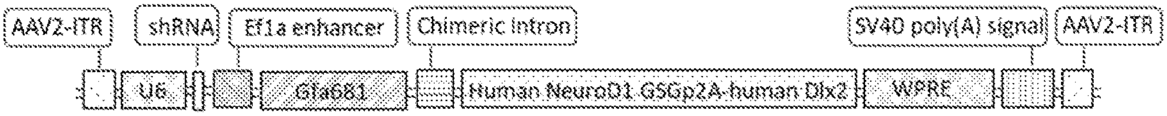
FIG. 5D depicts a map of a U6:shRNA:EF-1α:Gfa681:NeuroD1:GSG-P2A:Dlx2:SV40.
Figure 6A:
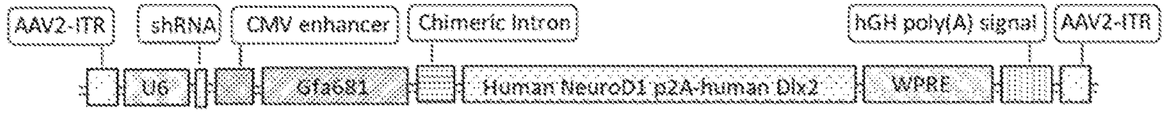
FIG. 6A depicts a map of a U6:shRNA:CE:Gfa681:NeuroD1:P2A:Dlx2:hGh.
Figure 6B:
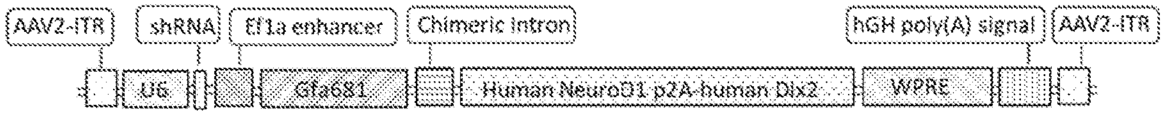
FIG. 6B depicts a map of a U6:shRNA:EF-1α:Gfa681:NeuroD1:P2A:Dlx2:hGh.
Figure 6C:
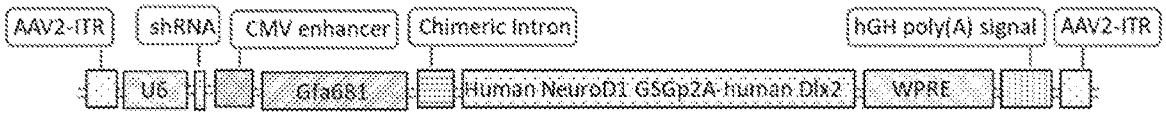
FIG. 6C depicts a map of a U6:shRNA:CE:Gfa681:NeuroD1:GSG-P2A:Dlx2:hGh.
Figure 6D:
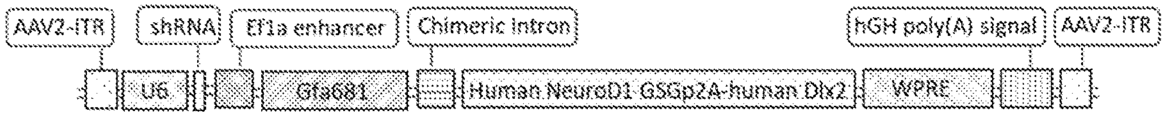
FIG. 6D depicts a map of a U6:shRNA: EF-1α:Gfa681:NeuroD1:GSG-P2A:Dlx2:hGh.
Figure 7A:
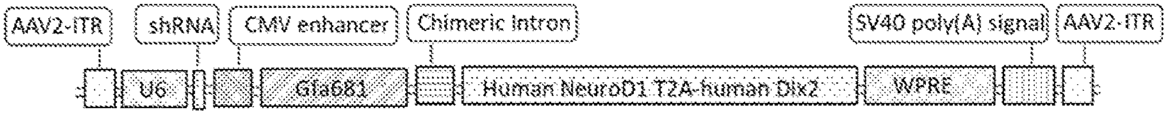
FIG. 7A depicts a map of a U6:shRNA:CE:Gfa681:NeuroD1:T2A:Dlx2:SV40.
Figure 7B:
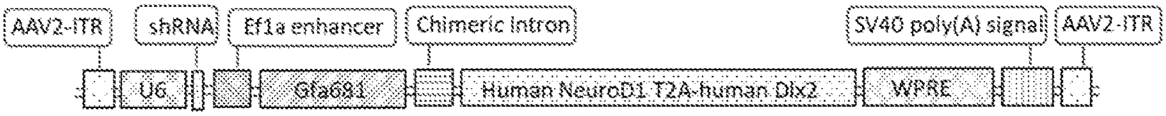
FIG. 7B depicts a map of a U6:shRNA:EF-1α:Gfa681:NeuroD1:T2A:Dlx2:SV40.
Figure 7C:
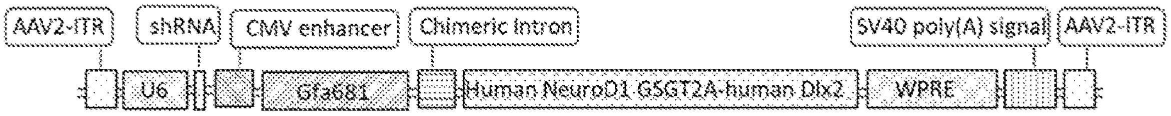
FIG. 7C depicts a map of a U6:shRNA:CE:Gfa681:NeuroD1:GSG-T2A:Dlx2:SV40.
Figure 7D:
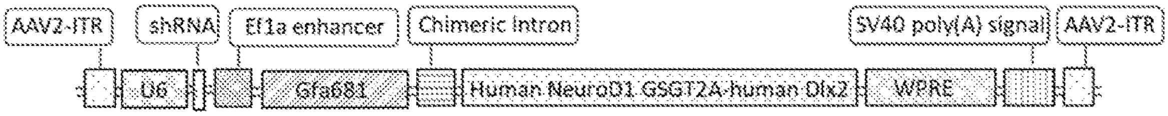
FIG. 7D depicts a map of a EF-1α:Gfa681:NeuroD1:GSG-T2A:Dlx2:SV40.
Figure 8A:
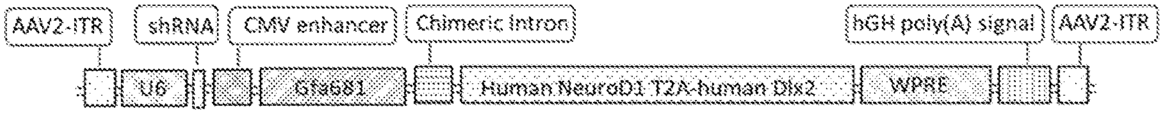
FIG. 8A depicts a map of a U6:shRNA:CE:Gfa681:NeuroD1:T2A:Dlx2:hGh.
Figure 8B:
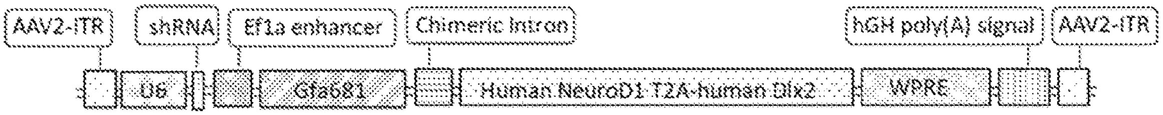
FIG. 8B depicts a map of a U6:shRNA:EF-1α:Gfa681:NeuroD1:T2A:Dlx2:hGh.
Figure 8C:
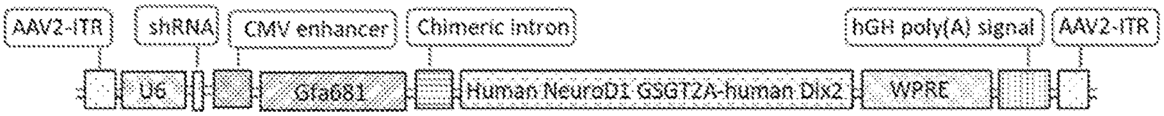
FIG. 8C depicts a map of a U6:shRNA:CE:Gfa681:NeuroD1:GSG-T2A:Dlx2:hGh.
Figure 8D:
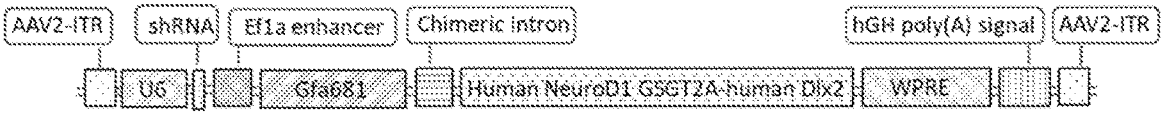
FIG. 8D depicts a vector map of a U6:shRNA:EF-1α:Gfa681:NeuroD1:GSG-T2A:Dlx2:hGh.

Forty eight AAV vector constructs:

EF-1α:GfaABC1D:NeuroD1:P2A:Dlx2:WPRE:SV40 (FIG. 1B);
EF-1α:Gfa1.6:NeuroD1:P2A:Dlx2:WPRE:SV40;
EF-1α:GFA2.2:NeuroD1:P2A:Dlx2:WPRE:SV40;
EF-1α:GfaABC1D:NeuroD1:P2A:Dlx2:WPRE:hGH;
EF-1α:Gfa1.6:NeuroD1:P2A:Dlx2:WPRE:hGH;
EF-1α:GFA2.2:NeuroD1:P2A:Dlx2:WPRE:hGH;
CE:GfaABC1D:NeuroD1:P2A:Dlx2:WPRE:SV40 (P31) (FIG. 1A);
CE:Gfa1.6:NeuroD1:P2A:Dlx2:WPRE:SV40;
CE:GFA2.2:NeuroD1:P2A:Dlx2:WPRE:SV40;
CE:GfaABC1D:NeuroD1:P2A:Dlx2:WPRE:hGH
CE:Gfa1.6:NeuroD1:P2A:Dlx2:WPRE:hGH;
CE:GFA2.2:NeuroD1:P2A:Dlx2:WPRE:hGH;
EF-1α:GfaABC1D:NeuroD1:T2A:Dlx2:WPRE:SV40 (FIG. 3B);
EF-1α:Gfa1.6:NeuroD1:T2A:Dlx2:WPRE:SV40;
EF-1α:GFA2.2:NeuroD1:T2A:Dlx2:WPRE:SV40;
EF-1α:GfaABC1D:NeuroD1:T2A:Dlx2:WPRE:hGH (FIG. 3D);
EF-1α:Gfa1.6:NeuroD1:T2A:Dlx2:WPRE:hGH;
EF-1α:GFA2.2:NeuroD1:T2A:Dlx2:WPRE:hGH;
CE:GfaABC1D:NeuroD1:T2A:Dlx2:WPRE:SV40 (FIG. 3A);
CE:Gfa1.6:NeuroD1:T2A:Dlx2:WPRE:SV40;
CE:GFA2.2:NeuroD1:T2A:Dlx2:WPRE:SV40;
CE:GfaABC1D:NeuroD1:T2A:Dlx2:WPRE:hGH (FIG. 3C);
CE:Gfa1.6:NeuroD1:T2A:Dlx2:WPRE:hGH;
CE:GFA2.2:NeuroD1:T2A:Dlx2:WPRE:hGH;
EF-1α:GfaABC1D:NeuroD1:GSG-P2A:Dlx2:WPRE:SV40 (FIG. 2B);
EF-1α:Gfa1.6:NeuroD1:GSG-P2A:Dlx2:WPRE:SV40;
EF-1α:GFA2.2:NeuroD1:GSG-P2A:Dlx2:WPRE:SV40
EF-1α:GfaABC1D:NeuroD1:GSG-P2A:Dlx2:WPRE:hGH (FIG. 2D);
EF-1α:Gfa1.6:NeuroD1:GSG-P2A:Dlx2:WPRE:hGH;
EF-1α:GFA2.2:NeuroD1:GSG-P2A:Dlx2:WPRE:hGH;
CE:GfaABC1D:NeuroD1:GSG-P2A:Dlx2:WPRE:SV40 (FIG. 2A); CE:Gfa1.6:NeuroD1:GSG-P2A:Dlx2:WPRE:SV40;
CE:GFA2.2:NeuroD1:GSG-P2A:Dlx2:WPRE:SV40;
CE:GfaABC1D:NeuroD1:GSG-P2A:Dlx2:WPRE:hGH (FIG. 2C);
CE:Gfa1.6:NeuroD1:GSG-P2A:Dlx2:WPRE:hGH;
CE:GFA2.2:NeuroD1:GSG-P2A:Dlx2:WPRE:hGH;
EF-1α:GfaABC1D:NeuroD1:GSG-T2A:Dlx2:WPRE:hGH;
EF-1α:Gfa1.6:NeuroD1:GSG-T2A:Dlx2:WPRE:hGH (FIG. 4D);
EF-1α:GFA2.2:NeuroD1:GSG-T2A:Dlx2:WPRE:SV40;
EF-1α:GfaABC1D:NeuroD1:GSG-T2A:Dlx2:WPRE:hGH (FIG. 4D);
EF-1α:Gfa1.6:NeuroD1:GSG-T2A:Dlx2:WPRE:hGH;
EF-1α:GFA2.2:NeuroD1:GSG-T2A:Dlx2:WPRE:hGH;
CE:GfaABC1D:NeuroD1:GSG-T2A:Dlx2:WPRE:SV40 (FIG. 4A); CE:Gfa1.6:NeuroD1:GSG-T2A:Dlx2:WPRE:SV40;
CE:GFA2.2:NeuroD1:GSG-T2A:Dlx2:WPRE:SV40;
CE:GfaABC1D:NeuroD1:GSG-T2A:Dlx2:WPRE:hGH (FIG. 4C);
CE:Gfa1.6:NeuroD1:GSG-T2A:Dlx2:WPRE:hGH; and CE:GFA2.2:NeuroD1:GSG-T2A:Dlx2:WPRE:hGH, are constructed.

All 48 vectors constructs utilize pHSG-299 (Takara, Mountain View, CA), a pUC based vector constructs which contains an origin of replication, a Kanamycin resistance gene and a multiple cloning site (MSC) with lacZ gene as backbone.

The 5' end of the expression cassette is an enhancer from a human elongation factor-1 alpha promoter (EF-1 alpha enhancer; SEQ ID NO: 2) or the cytomegalovirus enhancer (CMV enhancer; SEQ ID NO: 11) placed 5' to either a 758-nucleotide GFAP promoter (GfaABC1D; SEQ ID NO: 26), 1667-nucleotide GFAP promoter (Gfa1.6; SEQ ID NO: 4), or a 2214-nucleotide GFAP promoter (GFA2.2 SEQ ID NO: 12).

Following (e.g., 3' to) the enhancer/GFAP promoter, several additional sequences are introduced into the expression cassette in 5' to 3' direction, including: a chimeric intron (SEQ ID NO: 5); a human NeuroD1 coding sequence (hNeuroD1; SEQ ID NO: 6); a human Dlx2 coding sequence (hDlx2; SEQ ID NO: 13); a linker sequence (P2A; SEQ ID NO: 15), (GSG-P2A; SEQ ID NO:18), (T2A; SEQ ID NO: 16), or (GSG-T2A; SEQ ID NO: 19); and a woodchuck hepatitis virus posttranscriptional regulatory element (WPRE; SEQ ID NO: 7). These sequences are all operably linked to an SV40 poly(A) signal (SEQ ID NO: 8) or hGH poly (A) signal (SEQ ID NO: 17) or bGH poly (A) signal (SEQ ID NO: 30). The enhancer, GFAP promoter, chimeric intron, hNeuroD1 coding sequence, hDlx2 coding sequence, linker, WPRE, and SV40 poly(A) signal are flanked by two AAV ITR sequences.

Example 2. AAV Virus Production

Each of the 24 plasmids is co-transfected into 293AAV cells using polyethylenimine along with Rep-Cap plasmid (a plasmid comprising a promoter driving the expression of AAV rep and cap genes) and Helper plasmid (a plasmid comprising a promoter driving the expression of E2A, E4, and VA RNA (of Adenovirus) to produce recombinant AAV virus particles.

Transfected cells are scraped and centrifuged at 72 hours after transfection. *Cell* pellets are frozen and thawed being placed in a dry ice/ethanol mixture followed by being placed in a 37° C. water bath. The freeze/thaw cycle is repeated three additional times. An AAV lysate is purified (e.g., cellular debris is removed) by ultra-centrifugation at 350,000 g for 1 hour in discontinuous iodixanol gradients. The virus-containing layer is collected and then concentrated by using Millipore Amicon Ultra Centrifugal Filters. Virus titers are then determined by qPCR using primers amplifying ITR region or gene/expression cassette specific sequences.

Example 3. Astrocytes Cell Cultures

Human cortical astrocytes (HA1800; ScienCell Research Laboratories, Inc., Carlsbad, California) are subcultured when they are over 90% confluent. For subculture, cells are trypsinized using TrypLE™ Select (Invitrogen, Carlsbad, California), centrifuged for 5 minutes at 200×g, then resuspended and plated on a medium comprising DMEM/F12 (Gibco); 10% fetal bovine serum (Gibco); penicillin/streptomycin (Gibco); 3.5 mM glucose (Sigma-Aldrich); B27 (Gibco); 10 ng/mL epidermal growth factor (Invitrogen); and 10 ng/mL fibroblast growth factor 2 (Invitrogen). The astrocytes are cultured on poly-D-lysine (Sigma-Aldrich) coated coverslips (12 mm) at a density of approximately 20,000 cells per coverslip in 24-well plates (BD Biosciences).

Rat primary astrocytes (isolated from Sprague Dawley Rat cortex or striatum) are cultured in media comprising DMEM/F12 (Gibco); 10% fetal bovine serum (Gibco), penicillin/streptomycin (Gibco); 3.5 mM glucose (Gibco).

All cells are maintained at 37° C. in humidified air with 5% carbon dioxide.

Example 4. Testing AAV Vector in Astrocyte Cell Cultures (In Vitro)

Recombinant AAV obtained from the method of Example 2 are used to infect human cortical astrocytes and rat primary astrocytes of Example 3 at a concentration range of $10^{10}$ particles/mL and $10^{14}$ particles/ml. Twenty-four hours after infection of the cells, the culture medium is replaced by differentiation medium comprising DMEM/F12 (Gibco); N2 supplement (Gibco); and 20 ng/mL brain-derived neurotrophic factor (Invitrogen). The differentiation medium is added to the cell cultures every four days. See Song et al., *Nature,* 417:39-44 (2002).

Empty space in the cell cultures is filled with additional human astrocytes to support the functional development of converted neurons as astrocytes or rat primary astrocytes convert to neurons.

Example 5. Testing of AAV Vector Potency

Recombinant AAV obtained from the method of Example 2 are used to infect human cortical astrocytes and rat primary astrocytes from Example 3 (or astrocytes from other brain regions or the spinal cord) at passage number 4 to 7 at a concentration range of $10^{10}$ particles/mL and $10^{14}$ particles/mL. qPCR, enzyme-linked immunosorbent (ELISA), and western blot are performed to determine expression of NeuroD1 transcript and protein levels.

Expression of NeuN, doublecortin (DCX), β3-tubulin, NF-200, and MAP2, are assessed by qPCR, ELISA, western blot, and immunostaining to determine functional output of recombinant AAV.

Example 6. Testing of AAV Vector Titration and Infection Rate

A purified AAV vector is treated with DNaseI to eliminate remnant plasmid contamination. A series of AAV vector dilutions are performed at 100 times, 500 times, 2500 times, and 12500 times. The AAV plasmid is diluted to generate a standard curve by serial dilutions. The plasmid is diluted to 104, 105, $10^6$, $10^7$, and $10^8$ molecules/ul. qPCR is performed on the diluted AAV vectors and the diluted AAV plasmid. The primers used are against the ITR region (Forward ITR primer, 5'-GGAACCCCTAGTGATGGAGTT, reverse ITR primer, 5'-CGGCCTCAGTGAGCGA). The qPCR mix comprises 10 uL Universal SYBR Master Mix 2×, 2 uL of 5 uM forward ITR primer, 2 uL of 5 uM reverse ITR primer, 5 uL of tested sample or diluted standard and 1 uL $H_2O$. The qPCR program is 95° C. for 10 minutes followed by 40 cycles of 95° C. for 15 seconds, 60° C. for 30 seconds followed by a melt curve. The data is analyzed using the qPCR cyclers software. The physical titer of the AAV sample (viral genomes (vg)/ml) is calculated based on the standard curve.

The AAV vector infection rate is tested by using the 50% tissue culture infection dose (TCID50) assay performed using a standard protocol from the American Type Culture Collection (ATCC; Manassas, VA).

Example 7. Testing of AAV Dose Range (In Vivo)

Recombinant AAV obtained from the method of Example 2 is injected into C57/BL6 mice by bilateral intracranial injection into the motor cortex. Each AAV is injected at a dosage of $1\times10^{11}$, $3\times10^{11}$, $1\times10^{12}$, $3\times10^{12}$, $1\times10^{12}$, $3\times10^{12}$, $1\times10^{13}$ viral genomes/mL at 1 uL of volume. Each dosage is assessed at 4 days, 20 days, and 60 days post injection to determine the optimal effective dose (OED), maximum tolerable dose (MTD), and minimum effective dose (MED) at a cell and tissue level. There are three mice per time point. The OED, MTD, and MED are determined by assessment of astrocyte-to-neuron conversion efficiency and potential toxicity via immunostaining of NeuroD1, GFAP, NeuN, and Iba1. If the first dose range is not sufficient to determine the OED, MTD, and MED, a second dosage range is performed at $1\times10^{10}$ viral genomes/mL to $1\times10^{14}$ GC/mL, at 1 uL of volume.

Example 8. Comparison of Neuron Conversion Rate of Recombinant AAVs Obtained from Various AAV Vector Constructs in Human Cell Cultures (In Vitro)

AAV vector constructs are design as described in Example 1 to express either NeuroD1 alone or Dlx2 alone. Recombinant AAV is obtained as described in Example 2 for (1) AAV vector constructs expressing NeuroD1 alone; (2) AAV vector constructs expressing Dlx2 alone; (3) a combination of AAV vector constructs (1) and (2); and (4) AAV vector constructs expressing NeuroD1 and a linker with Dlx2. Resulting recombinant AAVs are used to infect human cortical astrocytes and rat primary astrocytes of Example 3. Twenty-four hours after infection of the cells, the culture medium is replaced by differentiation medium comprising DMEM/F12 (Gibco); N2 supplement (Gibco); and 20 ng/mL brain-derived neurotrophic factor (Invitrogen). The differentiation medium is added to the cell cultures every four days. See Song et al., *Nature,* 417:39-44 (2002). Empty space in the cell cultures is filled with additional human astrocytes to support the functional development of converted neurons as astrocytes or microglial cells convert to neurons. Neuron conversion levels of each treatment are measured and compared.

Example 9. Testing AAV Vector in Human Subjects (In Vivo)

Recombinant AAV obtained from the method of Example 2 are used to infect human brain or spinal cord astrocytes in vivo. Recombinant AAV is injected at a concentration range of $10^{10}$ particles/mL and $10^{14}$ particles/mL with a volume ranging from 10 μL to 1 mL into the brain or spinal cord of a human subject with a neurological condition. The human subject's neurological condition symptoms, brain imaging including MRI, PET scan, or combination of MRI and PET, and behavioral metrics are observed before, during, and post injection. Post injection observations are performed once a week until the first month post injection. After the first month post injection, observations are performed once a month for the next 11 months, and may be extended to 2 years following viral injection.

Example 10. Dose Scale Assay in Non-Human Primates

The volume of brain tissue expressing NeuroD1 from Example 7 divided by the number of vector genomes ($mm^3$/vector genomes) is used to determine the viral infection rate of brain tissue. The volume ($mm^3$) of specific brain region to be treated in non-human primates is calculated and a dose range of vector genomes is scaled according to the infection rate obtained in Example 7. A dose range study is performed as in Example 7 and the OED, MTD, and MED are determined by assessment of astrocyte-to-neuron conversion efficiency and potential toxicity via immunostaining of NeuroD1, GFAP, NeuN, and Iba1.

Example 11. Treatment of a Subject in Need Thereof with Huntington's Disease (In Vivo)

A subject with Huntington's Disease is treated with recombinant AAV obtained from the method of Example 2. The subject's neurological symptoms include involuntary movement such as chorea movement, uncontrolled posture, mood change, sleep disorder, speech changes, difficulty with swallowing, and impairment of cognitive functions such as deficits in learning and memory. Recombinant AAV is injected at a concentration range of $10^{10}$ particles/mL and $10^{14}$ particles/mL with a volume ranging from 10 μL to 1000 μL into the striatum (putamen and caudate nucleus) of a human subject with a neurological condition. The human subject's neurological condition symptoms, brain imaging including MRI, PET scan, or combination of MRI and PET, and behavioral metric's are observed before, during, and post injection. Post injection observations are performed once a week until the first month post injection. After the first month post injection, observations are performed once a month for the next 11 months, and may be extended to 2 years following viral injection.

Example 12. A Combination Approach to Directly Converting Glial Cells to Neurons Coupled with shRNA for Knockdown of the Htt Gene Expression A target sequence is identified that is complementary to the Htt gene. An shRNA is designed to target the Htt gene. NeuroD1, Dlx2, and the target shRNA are packaged in to an AAV vector (hU6::Htt shRNA-hGFAP::hNeuroD1-P2A-hDlx2)(FIGS. 5A-8D) and recombinant AAV is produced as described in Example 2. Recombinant AAV is injected into the striatum of mice with mutant Htt gene. Mice receiving the treatment are tested for behavioral metrics, such as cat walk, open field test, clasping, mouse weight, and grip strength and brain imaging including MRI, PET scan, or combination of MRI and PET. Behavioral test results and brain imaging are compared among the groups (i) receiving no treatment, (ii) receiving recombinant AAV from Example 2, and (iii) receiving recombinant AAV (hU6::Htt shRNA-hGFAP::hNeuroD1-P2A-hDlx2)(FIG. 5A-8D).

Alternatively, the target shRNA is packaged in to an AAV vector (hU6::hHtt shRNA) and another recombinant AAV is produced as described in Example 2. The two recombinant AAVs are injected into the striatum of mice with mutant Htt. Mice receiving the treatment are tested for behavioral metrics, such as cat walk, open field test, clasping, mouse weight, and grip strength and brain imaging including MRI, PET scan, or combination of MRI and PET. Behavioral test results and brain imaging are compared among the groups (i) receiving no treatment, (ii) receiving recombinant AAV from Example 2 alone, and (iii) receiving recombinant AAV (hU6::hHtt shRNA) in combination with recombinant AAV from Example 2.

Example 13. A Combination Approach to Directly Converting Glial Cells to Neurons Coupled with CRISPR/CAS Gene Editing of the Htt Gene A target sequence is identified that is complementary to the Htt gene. A guide RNA (gRNA) sequence is designed to target the Htt gene. A donor sequence is designed to modify the number of CAG repeats of the Htt gene to less than 36. The Cas9 nuclease, an Htt specific gRNA, and donor sequence are packaged into AAV vectors (AAV-Cas9-HTT). Recombinant AAV is produced as described in Example 2.

Recombinant AAV (AAV-Cas9-HTT) is injected into the striatum of mice with mutant Htt simultaneously with recombinant AAV from Example 2. Mice receiving the treatment are tested for behavioral metrics, such as cat walk, open field test, clasping, mouse weight, and grip strength and brain imaging including MRI, PET scan, or combination of MRI and PET. Behavioral test results and brain imaging are compared among the groups (i) receiving no treatment, (ii) receiving recombinant AAV from Example 2, and (iii) receiving recombinant AAV-Cas9-HTT with recombinant AAV from Example 2 to identify synergistic effects between mutant Htt gene editing and glia-to-neuron conversion. Recombinant AAV-Cas9-HTT and recombinant AAV from Example 2 can be injected simultaneously or at different times.

Alternatively, NeuroD1, a linker (P2A), Dlx2, a second linker (P2A), Cas9 nuclease, the Htt specific gRNA, and the donor sequence are packaged into AAV vectors (AAV-hNeuroD1-P2A-hDlx2-P2A-Cas9-HTT). Recombinant AAV is produced as described in Example 2. Recombinant AAV (AAV-hNeuroD1-P2A-hDlx2-P2A-Cas9-HTT) is injected into the striatum of mice with mutant Htt simultaneously with recombinant AAV from Example 2. Mice receiving the treatment are tested for behavioral metrics, such as cat walk, open field test, clasping, mouse weight, and grip strength and brain imaging including MRI, PET scan, or combination of MRI and PET. Behavioral test results and brain imaging are compared among the groups (i) receiving no treatment, (ii) receiving recombinant AAV from Example 2, and (iii) receiving recombinant AAV-hNeuroD1-P2A-hDlx2-P2A-Cas9-HTT with recombinant AAV from Example 2 to identify synergistic effects between mutant Htt gene editing and glia-to-neuron conversion.

Example 14. A Combination Approach to Directly Converting Glial Cells to Neurons Coupled with Antisense Oligonucleotide (ASO) to Knock Down the Htt Gene Expression A target sequence is identified that is complementary to the Htt gene. An ASO is designed and synthesized to knock down the Htt gene expression. Recombinant AAV from Example 2 is injected together with Htt ASO into the striatum of mice with mutant Htt. Mice receiving the treatment are tested for behavioral metrics, such as cat walk, open field test, clasping, mouse weight, and grip strength and brain imaging including MRI, PET scan, or combination of MRI and PET. Behavioral test results and brain imaging are compared among the groups (i) receiving no treatment, (ii) receiving recombinant AAV from Example 2, and (iii) receiving recombinant AAV from Example 2 together with Htt ASO.

Example 15. A Combination Approach to Directly Converting Glial Cells to Neurons Coupled with siRNA to Knock Down the Htt Gene Expression A target sequence is identified that is complementary to the Htt gene. An siRNA is designed and synthesized to knock down the Htt gene expression. Recombinant AAV from example 2 is injected together with Htt siRNA into the striatum of mice with mutant Htt. Mice receiving the treatment are tested for behavioral metrics, such as cat walk, open field test, clasping, mouse weight, and grip strength and brain imaging including MRI, PET scan, or combination of MRI and PET. Behavioral test results and brain imaging are compared among the groups (i) receiving no treatment, (ii) receiving recombinant AAV from Example 2, and (iii) receiving recombinant AAV from Example 2 together with Htt siRNA.

Example 16. A Combination Approach to Directly Converting Glial Cells to Neurons Coupled with miRNA to Knock Down the Htt Gene Expression A miRNA is identified that is regulating the Htt gene expression. NeuroD1, Dlx2, and the miRNA are packaged into an AAV vector (CAG::Htt miRNA-hGFAP::hNeuroD1-P2A-hDlx2) and recombinant AAV is produced as described in Example 2. Recombinant AAV is injected into the striatum of mice with mutant Htt. Mice receiving the treatment are tested for behavioral metrics, such as cat walk, open field test, clasping, mouse weight, and grip strength and brain imaging including MRI, PET scan, or combination of MRI and PET. Behavioral test results and brain imaging are compared among the groups (i) receiving no treatment, (ii) receiving recombinant AAV from Example 2, and (iii) receiving recombinant AAV (CAG::Htt miRNA-hGFAP::hNeuroD1-P2A-hDlx2).

Alternatively, the target miRNA is packaged in to an AAV vector (CAG::hHtt miRNA) and recombinant AAV is produced as described in Example 2. Recombinant AAV is injected into the striatum of mice with mutant Htt. Mice receiving the treatment are tested for behavioral metrics, such as cat walk, open field test, clasping, mouse weight, and grip strength and brain imaging including MRI, PET scan, or combination of MRI and PET. Behavioral test results and brain imaging are compared among the groups (i) receiving no treatment, (ii) receiving recombinant AAV from Example 2 alone, and (iii) receiving recombinant AAV (CAG::hHtt miRNA) in combination with recombinant AAV from Example 2.

Example 17. AAV Virus Production of P31

Figure 9:
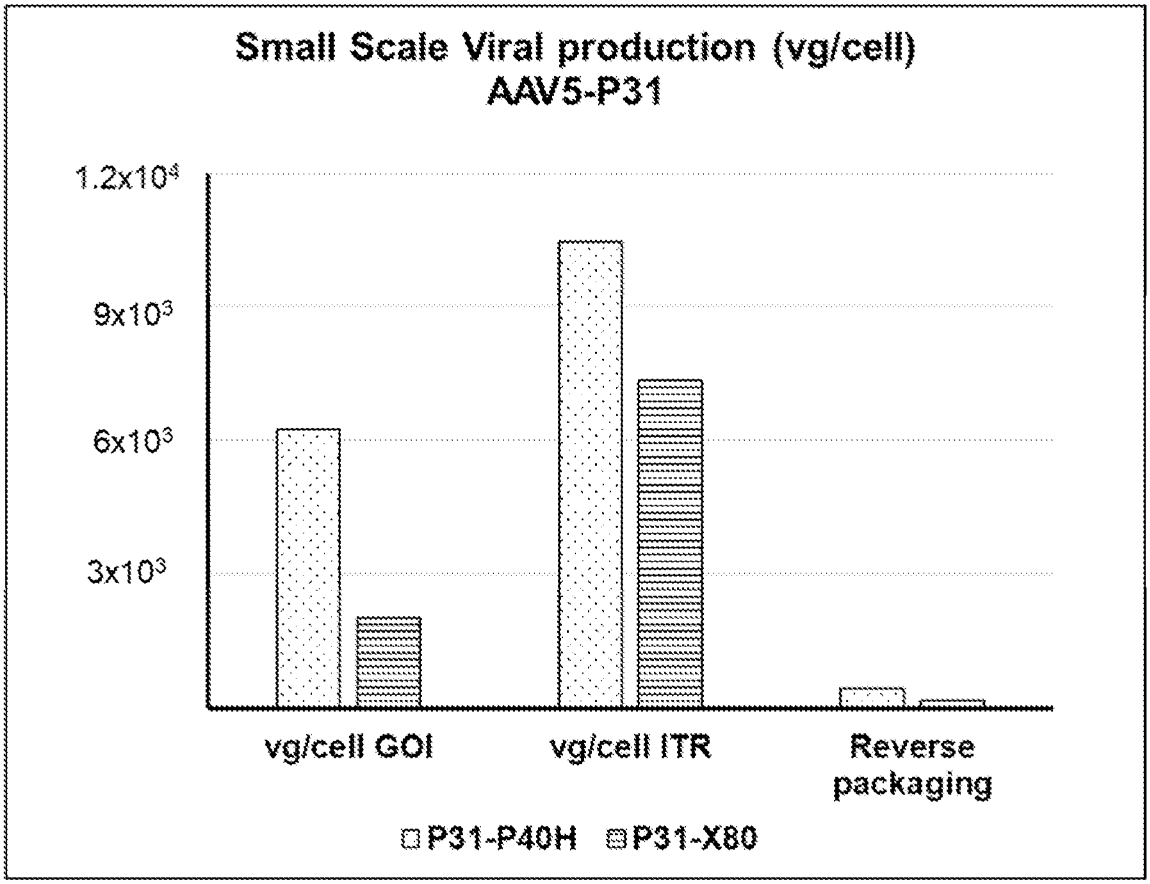
FIG. 9 measures AAV virus production of the P31 plasmid. Titer analysis is performed using gene of interest (GOI) primers, ITR region primers, and reverse packaging primers. Virus titer is calculated as vg/cell.

Recombinant AAV is obtained as described in Example 2. The P31 plasmid is co-transfected into AAV293 cells with a Rep-Cap plasmid expressing serotype 5 capsid protein and the Helper plasmid P40Helper (P40H) or pALD-X80 (X80) to produce recombinant AAV virus particles (P31-P40H or P31-X80). Virus titers are determined by qPCR using primers amplifying gene of interest (GOI) primers specific to the P31 plasmid and the ITR region. Reverse packaging primers are used to evaluate nonspecific packaging. Increased viral production is observed with the X80 helper plasmid compared to the P40H helper plasmid (FIG. 9).

Example 18. Successful Establishment of Rat Astrocytes Primary Culture

Figure 10:
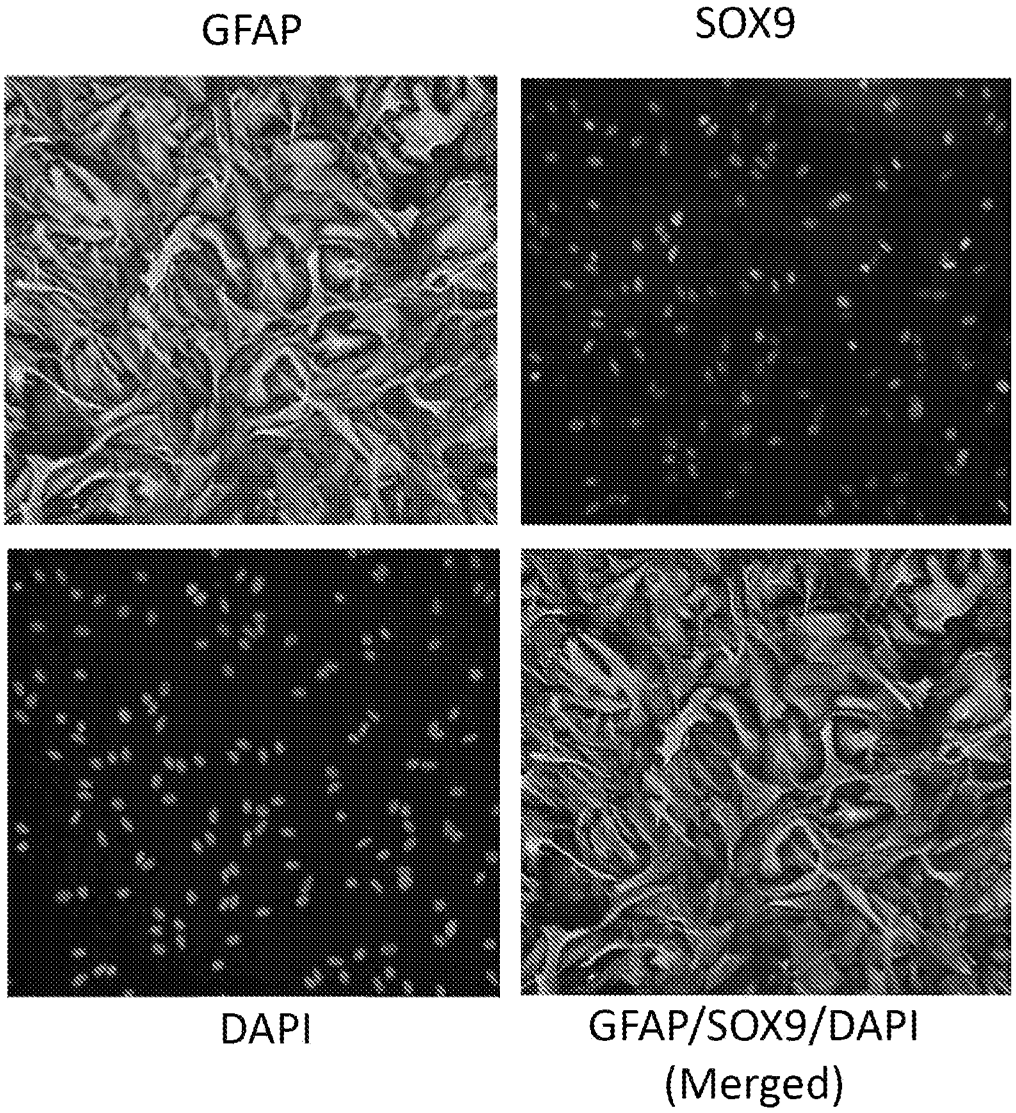
FIG. 10 depicts establishment of rat astrocyte primary culture from 3 day post-natal Sprague-Dawley rat brains. Upper left panel presents an image of GFAP stained cells. Upper right panel presents an image of SOX9 stained cells. Lower left panel presents an image of DAPI stained cells. Lower right panel presents a merge image of GFAP, SOX9, and DAPI stained cells.

Cortical and striatum tissue is isolated from 3 day postnatal Sprague-Dawley rat brains. Tissue is treated with papain to generate single cell suspension and seeded in flasks coated with poly-D-lysine. Cells are immunostained with GFAP antibody and SOX9 antibody. Cells are counter stained with DAPI antibody. More than 95% of cells are astrocytes identified by GFAP and SOX9 staining (FIG. 10). Far left panel presents an image of GFAP stained cells. Middle left panel presents an image of SOX9 stained cells. Middle right panel presents an image of DAPI stained cells. Far right panel presents a merge image of GFAP, SOX9, and DAPI stained cells.

Example 19. Comparison of Plasmid Transfection

Figure 11:
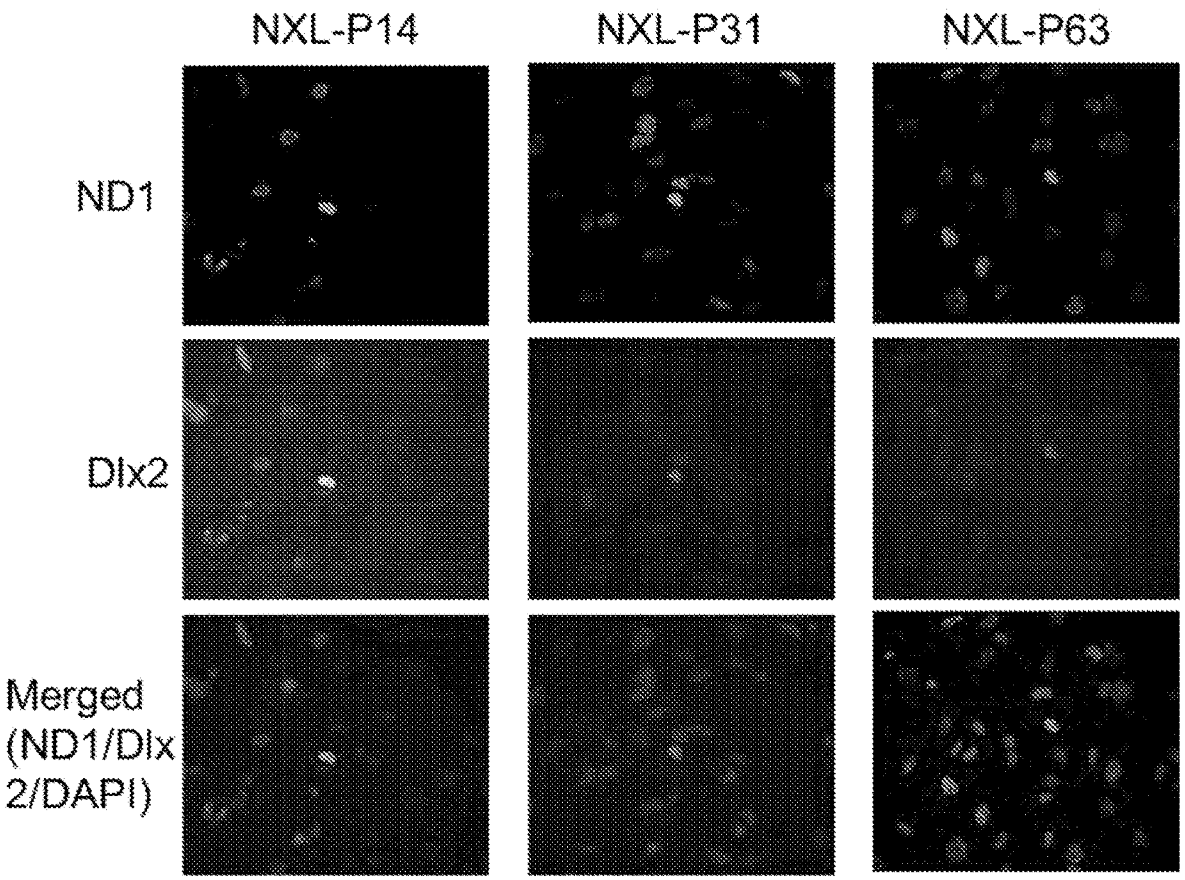
FIG. 11 depicts comparison of NeuroD1 expression efficiency of plasmids. Primary rat astrocyte cells are transfected with either the P14 (CE:GfaABC1D:hNeuroD1-P2A-Dlx2:WPRE:SV40), P31 (EF-1αE:GfaABC1D:NeuroD1-P2A-Dx2:WPRE:SV40), and P63 (CE:GfaABC1D:NeuroD1-GSG P2A-Dlx2: WPRE:SV40). Top panels show NeuroD1 staining of cells, middle panels show Dlx2 staining of cells and bottom panels show merged NeuroD1, Dlx2 and DAPI staining of cells.

Primary rat astrocytes are seeded and transfected as described in Example 18 with expression vectors P14 (CE:GfaABC1D:hNeuroD1-P2A-Dlx2:WPRE:SV40), P31 (EF- 1α:GfaABC1D:NeuroD1-P2A-Dx2:WPRE:SV40), and P63 (CE:GfaABC1D:NeuroD1-GSG P2A-Dx2:WPRE:SV40) to test the expression efficiency of NeuroD1 and Dlx2 in transfected cells. P14 resulted in the NeuroD1 and Dlx2 expression shown by NeuroD1 staining and Dlx2 staining of cells (FIG. 11; top panels show NeuroD1 staining of cells, middle panels show Dlx2 staining of cells, and bottom panels show merged NeuroD1, Dlx2, and DAPI staining of cells).

Figure 12:
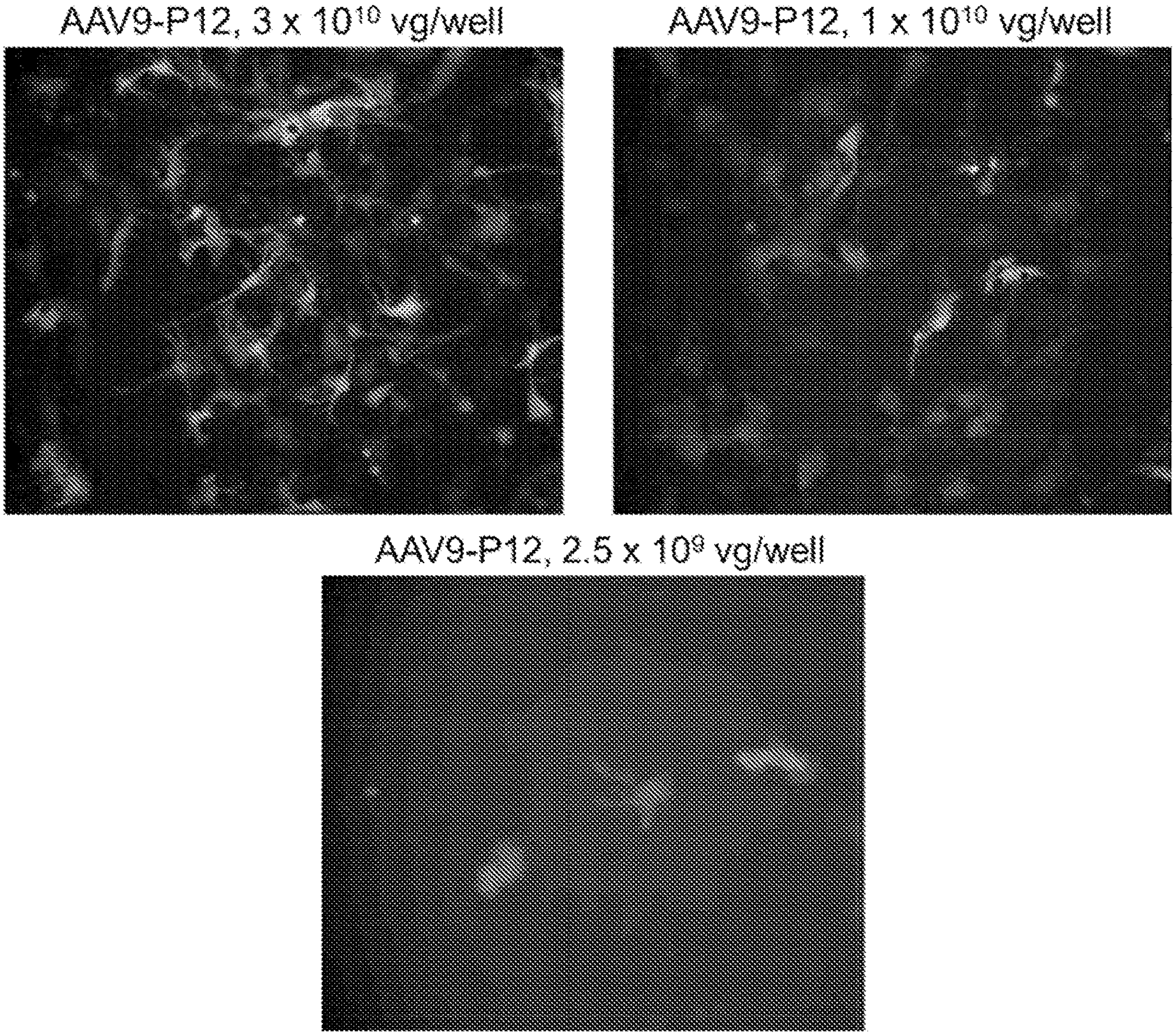
FIG. 12 depicts comparison of AAV virus particle transduction at different doses using AAV9-P12 (pGfaABC1D:GFP). Upper left panel shows a dose of $3\times10^{10}$ vg/well. Upper right panel shows a dose of $1\times10^{10}$ vg/well. Lower panel shows a dose of $2.5\times10^{9}$ vg/well.

Example 20. Successful Transduction of AAV Virus Particles into Primary Rat Astrocytes Recombinant AAV obtained from the method of Example 2 is transduced into primary rat astrocytes seeded in a 96 well plate with AAV9-P12 (pGfaABC1D:GFP) at various doses of either $3\times10^{10}$ vg/well, $1\times10^{10}$ vg/well, and $2.5\times10^{9}$ vg/well. RCAs of passage 5-7 are seeded on glass cover slips coated with poly-D-lysine (PDL) in 96-well plates at 50% confluency 24 hours prior to transduction. Cells are transduced with virus in fresh astrocyte media at the designated titer. Media are refreshed the next day and every 3-4 days. Images acquired six days post transduction of GFP positives cells show that the transduction rate is higher when virus titer is higher (FIG. 12).

Figure 13A:
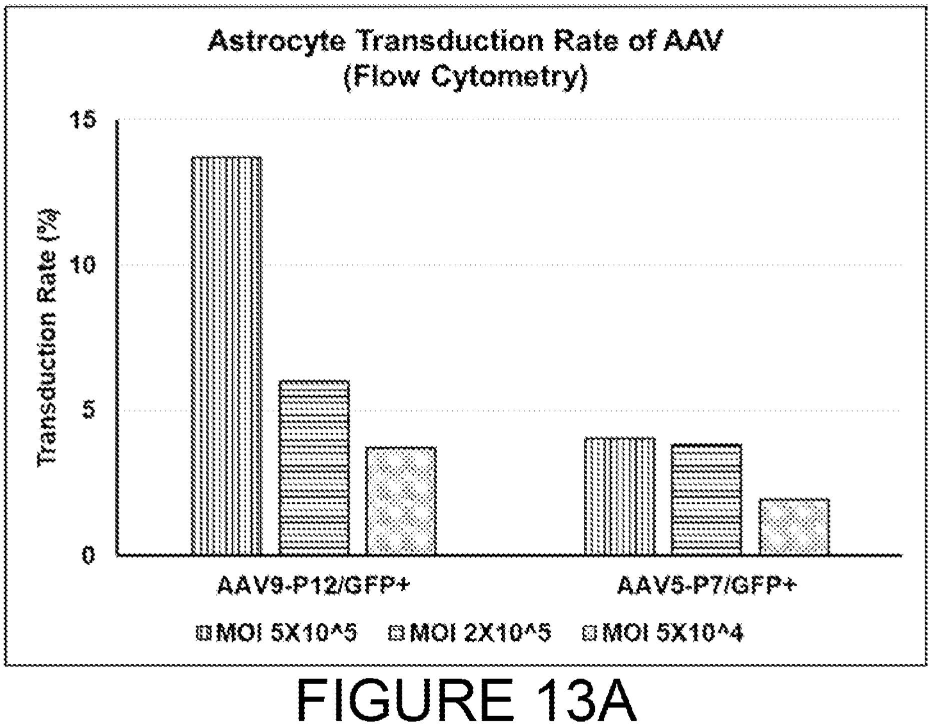
FIGS. 13A and 13B depict quantitative analysis of AAV particle transduction into primary rate astrocytes.
Figure 13B:
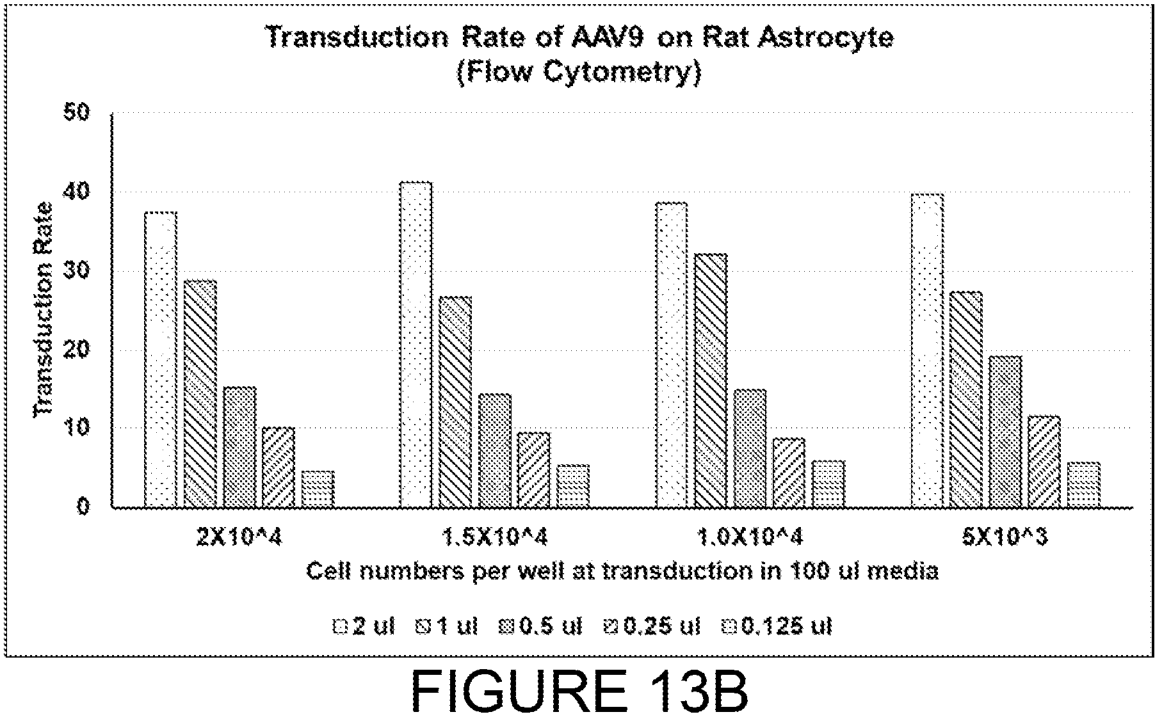

Example 21. Quantitative Analysis of Transduction of AAV Virus Particles into Primary Rat Astrocytes Recombinant AAV obtained from the method of Example 2 is transduced into primary rat astrocytes seeded in 24-well plates or 96-well plates with viral particles AAV9-P12 (pGfaABC1D:GFP) and AAV5-P7 (pEF-1α:GFP). Cells are harvested seven days post-infection by trypsinization. The cells are fixed, washed, and suspended in PBS. The viral transduction rate is analyzed using flow cytometry to count GFP positive cells compared with all cells (FIGS. 13A and 13B). FIG. 13A shows the % transduction rate at different MOI. Cells seeded in 24-well plates at $1\times10^{5}$ cells/well are infected at MOI of either $5\times10^{5}$ vg/cell, $2\times10^{5}$ vg/cell and $5\times10^{4}$ vg/cell. The viral transduction rate decreases as the MOI decreases. FIG. 13B shows the transduction rate of AAV viral particles in cells seeded in 96 well plates at a series of densities of $2\times10^{4}$ cell/well, $1.5\times10^{4}$ cell/well, $1\times10^{4}$ cell/well, and $5\times10^{3}$ cell/well, and infected with virus at a series of amounts of 2 μl, 1 μl, 0.5 μl, 0.25 μl, 0.125 μl of $1\times10^{13}$ vg/ml virus in 100 μl of medium. This is equivalent to $2\times10^{10}$ vg, $1\times10^{10}$ vg, $5\times10^{9}$ vg, $2.5\times10^{9}$ vg, and $1.25\times10^{9}$ vg each well respectively. The viral transduction rate is unchanged as the number of cells per well decreases.

Figure 14:
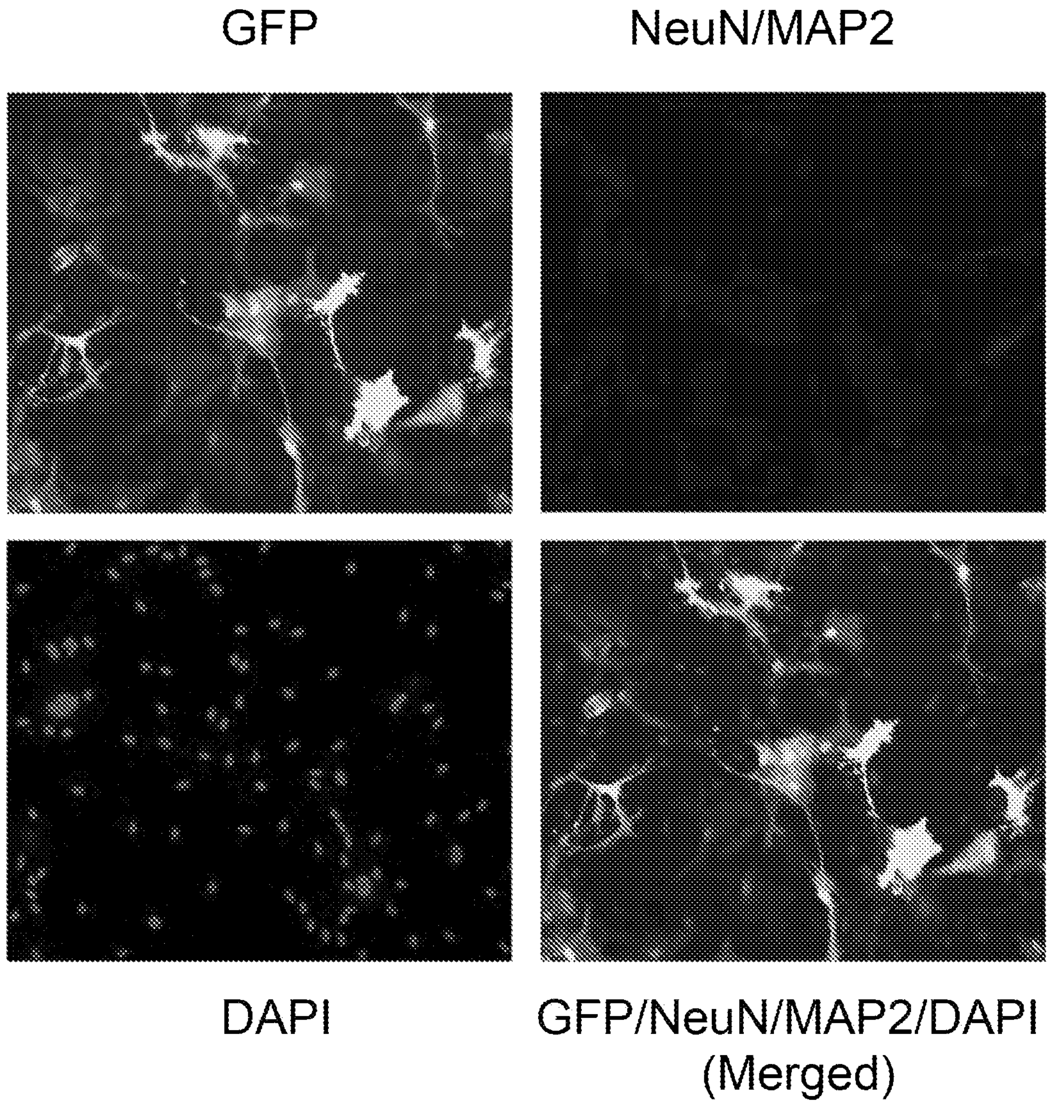
FIG. 14 depicts RCAs three weeks post transduction with control plasmid AAV9-P21 (CE-pGFA681-CI-GFP-WPRE-SV40 pA) at $2\times10^{10}$ vg/ml. Cells are immunostained with antibodies against neuronal markers NeuN and MAP2, and with DAPI (nuclear stain). GFP fluorescence indicates the presence of cells transduced with the control plasmid.
Figure 15:
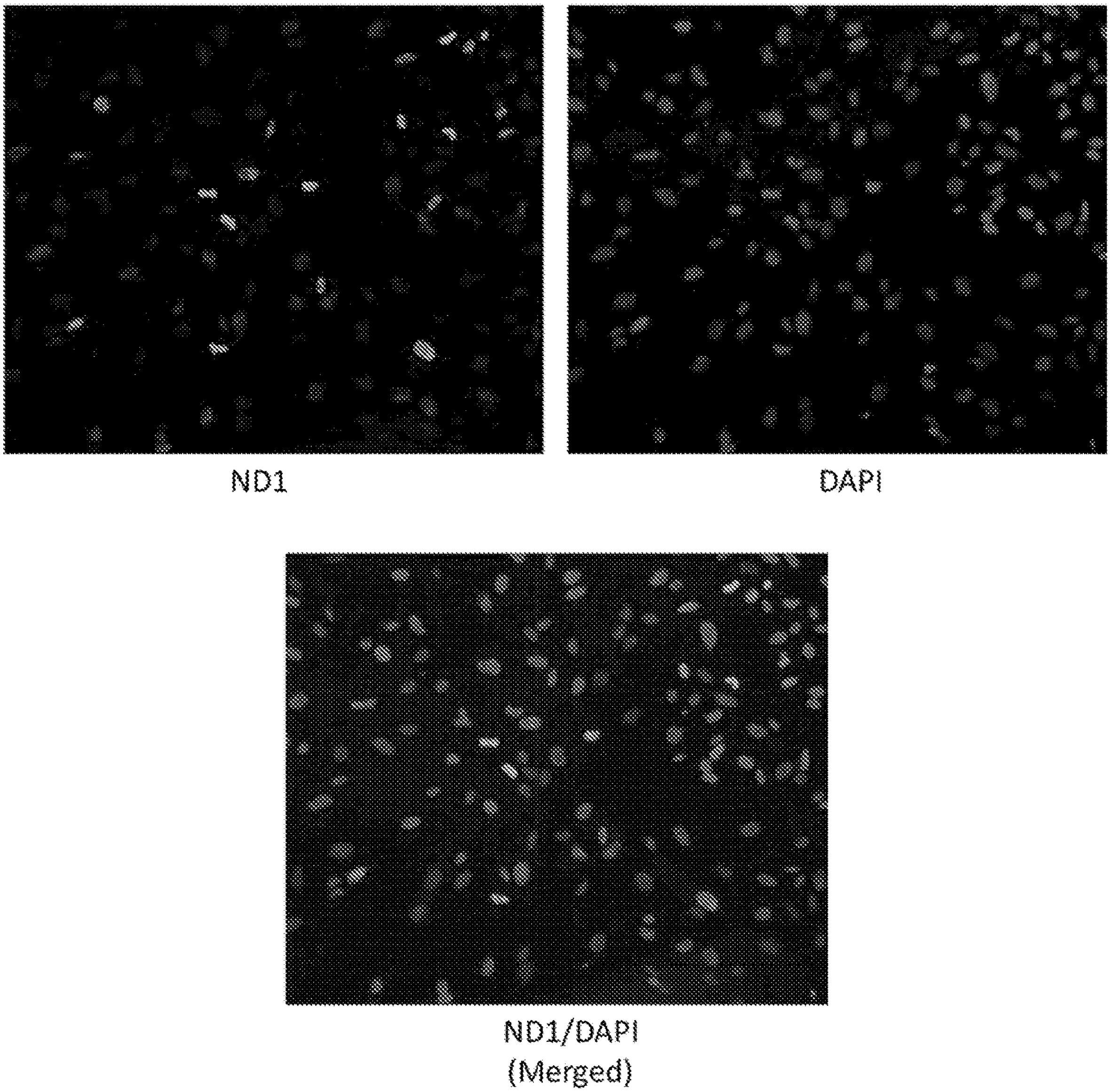
FIG. 15 depicts RCAs immunostained with an anti-NeuroD1 (ND1) antibody and DAPI (nuclear stain) 24 hours post transfection with NXL-P134 (CE-pGfa681-CRGI-hND1-oPRE-bGHpA).
Figure 16:
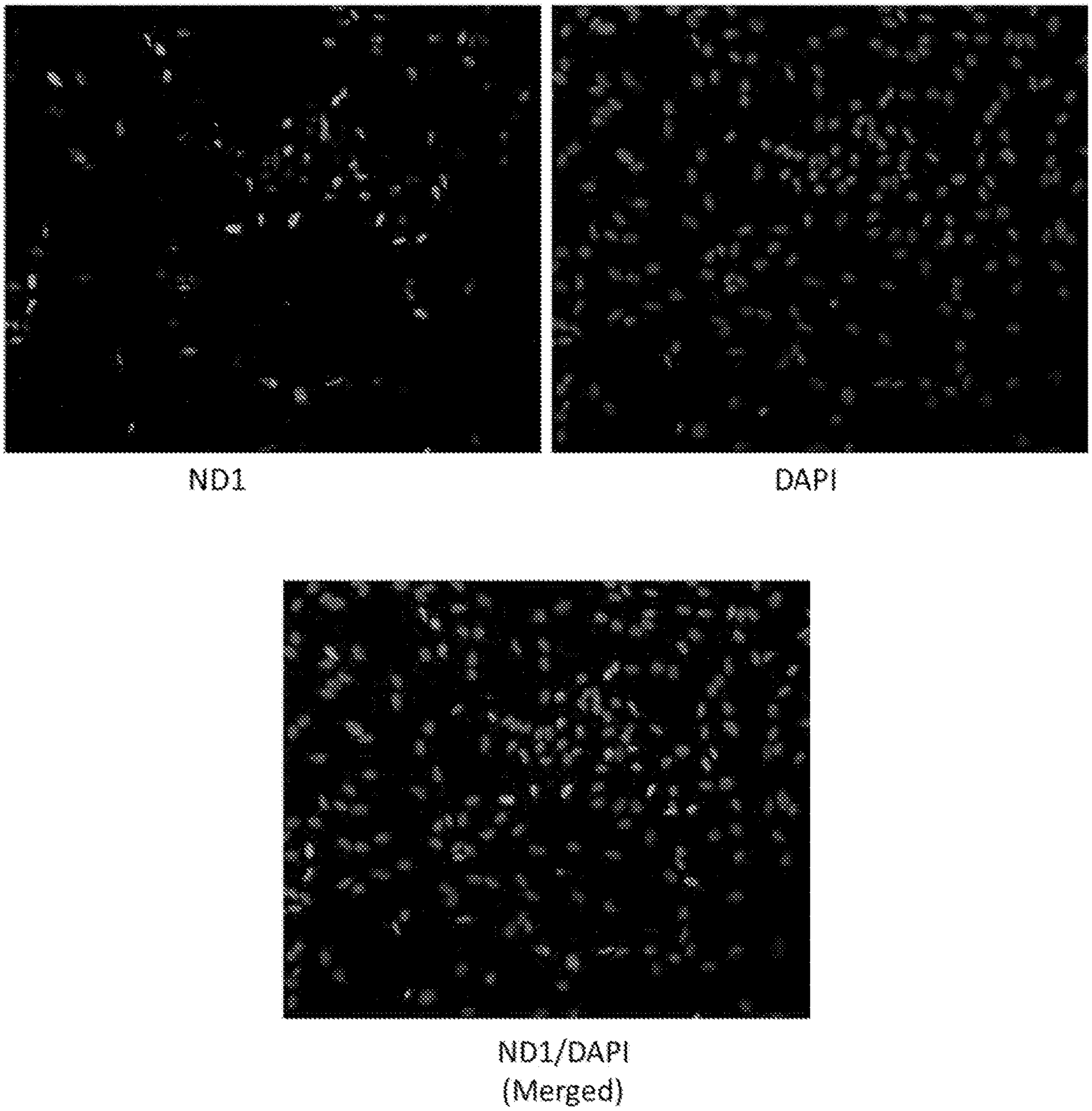
FIG. 16 depicts RCAs immunostained with an anti-ND1 antibody and DAPI (nuclear stain) 6 days post transduction with AAV9-P134 (CE-pGfa681-CRGI-hND1-oPRE-bGHpA) at $2\times10^{10}$ vg/ml.
Figure 18:
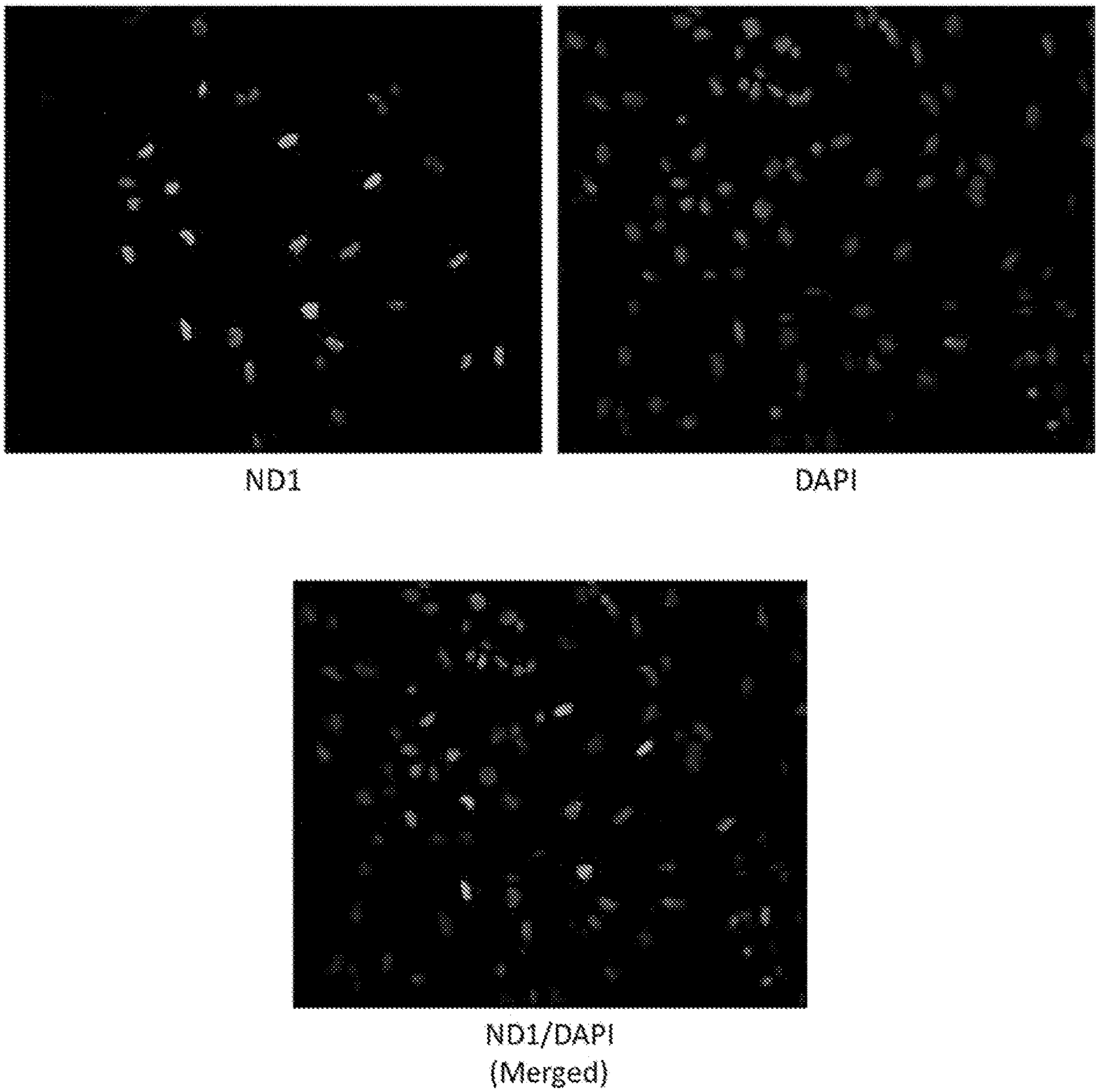
FIG. 18 depicts RCAs immunostained with an anti-ND1 antibody and DAPI (nuclear stain) 24 hours post transfection with NXL-P138 (EE-pGfa681-CRGI-hND1-oPRE-bGHpA).
Figure 21:
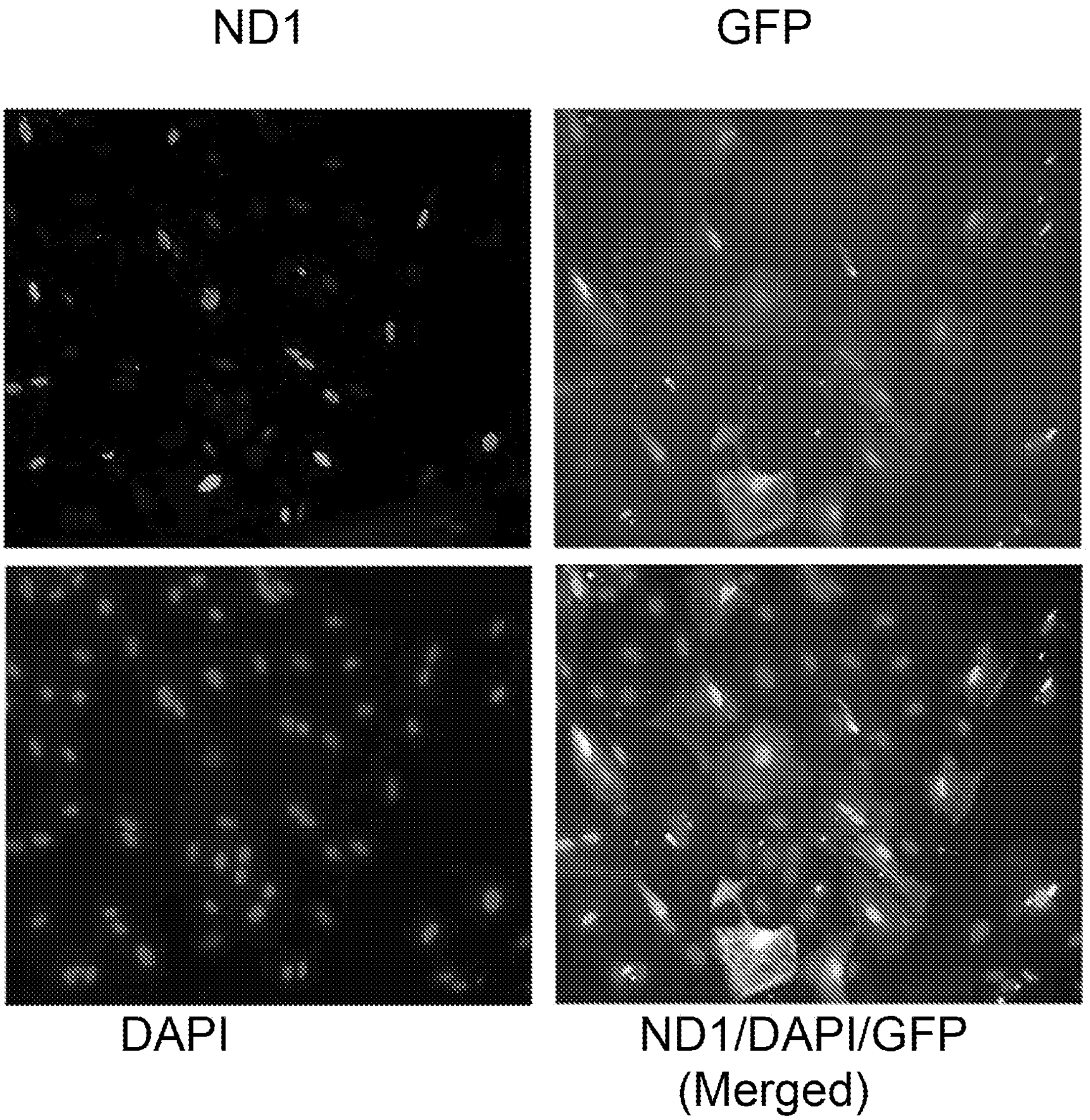
FIG. 21 depicts RCAs immunostained with an anti-ND1 antibody and DAPI (nuclear stain) 6 days post transduction with AAV9-P9 (CE-pGfa681-CI-hND1-p2A-GFP-WPRE-SV40 pA) at $2\times10^{10}$ vg/ml. GFP fluorescence indicates presence of transduced cells.
Figure 22:
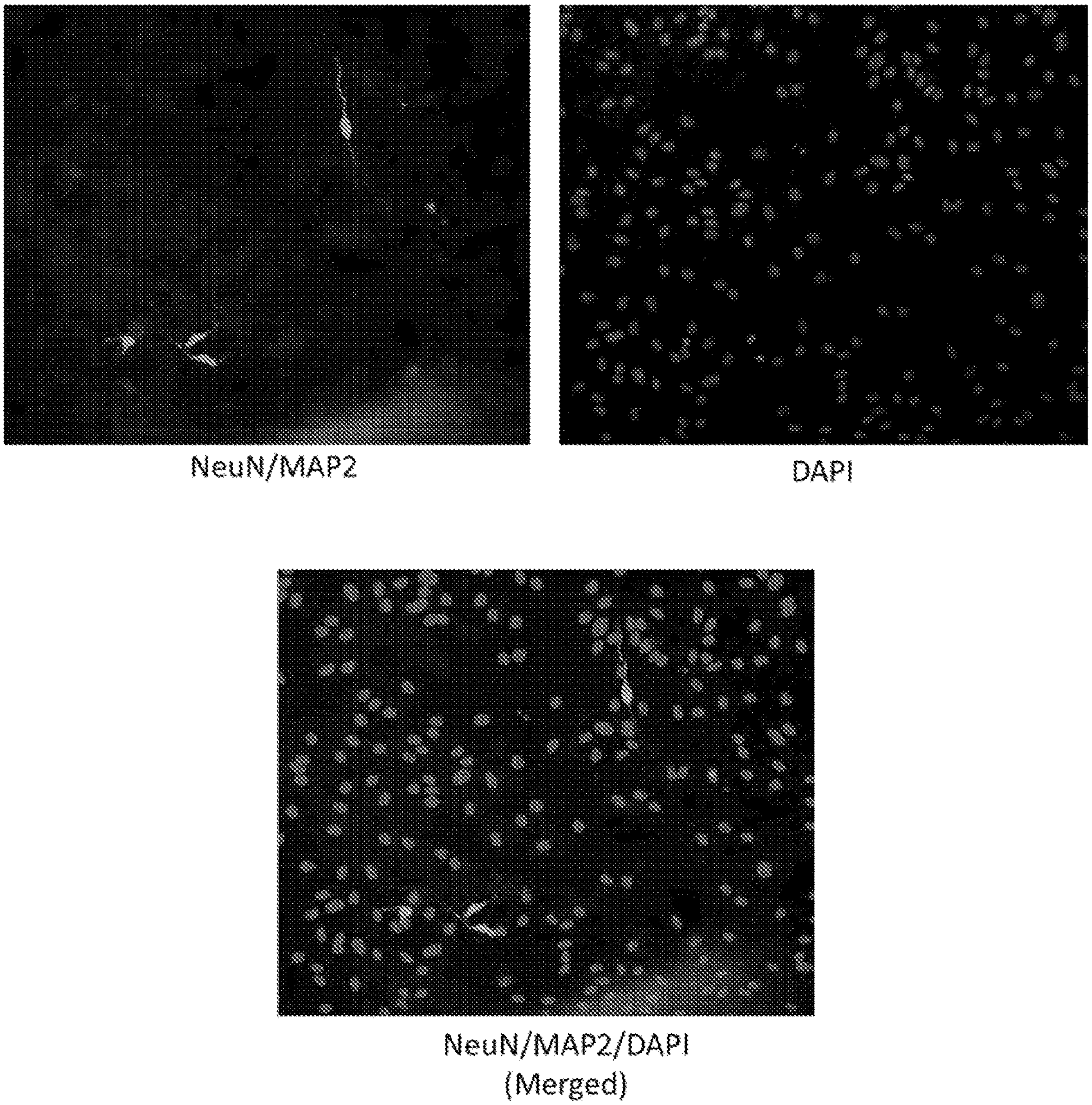
FIG. 22 depicts RCAs immunostained with anti-NeuN and anti-MAP2 antibodies and DAPI (nuclear stain) 3 weeks post transduction with AAV9-P9 (CE-pGfa681-CI-hND1-p2A-GFP-WPRE-SV40 pA) at $2\times10^{10}$ vg/ml. Transduction with the ND1-containing vector generates neurons (NeuN//MAP2+) from the astrocyte culture.
Figure 23:
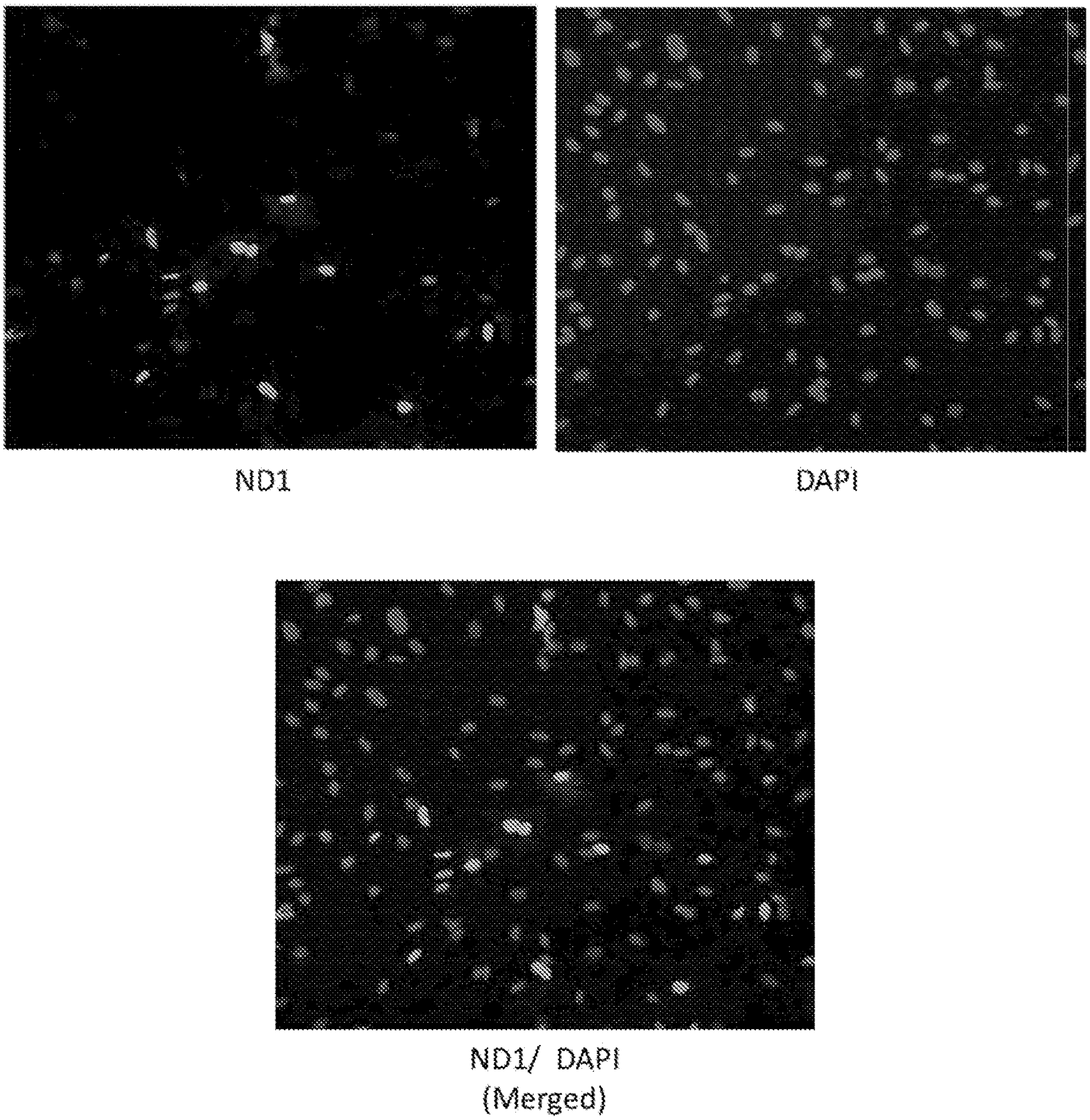
FIG. 23 depicts RCAs immunostained with an anti-ND1 antibody and DAPI (nuclear stain) 24 hours post transfection with NXL-P22 (CE-pGfa681-CI-hND1-WPRE-SV40 pA).
Figure 24:
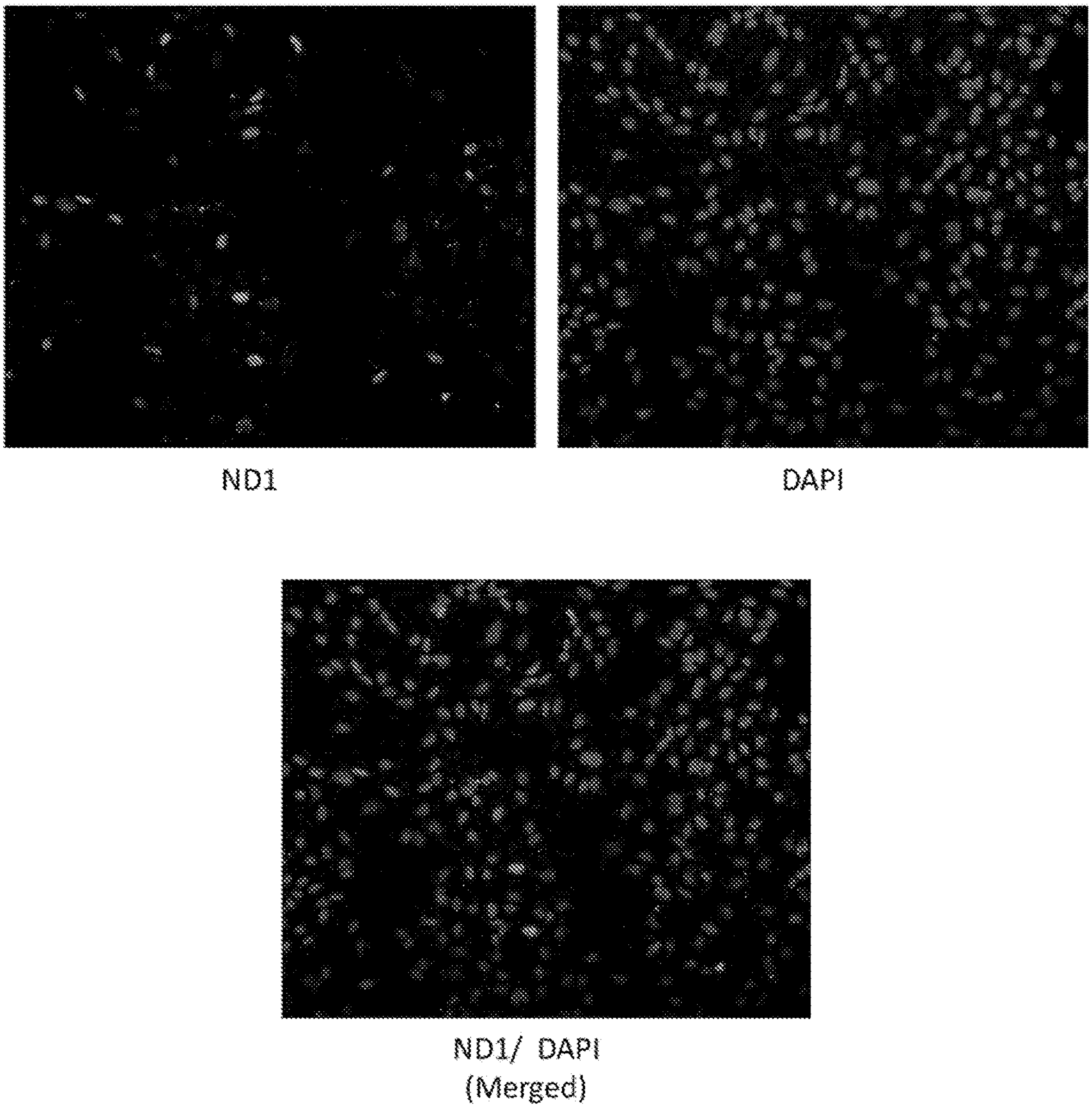
FIG. 24 depicts RCAs immunostained with an anti-ND1 antibody and DAPI (nuclear stain) 6 days post transduction with AAV9-P22 (CE-pGfa681-CI-hND1 WPRE-SV40 pA) at $2\times10^{10}$ vg/ml.
Figure 25:
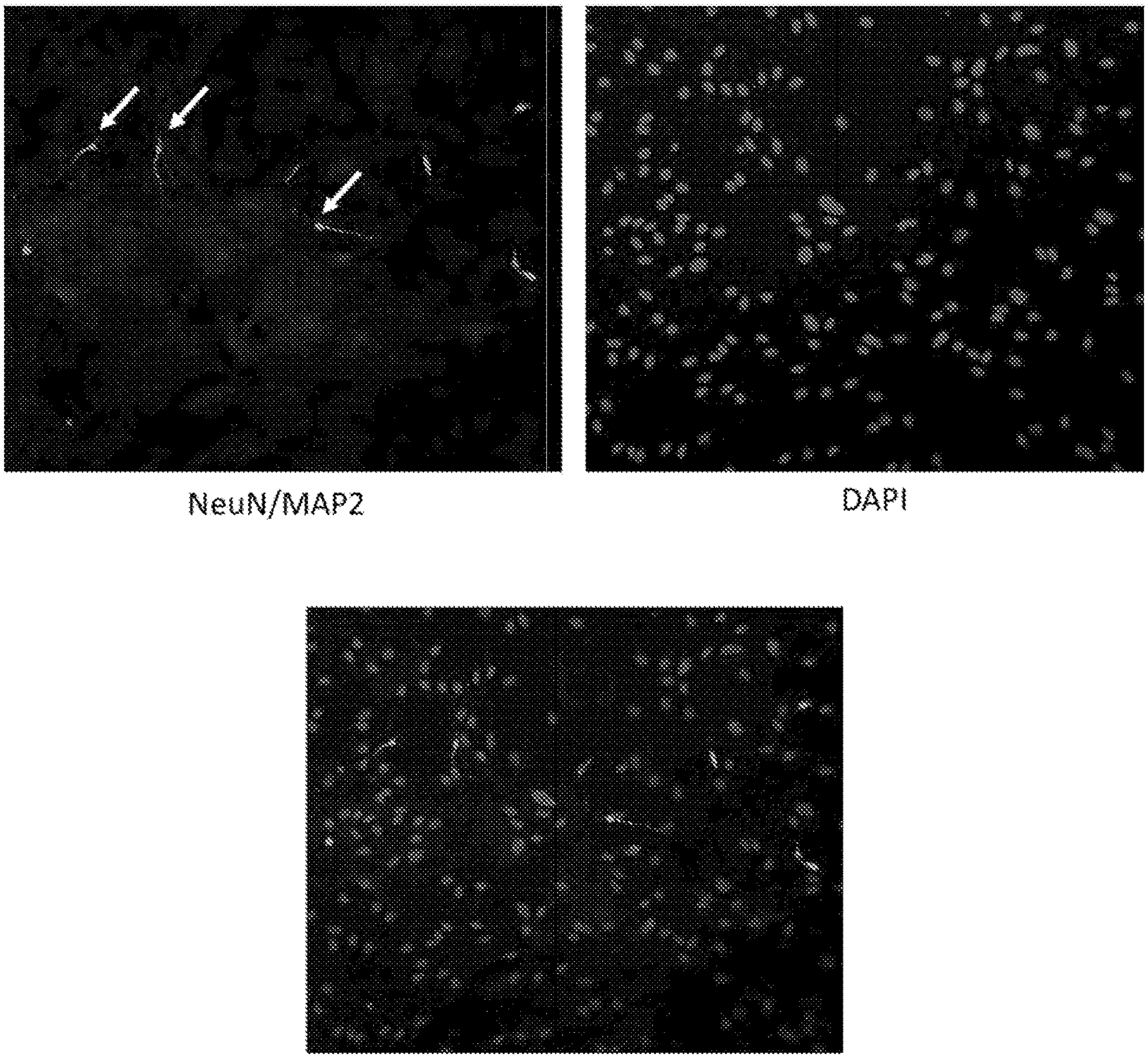
FIG. 25 depicts RCAs immunostained with anti-NeuN and anti-MAP2 antibodies and DAPI (nuclear stain) 3 weeks post transduction with AAV9-P22 (CE-pGfa681-CI-hND1-WPRE-SV40 pA) at $2\times10^{10}$ vg/ml. Transduction with the ND1-containing vector generates neurons (NeuN//MAP2+) from the astrocyte culture.
Figure 26:
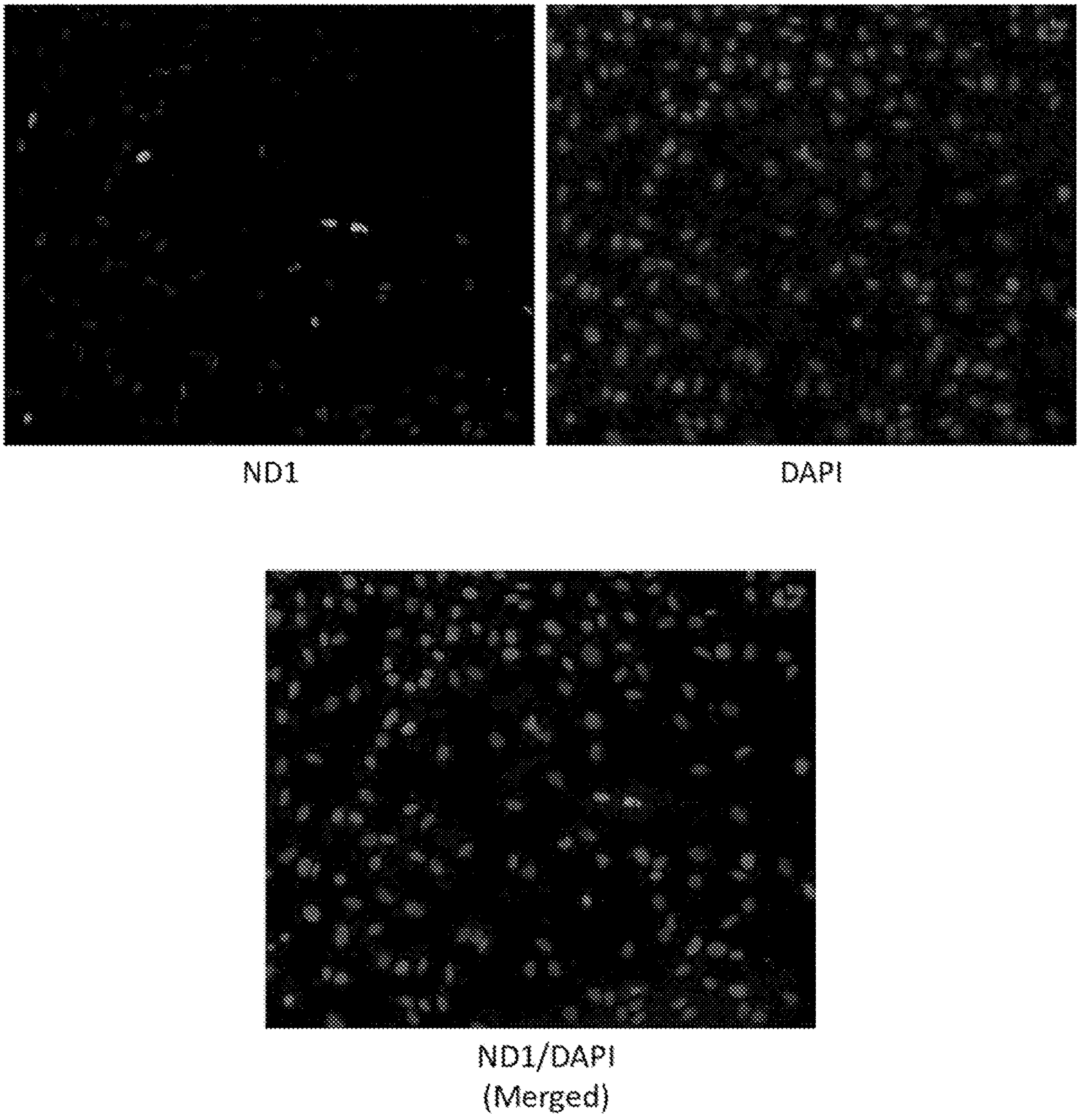
FIG. 26 depicts RCAs immunostained with an anti-ND1 antibody and DAPI (nuclear stain) 24 hours post transfection with NXL-P35 (EE-pGfa681-CI-hND1-WPRE-SV40 pA).
Figure 27:
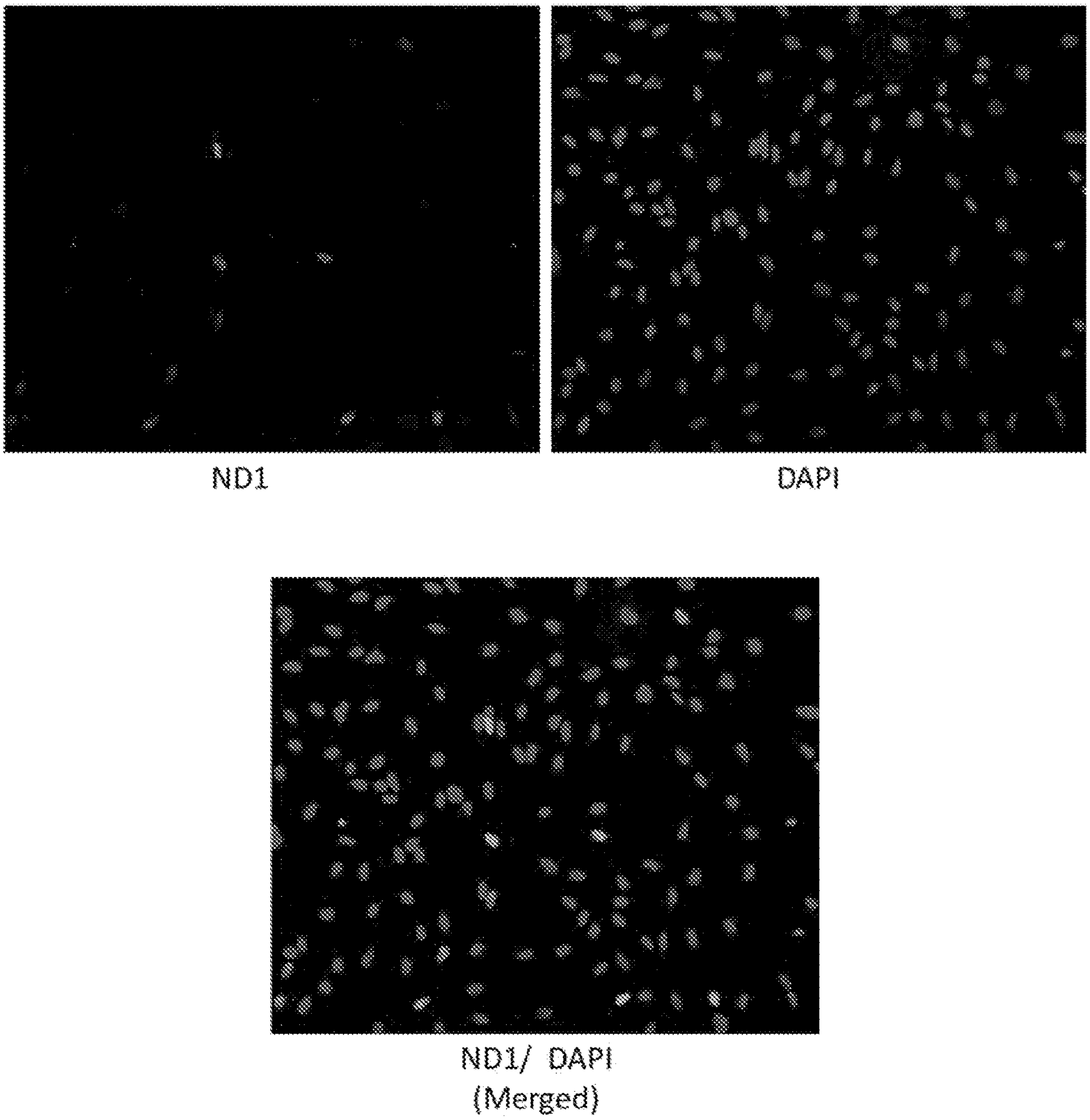
FIG. 27 depicts RCAs immunostained with an anti-ND1 antibody and DAPI (nuclear stain) 6 days post transduction with AAV9-P35 (EE-pGfa681-CI-hND1 WPRE-SV40 pA) at $2\times10^{10}$ vg/ml.
Figure 30:
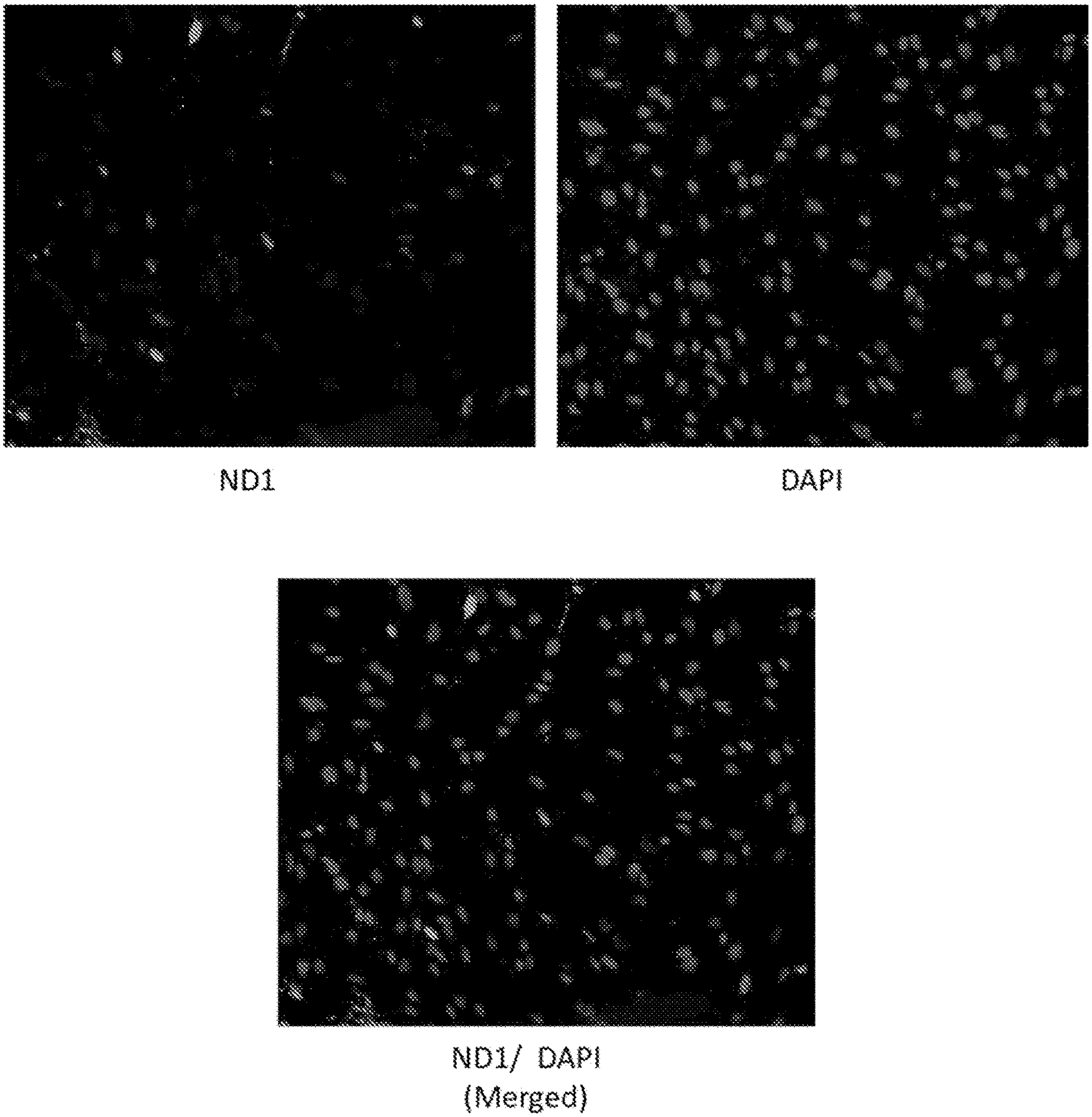
FIG. 30 depicts RCAs immunostained with an anti-ND1 antibody and DAPI (nuclear stain) 24 hours post transfection with NXL-P108 (CE-pGfa681-CI-hND1-oPRE-bGHpA).
Figure 31:
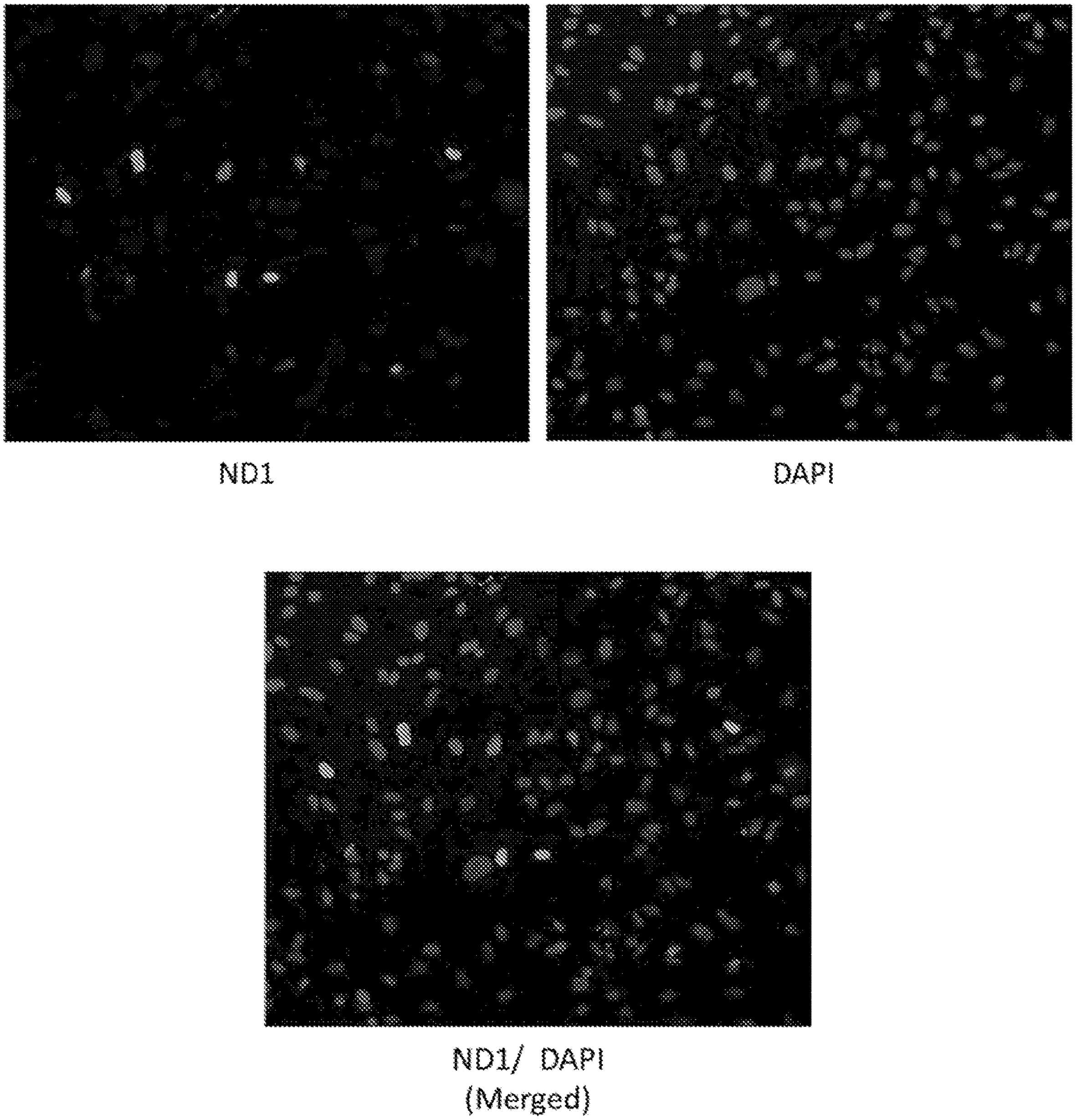
FIG. 31 depicts RCAs immunostained with an anti-ND1 antibody and DAPI (nuclear stain) 24 hours post transfection with NXL-P109 (CE-pGfa681-CRGI-hND1-bGHpA).

Example 22. In Vitro Transgene Expression and Astrocyte-to-Neuron Conversion Induced by NeuroD1 Vectors Materials and Methods Primary Rat Astrocyte Culture: Rat cortical astrocytes (RCA) are isolated from 3-day postnatal Sprague Dawley rat cortical tissue. Cells are maintained in astrocyte media (AM) composed of DMEM supplemented with 10% FBS, 2.5 mM Glutamine, 3.5 mM Glucose, penn/strep. Cells are subcultured at 1:3-1:4 ratio for first two passages at low cell density to promote residual progenitor differentiation. Subsequent sub-cultures are at 1:2 or 1:3 ratio when reaching 90-100% confluent. Cells at passage 5-7 are used for transfection and transduction. Immunostaining with a GFAP antibody shows that >90% cells are GFAP positive astrocytes. Culture astrocytes are immunostained with astrocyte markers GFAP and Sox9 at passage 6 (FIG. 14).

Vectors: AAVs are produced with selected vectors and tested in vitro using rat astrocytes:

NXL-P9 (CE-pGfa681-CI-hND1-p2A-GFP-WPRE-SV40 pA)
NXL-P22 (CE-pGfa681-CI-hND1-WRPE-SV40 pA)
NXL-P35 (EE-pGfa681-CI-hND1-WRPE-SV40 pA)
NXL-P37 (EE-pGfa681-CI-hND1-p2A-GFP-WPRE-SV40 pA
NXL-P107 (CE-pGfa681-CI-hND1-bGHpA)
NXL-P108 (CE-pGfa681-CI-hND1-oPRE-bGHpA)
NXL-P109 (CE-pGfa681-CRGI-hND1-bGHpA)
NXL-P130 (CE-pGfa681-GI-hND1-oPRE-bGHpA)
NXL-P134 (CE-pGfa681-CRGI-hND1-oPRE-bGHpA)
NXL-P136 (EE-Gfa681-CRGI-hND1-bGHpA)
NXL-P138 (EE-Gfa681-CRGI-hND1-oPRE-bGHpA)

Viral Production: Virus used for in vitro studies are produced using adherent AAV293 cells by triple transfections (GOI, helper, and Rep/Cap plasmids) with polyethylenimine (PEI). Virus recovery and purification is achieved via ultra-centrifugation or the use of commercial purification kits.

Specifically, AAV293 cells (*Cell* Biolabs, Cat #AAV-100) are seeded in 15-cm culture dishes 24 hours prior to transfection. Cells at 70-85% confluency are transfected per dish with 10 ug GOI, 10 ug of Rep/Cap, and 14 ug of pALD-X80 (Aldevron) or pHelper (Cell Biolabs) using polyethylenimine (PEI) at a DNA:PEI ratio of 1:4. Multiple dishes are transfected for production based on the scale needed. Culture media is refreshed daily. Seventy-two hours post transfection, cells are collected and lysed to harvest the virus using an AAVpro purification kit (Takara, Cat #6666, 6675, 6235) following the manufacturer's protocol.

Figure 35:
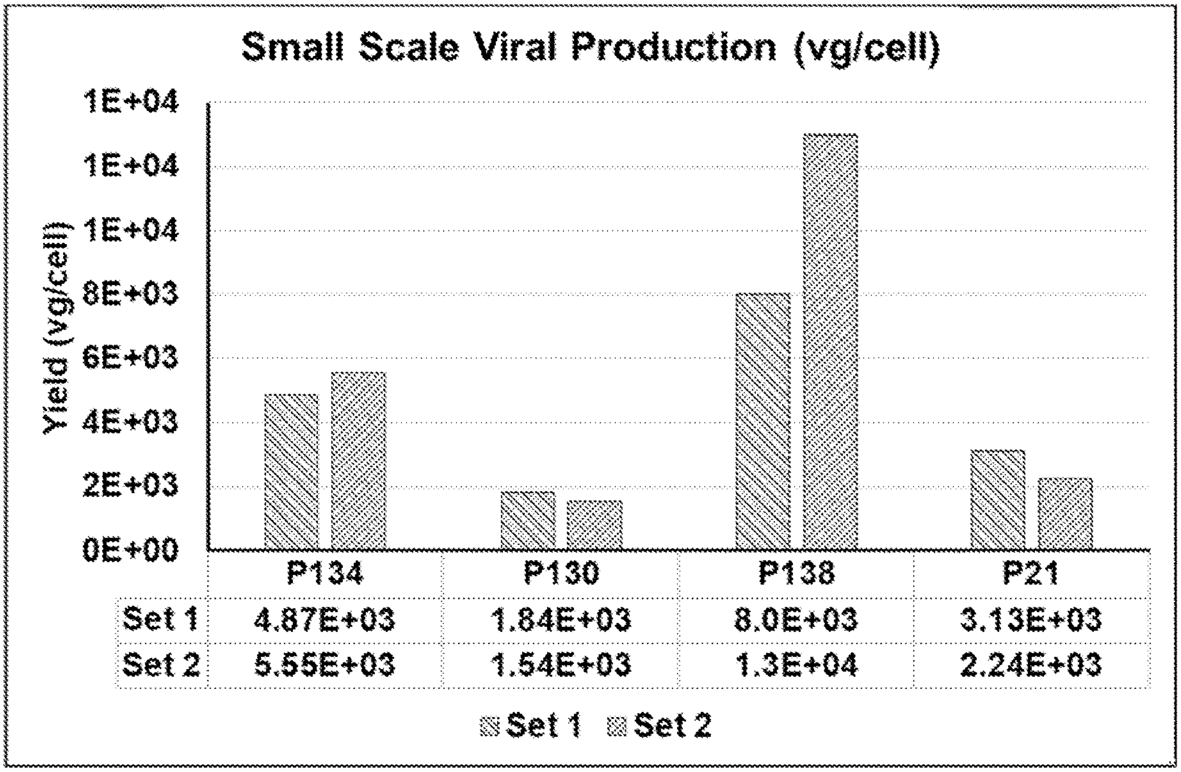
FIG. 35 is a plot of measurements of AAV virus production of the P134, P130, P138 and P21 plasmids. Titer analysis is performed by qPCR using primers amplifying gene of interest (GOI) and primers specific to the plasmids. Virus yield is calculated as vg/cell.

Viral titers are determined by real-time quantitative PCR using a primer pair in the ITR region, primers amplifying a gene of interest (GOI), or vector specific primers. Plasmid DNA is used as a standard. The production yield is ~$10^{3}$-$10^{4}$ vg/cell level. FIG. 35 depicts how each of the P134, P130, P138 and P21 plasmids co-transfected into AAV293 cells with a Rep-Cap plasmid expressing a serotype 9 capsid protein and the Helper plasmid pALD-X80 (X80) produced recombinant AAV virus particles as measured by qPCR.

Transfection and Immunofluorescence: Rat cortical astrocytes (RCAs) of passage 5-7 are seeded on glass cover slips coated with poly-D-lysine (PDL) in 24-well plates at 30-50% confluency 24-48 hours prior to transfection. Cells are transfected with 300 ng of vector DNA using Lipofectamine reagent (Thermo Fisher Cat #15338) following the manufacturer's protocol. At 24-48 hours post transfection, cells are fixed with 4% paraformaldehyde in PBS and subsequently washed and immunostained with anti-NeuroD1 (anti-ND1) antibody (Abcam Cat #ab60704) and followed with secondary antibodies conjugated with fluorescent dyes (Invitrogen, Alexa Fluor). Images are captured under a fluorescent microscope (Zeiss Axiovert Al, Zen Blue). Gene expression levels are assessed by comparing the fluorescence intensity.

Transduction and Immunofluorescence: RCAs of passage 5-7 are seeded on glass cover slips coated with poly-D-lysine (PDL) in 24-well plates at 30-50% confluency 24-48 hours prior to transduction. Cells are transduced with AAVs at $2\text{-}6\times10^{10}$ viral genome (vg)/ml in fresh astrocyte media. Media are refreshed the next day and every 3-4 days. Three to six days post transduction, cells are fixed with 4% paraformaldehyde in PBS and subsequently washed and immunostained with anti-ND1 antibody (Abcam Cat #ab60704) and followed with secondary antibodies conjugated with fluorescent dyes (Invitrogen, Alexafluor) for observation and image capturing under a fluorescent microscope (Zeiss Axiovert Al, Zen Blue). Gene expression levels are assessed by comparing the fluorescence intensity.

Astrocyte-to-neuron conversion assessment RCAs of passage 5-7 are seeded on glass cover slips coated with poly-D-lysine (PDL) in 24-well plates at 30-50% confluency 24-48 hours prior to transduction. Cells are transduced with virus at 2-6×$10^{10}$ vg/ml in 500 ul of fresh astrocyte media (DMEM supplemented with 10% FBS, 2.5 mM Glutamine, 3.5 mM Glucose, penn/strep). At 48 hours post transduction, media is replaced with 5% FBS astrocyte media. Subsequently, 100 ul of conversion media (DMEM/F12+1% FBS+B27+N2 and 1 uM Rock inhibitor and 10 ng/ml BDNF) is added daily for 4 days. After the 4 days, the media is completely replaced with conversion media.

Cells are fixed with 4% paraformaldehyde in PBS at various desired time points (three days, one to five weeks post transduction) and subsequently washed and immunostained with antibodies against ND1 (Abcam Cat #ab60704), NeuN (Millipore, Cat #ABN78), Map2 (Invitrogen, Cat #PA5-17646), followed with secondary antibodies conjugated with fluorescent dyes (Invitrogen, Alexafluor) for observation and imaging under a fluorescent microscope (Zeiss Axiovert Al, Zen Blue).

In Vitro Studies Results:

All tested NeuroD1 (ND1) plasmids are effective in driving the expression of NeuroD1 (FIGS. 16-31). The expression level of NeuroD1 is affected by the elements in the vector. Among three versions of the GFA promoter, the 681 bp promoter shows the highest NeuroD1 expression level and the 1.6 kb promoter shows the weakest NeuroD1 expression level. Promoter enhancer elements significantly affect the expression level of NeuroD1. The CMV enhancer increases the expression level of NeuroD1 more than the ef1α enhancer. Chimeric introns and WPREs also increase the expression level of NeuroD1.

All tested ND1-containing AAVs are effective in driving the expression of ND1 and inducing an astrocyte-to-neuron conversion in cultured rat astrocytes as shown by positive staining of NeuN and/or MAP2 (FIGS. 17, 30, 22, 25, and 28). The conversion rate is higher when astrocytes are transduced by the vectors driving a higher ND1 expression. Vectors NXL-P134 and NXL-P138, and the viruses generated using these vectors, i.e., AAV9-P134 and AAV9-P138 respectively, are the most effective in driving expression of ND1 and inducing astrocyte-to-neuron conversion, with AAV-P134 being the most effective (FIGS. 15-20). Plasmid AAV9-P21 (CE-pGFA681-CI-GFP-WPRE-SV40 pA), which does not contain an ND1 sequence, is used as a control, and it does not induce an astrocyte-to-neuron conversion, as shown by the lack of positive staining for NeuN and/or Map2 (FIG. 14).

NeuN/RBFOX3 (Neuronal nuclear protein) is a neuron differentiation marker, which stains nuclei and perinuclear cytoplasm in neurons. MAP2 (microtubule associated protein 2) is another neuronal marker which stains cytoplasm microtubules including dendrites in neurons.

One week post transduction by ND1-containing AAVs, small number of NeuN and MAP2 positive cells (neurons) are observed. By two and three weeks, more NeuN/MAP2 positive cells are observed. Some NeuN/MAP2 positive cells show typical neuronal morphology.

Example 23. In Vivo Transgene Expression and Astrocyte-to-Neuron Conversion Induced by NeuroD1 Viral Vectors AAV9-P134 and AAV9-P138 viruses are used for the in vivo studies. AAV9-P12, which drives the expression of GFP alone (no ND1) under a GFAP promoter, is used for the control and to identify cells expressing GFAP (astrocytes).

Single strand adenovirus-associated viral (ssAAV, AAV for short) vectors NXL-P12, NXL-P134 and NXL-P138 are packaged into AAV, serotype 9 (AAV9), followed by a subsequent iodixanol gradient ultracentrifuge and concentration. Purified AAV viruses are titered using a quantitative PCR-based method. All AAV used in this study is prepared in 0.001% Pluronic F-68 (Poloxamer 188 Solution, PFL01-100ML, Caisson Laboratories, Smithfield, UT, USA) in PBS (pH 7.4)

Normal C57BL/6 mice older than 8 weeks are injected with AAV9-P134, AAV-P138, and AAV9-P12 viruses as follows:

- P12 control group: AAV9-P12 5×$10^{11}$ GC/ml, 1 μL, 1 injection in cortex (unilateral) (n=6)
- P134 group: AAV9-P12 2.5×$10^{11}$ GC/ml+AAV9-P134 2.5×$10^{11}$ GC/ml, 1 μL, 1 injection in cortex (unilateral) (n=6)
- P138 group: AAV9-P12 2.5×$10^{11}$ GC/ml+AAV9-P138 2.5×$10^{11}$ GC/ml, 1 μL, 1 injection in cortex (unilateral) (n=6)

Mice are sacrificed and brain cortex tissue analyzed at 10 days post infection (dpi) and at 30 dpi. The animals are anesthetized with 1.25% Avertin and then sequentially perfused intracardially first with saline solution (0.9% NaCl) and then with 4% paraformaldehyde (PFA). The brains are collected and post-fixed in 4% PFA overnight and are sequentially placed in 20% and 30% sucrose at 4° C. until the tissue sank. The dehydrated brains are embedded in Optimal Cutting Temperature (Tissue-Tek® O.C.T. Compound, Sakura® Finetek, Torrance, CA, USA), and then serially sectioned at the coronal plane on the cryostat (Thermo Scientific, Shanghai, China) at 30 μm thickness. For immunofluorescence, free floating brain sections are first washed with PBS and blocked for 1 hour at room temperature (RT) in 5% normal donkey serum, 3% bovine serum albumin and 0.3% TritonX-100 prepared in PBS, and then incubated overnight at 4° C. with primary antibodies diluted in blocking solution. After additional washing with 0.2% PBST (0.2% tween-20 in PBS), the samples are incubated with 0.5 μg/μL 4',6-diamidino-2-phenylindole (DAPI; F. Hoffmann-La Roche, Natley, NJ, USA) and appropriate donkey anti-mouse/rabbit secondary antibodies conjugated to Alexa Fluor 555, goat anti-chicken secondary antibodies conjugated to Alexa Fluor 488 (1:1000, Life technologies, Carlsbad, CA, USA), and goat anti-rat (Life technologies)/guinea pig (Jackson immune research) secondary antibodies conjugated to Alexa Fluor 647(1:500) for 2 hours at room temperature, followed by extensive washing with PBS. Samples are finally mounted with VECTASHIELD® mounting medium (VECTOR Laboratories, Burlingame, CA, USA) and sealed with nail polish. Representative Images are taken with a confocal microscope (LSM880, Zeiss, Jena, Germany). Primary antibodies used are as follow: rat anti-GFAP (a marker for astrocytes, 1:1000, Cat #13-0300, Invitrogen), guinea pig anti-NeuN (a marker for neurons 1:1000, Cat #ABN90, Millipore), mouse anti-NeuroD1 (1:500, Cat #ab60704, Abcam), and chicken anti-GFP (1:1000, Cat #ab13970, Abcam). Representative images are captured by either Zeiss Axioplan fluorescent microscope (Axio Imager Z2, Zeiss, Gottingen, Germany) or confocal microscope (LSM880, Zeiss, Jena, Germany). Quantitative analysis is performed based on 4 randomly chosen fields (212 μm×212 μm, acquired at 400 magnification from LSM880 confocal microscope) from 3 brain slices per mouse (3 mice per group). The data is shown as mean f SEM.

Figure 36:
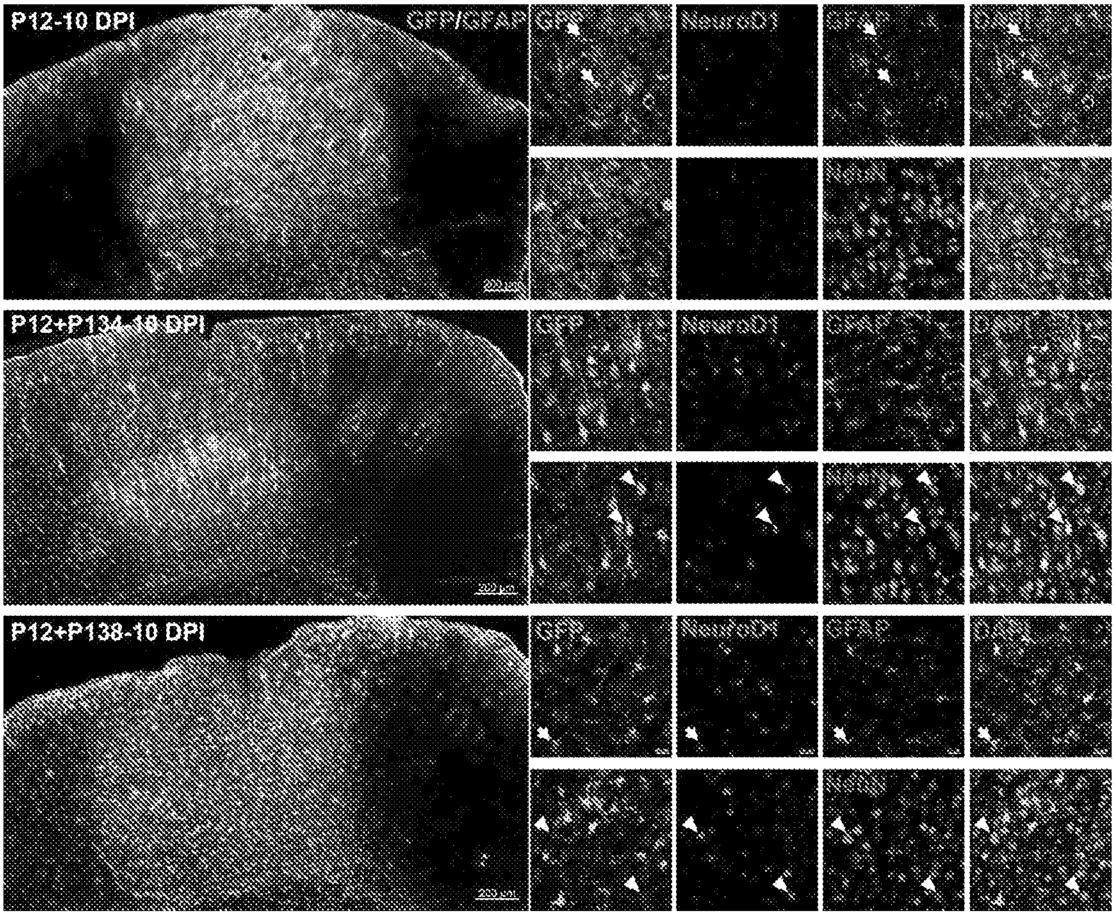
FIG. 36 depicts the brain cortex tissue of mice infected with AAV9-P12 (P12 control group), AAV9-P12+AAV9-P134 (P134 group), and AAV9-P12+AAV9-P138 (P138 group) at 10 days post infection (dpi). Cells are immunostained with antibodies against NeuroD1, GFAP, NeuN, and with DAPI (nuclear stain). GFP fluorescence indicates the presence of cells infected with the control virus.

Control virus P12, which expresses GFP reporter alone, is first compared with NeuroD1-expressing viruses P134 and P138 (both added P12 together to trace converted neurons). When the control virus P12 is injected in the uninjured mouse cortex, the infected cells are primarily astrocytes without NeuroD1 expression at 10 dpi (days post injection, FIG. 36). In contrast, NeuroD1 expression is detected clearly in both P134 and P138 groups. While most NeuroD1-expressing cells in the P138 group at 10 dpi are still astrocytes, a portion of NeuroD1-expressing cells in P134 group are NeuN+ neurons already (FIG. 36), suggesting that P134 might have better conversion capability than P138. Additionally, at 10 dpi, analysis of the cortex brain tissue of the mice in the P134 group shows a high level of conversion of astrocytes into neurons, as demonstrated by the morphological changes, such as the presence of long processes, in GFP positive cells (FIG. 32). The P138 group shows a lower level of conversion.

Figure 37:
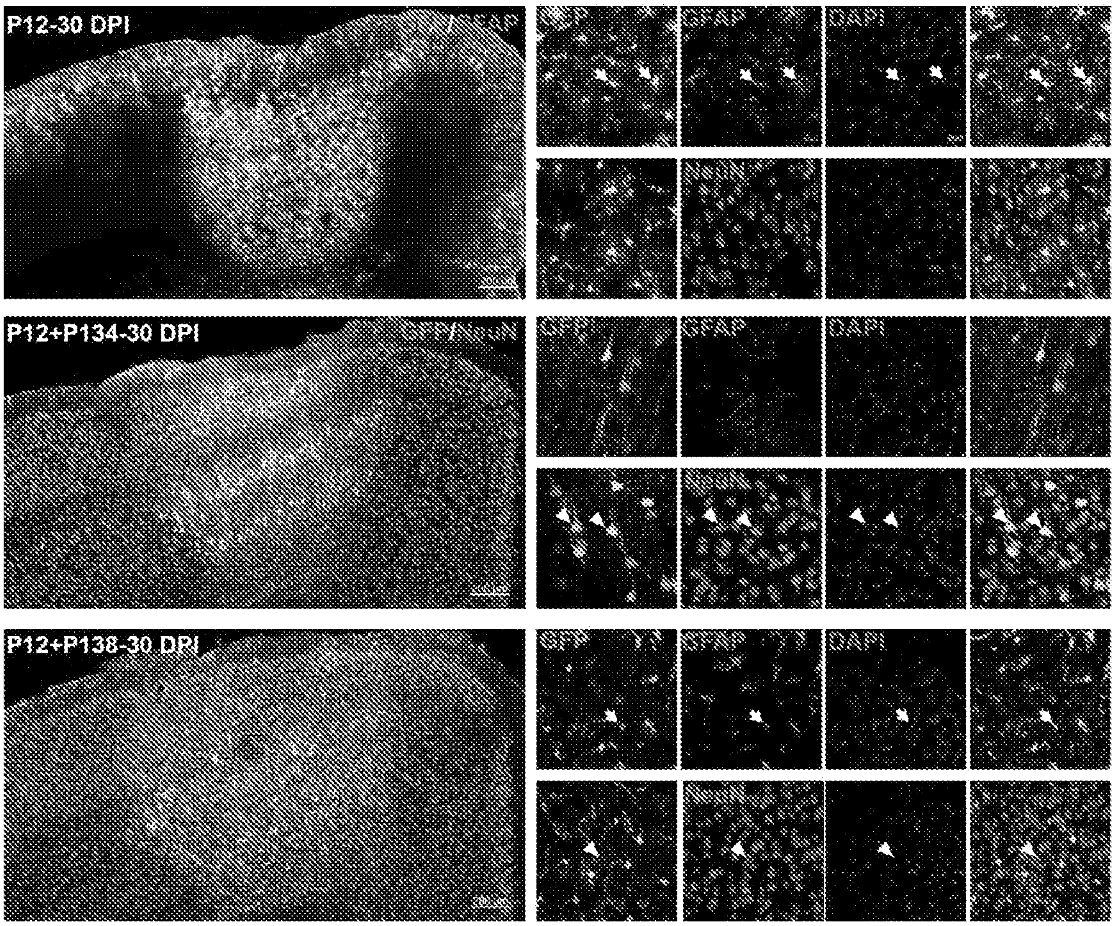
FIG. 37 depicts the brain cortex tissue of mice infected with AAV9-P12 (P12 control group), AAV9-P12+AAV9-P134 (P134 group), and AAV9-P12+AAV9-P138 (P138 group) at 30 days post infection (dpi). Cells are immunostained with antibodies against NeuroD1, GFAP, NeuN, and with DAPI (nuclear stain). GFP fluorescence indicates the presence of cells infected with the control virus.

At 30 days after virus injection, the infected cells in the control group (P12) remain as astrocytes, but most GFP positive cells in the P134 group are neurons expressing NeuN (FIG. 37). However, the conversion rate of the P138 group is lower than the P134. Most infected cells in the P138 group at this stage are still astrocytes, and the GFP signal in the converted neurons is weak (FIG. 37). Additionally, at 30 dpi, analysis of the cortex brain tissue of the mice in the P134 group shows an even higher level of conversion of astrocytes into neurons, as demonstrated by the presence of long processes in GFP positive cells (FIG. 33)

The AAV9-P134 virus is also effective in a bilateral injury mouse model. Ischemic stroke is induced in normal C57BL/6J mice (older than 8 weeks) by injecting 1 μL of Endothelin 1, 1-31 aa (1 μg/μL) in each side of the cortex. Mice are anesthetized with 20 mg/kg 1.25% Avertin (a mixture of 12.5 mg/mL of 2,2,2-Tribromoethanol and 25 μL/mL 2-Methyl-2-butanol, Sigma, St. Louis, MO, USA) through intraperitoneal injection and then placed in a prone position in the stereotaxic frame. Endothelin-1 (ET-1) and virus is injected through glass pipette into motor cortex at the coordinate +0.2 mm anterior-posterior (AP from Bregma), −1.5 mm medial-lateral (ML from Bregma, left side), −0.7 mm dorsal-lateral (DV from dura). The injection speed is 80 nL/min. The pipette is kept in place after injection for about 10 minutes and then slowly withdrawn. Seven days after injection of Endothelin 1, mice are injected with the AAV9-P12 and AAV9-P134 viruses as follow:

P12 Group: AAV9-P12 $5\times10^{11}$ GC/ml, 1 μL, 1 injection in each side of cortex (bilateral)

P14 Group: AAV9-P12 $2.5\times10^{11}$ GC/ml+AAV9-P134 $2.5\times10^{11}$ GC/ml, 1 μL, 1 injection in each side of cortex (bilateral)

Figure 34:
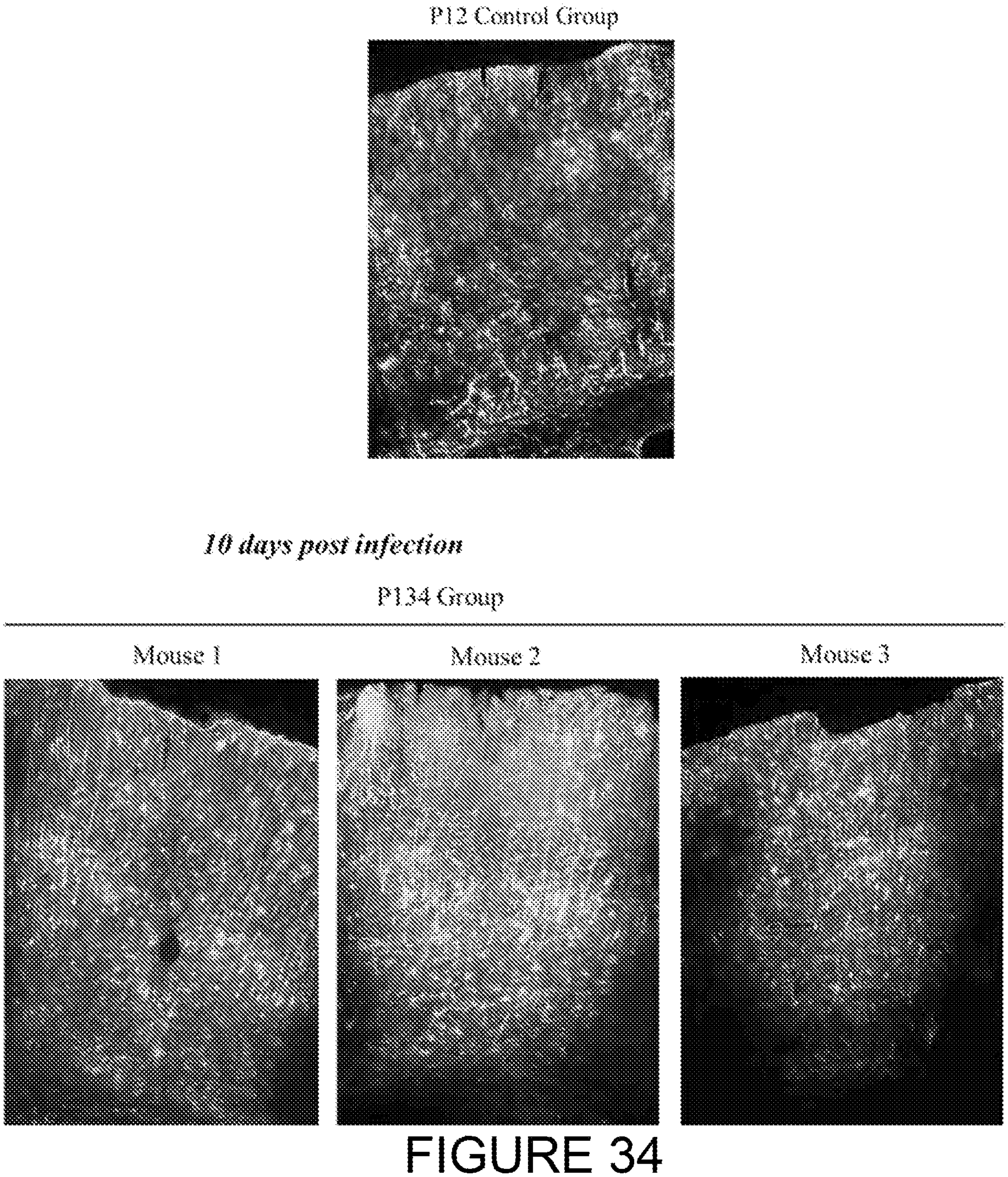
FIG. 34 depicts the brain cortex tissue of mice (bilateral injury model) infected with AAV9-P12 (P12 control group), and AAV9-P12+AAV9-P134 (P134 group) at 10 dpi.
Figure 38:
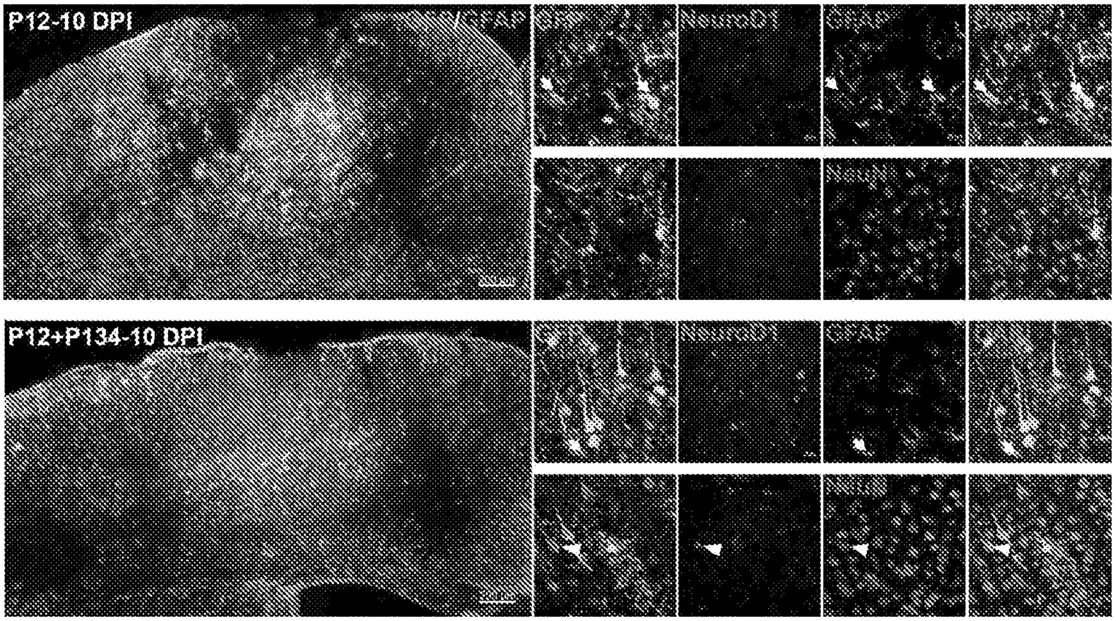
FIG. 38 depicts the brain cortex tissue of mice (bilateral injury model) infected with AAV9-P12 (P12 control group), and AAV9-P12+AAV9-P134 (P134 group) at 10 dpi. Cells are immunostained with antibodies against NeuroD1, GFAP, NeuN, and with DAPI (nuclear stain). GFP fluorescence indicates the presence of cells infected with the control virus.
Figure 39A:
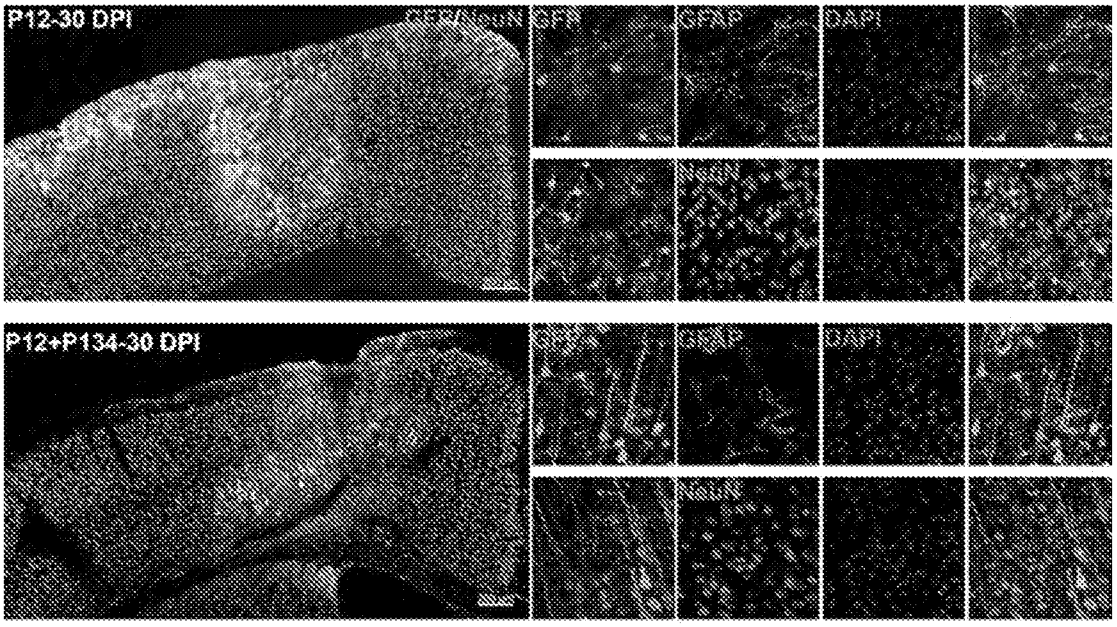
FIGS. 39A and 39B depict the brain cortex tissue of mice (bilateral injury model) infected with AAV9-P12 (P12 control group), and AAV9-P12+AAV9-P134 (P134 group) at 30 dpi.
Figure 39B:
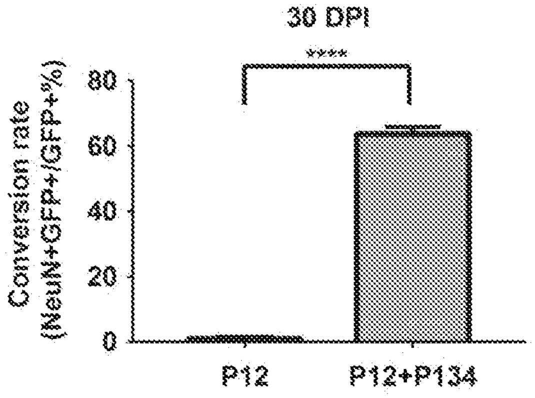

Mice are sacrificed at 10 days post injection (dpi) of the viruses and the brain cortex tissue analyzed. When the control virus P12 is injected in the ET-1 lesioned mouse cortex, the infected cells are primarily astrocytes without NeuroD1 expression at 10 dpi (days post injection, FIG. 38). In contrast, NeuroD1 expression is detected in the P134 group (FIG. 38). Mice are sacrificed at 10 days post injection (dpi) of the viruses and the brain cortex tissue analyzed. At 10 dpi, analysis of the cortex brain tissue of the mice in the P134 group shows a high level of conversion of astrocytes into neurons, as demonstrated by the morphological changes observed in GFP positive cells, such as the presence of long processes (FIG. 34).

Example 24. In Vitro Transgene Expression and Astrocyte-to-Neuron Conversion Induced by Expression of NeuroD1 and Dlx2

Materials and Methods

Vectors: The vectors are tested via transfection of rat cortical astrocytes (RCAs). Additionally, AAVs are produced with selected vectors and tested in vitro using rat astrocytes via transduction:

NXL-P20 (CE-pGfa681-CI-hND1-p2A-hDLX2-WPRE-SV40 pA)

NXL-P31 (EE-pGfa681-CI-hND1-p2A-hDlx2-WPRE-SV40 pA)

NXL-P111 (CE-pGfa1681-CI-hDlx2-IRES-hND1-SV40 pA)

NXL-P112 (CE-pGfa1681-CI-hDlx2-IRES-hND1-bGHpA)

NXL-P113 (EE-pGfa1681-CI-hDlx2-IRES-hND1-bGHpA)

NXL-P122 (CE-pGfa681-CI-hDlx2-P2A-hND1-bGHpA)

NXL-P123 (EE-pGfa681-CI-hDlx2-P2A-hND1-bGHpA)

NXL-P124 (CE-pGfa681-CI-hND1-P2A-hDlx2-bGHpA)

Figure 40:
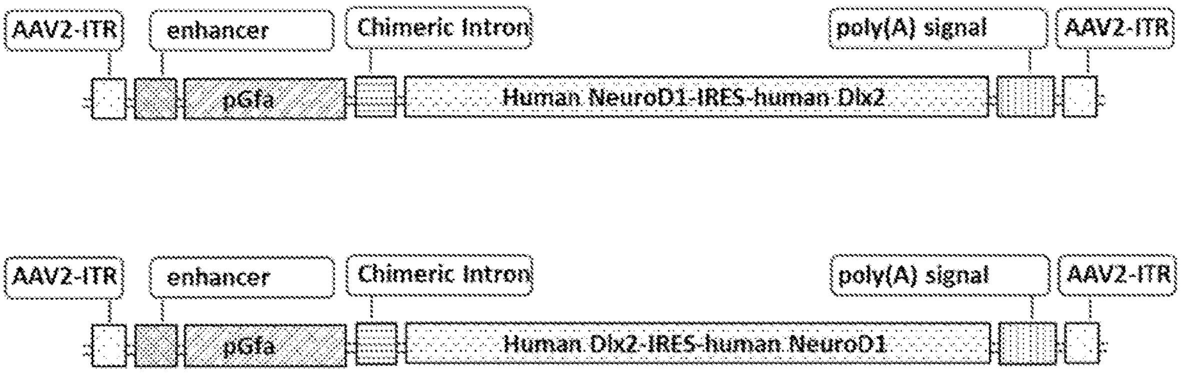
FIG. 40 depicts two general maps of ND1 and Dlx2 constructs. Enhancer refers to an ef1a enhancer or CMV enhancer. pGfa refers to a 2.2 kb or 1.6 kb Gfa promoter. poly(A) signal refers to SV40, bGH or an hGH poly(A) signal.
Figure 41:
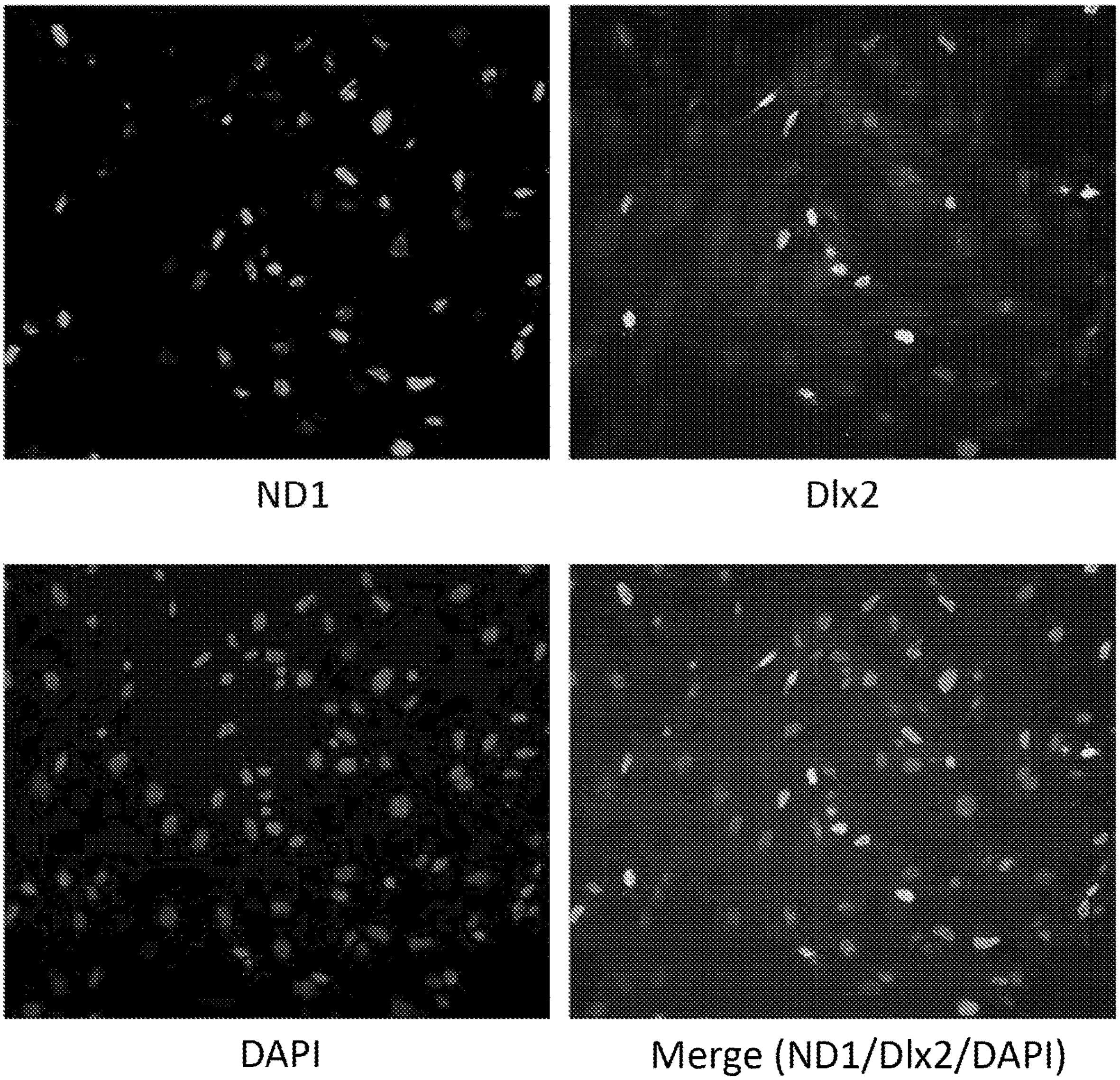
FIG. 41 depicts RCAs immunostained with an anti-ND1 antibody, an anti-Dlx2 antibody, and DAPI (nuclear stain) 24 hours post transfection with NXL-P112 (CE-pGfa681-CI-hDlx2-IRES-hND1-bGHpA).
Figure 42:
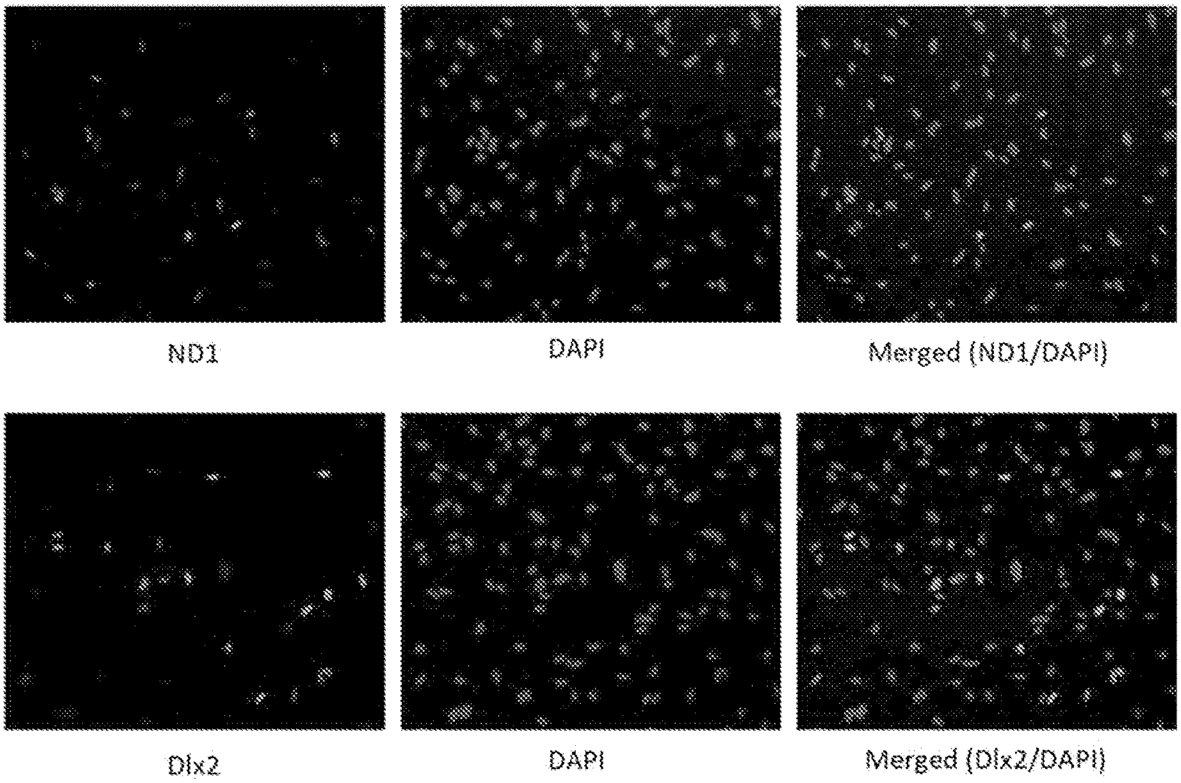
FIG. 42 depicts RCAs immunostained with an anti-ND1 antibody, an anti-Dlx2 antibody, and DAPI (nuclear stain) 6 days post transduction with AAV9-P112 (CE-pGfa681-CI-hDlx2-IRES-hND1-bGHpA) at $2\times10^{10}$ vg/ml.
Figure 43:
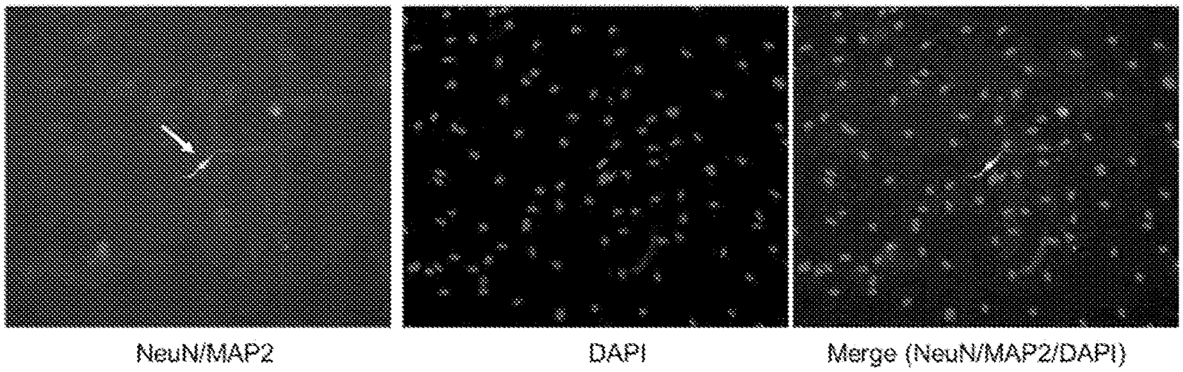
FIG. 43 depicts RCAs immunostained with an anti-NeuN antibody, an anti-MAP2 antibody, and DAPI (nuclear stain) 3 weeks post transduction with AAV9-P112 (CE-pGfa681-CI-hDlx2-IRES-hND1-bGHpA) at $2\times10^{10}$ vg/ml.
Figure 44:
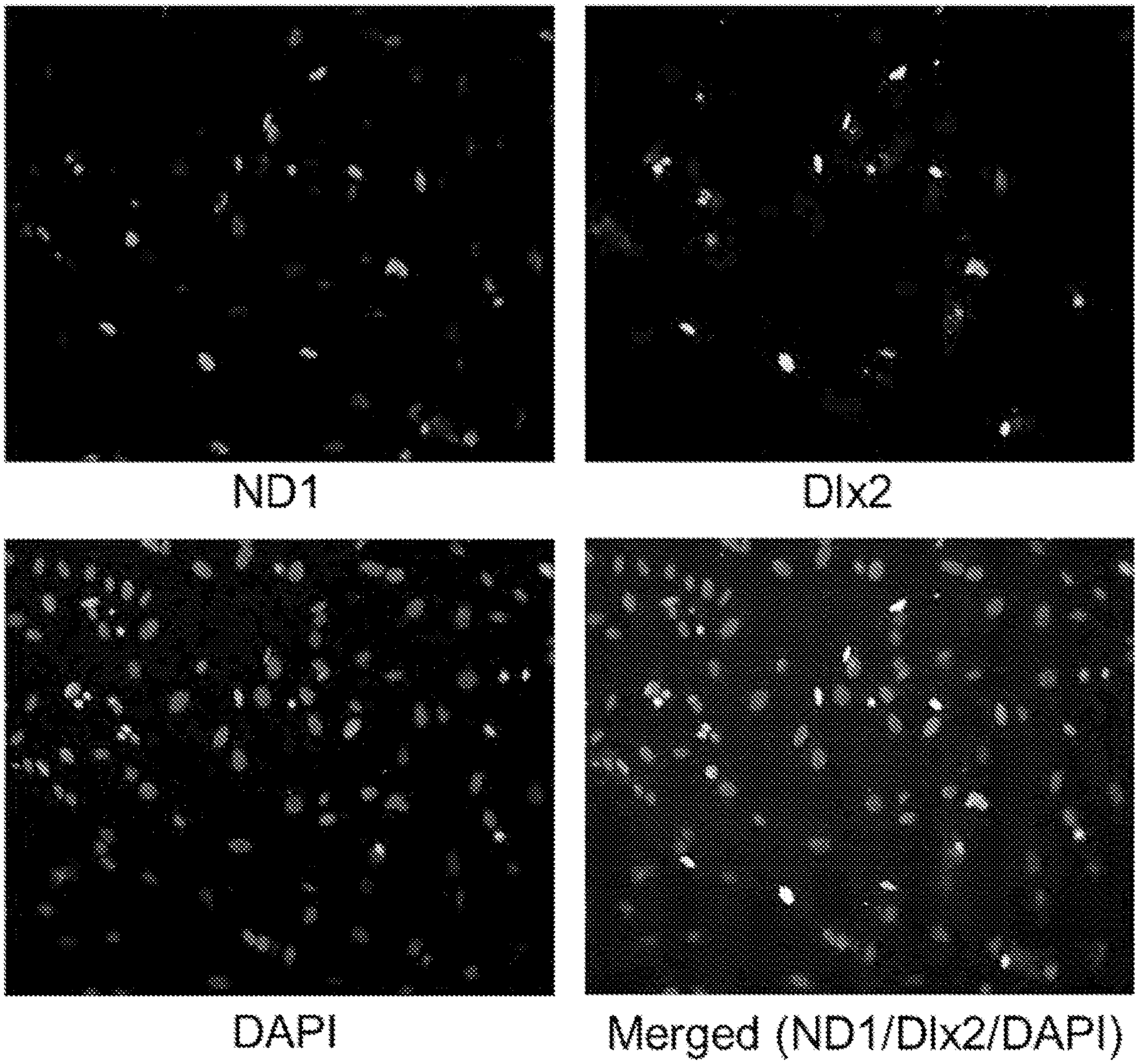
FIG. 44 depicts RCAs immunostained with an anti-ND1 antibody, an anti-Dlx2 antibody, and DAPI (nuclear stain) 24 hours post transfection with NXL-P122 (CE-pGfa681-CI-hDlx2-P2A-hND1-bGHpA).
Figure 45:
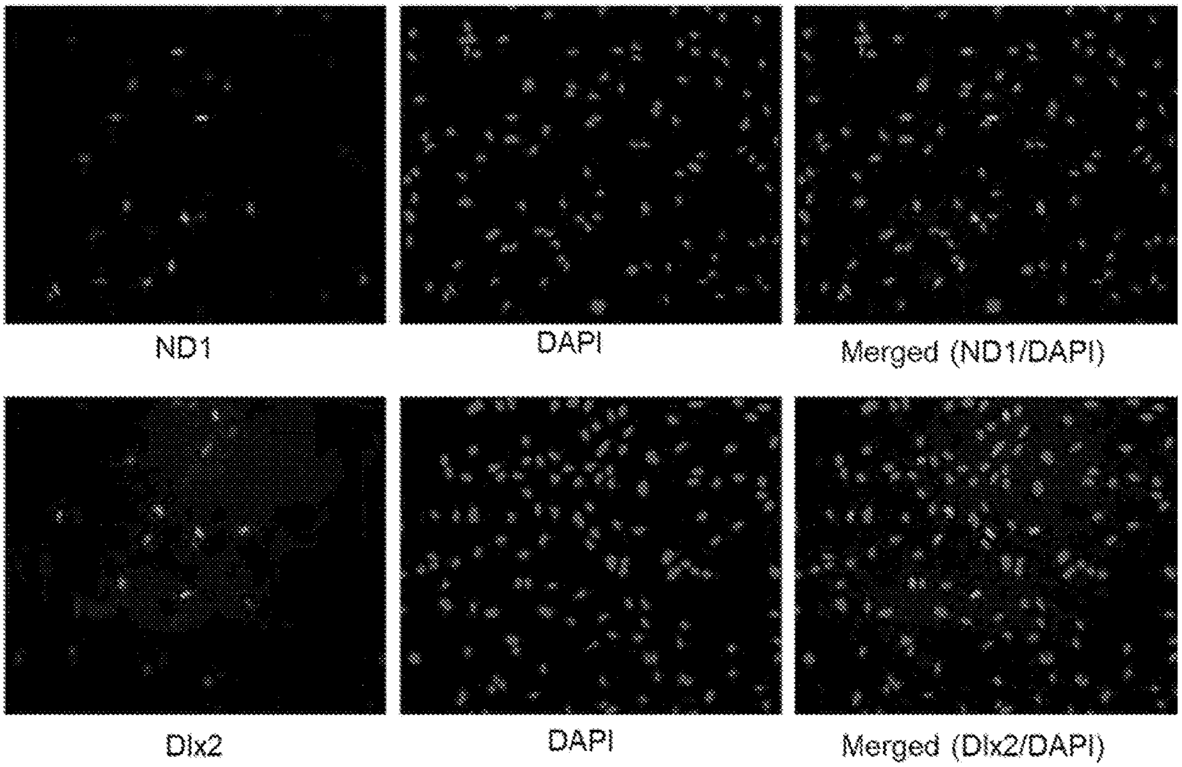
FIG. 45 depicts RCAs immunostained with an anti-ND1 antibody, an anti-Dlx2 antibody, and DAPI (nuclear stain) 6 days post transduction with AAV9-P122 (CE-pGfa681-CI-hDlx2-p2A-hND1-bGHpA) at $2\times10^{10}$ vg/ml.
Figure 46:
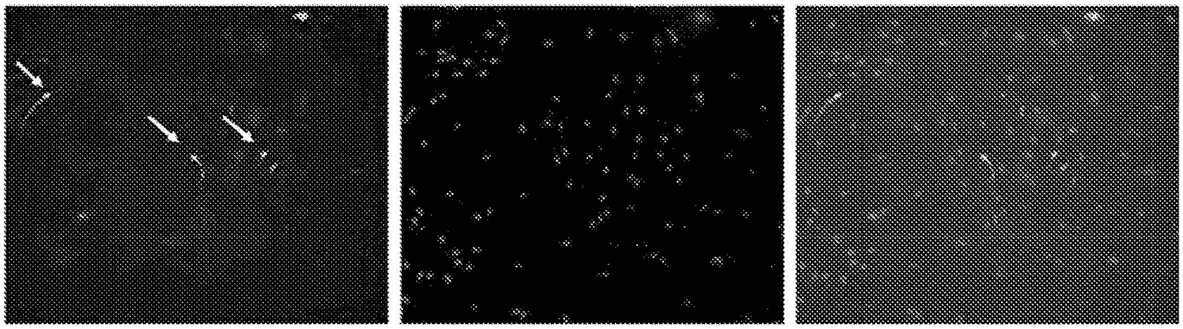
FIG. 46 depicts RCAs immunostained with an anti-NeuN antibody, an anti-MAP2 antibody, and DAPI (nuclear stain) 3 weeks post transduction with AAV9-P122 (CE-pGfa681-CI-hDlx2-P2A-hND1-bGHpA) at $2\times10^{10}$ vg/ml.
Figure 47:
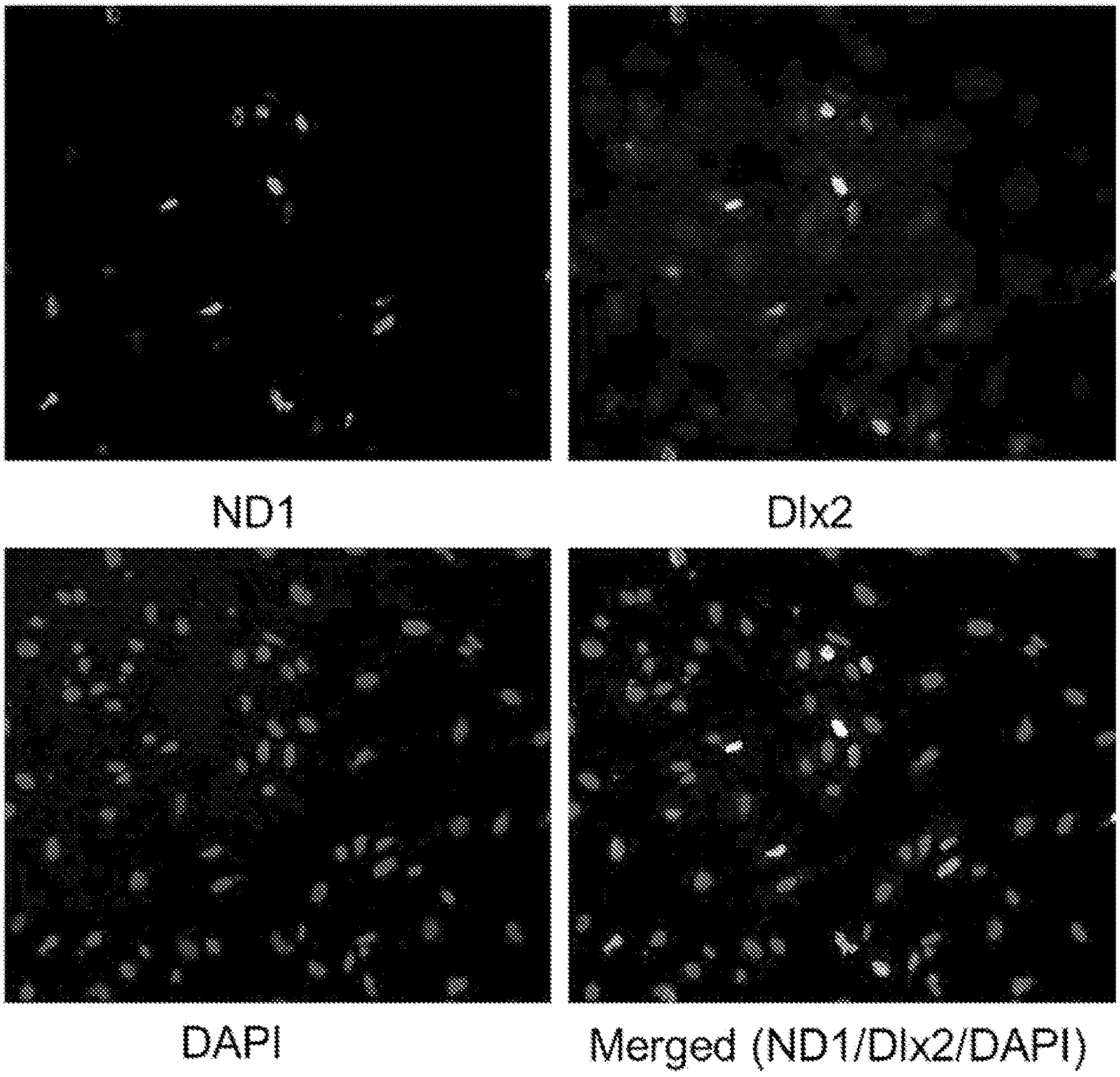
FIG. 47 depicts RCAs immunostained with an anti-ND1 antibody, an anti-Dlx2 antibody, and DAPI (nuclear stain) 24 hours post transfection with NXL-P124 (CE-pGfa681-CI-hND1-P2A-hDlx2-bGHpA).
Figure 48:
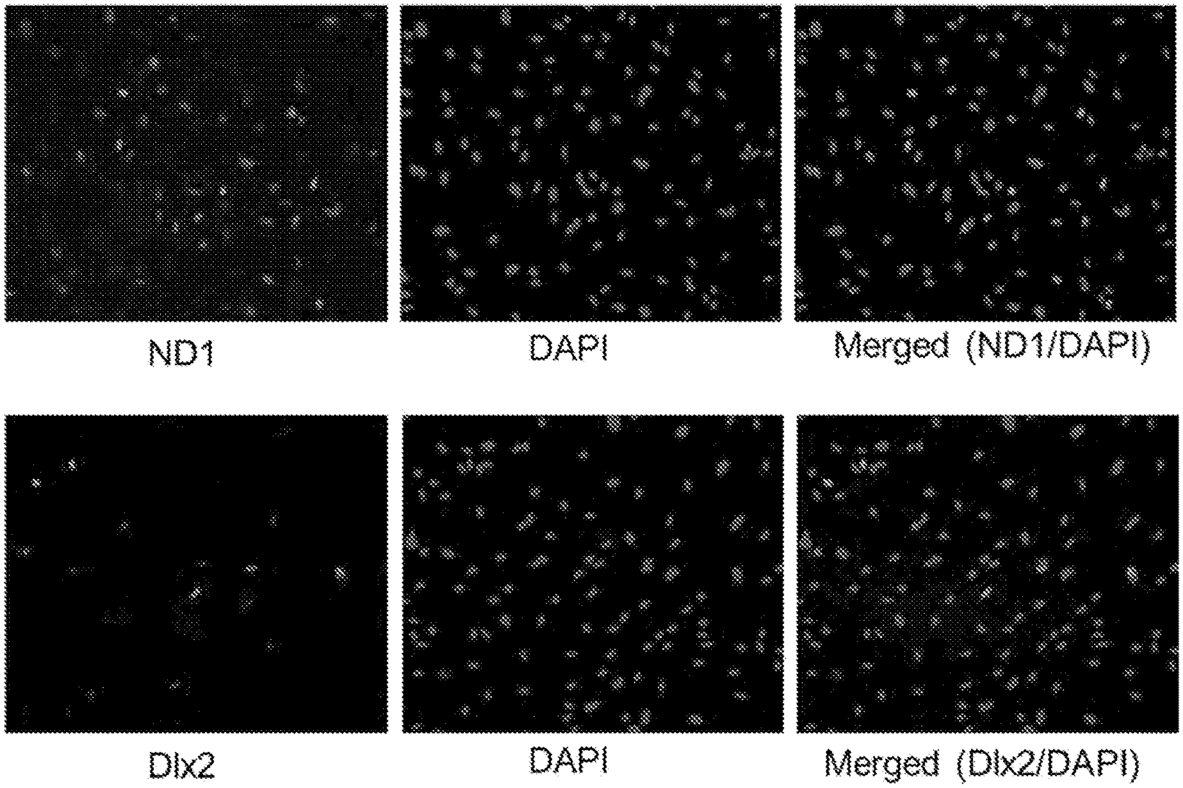
FIG. 48 depicts RCAs immunostained with an anti-ND1 antibody, an anti-Dlx2 antibody, and DAPI (nuclear stain) 6 days post transduction with AAV9-P124 (CE-pGfa681-CI-hND1-p2A-hDlx2-bGHpA) at $2\times10^{10}$ vg/ml.
Figure 49:
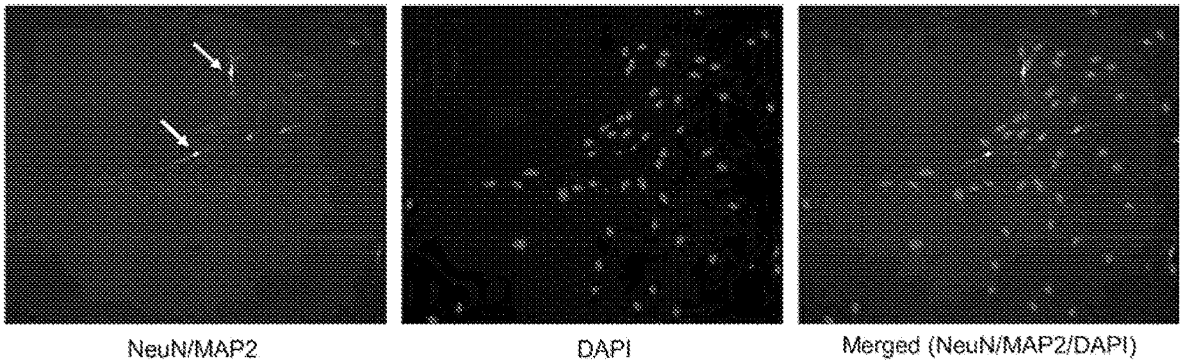
FIG. 49 depicts RCAs immunostained with an anti-NeuN antibody, an anti-MAP2 antibody, and DAPI (nuclear stain) 3 weeks post transduction with AAV9-P124 (CE-pGfa681-CI-hND1-P2A-hDlx2-bGHpA) at $2\times10^{10}$ vg/ml.
Figure 50:
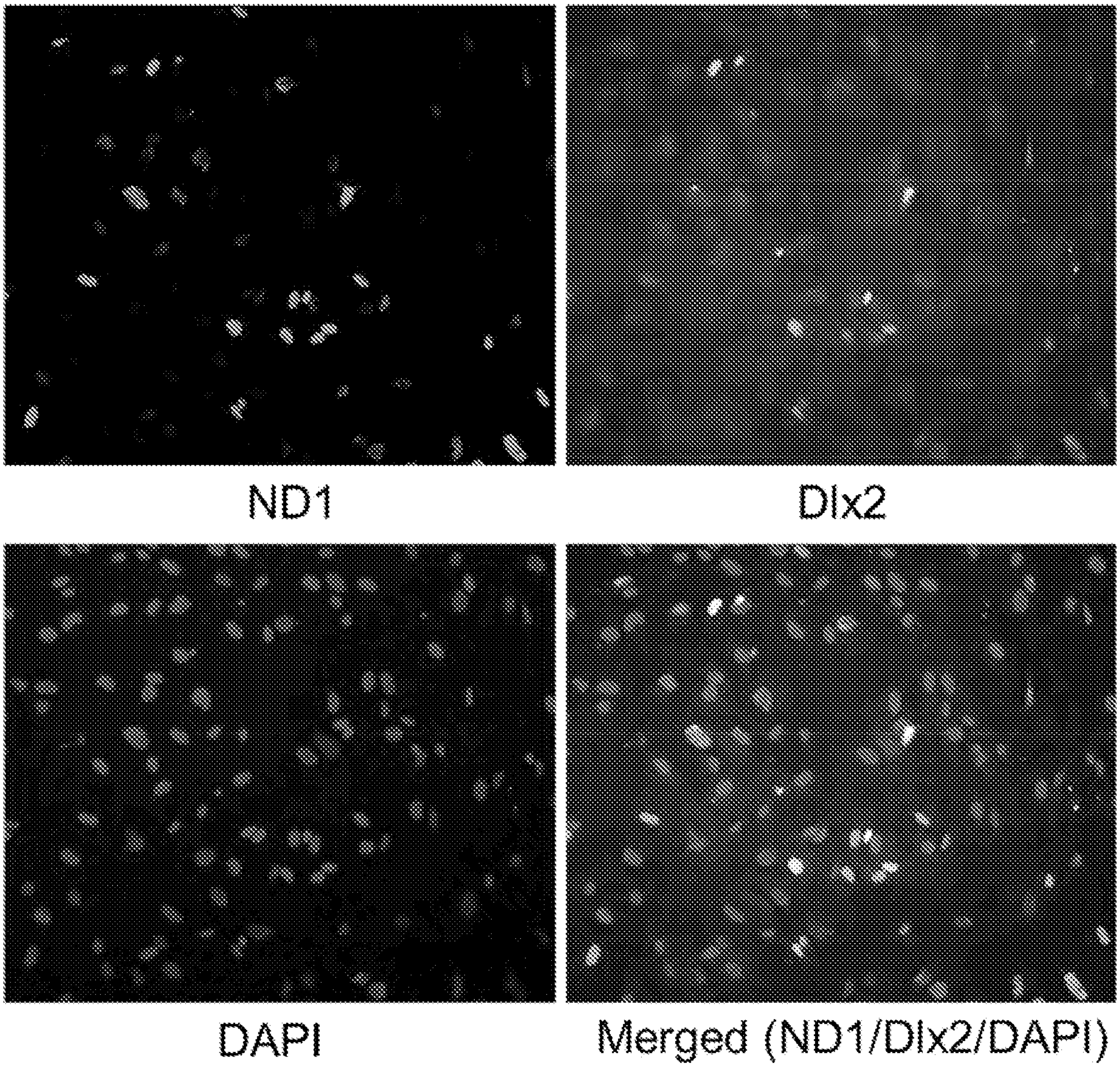
FIG. 50 depicts RCAs immunostained with an anti-ND1 antibody, an anti-Dlx2 antibody, and DAPI (nuclear stain)

FIG. 40 depicts two general maps of the constructs.

Cell Culture: Rat cortical astrocytes (RCAs) of passage 5-7 are seeded on glass cover slips coated with poly-D-lysine (PDL) in 24-well plates at 30-50% confluency 24-48 hours prior to transduction.

Transduction and Immunofluorescence: Cells are transduced with virus at $2\text{-}6\times10^{10}$ vg/ml in 500 ul of fresh astrocyte media (DMEM supplemented with 10% FBS, 2.5 mM Glutamine, 3.5 mM Glucose, penn/strep). At 48 hours post transduction, media is replaced with 5% FBS astrocyte media. For the next 4 days, 100 ul of conversion media (DMEM/F12+1% FBS+B27+N2 and 1 uM Rock inhibitor and 10 ng/ml BDNF) is added daily. Then the media is completely replaced with conversion media.

Cells are fixed with 4% paraformaldehyde in PBS at various desired time points (e.g., three days, one to five weeks post transduction) and subsequently washed and immunostained with antibodies against ND1 (Abcam Cat #ab60704), Dlx2 (Millipore Cat #AB5726), NeuN (Millipore, Cat #ABN78), Map2 (Invitrogen, Cat #PA5-17646) and followed with secondary antibodies conjugated with fluorescent dyes (Invitrogen, Alexafluor). Images are captured under a fluorescent microscope (Zeiss Axiovert Al, Zen Blue). Gene expression levels are assessed by comparing the fluorescence intensity.

In Vitro Studies Results:

The tested ND1-Dlx2 constructs are effective in driving the expression of ND1 and Dlx2 by transfection and/or transduction of the cultured rat astrocytes as demonstrated by the positive stating of ND1 and Dlx2 in these cells (FIGS. 41-56). Additionally, ND1/Dlx2-containing AAVs (AAV9-P122, AAV-P122, AAV-P124, and AAV-P20) are effective in driving the expression of ND1, Dlx2, and inducing an astrocyte-to-neuron conversion in cultured rat astrocytes as shown by positive staining of neuronal markers NeuN and/or MAP2 (FIGS. 43, 46, and 49, and 52). Some NeuN/MAP2 positive cells show typical neuronal morphology.

Example 25. In Vivo Transgene Expression and Astrocyte-to-Neuron Conversion Induced by Expression of NeuroD1 and Dlx2

AAV9-P112 and AAV9-P122 viruses are used for the in vivo studies. AAV9-P12, which drives the expression of GFP alone (no ND1 nor Dlx2) under a GFAP promoter, is used for the control and to identify cells expressing GFAP (astrocytes).

Normal C57BL/6 mice older than 8 weeks are injected with AAV-P12, AAV9-P112, and AAV9-P122 viruses as follows:

P12 control group: AAV9-P12 $2.5\times10^{11}$ GC/ml, 2 μL, 1 injection in striatum (n=6)

P112 group: AAV9-P12 $2.5\times10^{11}$ GC/ml+AAV9-P12 $2.5\times10^{11}$ GC/ml, 2 μL, 1 injection in striatum (n=6)

P122 group: AAV9-P12 $2.5\times10^{11}$ GC/ml+AAV9-P122 $2.5\times^{11}$ GC/ml, 2 μL, 1 injection in striatum (n=6)

Mice are sacrificed and brain cortex tissue are analyzed at 10 days post infection (dpi) and at 30 dpi. The infection of mouse striatum by AAV9-P12 is confirmed at 10 dpi by the presence of GFP fluorescence. At 30 dpi, AAV9-P12 infected cells are still GFAP-positive astrocytes, suggesting that AAV9-P12 is specific in infecting astrocytes (FIG. 57A-B). In the P112 group, the majority of cells co-infected with AAV9-P12 and AAV9-P112 are GFAP-positive stained astrocytes at 10 dpi (FIG. 58). By 30 days post viral infection, many cells co-infected with AAV9-P12 and AAV9-P112 become NeuN-positive neurons (FIG. 59, white arrows). In the P122 group, the majority of cells co-infected with AAV9-P12 and AAV9-P122 are GFAP-positive stained astrocytes at 10 dpi (FIG. 60). By 30 days post viral infection, many cells co-infected with AAV9-P12 and AAV9-P122 become NeuN-positive neurons (FIG. 61, white arrows).

Example 26. In Vitro Transgene Expression of Dlx2

Vectors: The vectors are tested via transfection of rat cortical astrocytes (RACs). Additionally, AAVs are produced with selected vectors and tested in vitro via transduction: NXL-P44: EE-pGfa681-CI-Dlx2-WPRE-SV40 pA NXL-P60: EE-pGfa681-Dlx2-WPRE-SV40 pA NXL-P75: CE-pGfa681-CI-Dlx2-WPRE-SV40 pA NXL-P104: CE-pGfa681-CGRI-Dlx2-bGHpA NXL-P105: CE-pGfa681-CI-Dlx2-oPRE-bGHpA NXL-P131: EE-pGfa681-CI-Dlx2-oPRE-bGHpA NXL-P133: CE-pGfa681-CGRI-Dlx2-oPRE-bGHpA NXL-P137: EE-pGfa681-CGRI-Dlx2-oPRE-bGHpA NXL-P104 and NXL-P105 constructs are effective in driving the expression of Dlx2 24 hours post transfection of the cultured RACs, as demonstrated by the positive Dlx2 staining in these cells (FIG. 62). NXL-P133, NXL-P137, and NXL-P131 constructs are effective in driving the expression of Dlx2 24 hours post transfection of the cultured RACs, as demonstrated by the positive Dlx2 staining in these cells (FIG. 63). AAV9-P133 (the AAV produced with NLX-P133) is effective in driving the expression of Dlx2 after transducing cultured RACs with this virus, as demonstrated by the positive Dlx2 staining in these cells (FIG. 64).

A variety of further modifications and improvements in and to the compositions and methods of the present disclosure will be apparent to those skilled in the art based. The following non-limiting embodiments are envisioned:

1. An adeno-associated virus (AAV) vector comprising a human neurogenic differentiation 1 (hNeuroD1) sequence comprising the nucleic acid sequence of SEQ ID NO: 6 and a human distal-less homeobox 2 (hDlx2) sequence comprising the nucleic acid sequence of SEQ ID NO: 13, wherein said hNeuroD1 sequence and said hDlx2 sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, wherein said hNeuroD1 sequence and said hDlx2 sequence are operably linked to regulatory elements comprising:
   (a) a glial fibrillary acidic protein (GFAP) promoter comprising a nucleic acid sequence selected from the group consisting of SEQ ID NOs: 4, 12, and 26;
   (b) an enhancer from a human elongation factor-1 alpha (EF1-α) promoter comprising the nucleic acid sequence of SEQ ID NO: 2 or a cytomegalovirus (CMV) enhancer comprising the nucleic acid sequence of SEQ ID NO: 11;
   (c) a chimeric intron comprising the nucleic acid sequence selected from the group consisting of SEQ ID NOs: 5 and 27;
   (d) a woodchuck hepatitis virus posttranscriptional regulatory element (WPRE) comprising the nucleic acid sequence selected from the group consisting of SEQ ID NOs: 7 and 29; and
   (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.
2. An adeno-associated virus (AAV) vector comprising a nucleic acid sequence encoding a human neurogenic differentiation 1 (hNeuroD1) protein comprising the amino acid coding sequence of SEQ ID NO: 10 and a nucleic acid coding sequence encoding a human distal-less homeobox 2 (hDlx2) protein comprising the amino acid sequence of SEQ ID NO: 14, wherein said hNeuroD1 coding sequence and said hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, (iii) or an internal ribosomal entry site of the encephalomyocarditis virus (IRES) sequence comprising SEQ ID NO: 3, wherein said hNeuroD1 coding sequence and said hDlx2 coding sequence is operably linked to regulatory elements comprising:
   (a) a glial fibrillary acidic protein (GFAP) promoter comprising a nucleic acid sequence selected from the group consisting of SEQ ID NOs: 4, 12, and 26;
   (b) an enhancer from a human elongation factor-1 alpha (EF1-α) promoter comprising the nucleic acid sequence of SEQ ID NO: 2 or a cytomegalovirus (CMV) enhancer comprising the nucleic acid sequence of SEQ ID NO: 11;
   (c) a chimeric intron comprising the nucleic acid sequence selected from the group consisting of SEQ ID NOs: 5 and 27;
   (d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

3. An adeno-associated virus (AAV) vector comprising a neurogenic differentiation 1 (NeuroD1) nucleic acid coding sequence encoding a NeuroD1 protein and a distal-less homeobox 2 (Dlx2) nucleic acid coding sequence encoding a Dlx2 protein, wherein said NeuroD1 coding sequence and said Dlx2 coding sequence are separated by a linker sequence, wherein said NeuroD1 coding sequence and said Dlx2 coding sequence are operably linked to regulatory elements comprising:

(a) a glial fibrillary acidic protein (GFAP) promoter;

(b) an enhancer;

(c) a chimeric intron;

(d) a woodchuck hepatitis virus posttranscriptional regulatory element (WPRE); and (e) a polyadenylation signal sequence.

4. A composition comprising an adeno-associated virus (AAV) vector for converting glial cells to functional neurons in a human, wherein said AAV vector comprises a human neurogenic differentiation 1 (hNeuroD1) sequence having a nucleic acid sequence of SEQ ID NO: 6 and a human distal-less homeobox 2 (hDlx2) sequence having a nucleic acid sequence of SEQ ID NO: 13, wherein said hNeuroD1 sequence and said hDlx2 sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, wherein said hNeuroD1 sequence and hDlx2 sequence are operably linked to regulatory elements comprising:

(a) a human glial fibrillary acidic protein (GFAP) promoter comprising a nucleic acid sequence selected from the group consisting of SEQ ID NOs: 4, 12, and 26;

(b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11;

(c) a chimeric intron comprising the nucleic acid sequence selected from the group consisting of SEQ ID NOs: 5 and 27;

(d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

5. A composition comprising an adeno-associated-virus (AAV) vector for converting glial cells to functional neurons in a human, wherein said AAV vector comprises a nucleic acid coding sequence encoding a human neurogenic differentiation 1 (hNeuroD1) protein comprising the amino acid sequence of SEQ ID NO: 10 and a nucleic acid coding sequence encoding a human distal-less homeobox 2 (hDlx2) protein comprising the amino acid sequence of SEQ ID NO: 14, wherein said hNeuroD1 coding sequence and said hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, wherein said hNeuroD1 coding sequence and said hDlx2 coding sequence are operably linked to regulatory elements comprising:

(a) a human glial fibrillary acidic protein (GFAP) promoter comprising a nucleic acid sequence selected from the group consisting of SEQ ID NOs: 4, 12, and 26;

(b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11;

(c) a chimeric intron comprising the nucleic acid sequence selected from the group consisting of SEQ ID NOs: 5 and 27;

(d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

6. A composition comprising an adeno-associated virus (AAV) vector for the treatment of a subject in need thereof, wherein said AAV vector comprises a neurogenic differentiation 1 (NeuroD1) sequence and a distal-less homeobox 2 (Dlx2) sequence, wherein said NeuroD1 sequence and said Dlx2 sequence are separated by a linker sequence, wherein said NeuroD1 sequence and Dlx2 sequence are operably linked to expression control elements comprising:

(a) a glial fibrillary acidic protein (GFAP) promoter;

(b) an enhancer;

(c) a chimeric intron;

(d) a woodchuck hepatitis virus posttranscriptional regulatory element (WPRE); and (e) a polyadenylation signal.

7. The AAV vector of any one of embodiments 1-3, or the composition of any one of embodiments 4-6, wherein said AAV vector is selected from the group consisting of AAV serotype 2, AAV serotype 5, and AAV serotype 9.

8. The AAV vector or composition of embodiment 7, wherein said AAV vector is AAV serotype 2.

9. The AAV vector or composition of embodiment 7, wherein said AAV vector is AAV serotype 5.

10. The AAV vector or composition of embodiment 7, wherein said AAV vector is AAV serotype 9.

11. The composition of embodiment 4 or 5, wherein said glial cells are reactive astrocytes.

12. The composition of embodiment 4 or 5, wherein said functional neurons are selected from the group consisting of glutamatergic neurons, GABAergic neurons, dopaminergic neurons, cholinergic neurons, seratonergic neurons, epinephrinergic neurons, motor neurons, and peptidergic neurons.
13. The composition of embodiment 4 or 5, wherein said human has a neurological condition.
14. The AAV vector of embodiment 3, or the composition of embodiment 6, wherein said NeuroD1 is a human NeuroD1 (hNeuroD1).
15. The AAV vector of embodiment 3, or the composition of embodiment 6, wherein said Dlx2 is a human Dlx2 (hDlx2).
16. The AAV vector of embodiment 3, or the composition of embodiment 6, wherein said NeuroD1 is selected from the group consisting of a chimpanzee NeuroD1, a bonobo NeuroD1, an orangutan NeuroD1, a gorilla NeuroD1, a macaque NeuroD1, a marmoset NeuroD1, a capuchin NeuroD1, a baboon NeuroD1, a gibbon NeuroD1, and a lemur NeuroD1.
17. The AAV vector of embodiment 3, or the composition of embodiment 6, wherein said Dlx2 is selected from the group consisting of a chimpanzee Dlx2, a bonobo Dlx2, an orangutan Dlx2, a gorilla Dlx2, a macaque Dlx2, a marmoset Dlx2, a capuchin Dlx2, a baboon Dlx2, a gibbon Dlx2, and a lemur Dlx2.
18. The AAV vector or composition of embodiment 14, wherein said hNeuroD1 comprises a nucleic acid sequence encoding an amino acid sequence at least 80% identical or similar to SEQ ID NO: 10.
19. The AAV vector or composition of embodiment 15, wherein said hDlx2 comprises a nucleic acid sequence encoding an amino acid sequence at least 80% identical or similar to SEQ ID NO: 14.
20. The AAV vector or composition of embodiment 14, wherein said hNeuroD1 coding sequence comprises a nucleic acid sequence at least 80% identical to SEQ ID NO: 6, or the complement thereof.
21. The AAV vector or composition of embodiment 15, said hDlx2 coding sequence comprises a nucleic acid sequence at least 80% identical to SEQ ID NO: 13, or the complement thereof.
22. The AAV vector of embodiment 3, or the composition of embodiment 6, wherein said linker is selected from the group consisting of P2A and T2A.
23. The AAV vector or composition of embodiment 22, wherein said linker is said P2A.
24. The AAV vector or composition of embodiment 22, wherein said linker is said T2A
25. The AAV vector or composition of embodiment 22, wherein said P2A linker comprises a nucleic acid sequence at least 80% identical to the sequence selected from the group consisting of SEQ ID NO: 15 and 18, or the complement thereof.
26. The AAV vector or composition of embodiment 22, wherein said T2A linker comprises a nucleic acid sequence at least 80% identical to the sequence selected from the group consisting of SEQ ID NO: 16 and 19, or the complement thereof.
27. The AAV vector of embodiment 3, or the composition of embodiment 6, wherein said GFAP promoter is a human GFAP (hGFAP) promoter.
28. The AAV vector of embodiment 3, or the composition of embodiment 6, wherein said GFAP promoter is selected from the group consisting of a chimpanzee GFAP promoter, a bonobo GFAP promoter, an orangutan GFAP promoter, a gorilla GFAP promoter, a macaque GFAP promoter, a marmoset GFAP promoter, a capuchin GFAP promoter, a baboon GFAP promoter, a gibbon GFAP promoter, and a lemur GFAP promoter.
29. The AAV vector or composition of any one of the preceding embodiments, wherein said IRES sequence comprises a nucleic acid sequence at least 80% identical to SEQ ID NO: 3, or the complement thereof.
30. The AAV vector or composition of embodiment 27, wherein said hGFAP promoter comprises a nucleic acid sequence at least 80% identical to SEQ ID NOs: 4 or the complement thereof.
31. The AAV vector or composition of embodiment 27, wherein said hGFAP promoter comprises a nucleic acid sequence at least 80% identical to SEQ ID NOs: 12 or the complement thereof.
32. The AAV vector or composition of embodiment 27, wherein said hGFAP promoter comprises a nucleic acid sequence at least 80% identical to SEQ ID NOs: 26 or the complement thereof.
33. The AAV vector of embodiment 3, or the composition of embodiment 6, wherein said enhancer is selected from the group consisting of an enhancer from human elongation factor-1 alpha (EF1-α) promoter and cytomegalovirus (CMV) enhancer
34. The AAV vector or composition of embodiment 33, wherein said EF1-α comprises a nucleic acid sequence at least 80% identical to SEQ ID NO: 2, or the complement thereof.
35. The AAV vector or composition of embodiment 33, wherein said CMV enhancer comprises a nucleic acid sequence at least 80% identical to SEQ ID NO: 11, or the complement thereof.
36. The AAV vector of embodiment 3, or the composition of embodiment 6, wherein said chimeric intron comprises a nucleic acid sequence at least 80% identical to a nucleic acid selected form the group consisting of SEQ ID NOs: 5 and 27, or the complement thereof.
37. The AAV vector of embodiment 3, or the composition of embodiment 6, wherein said WPRE comprises a nucleic acid sequence at least 80% identical to a nucleic acid selected from the group consisting of SEQ ID NOs: 7 and 29, or the complement thereof.
38. The AAV vector of embodiment 3, or the composition of embodiment 6, wherein said polyadenylated signal is selected from the group consisting of SV40 polyadenylation signal, a hGH polyadenylation signal, and a bGH polyadenylation signal.
39. The AAV vector or composition of embodiment 38, wherein said SV40 polyadenylated signal comprises a nucleic acid sequence at least 80% identical to SEQ ID NO: 8, or the complement thereof.
40. The AAV vector or composition of embodiment 38, wherein said hGH polyadenylated signal comprises a nucleic acid sequence at least 80% identical to SEQ ID NO: 17, or the complement thereof.
41. The AAV vector or composition of embodiment 38, wherein said bGH polyadenylated signal comprises a nucleic acid sequence at least 80% identical to SEQ ID NO: 30, or the complement thereof.
42. The AAV vector of embodiment 3, or the composition of embodiment 6, wherein said AAV vector further comprises a nucleic acid sequence encoding an AAV protein sequence.
43. The AAV vector of any one of embodiments 1-3, or the composition of any one of embodiments 4-6, wherein said AAV vector comprises AAV serotype 2 inverted terminal repeats (ITRs).

44. The AAV vector of any one of embodiments 1-3, or the composition of any one of embodiments 4-6, wherein said AAV vector comprises AAV serotype 5 inverted terminal repeats (ITRs).

45. The AAV vector of any one of embodiments 1-3, or the composition of any one of embodiments 4-6, wherein said AAV vector comprises AAV serotype 9 inverted terminal repeats (ITRs).

46. The AAV vector of any one of embodiments 1-3, or the composition of any one of embodiments 4-6, wherein said AAV vector comprises at least one ITR nucleic acid sequence at least 80% identical to SEQ ID NO: 1.

47. The AAV vector of any one of embodiments 1-3, or the composition of any one of embodiments 4-6, wherein said AAV vector comprises at least one ITR nucleic acid sequence at least 80% identical to SEQ ID NO: 9.

48. The composition of embodiment 6, wherein said subject in need thereof is a mammal.

49. The composition of embodiment 48, wherein said mammal is a human.

50. The composition of embodiment 48, wherein said mammal is a non-human primate.

51. The composition of embodiment 6, wherein said subject in need thereof has a neurological condition.

52. The composition of embodiment 13 or 51, wherein said neurological condition comprises an injury to the central nervous system (CNS) or peripheral nervous system.

53. The composition of embodiment 13 or 51, wherein said wherein said neurological condition comprises an injury to the CNS.

54. The composition of embodiment 13 or 51, wherein said neurological condition is selected from the group consisting of Alzheimer's Disease, Parkinson's Disease, amyotrophic lateral sclerosis (ALS), Huntington's Disease, epilepsy, physical injury, stroke, cerebral aneurysm, traumatic brain injury, concussion, a tumor, inflammation, infection, ataxia, brain atrophy, spinal cord atrophy, multiple sclerosis, traumatic spinal cord injury, ischemic or hemorrhagic myelopathy (myelopathy), global ischemia, hypoxic ischemic encephalopathy, embolism, fibrocartilage embolism myelopathy, thrombosis, nephropathy, chronic inflammatory disease, meningitis, and cerebral venous sinus thrombosis.

55. The composition of embodiment 13 or 51, wherein said neurological condition is Alzheimer's Disease.

56. The composition of embodiment 13 or 51, wherein said neurological condition is Parkinson's Disease.

57. The composition of embodiment 13 or 51, wherein said neurological condition is ALS.

58. The composition of embodiment 13 or 51, wherein said neurological condition is Huntington's Disease.

59. The composition of embodiment 13 or 51, wherein said neurological condition is a stroke.

60. The composition of embodiment 59, wherein said stroke is an ischemic stroke.

61. The composition of embodiment 59, wherein said stroke is a hemorrhagic stroke.

62. The composition of embodiment 51, wherein said composition is capable of converting at least one glial cell to a neuron.

63. The composition of embodiment 62, wherein said glial cells are selected from the group consisting of astrocytes and NG2 cells.

64. The composition of embodiment 62, wherein said glial cells are astrocytes.

65. The composition of embodiment 62, wherein said astrocytes are reactive astrocytes.

66. The composition of embodiment 62, wherein said glial cells are GFAP positive.

67. The composition of embodiment 62, wherein said neurons are functional neurons.

68. The composition of embodiment 62, wherein said functional neurons are selected from the group consisting of glutamatergic neurons, GABAergic neurons. dopaminergic neurons, cholinergic neurons, seratonergic neurons, epinephrinergic neurons, motor neurons, and peptidergic neurons.

69. The composition of embodiment 68, wherein said functional neurons are glutamatergic neurons.

70. The composition of embodiment 6, wherein said composition is formulated to be delivered to a subject in need thereof.

71. The composition of embodiment 70, wherein said composition is formulated for local delivery.

72. The composition of embodiment 70, wherein said composition is formulated for systemic delivery.

73. The composition of any one of embodiments 70-72, wherein said composition is formulated for delivery via intraperitoneal, intramuscular, intravenous, intrathecal, intracerebral, intracranial, intra lateral ventricle of the brain, intra cisterna magna, intra vitreous, intra-subretina, intraparenchymal, intranasal, or oral administration.

74. A method comprising delivering the composition of embodiment 6 to said subject in need thereof.

75. The method of embodiment 74, wherein said composition is formulated to be delivered to a subject in need thereof.

76. The method of embodiment 74, wherein said delivering comprises local administration.

77. The method of embodiment 74, wherein said delivering comprises systemic administration.

78. The method of any one of embodiments 74-77, wherein said delivering comprises an intraperitoneal, intramuscular, intravenous, intrathecal, intracerebral, intracranial, intra lateral ventricle of the brain, intra cisterna magna, intra vitreous, intra-subretina, intraparenchymal, intranasal, or oral administration.

79. A method of converting reactive astrocytes to functional neurons in a brain of a living human comprising: injecting an adeno-associated virus (AAV) into a subject in need thereof, wherein said AAV comprises a DNA vector construct comprising a human neurogenic differentiation 1 (hNeuroD1) sequence comprising the nucleic acid sequence of SEQ ID NO: 6 and a human distal-less homeobox 2 (hDlx2) sequence comprising the nucleic acid sequence of SEQ ID NO: 13, wherein said hNeuroD1 sequence and said hDlx2 sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, wherein said hNeuroD1 sequence and said hDlx2 sequence are operably linked to regulatory elements comprising:

(a) a human glial fibrillary acidic protein (GFAP) promoter comprising a nucleic acid sequence selected from the group consisting of SEQ ID NOs: 4, 12, and 26;

(b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11;

(c) a chimeric intron comprising the nucleic acid sequence selected from the group consisting of SEQ ID NOs: 5 and 27;

(d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

80. A method of converting reactive astrocytes to functional neurons in a brain of a living human comprising: injecting an adeno-associated virus (AAV) into a subject in need thereof, wherein said AAV comprises a DNA vector construct comprising a nucleic acid coding sequence encoding a human neurogenic differentiation 1 (hNeuroD1) protein comprising the amino acid sequence of SEQ ID NO: 10 and a nucleic acid coding sequence encoding a human distal-less homeobox 2 (hDlx2) protein comprising the amino acid sequence of SEQ ID NO: 14, wherein said hNeuroD1 coding sequence and said hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, wherein said hNeuroD1 coding sequence and hDlx2 coding sequence are operably linked to expression control elements comprising:

(a) a human glial fibrillary acidic protein (GFAP) promoter comprising a nucleic acid sequence selected from the group consisting of SEQ ID NOs: 4, 12, and 26;

(b) an enhancer from the human elongation factor-1 alpha (EF-1 alpha) promoter comprising the nucleic acid sequence of SEQ ID NO: 2 or a cytomegalovirus (CMV) enhancer comprising the nucleic acid sequence of SEQ ID NO: 11;

(c) a chimeric intron comprising the nucleic acid sequence selected from the group consisting of SEQ ID NOs: 5 and 27;

(d) a woodchuck hepatitis virus posttranscriptional regulatory element (WPRE) comprising the nucleic acid sequence selected from the group consisting of SEQ ID NOs: 7 and 29; and (e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

81. A method of converting glial cells to neurons in a subject in need thereof comprising: delivering an adeno-associated virus (AAV) to said subject in need thereof, wherein said AAV comprises a DNA vector construct comprising a neurogenic differentiation 1 (NeuroD1) sequence and a distal-less homeobox 2 (Dlx2) sequence, wherein said NeuroD1 sequence and Dlx2 sequence are separated by a linker sequence, wherein said NeuroD1 sequence and Dlx2 sequence are operably linked to expression control elements comprising:

(a) a glial fibrillary acid protein (GFAP) promoter;

(b) an enhancer;

(c) a chimeric intron;

(d) a woodchuck hepatitis virus posttranscriptional regulatory element (WPRE); and (e) and a polyadenylation signal sequence, wherein said AAV vector is capable of converting at least one glial cell to a neuron in said subject in need thereof.

82. A method of treating a neurological condition in a subject in need thereof comprising: delivering an adeno-associated virus (AAV) to said subject, wherein said AAV comprises a DNA vector construct comprising a neurogenic differentiation 1 (NeuroD1) sequence and distal-less homeobox 2 (Dlx2) sequence, wherein said NeuroD1 sequence and Dlx2 sequence are separated by a linker sequence, wherein said NeuroD1 sequence and said Dlx2 sequence are operably linked to expression control elements comprising:

(a) a glial fibrillary acid protein (GFAP) promoter;

(b) an enhancer;

(c) a chimeric intron;

(d) a woodchuck hepatitis virus posttranscriptional regulatory element (WPRE); and (e) a polyadenylation signal to said subject in need thereof.

83. The method of any one of embodiments 79-82, wherein said AAV is selected from the group consisting of AAV serotype 2, AAV serotype 5, and AAV serotype 9.

84. The method of embodiment 83, wherein said AAV is AAV serotype 2.

85. The method of embodiment 83, wherein said AAV is AAV serotype 5.

86. The method of embodiment 83, wherein said AAV is AAV serotype 9.

87. The method of embodiments 79 or 80, wherein said functional neurons are glutamatergic neurons, GABAergic neurons, dopaminergic neurons, cholinergic neurons, seratonergic neurons, epinephrinergic neurons, motor neurons, and peptidergic neurons.

88. The method of embodiments 81 or 82, wherein said NeuroD1 is human NeuroD1 (hNeuroD1).

89. The method of embodiments 81 or 82 wherein said Dlx2 is human Dlx2 (hDlx2).

90. The method of embodiments 81 or 82, wherein said NeuroD1 is selected from the group consisting of a chimpanzee NeuroD1, a bonobo NeuroD1, an orangutan NeuroD1, a gorilla NeuroD1, a macaque NeuroD1, a marmoset NeuroD1, a capuchin NeuroD1, a baboon NeuroD1, a gibbon NeuroD1, and a lemur NeuroD1.

91. The method of embodiments 75 or 76, wherein said Dlx2 is selected from the group consisting of a chimpanzee Dlx2, a bonobo Dlx2, an orangutan Dlx2, a gorilla Dlx2, a macaque Dlx2, a marmoset Dlx2, a capuchin Dlx2, a baboon Dlx2, a gibbon Dlx2, and a lemur Dlx2.

92. The method of embodiment 88, wherein said hNeuroD1 comprises an amino acid sequence encoding an amino acid coding sequence at least 80% identical or similar to SEQ ID NO: 10.

93. The method of embodiment 89, said hDlx2 comprises a amino acid sequence encoding an amino acid sequence at least 80% identical or similar to SEQ ID NO: 14.

94. The method of embodiment 88, wherein said hNeuroD1 coding sequence comprises a nucleic acid sequence at least 80% identical to SEQ ID NO: 6, or the complement thereof.

95. The method of embodiment 89, said hDlx2 coding sequence comprises a nucleic acid sequence at least 80% identical to SEQ ID NO: 13, or the complement thereof.

96. The method of embodiments 81 or 82, wherein said GFAP promoter is a human GFAP (hGFAP) promoter.

97. The method of embodiments 81 or 82, wherein said GFAP promoter is selected from the group consisting of a chimpanzee GFAP promoter, a bonobo GFAP promoter, an orangutan GFAP promoter, a gorilla GFAP promoter, a macaque GFAP promoter, a marmoset GFAP promoter, a capuchin GFAP promoter, a baboon GFAP promoter, a gibbon GFAP promoter, and a lemur GFAP promoter.

98. The method of any one of embodiments 79-97, wherein said IRES sequence comprises a nucleic acid sequence at least 80% identical to SEQ ID NO: 3, or the complement thereof.

99. The method of embodiment 96, wherein said hGFAP promoter comprises a nucleic acid sequence at least 80% identical to SEQ ID NOs: 4, or the complement thereof.

100. The method of embodiment 96, wherein said hGFAP promoter comprises a nucleic acid sequence at least 80% identical to SEQ ID NOs: 12, or the complement thereof.

101. The method of embodiment 96, wherein said hGFAP promoter comprises a nucleic acid sequence at least 80% identical to SEQ ID NOs: 26, or the complement thereof.

102. The method of embodiments 81 or 82, wherein said linker is selected from the group consisting of P2A and T2A.

103. The method of embodiment 102, wherein said P2A linker comprises a nucleic acid sequence at least 80% identical to the sequence selected from the group consisting of SEQ ID NO: 15 and 18, or the complement thereof.

104. The method of embodiment 102, wherein said T2A linker comprises a nucleic acid sequence at least 80% identical to the sequence selected from the group consisting of SEQ ID NO: 16 and 19, or the complement thereof.

105. The method of embodiments 81 or 82, wherein said enhancer is selected from the group consisting of an enhancer from human elongation factor-1 alpha (EF1-α) promoter and cytomegalovirus (CMV) enhancer.

106. The method of embodiment 105, wherein said EF1-α comprises a nucleic acid sequence at least 80% identical to SEQ ID NO: 2, or the complement thereof.

107. The method of embodiment 105, wherein said CMV enhancer comprises a nucleic acid sequence at least 80% identical to SEQ ID NO: 11, or the complement thereof.

108. The method of embodiments 81 or 82, wherein said chimeric intron comprises a nucleic acid sequence at least 80% identical to nucleic acid selected from the group consisting of SEQ ID NOs: 5 and 27, or the complement thereof.

109. The method of embodiments 81 or 82, wherein said WPRE comprises a nucleic acid sequence at least 80% identical to a nucleic acid selected from the group consisting of SEQ ID NOs: 7 and 29, or the complement thereof.

110. The method of embodiments 81 or 82, wherein said polyadenylated signal selected from the group consisting of SV40 polyadenylation signal and a hGH polyadenylation signal 111. The method of embodiment 110, wherein said SV40 polyadenylated signal comprises a nucleic acid sequence at least 80% identical to SEQ ID NO: 8, or the complement thereof.

112. The method of embodiment 110, wherein said hGH polyadenylated signal comprises a nucleic acid sequence at least 80% identical to SEQ ID NO: 13, or the complement thereof.

113. The method of embodiments 81 or 82, wherein said vector further comprises a nucleic acid sequence encoding an AAV protein sequence.

114. The method of any one of embodiments 79-82, wherein said vector comprises AAV serotype 2 inverted terminal repeats (ITRs).

115. The method of any one of embodiments 79-82, wherein said vector comprises AAV serotype 5 inverted terminal repeats (ITRs).

116. The method of any one of embodiments 79-82, wherein said vector comprises AAV serotype 9 inverted terminal repeats (ITRs).

117. The method of any one of embodiments 79-82, wherein said vector comprises at least one ITR nucleic acid sequence at least 80% identical to SEQ ID NO: 1.

118. The method of any one of embodiments 79-82, wherein said vector comprises at least one ITR nucleic acid sequence at least 80% identical to SEQ ID NO: 9.

119. The method of embodiment 81, wherein said converting occurs in the central nervous system (CNS) or peripheral nervous system.

120. The method of embodiment 81, wherein said converting occurs in the CNS.

121. The method of embodiment 81 or 82, wherein said subject in need thereof is a mammal.

122. The method of embodiment 121, wherein said mammal is a human.

123. The method of embodiment 121, wherein said mammal is a non-human primate.

124. The method of embodiment 81 or 82, wherein said delivering comprises a local administration.

125. The method of embodiment 81 or 82, wherein said delivering comprises systemic administration.

126. The method of embodiment 81 or 82, wherein said delivering comprises an administration selected from the group consisting of an intraperitoneal administration, intramuscular administration, intravenous administration, intrathecal administration, intracerebral administration, intracranial, intra lateral ventricle of the brain, intra cisterna magna, intra vitreous, intra-subretina, intraparenchymal administration, intranasal administration, and oral administration.

127. The method of embodiment 79 or 80, wherein said injecting comprises an injection selected from the group consisting of an intraperitoneal injection, intramuscular injection, intravenous injection, intrathecal injection, intracerebral injection, intracranial, intra lateral ventricle of the brain, intra cisterna magna, intra vitreous, intra-subretina, intraparenchymal injection, intranasal injection, and oral injection.

128. The method of embodiments 81 or 82, wherein said delivering comprises injecting.

129. The method of any one of embodiments 79, 80 or 128, wherein said injecting is performed at a concentration of between $10^{10}$ particles/mL and $10^{14}$ particles/mL.

130. The method of embodiment 129, wherein said injecting further comprises a flow rate of between 0.1 μL/minute and 5.0 μL/minute.

131. The method of embodiment 81, wherein said at least one glial cell is selected from the group consisting of at least one astrocyte and at least one NG2 cell.

132. The method of embodiment 131, wherein said at least one glial cell is at least one astrocyte.

133. The method of embodiment 131 or 132, wherein said at least one astrocyte is a reactive astrocyte.

134. The method of embodiment 81, wherein said neuron is a functional neuron.

135. The method of any one of embodiments 79, 80 and 134, wherein said functional neurons are selected from the group consisting of glutamatergic neurons, GABAergic neurons, dopaminergic neurons, cholinergic neurons, seratonergic neurons, epinephrinergic neurons, motor neurons, and peptidergic neurons.

136. The method of embodiment 81, wherein said subject exhibits an improvement of at least one neurological condition symptom as compared to said subject prior to said delivering.

137. The method of embodiment 136, wherein said improvement is measured within 1 year of said delivering.

138. The method of any one of embodiments 79, 80, or 128, wherein said method comprises directly injecting said AAV into the brain of said subject.

139. The method of any one of embodiments 79 or 80 wherein said wherein said converting is in the striatum of said brain.

140. The method of any one of embodiments 79, 80, or 128, wherein said method comprises directly injecting said AAV into the spinal cord of said subject.

141. The method of embodiment 82, wherein said neurological condition comprises an injury to the central nervous system (CNS) or peripheral nervous system.

142. The method of embodiment 82, wherein said neurological condition is selected from the group consisting of Alzheimer's Disease, Parkinson's Disease, amyotrophic lateral sclerosis (ALS), Huntington's Disease, epilepsy, physical injury, stroke, cerebral aneurysm, traumatic brain injury, concussion, a tumor, inflammation, infection, ataxia, brain atrophy, spinal cord atrophy, multiple sclerosis, traumatic spinal cord injury, ischemic or hemorrhagic myelopathy (myelopathy), global ischemia, hypoxic ischemic encephalopathy, embolism, fibrocartilage embolism myelopathy, thrombosis, nephropathy, chronic inflammatory disease, meningitis, and cerebral venous sinus thrombosis.

143. The method of embodiment 82, wherein said neurological condition is Alzheimer's Disease.

144. The method of embodiment 82, wherein said neurological condition is Parkinson's Disease.

145. The method of embodiment 82, wherein said neurological condition is ALS.

146. The method of embodiment 82, wherein said neurological condition is Huntington's Disease.

147. The method of embodiment 82, wherein said neurological condition is a stroke.

148. The method of embodiment 147, wherein said stroke is an ischemic stroke.

149. The method of embodiment 147, wherein said stroke is a hemorrhagic stroke.

150. The method of embodiment 82, wherein said method is capable of converting at least one glial cell into a neuron.

151. The method of embodiment 150, wherein said glial cells are selected from the group consisting of astrocytes and NG2 cells.

152. The method of embodiment 150, wherein said glial cells are astrocytes.

153. The method of embodiment 152, wherein said astrocytes are reactive astrocytes.

154. The method of embodiment 150, wherein said glial cells are GFAP positive.

155. The method of embodiment 150, wherein said neurons are functional neurons.

156. The method of embodiment 145, wherein said functional neurons are selected from the group consisting of glutamatergic neurons, GABAergic neurons, dopaminergic neurons, cholinergic neurons, seratonergic neurons, epinephrinergic neurons, motor neurons, and peptidergic neurons.

157. The method of embodiments 79 or 80, wherein a therapeutically effective dose of said AAV is injected into said subject.

158. The method of embodiments 81 or 82, wherein a therapeutically effective dose of said AAV is delivered to said subject.

159. The method of embodiment 147 or 148, wherein said therapeutically effective dose is administered with a pharmaceutically acceptable carrier.

160. A composition comprising (i) an adeno-associated virus (AAV) vector comprising a human neurogenic differentiation 1 (hNeuroD1) sequence comprising the nucleic acid sequence of SEQ ID NO: 6, and (ii) an adeno-associated virus (AAV) vector comprising a human distal-less homeobox 2 (hDlx2) sequence comprising the nucleic acid sequence of SEQ ID NO: 13; wherein the hNeuroD1 sequence is operably linked to regulatory elements comprising:

(a) a glial fibrillary acidic protein (GFAP) promoter comprising the nucleic acid sequence of SEQ ID NO: 26;

(b) an enhancer from a human elongation factor-1 alpha (EF1-α) promoter comprising the nucleic acid sequence of SEQ ID NO: 2;

(c) a chimeric intron comprising the nucleic acid sequence of SEQ ID NO: 5 or SEQ ID NO: 27;

(d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

161. A composition comprising (i) an adeno-associated virus (AAV) vector comprising a human neurogenic differentiation 1 (hNeuroD1) sequence comprising the nucleic acid sequence of SEQ ID NO: 6, and (ii) an adeno-associated virus (AAV) vector comprising a human distal-less homeobox 2 (hDlx2) sequence comprising the nucleic acid sequence of SEQ ID NO: 13; wherein the hNeuroD1 sequence is operably linked to regulatory elements comprising:
(a) a glial fibrillary acidic protein (GFAP) promoter comprising the nucleic acid sequence of SEQ ID NO: 26;
(b) a cytomegalovirus (CMV) enhancer comprising the nucleic acid sequence of SEQ ID NO: 11;
(c) a chimeric intron comprising the nucleic acid sequence of SEQ ID NO: 5 or SEQ ID NO: 27;
(d) a woodchuck hepatitis virus posttranscriptional regulatory element (WPRE) comprising the nucleic acid sequence of SEQ ID NO: 29; and
(e) a bGH polyadenylation sequence comprising the nucleic acid sequence of SEQ ID NO: 30.

162. The composition of embodiment 160 or 161, wherein (ii) comprises an AAV vector comprising the hDlx2 sequence comprising the nucleic acid sequence of SEQ ID NO: 13 operably linked to regulatory elements comprising:
(a) a glial fibrillary acidic protein (GFAP) promoter comprising a nucleic acid sequence of SEQ ID NO: 26;
(b) an enhancer from a human elongation factor-1 alpha (EF1-α) promoter comprising the nucleic acid sequence of SEQ ID NO: 2 or a cytomegalovirus (CMV) enhancer comprising the nucleic acid sequence of SEQ ID NO: 11;
(c) a chimeric intron comprising the nucleic acid sequence selected from the group consisting of SEQ ID NOs: 5 and 27;
(d) a woodchuck hepatitis virus posttranscriptional regulatory element (WPRE) comprising the nucleic acid sequence selected from the group consisting of SEQ ID NOs: 7 and 29; and
(e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

163. A composition comprising (i) an adeno-associated virus (AAV) vector comprising a nucleic acid sequence encoding a human neurogenic differentiation 1 (hNeuroD1) protein comprising the amino acid coding sequence of SEQ ID NO: 10, and (ii) an adeno-associated virus (AAV) vector comprising a nucleic acid coding sequence encoding a human distal-less homeobox 2 (hDlx2) protein comprising the amino acid sequence of SEQ ID NO: 14;
wherein the nucleic acid sequence encoding an hNeuroD1 protein is operably linked to regulatory elements comprising:
(a) a glial fibrillary acidic protein (GFAP) promoter comprising the nucleic acid sequence of SEQ ID NO: 26;
(b) an enhancer from a human elongation factor-1 alpha (EF1-α) promoter comprising the nucleic acid sequence of SEQ ID NO: 2;
(c) a chimeric intron comprising the nucleic acid sequence of SEQ ID NO: 5 or SEQ ID NO: 27;
(d) a woodchuck hepatitis virus posttranscriptional regulatory element (WPRE) comprising the nucleic acid sequence of SEQ ID NO: 29; and
(e) a bGH polyadenylation sequence comprising the nucleic acid sequence of SEQ ID NO: 30.

164. A composition comprising (i) an adeno-associated virus (AAV) vector comprising a nucleic acid sequence encoding a human neurogenic differentiation 1 (hNeuroD1) protein comprising the amino acid coding sequence of SEQ ID NO: 10, and (ii) an adeno-associated virus (AAV) vector comprising a nucleic acid coding sequence encoding a human distal-less homeobox 2 (hDlx2) protein comprising the amino acid sequence of SEQ ID NO: 14;
wherein the nucleic acid sequencing encoding an hNeuroD1 protein is operably linked to regulatory elements comprising:
(a) a glial fibrillary acidic protein (GFAP) promoter comprising the nucleic acid sequence of SEQ ID NO: 26;
(b) a cytomegalovirus (CMV) enhancer comprising the nucleic acid sequence of SEQ ID NO: 11;
(c) a chimeric intron comprising the nucleic acid sequence of SEQ ID NO: 5 or SEQ ID NO: 27;
(d) a woodchuck hepatitis virus posttranscriptional regulatory element (WPRE) comprising the nucleic acid sequence of SEQ ID NO: 29; and
(e) a bGH polyadenylation sequence comprising the nucleic acid sequence of SEQ ID NO: 30

165. The composition of embodiment 163 or 164, wherein (ii) comprises an AAV vector comprising a nucleic acid coding sequence encoding the hDlx2 protein, wherein the nucleic acid is operably linked to regulatory elements comprising:
(a) a glial fibrillary acidic protein (GFAP) promoter comprising a nucleic acid sequence of SEQ ID NO: 26;
(b) an enhancer from a human elongation factor-1 alpha (EF1-α) promoter comprising the nucleic acid sequence of SEQ ID NO: 2 or a cytomegalovirus (CMV) enhancer comprising the nucleic acid sequence of SEQ ID NO: 11;
(c) a chimeric intron comprising the nucleic acid sequence selected from the group consisting of SEQ ID NOs: 5 and 27;
(d) a woodchuck hepatitis virus posttranscriptional regulatory element (WPRE) comprising the nucleic acid sequence selected from the group consisting of SEQ ID NOs: 7 and 29; and
(e) a SV40 polyadenylation signal sequence comprising the nucleic acid sequence of SEQ ID NO: 8, a hGH polyadenylation sequence comprising the nucleic acid sequence of SEQ ID NO: 17, or a bGH polyadenylation sequence comprising the nucleic acid sequence of SEQ ID NO: 30.

166. An adeno-associated virus (AAV) vector comprising a human neurogenic differentiation 1 (hNeuroD1) sequence comprising the nucleic acid sequence of SEQ ID NO: 6 and a human distal-less homeobox 2 (hDlx2) sequence comprising the nucleic acid sequence of SEQ ID NO: 13, wherein said hNeuroD1 sequence and said hDlx2 sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, wherein said hNeuroD1 sequence and said hDlx2 sequence are operably linked to regulatory elements comprising:

(a) a glial fibrillary acidic protein (GFAP) promoter comprising the nucleic acid sequence of SEQ ID NO: 26;

(b) an enhancer from a human elongation factor-1 alpha (EF1-α) promoter comprising the nucleic acid sequence of SEQ ID NO: 2;

(c) a chimeric intron comprising the nucleic acid sequence of SEQ ID NO: 5 or SEQ ID NO: 5;

(d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

167. An adeno-associated virus (AAV) vector comprising a human neurogenic differentiation 1 (hNeuroD1) sequence comprising the nucleic acid sequence of SEQ ID NO: 6 and a human distal-less homeobox 2 (hDlx2) sequence comprising the nucleic acid sequence of SEQ ID NO: 13, wherein said hNeuroD1 sequence and said hDlx2 sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, wherein said hNeuroD1 sequence and said hDlx2 sequence are operably linked to regulatory elements comprising:

(a) a glial fibrillary acidic protein (GFAP) promoter comprising the nucleic acid sequence of SEQ ID NO: 26;

(b) a cytomegalovirus (CMV) enhancer comprising the nucleic acid sequence of SEQ ID NO: 11;

(c) a chimeric intron comprising the nucleic acid sequence of SEQ ID NO: 5;

(d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

168. An adeno-associated virus (AAV) vector comprising a nucleic acid sequence encoding a human neurogenic differentiation 1 (hNeuroD1) protein comprising the amino acid coding sequence of SEQ ID NO: 10 and a nucleic acid coding sequence encoding a human distal-less homeobox 2 (hDlx2) protein comprising the amino acid sequence of SEQ ID NO: 14, wherein said hNeuroD1 coding sequence and said hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, wherein said hNeuroD1 coding sequence and said hDlx2 coding sequence is operably linked to regulatory elements comprising:

(a) a glial fibrillary acidic protein (GFAP) promoter comprising the nucleic acid sequence of SEQ ID NO: 26;

(b) an enhancer from a human elongation factor-1 alpha (EF1-α) promoter comprising the nucleic acid sequence of SEQ ID NO: 2;

(c) a chimeric intron comprising the nucleic acid sequence of SEQ ID NO: 5;

(d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

169. An adeno-associated virus (AAV) vector comprising a nucleic acid sequence encoding a human neurogenic differentiation 1 (hNeuroD1) protein comprising the amino acid coding sequence of SEQ ID NO: 10 and a nucleic acid coding sequence encoding a human distal-less homeobox 2 (hDlx2) protein comprising the amino acid sequence of SEQ ID NO: 14, wherein said hNeuroD1 coding sequence and said hDlx2 coding sequence are separated by (i) a P2A linker comprising the nucleic acid sequence selected from the group consisting of SEQ ID NO: 15 and 18, (ii) a T2A linker comprising the nucleic acid sequence selected from the group consisting of SEQ ID NO: 16 and 19, or (iii) an internal ribosomal entry site of the encephalomyocarditis virus (IRES) sequence comprising SEQ ID NO: 3, wherein said hNeuroD1 coding sequence and said hDlx2 coding sequence is operably linked to regulatory elements comprising:

(a) a glial fibrillary acidic protein (GFAP) promoter comprising the nucleic acid sequence of SEQ ID NO: 26;

(b) a cytomegalovirus (CMV) enhancer comprising the nucleic acid sequence of SEQ ID NO: 11;

(c) a chimeric intron comprising the nucleic acid sequence of SEQ ID NO: 5;

(d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

170. An adeno-associated virus (AAV) vector comprising a human neurogenic differentiation 1 (hNeuroD1) sequence comprising the nucleic acid sequence of SEQ ID NO: 6 and a human distal-less homeobox 2 (hDlx2) sequence comprising the nucleic acid sequence of SEQ ID NO: 13, wherein said hNeuroD1 sequence and said hDlx2 sequence are separated by a P2A linker comprising the nucleic acid sequence selected from the group consisting of SEQ ID NO: 15 and 18 or an internal ribosomal entry site of the encephalomyocarditis virus (IRES) sequence comprising SEQ ID NO: 3, wherein said hNeuroD1 sequence and said hDlx2 sequence are operably linked to regulatory elements comprising:

(a) a glial fibrillary acidic protein (GFAP) promoter comprising the nucleic acid sequence of SEQ ID NO: 26;

(b) a cytomegalovirus (CMV) enhancer comprising the nucleic acid sequence of SEQ ID NO: 11;

(c) a chimeric intron comprising the nucleic acid sequence of SEQ ID NO: 5; and (d) a bGH polyadenylation sequence comprising the nucleic acid sequence of SEQ ID NO: 30.

171. An adeno-associated virus (AAV) vector comprising a nucleic acid sequence encoding a human neurogenic differentiation 1 (hNeuroD1) protein comprising the amino acid coding sequence of SEQ ID NO: 10 and a nucleic acid coding sequence encoding a human distal-less homeobox 2 (hDlx2) protein comprising the amino acid sequence of SEQ ID NO: 14, wherein said hNeuroD1 coding sequence and said hDlx2 coding sequence are separated by a P2A linker comprising the nucleic acid sequence selected from the group consisting of SEQ ID NO: 15 and 18 or an internal ribosomal entry site of the encephalomyocarditis virus (IRES) sequence comprising SEQ ID NO: 3, wherein said hNeuroD1 coding sequence and said hDlx2 coding sequence is operably linked to regulatory elements comprising:

(a) a glial fibrillary acidic protein (GFAP) promoter comprising the nucleic acid sequence of SEQ ID NO: 26;
(b) a cytomegalovirus (CMV) enhancer comprising the nucleic acid sequence of SEQ ID NO: 11;
(c) a chimeric intron comprising the nucleic acid sequence of SEQ ID NO: 5; and
(d) a bGH polyadenylation sequence comprising the nucleic acid sequence of SEQ ID NO: 30.

The invention claimed is:

1. An adeno-associated virus (AAV) vector comprising (i) a first nucleic acid sequence encoding human neurogenic differentiation 1 (hNeuroD1) sequence comprising a nucleic acid sequence at least 99% identical to the sequence set forth in SEQ ID NO: 6 and (ii) a second nucleic acid sequence encoding human distal-less homeobox 2 (hDlx2) sequence comprising a nucleic acid sequence at least 99% identical to the sequence set forth in SEQ ID NO: 13;

wherein said first nucleic acid sequence and said second nucleic acid sequence are separated by a P2A linker comprising the nucleic acid sequence of SEQ ID NO: 15, or an internal ribosomal entry site of an encephalomyocarditis virus (IRES) sequence comprising the nucleic acid sequence of SEQ ID NO: 3; and wherein said first nucleic acid sequence and said second nucleic acid sequence are operably linked to regulatory elements comprising:

(a) a glial fibrillary acidic protein (GFAP) promoter comprising the nucleic acid sequence of SEQ ID NO: 26;

(b) an enhancer from a human elongation factor-1 alpha (EF1-$\alpha$) promoter comprising the nucleic acid sequence of SEQ ID NO: 2 or a cytomegalovirus (CMV) enhancer comprising the nucleic acid sequence of SEQ ID NO: 11;

(c) a chimeric intron comprising the nucleic acid sequence of SEQ ID NO: 5;

(d) a woodchuck hepatitis virus posttranscriptional regulatory element (WPRE) comprising the nucleic acid sequence of SEQ ID NO: 29; and (e) a bGH polyadenylation sequence comprising the nucleic acid sequence of SEQ ID NO: 30.

2. The AAV vector of claim 1, wherein said AAV vector is selected from the group consisting of AAV serotype 2, AAV serotype 5, and AAV serotype 9.

3. The AAV vector of claim 2, wherein said AAV vector is AAV serotype 2.

4. The AAV vector of claim 2, wherein said AAV vector is AAV serotype 5.

5. The AAV vector of claim 2, wherein said AAV vector is AAV serotype 9.

6. The AAV vector of claim 1, wherein said AAV vector comprises at least one ITR nucleic acid sequence at least 80% identical to SEQ ID NO: 1 or SEQ ID NO: 9.

7. The AAV vector of claim 1, wherein said AAV vector comprises AAV serotype 2 inverted terminal repeats (ITRs).

8. The AAV vector of claim 1, wherein said AAV vector comprises AAV serotype 5 inverted terminal repeats (ITRs).

9. The AAV vector of claim 1, wherein said AAV vector comprises AAV serotype 9 inverted terminal repeats (ITRs).

10. The AAV vector of claim 1, wherein said AAV vector is arranged in order from 5' to 3' as follows: (a) said CMV enhancer; (b) said GFAP promoter; (c) said chimeric intron; (d) said hDlx2 sequence; (e) said IRES sequence; (f) said hNeuroD1 sequence; and (g) said bGH polyadenylation sequence.

11. The AAV vector of claim 1, wherein said AAV vector is arranged in order from 5' to 3' as follows: (a) said CMV enhancer; (b) said GFAP promoter; (c) said chimeric intron; (d) said hDlx2 sequence; (e) said P2A linker; (f) said hNeuroD1 sequence; and (g) said bGH polyadenylation sequence.

* * * * *